US008772006B2

(12) United States Patent
Sorge et al.

(10) Patent No.: US 8,772,006 B2
(45) Date of Patent: *Jul. 8, 2014

(54) COMPOSITIONS AND METHODS UTILIZING DNA POLYMERASES

(75) Inventors: Joseph A. Sorge, Del Mar, CA (US); Connie Jo Hansen, San Diego, CA (US); Holly Hogrefe, San Diego, CA (US)

(73) Assignee: Agilent Technologies, Inc., Loveland, CO (US)

(*) Notice: Subject to any disclaimer, the term of this patent is extended or adjusted under 35 U.S.C. 154(b) by 1364 days.

This patent is subject to a terminal disclaimer.

(21) Appl. No.: 11/435,018

(22) Filed: May 15, 2006

(65) Prior Publication Data

US 2008/0280291 A1 Nov. 13, 2008

Related U.S. Application Data

(63) Continuation of application No. 10/223,650, filed on Aug. 19, 2002, now abandoned, which is a continuation-in-part of application No. 09/896,923, filed on Jun. 29, 2001, which is a continuation-in-part of application No. 09/698,341, filed on Oct. 27, 2000, now Pat. No. 6,946,273.

(60) Provisional application No. 60/162,600, filed on Oct. 29, 1999.

(51) Int. Cl.
*C12N 9/12* (2006.01)
*C12P 19/34* (2006.01)

(52) U.S. Cl.
USPC ............................ 435/194; 435/183; 530/350

(58) Field of Classification Search
None
See application file for complete search history.

(56) References Cited

U.S. PATENT DOCUMENTS

| | | | | |
|---|---|---|---|---|
| 2,310,652 | A | | 2/1943 | Peter |
| 5,210,036 | A | | 5/1993 | Comb et al. |
| 5,310,652 | A | | 5/1994 | Gelfand et al. |
| 5,322,770 | A | | 6/1994 | Gelfand et al. |
| 5,322,785 | A | | 6/1994 | Comb et al. |
| 5,436,149 | A | | 7/1995 | Barnes |
| 5,545,552 | A | | 8/1996 | Mathur |
| 5,556,772 | A | | 9/1996 | Sorge et al. |
| 5,602,011 | A | | 2/1997 | Luhm et al. |
| 5,674,679 | A | | 10/1997 | Fuller |
| 5,866,395 | A | | 2/1999 | Mathur |
| 5,882,904 | A | * | 3/1999 | Riedl et al. .................. 435/91.2 |
| 5,948,663 | A | | 9/1999 | Mathur |
| 6,027,913 | A | | 2/2000 | Sommer |
| 6,300,073 | B1 | | 10/2001 | Zhao et al. |
| 6,333,158 | B1 | | 12/2001 | Uemori et al. |
| 6,399,320 | B1 | | 6/2002 | Markau et al. |
| 6,436,677 | B1 | | 8/2002 | Gu et al. |
| 6,468,775 | B1 | | 10/2002 | Ankenbauer et al. |
| 6,627,424 | B1 | | 9/2003 | Wang |
| 6,946,273 | B1 | | 9/2005 | Sorge |
| 2002/0012970 | A1 | | 1/2002 | Smith et al. |
| 2002/0119465 | A1 | | 8/2002 | Zhao et al. |
| 2004/0091865 | A1 | | 5/2004 | Gretarsdottir et al. |

FOREIGN PATENT DOCUMENTS

| | | | |
|---|---|---|---|
| EP | 0655506 | A1 | 5/1995 |
| EP | 0727496 | A2 | 8/1996 |
| EP | 1132470 | | 12/2001 |
| EP | 0745676 | | 7/2003 |
| EP | 02803260 | | 12/2004 |
| EP | 05755004.8 | | 7/2009 |
| WO | 92/09689 | | 6/1992 |
| WO | 95/04162 | | 2/1995 |
| WO | 97/39150 | | 10/1997 |
| WO | WO 97/39150 | | 10/1997 |
| WO | 98/14588 | | 4/1998 |
| WO | 99/06538 | | 2/1999 |
| WO | 00/71739 | | 11/2000 |
| WO | 01/09347 | | 2/2001 |
| WO | PCT/US0029706 | | 3/2001 |
| WO | 01/23411 | | 4/2001 |
| WO | 01/32887 | | 5/2001 |
| WO | 01/38546 | | 5/2001 |
| WO | 01/92501 | | 12/2001 |
| WO | 03054139 | | 6/2003 |
| WO | 2004039947 | | 5/2004 |

OTHER PUBLICATIONS

Dong, Qun et al., "Mutational Studies of Human DNA Polymerase," Journal of Biological Chemistry, vol. 268, N. 32, 24163-24174, 1993.

Ngo et al., The Protein Folding Problem and Tertiary Structure Prediction, 1994, Merz et al. (ed.), Birkhauser, Boston, MA, pp. 433 and 492-495.

U.S. Appl. No. 10/839,456, filed May 5, 2004. Office Action mailed Dec. 13, 2007.

U.S. Appl. No. 10/435,766, filed May 12, 2003 Office Action mailed Jun. 28, 2007.

U.S. Appl. No. 10/435,766, filed May 12, 3003 Office Action mailed Jan. 31, 2008.

Gardner, A.F. et al., (1999), "Determinants of Nucleotide Sugar Recognition in an Archaeon DNA Polymerase," Nucleic Acids Research, 27 (12): 2545-2553.

International Search Report of International Application No. PCT/US02/20562 dated Sep. 22, 2003.

(Continued)

*Primary Examiner* — Richard Hutson

(74) *Attorney, Agent, or Firm* — Fox Rothschild LLP

(57) ABSTRACT

The invention features a novel isolated Family B DNA polymerase, a *Thermococcus* polymerase JDF-3, and mutant recombinant forms thereof. Mutant polymerases of the invention are deficient in 3' to 5' exonuclease activity and/or exhibit reduced discrimination against non-conventional nucleotides relative to the wild-type form of the polymerase.

66 Claims, 39 Drawing Sheets

(56) References Cited

OTHER PUBLICATIONS

Stryer, Biochemisty, Third Edition, 1988, W.H. Freeman and Co., New York, p. 72.
Supplemental EP Search Report from EPO2803260 dated Dec. 13, 2004.
Syvanen, A., "From Gels to Chips: "Minisequencing" Primer Extension for Analysis of Point Mutations and Single Nucleotide Polymorphisms," Human Mutation 13:1-10 (1999).
Ngo, et al, Computational Complexity, Protein Structure Prediction, and The Levinthal Paradox, in The Protein Folding Problem and Tertiary Structure Prediction, 1994, Merz et al. (ed.), Birkhauser, Boston, MA, pp. 433 and 492-495.
Tabor, Stanley and Richardson, Charles, C., "A Single Residue in DNA Polymerases of the *Escherichia coli* DNA Polymerase I Family is Critical for Distinguishing Between Deoxy- and Dideoxyribonucleotides," Proc. Natl. Acad. Sci. USA (1995) vol. 92, 6339-6343.
PCT International Search Report received in International Application No. PCT/US2007/087738, dated Apr. 16, 2008.
Southworth, M.W., "Cloning of Thermostable DNA Polymerases From Hyperthermophilic Marine Archaea With Emphasis on *Themococcus sp. 9* Degrees N-7 and Mutations Affecting 3'-5' Exonuclease Activity." Proc. Natl. Acad. Sci. USA. May 28, 1996, vol. 93, No. 11. pp. 5281-5285.
Zhou, M. "Crystallization and Preliminary Diffraction Analysis of a Hyperthermostable DNA Polymerase From a *Thermococcus* Archaeon." Acta. Crystallogr. D. Biol. Crystallogr. Sep. 1, 1998., vol. 54, Pt. 5, pp. 994-995.
Lasken, R.S. "Archaebacterial DNA Polymerases Tightly Bind Uracil-Containing DNA." J. Biol. Chem. Jul 26, 1996, vol. 271, No. 30, pp. 17692-17696.
Hashimoto, H. "Crystal Structure of DNA Polymerase From Hyperthermophilic Archaeon *Pyrococcus kodakaraensis* KOD1." J. Mol. Biol. Feb. 23, 2001, vol. 306, No. 3 pp. 469-477.
Wang, et al., "Crystal Structure of a Pol & Family Replication DNA Polymerase From Bacteriophage RB69" (1997) Cell 89:1087-1099.
Braithwaite and Ito, "Compilation, Alignment, and Phylogenetic Relationships of DNA Polymerases," (1993) Nucleic Acids. Res. V. 21: 787-802.
Polesky, et al., "Side Chains Involved in Catalysis of the Polymerase Reaction of DNA Polymerase I From *Escherichia coli,*" (1992), Journal of Biological Chemistry V. 267: 8417-8428.
Gao, et al., Conferring RNA Polymerase Activity to a DNA Polymerase: A Single Residue in Reverse Transcriptase Controls Substrate Selection, (1997), Proc. Natl. Acad. Sci USA 94:407-411.
Hopfner, et. al., "Crystal Structure of a Thermostable Type B DNA Polymerase From *Thermococus gorgonarius,*" (1999) Proc. Natl. Acad. Sci. USA 96:3600-3605.
Joyce, Catherine M., "Choosing the Right Sugar: How Polymerases Select a Nucleotide Substrate," (1997), Proc. Natl. Acad. Sci. USA 94: 1619-1622.
Blasco, et al., "29 DNA Polymerase Active Site." (1993), J. Biol. Chem. 268:24106-24113.
Astatke, et al., "A Single Side Chain Prevents *Escherichia coli* DNA Polymerase I (Klenow Fragment) From Incorporating Ribonucleotides," (1998), Proc. Natl. Acad. Sci. USA 96:3402-3407.
Astatke, et al., Deoxynucleotide Triphosphate and Pyrophosphate Binding Sites in the Catalytically Competent Ternary Complex for the Polymerase Reaction Catalyzed by DNA Polymerase I (Klenow Fragment), (1995), J. Biol. Chem, 270: 1945-1954.
Stemmer, "Rapid Evolution of a Protein In Vitro by DNA Shufflin," (1994), Nature 370:389-391.
Reha-Krantz, et al., "Bacteriophage T4 DNA Polymerase Mutations That Confer Sensitivity to the Ppi Analog Phosphocoacetic Acid," (1993), J. Virol. 67:60-66.
Kaushik, et al., "Significance of the O-Helix Residues of *Escherichia coli* DNA Po.ymerase I in DNA Synthesis: Dynamics of the dNTP Binding Pocket," (1996), Biochem 35: 7256-7266.
Evans, et al., "Improving Dideoxynucleotide-Triphosphate Utilisation by the Hyper-Thermophilic DNA Polymerases From the Archaeon *Pyrococus furiosus,*" (2000), Nucleic Acids Res 28, 1059-66.
Pandey, et al., "Role of Lysine 758 of *Escherichia coli* DNA Polymerase I as Assessed by Site-Directed mutagenesis," (1994), J. Biol. Chem. 269: 13259-13265.
Polesky, et al., "Identification of Residues Critical for the polymerae Activity of the Klenow Fragment of DNA Polymerase I From *Escherichia coli,*" (1990), J. Biol. Chem. 265: 14579-14591.
Zhu, et al., Mutagenesis of a Highly Conserved Lysine 340 of the PRD1 DNA Polymerase, (1994) Biochem. Biophys Acta 1219:260-266.
Barnes, "DNA Sequencing by Partial Ribosubstitution," (1978) J. Mol. Biol. 119-83-99.
Astatke, et al., "How *E coli* DNA Polymerase I (Klenow Fragment) Distinguishes Between Deoxy- and Dideoxynucleotides," (1998), J. Mol. Biol. 278: 147-165.
Blain & Goff, "Nuclease Activities of Moloney Murine Leukemia Virus Reverse Transcriptase," J. Biol. Chem. (1993) 5:23585-23592.
Blain & Goff, "Effects on DNA Synthesis and Translocation Caused by Mutations in the RNase H Domain of Moloney Murine Leukemia Virus Reverse Transcriptase," J. Virol. (1995) 69:4440-4452.
Myers and Gelfand, "Reverse Transcription and DNA Amplification by a *Thermus thermophilus* DNA Polymerase," 1991, Biochem., 30:7661-7666.
Perler, et al., "Intervening Sequences in an Archaea DNA Polymerase Gene," (1992) Proc. Natl. Acad. Sci. USA 89:5577-5581.
Kong, et al., "Characterization of a DNA Polymerase From the Hyperthermophile Archaea *Thermococcus litoralis,*" (1993), J. Biol. Chem. 268:1965.
Xu, et al., "In Vitro Protein Splicing of Purified Precursor and the Identification of a Branched Intermediate," (1993), Cell 75 (7), 1371-1377.
Lundberg, et., "High-Fidelity Amplification Using a Thermostable DNA Polymerase Isolated From *Pyrococcus furiosus,*" (1991) Gene 108:1.
Blanco, et al., "A General Structure for DNA-Dependent DNA Polymerases," (1991), Gene 100:27-38.
Larder, et al., "Related Functional Domains in Virus DNA Polymerases," (1987), EMBO J. 6:169-175.
Rodriguez, et al., "Crystal Structure of a Pol a Family DNA Polymerae From the Hyperthermophilic Archaeon *Thermococcus* sp. 9 degrees N-7," (2000), J. Mol. Biol. 299:447-462.
Pavlov, et al., "Helix-Hairpin-Helix Motifs Confer Salt Resistance and Processivity on Chimeric DNA Polymerases," 2002, Proc. Natl. Acad. Sci. USA, 99:13510-13515.
Office Action dated May 13, 2009; U.S Appl. No. 09/896,923.
Dong, Q. et al., "Mutational Studies on Human DNA Polymerase Alpha", J. Biol. Chem. 268:32, 24163-24174, Nov. 15, 1993.
Office Action dated Nov. 1, 2011; Japanese patent application No. 2001-535569 (with English language translation).
Office Action dated Dec. 13, 2007; US patent application publication No. 20050158730.
Office Action dated Jun. 18, 2009; US patent application publication No. 20040081965.
Supplemental European Search Report dated Jul. 6, 2009; European Patent Application No. 05755004.
International Search Report dated Mar. 29, 2001; PCT/US00/29706.
Office Action (Notice of Allowance) dated May 14, 2012; U.S. Appl. No. 09/896,923.

* cited by examiner

| FIG. 1A |
| --- |
| FIG. 1B |

FIG. 1

JDF-3 DNA polymerase nucleotide sequence: 2331 nucleotides

ATGATCCTTGACGTTGATTACATCACCGAGAATGGAAAGCCCGTCATCAGGGTCTTCAAGAAGGAGAACGG
CGAGTTCAGGATTGAATACGACCGCGAGTTCGAGCCCTACTTCTACGCGCTCCTCAGGGACGACTCTGCCA
TCGAAGAAATCAAAAAGATAACCGCGGAGAGGCACGGCAGGGTCGTTAAGGTTAAGCGCGCGGAGAAGGTG
AAGAAAAAGTTCCTCGGCAGGTCTGTGGAGGTCTGGGTCCTCTACTTCACGCACCCGCAGGACGTTCCGGC
AATCCGCGACAAAATAAGGAAGCACCCCGCGGTCATCGACATCTACGAGTACGACATACCCTTCGCCAAGC
GCTACCTCATAGACAAGGGCCTAATCCCGATGGAAGGTGAGGAAGAGCTTAAACTCATGTCCTTCGACATC
GAGACGCTCTACCACGAGGGAGAAGAGTTTGGAACCGGGCCGATTCTGATGATAAGCTACGCCGATGAAAG
CGAGGCGCGCGTGATAACCTGGAAGAAGATCGACCTTCCTTACGTTGAGGTTGTCTCCACCGAGAAGGAGA
TGATTAAGCGCTTCTTGAGGGTCGTTAAGGAGAAGGACCCGGACGTGCTGATAACATACAACGGCGACAAC
TTCGACTTCGCCTACCTGAAAAAGCGCTGTGAGAAGCTTGGCGTGAGCTTTACCCTCGGGAGGGACGGGAG
CGAGCCGAAGATACAGCGCATGGGGGACAGGTTTGCGGTCGAGGTGAAGGGCAGGGTACACTTCGACCTTT
ATCCAGTCATAAGGCGCACCATAAACCTCCCGACCTACACCCTTGAGGCTGTATACGAGGCGGTTTTCGGC
AAGCCCAAGGAGAAGGTCTACGCCGAGGAGATAGCCACCGCCTGGGAGACCGGCGAGGGGCTTGAGAGGGT
CGCGCGCTACTCGATGGAGGACGCGAGGGTTACCTACGAGCTTGGCAGGGAGTTCTTCCCGATGGAGGCCC

FIG. 1A

AGCTTTCCAGGCTCATCGGCCAAGGCCTCTGGGACGTTTCCCGCTCCAGCACCGGCAACCTCGTCGAGTGG
TTCCTCCTAAGGAAGGCCTACGAGAGGAACGAACTCGCTCCCAACAAGCCCGACGAGAGGGAGCTGGCGAG
GAGAAGGGGGGGCTACgcCGGTGGCTACGTCAAGGAGCCGGAGCGGGACTGTGGACAATATCGTGTATC
TAGACTTTCGTAGTCTCTACCCTTCAATCATAATCACCCACAACGTCTCGCCAGATACGCTCAACCGCGAG
GGGTGTAGGAGCTACGACGTTGCCCCCGAGGTCGGTCACAAGTTCTGCAAGGACTTCCCCGGCTTCATTCC
GAGCCTGCTCGGAAACCTGCTGGAGGAAAGGCAGAAGATAAAGAGGAAGATGAAGGCAACTCTCGACCCGC
TGGAGAAGAATCTCCTCGATTACAGGCAACGCGCCATCAAGATTCTCGCCAACAGCTACTACGGCTACTAC
GGCTATGCCAGGGCAAGATGGTACTGCAGGGAGTGCGCCGAGAGCGTTACGGCATGGGAAGGGAGTACAT
CGAAATGGTCATCAGAGAGCTTGAGGAAAAGTTCGGTTTTAAAGTCCTCTATGCAGACACAGACGGTCTCC
ATGCCACCATTCCTGGAGCGGACGCTGAAACAGTCAAGAAAAAGGCAATGGAGTTCTTAAACTATATCAAT
CCCAAACTGCCCGGCCTTCTCGAACTCGAATACGAGGGCTTCTACGTCAGGGGCTTCTTCGTCACGAAGAA
AAAGTACGCGGTCATCGACGAGGAGGGCAAGATAACCACGCGCGGGCTTGAGATAGTCAGGCGCGACTGGA
GCGAGATAGCGAAGGAGACGCAGGCGAGGGTTTTGGAGGCGATACTCAGGCACGGTGACGTTGAAGAGGCC
GTCAGAATTGTCAGGGAAGTCACCGAAAAGCTGAGCAAGTACGAGGTTCCGCCGGAGAAGCTGGTTATCCA
CGAGCAGATAACGCGCGAGCTCAAGGACTACAAGGCCACCGGCCCGCACGTAGCCATAGCGAAgcGTTTGG
CCGCCAGAGGTGTTAAAATCCGGCCCGGAACTGTGATAAGCTACATCGTTCTGAAGGGCTCCGGAAGGATA
GGCGACAGGGCGATTCCCTTCGACGAGTTCGACCCGACGAAGCACAAGTACGATGCGGACTACTACATCGA
GAACCAGGTTCTGCCGGCAGTTGAGAGAATCCTCAGGGCCTTCGGCTACCGCAAGGAAGACCTGCGCTACC
AGAAGACGAGGCAGGTCGGGCTTGGCGCGTGGCTGAAGCCGAAGGGGAAGAAGAAGTGA

FIG. 1B

JDF-3 DNA polymerase amino acid sequence
Theoretical molecular weight: 90.3 kD

MILDVDYITENGKPVIRVFKKENGEFRIEYDREFEPYFYALLRDDSAIEEIKKITAERHGRVVKVKRAEKV
KKKFLGRSVEVWVLYFTHPQDVPAIRDKIRKHPAVIDIYEYDIPFAKRYLIDKGLIPMEGEEELKLMSFDI
ETLYHEGEEFGTGPILMISYADESEARVITWKKIDLPYVEVVSTEKEMIKRFLRVVKEKDPDVLITYNGDN
FDFAYLKKRCEKLGVSFTLGRDGSEPKIQRMGDRFAVEVKGRVHFDLYPVIRRTINLPTYTLEAVYEAVFG
KPKEKVYAEEIATAWETGEGLERVARYSMEDARVTYELGREFFPMEAQLSRLIGQGLWDVSRSSTGNLVEW
FLLRKAYERNELAPNKPDERELARRRGGYAGGYVKEPERGLWDNIVYLDFRSLYPSIIITHNVSPDTLNRE
GCRSYDVAPEVGHKFCKDFPGFIPSLLGNLLEERQKIKRKMKATLDPLEKNLLDYRQRAIKILANSYYGYY
GYARARWYCRECAESVTAWGREYIEMVIRELEEKFGFKVLYADTDGLHATIPGADAETVKKKAMEFLNYIN
PKLPGLLELEYEGFYVRGFFVTKKKYAVIDEEGKITTRGLEIVRRDWSEIAKETQARVLEAILRHGDVEEA
VRIVREVTEKLSKYEVPPEKLVIHEQITRELKDYKATGPHVAIAKRLAARGVKIRPGTVISYIVLKGSGRI
GDRAIPFDEFDPTKHKYDADYYIENQVLPAVERILRAFGYRKEDLRYQKTRQVGLGAWLKPKGKKK

FIG. 2

JDF-3 DNA polymerase with intein sequence

MILDVDYITENGKPVIRVFKKENGEFRIEYDREFEPYFYALLRDDSAIEE
IKKITAERHGRVVKVKRAEKVKKKFLGRSVEVWVLYFTHPQDVPAIRDKI
RKHPAVIDIYEYDIPFAKRYLIDKGLIPMEGEEELKLMSFDIETLYHEGE
EFGTGPILMISYADESEARVITWKKIDLPYVEVVSTEKEMIKRFLRVVKE
KDPDVLITYNGDNFDFAYLKKRCEKLGVSFTLGRDGSEPKIQRMGDRFAV Extein 1
EVKGRVHFDLYPVIRRTINLPTYTLEAVYEAVFGKPKEKVYAEEIATAWE
TGEGLERVARYSMEDARVTYELGREFFPMEAQLSRLIGQGLWDVSRSSTG
NLVEWFLLRKAYERNELAPNKPDERELARRRGGYAGGYVKEPERGLWDNI
VYLDFRSLYPSIIITHNVSPDTLNREGCRSYDVAPEVGHKFCKDFPGFIP
SLLGNLLEERQKIKRKMKATLDPLEKNLLDYRQRAIKILAN SLLPGEWVA
VIEGGKLRPVRIGELVDGLMEASGERVKRDGDTEVLEVEGLYASPSTGSP
RKPAQCR*KP**GTAMPGKFTE*LSTPEGGLSVTRGHSLFAYRDASLWR*
RGRRRFKPGDLLAVPSG*PSRRGGRGSTSLNCSSNCPRRKRPTCHRHSGK
GRKNFFRGMLRTLRWIFGEEKTGGRPGATWSTLRGLGYVKLRKIGYGVVD
REGLGKVPRFYERLVEVIRYNGNRGEFIADFNALRPVLRLMMPEKELEEW Intein 1
LVGTRNGFRIRPFIEVDWKFAKLLGYYVSEGSAGKWKNRTGGWSYSVRLY
NEDGSVLDDMERLARSSLGA*ARGELRRDFKEDGLHNLRGALRFTGREQE
GSVAYLHVP*GGPLGLP*GVLHRRRRRSPEQDGSALHQERASG*RPRPAP
ELAGRLSDKRPPRQRGLQGLRERGTALYRVPEAEERLTYSHVIPREVLEE
TSAGPSRRT*VTGNSGSWWKAGSSTRKGPVG*AGSSTGI*SSTGSRKSGR
KATRGTSTT*ALRRTRTSGGLWVPLRAQX

FIG. 3A

```
                                 SYYGYYGYARARWYCRECAES
VTAWGREYIEMVIRELEEKFGFKVLYADTDGLHATIPGADAETVKKKAME
FLNYINPKLPGLLELEYEGFYVRGFFVTKKKYAVIDEEGKITTRGLEIVR
RDWSEIAKETQARVLEAILRHGDVEEAVRIVREVTEKLSKYEVPPEKLVI   Extein 2
HEQITRELKDYKATGPHVAIAKRLAARGVKIRPGTVISYIVLKGSGRIGD
RAIPFDEFDPTKHKYDADYYIENQVLPAVERILRAFGYRKEDLRYQKTRQ
VGLGAWLKPKGKKK
```

FIG. 3B

JDF-3 DNA polymerase genomic sequence

```
AATTCCACTGCCGTGTTTAACCTTTCCACCGTTGAACTTGAGGGTGATTT
TCTGAGCCTCCTCAATCACTTAATCGAGACCGCGGATTACCTTGAACTGG
TACACGTTCAACGATTCGGTTCTTGTAATGGTCGATACTGGGCCGTGCTG
GATTTTCTAAACGTCTCAAGAACGGCTTTCATCAACGGAAACTGCCACGT   5' untranslated sequence
CTCCGCCGTCGTGAGGGTTAAACCTGAAGTTCAAGACTTTGCAACGGAAT
GGCGAGAGAACGGCGACTACCCCAGTGGAAGAGCTTTTGAAAGCCAAAGC
CGAGCTTCAGCGAATGTGCGGTGCCCTTGTTCAAGAGTTGTGAGCCCTTG
ATTGTTGTTTTCTCCTCTTTTCTGATAACATCGATGGCGAAGTTTATTAG
TTCTCAGTTCGATAATCAGGCAGGTGTTGGTC
```

FIG. 4A

ATGATCCTTGACGTTGAT
TACATCACCGAGAATGGAAAGCCCGTCATCAGGGTCTTCAAGAAGGAGAA
CGGCGAGTTCAGGATTGAATACGACCGCGAGTTCGAGCCCTACTTCTACG
CGCTCCTCAGGGACGACTCTGCCATCGAAGAAATCAAAAAGATAACCGCG
GAGAGGCACGGCAGGGTCGTTAAGGTTAAGCGCGCGGAGAAGGTGAAGAA
AAAGTTCCTCGGCAGGTCTGTGGAGGTCTGGGTCCTCTACTTCACGCACC
CGCAGGACGTTCCGGCAATCCGCGACAAAATAAGGAAGCACCCCGCGGTC
ATCGACATCTACGAGTACGACATACCCTTCGCCAAGCGCTACCTCATAGA
CAAGGGCCTAATCCCGATGGAAGGTGAGGAAGAGCTTAAACTCATGTCCT
TCGACATCGAGACGCTCTACCACGAGGGAGAAGAGTTTGGAACCGGGCCG
ATTCTGATGATAAGCTACGCCGATGAAAGCGAGGCGCGCGTGATAACCTG
GAAGAAGATCGACCTTCCTTACGTTGAGGTTGTCTCCACCGAGAAGGAGA
TGATTAAGCGCTTCTTGAGGGTCGTTAAGGAGAAGGACCCGGACGTGCTG
ATAACATACAACGGCGACAACTTCGACTTCGCCTACCTGAAAAAGCGCTG
TGAGAAGCTTGGCGTGAGCTTTACCCTCGGGAGGGACGGAGCGAGCCGA Extein 1
AGATACAGCGCATGGGGGACAGGTTTGCGGTCGAGGTGAAGGGCAGGGTA
CACTTCGACCTTTATCCAGTCATAAGGCGCACCATAAACCTCCCGACCTA
CACCCTTGAGGCTGTATACGAGGCGGTTTTCGGCAAGCCCAAGGAGAAGG
TCTACGCCGAGGAGATAGCCACCGCCTGGGAGACCGGCGAGGGGCTTGAG
AGGGTCGCGCGCTACTCGATGGAGGACGCGAGGGTTACCTACGAGCTTGG
CAGGGAGTTCTTCCCGATGGAGGCCCAGCTTTCCAGGCTCATCGGCCAAG
GCCTCTGGGACGTTTCCCGCTCCAGCACCGGCAACCTCGTCGAGTGGTTC
CTCCTAAGGAAGGCCTACGAGAGGAACGAACTCGCTCCCAACAAGCCCGA
CGAGAGGGAGCTGGCGAGGAGAAGGGGGGCTACGCCGGTGGCTACGTCA
AGGAGCCGGAGCGGGGACTGTGGGACAATATCGTGTATCTAGACTTTCGT
AGTCTCTACCCTTCAATCATAATCACCCACAACGTCTCGCCAGATACGCT

FIG. 4B

CAACCGCGAGGGGTGTAGGAGCTACGACGTTGCCCCCGAGGTCGGTCACA
AGTTCTGCAAGGACTTCCCCGGCTTCATTCCGAGCCTGCTCGGAAACCTG
CTGGAGGAAAGGCAGAAGATAAAGAGGAAGATGAAGGCAACTCTCGACCC
GCTGGAGAAGAATCTCCTCGATTACAGGCAACGCGCCATCAAGATTCTCG
CCAAC

AGCCTTCTTCCCGGGGAGTGGGTTGCGGTCATTGAAGGGGGGAAA
CTCAGGCCCGTCCGCATCGGCGAGCTGGTTGATGGACTGATGGAAGCCAG
CGGGGAGAGGGTGAAAAGAGACGGCGACACCGAGGTCCTTGAAGTCGAGG
GGCTTTACGCCTCTCCTTCGACAGGGAGTCCAAGAAAGCCCGCACAATGC
CGGTGAAAGCCGTGATAAGGCACCGCTATGCCGGGGAAGTTTACAGAATA
GCTCTCAACTCCGGAAGGAGGATTAAGCGTGACGCGCGGCCACAGCCTCT
TCGCGTACCGGGACGCGAGCTTGTGGAGGTGACGGGGGAGGAGGAGGTTC
AAGCCCGGCGACCTCCTGGCGGTGCCAAGCGGATAACCCTCCCGGAGAGG
AGGGAGAGGCTCAACATCGTTGAACTGCTCCTCGAACTGCCCGAGGAGGA
AACGGCCGACATGTCATCGACATTCCGGCAAGGGTAGAAAGAACTTCTTC
AGGGGAATGCTCAGAACCCTCCGCTGGATTTTCGGGGAGGAGAAGACCGG Intein 1
AGGGCGGCCAGGCGCTACCTGGAGCACCTTGCGTGGGCTCGGCTACGTGA
AGCTGAGGAAAATCGGCTACGGGGTGGTTGATAGGGAGGGACTGGGAAAG
GTACCGCGCTTCTACGAGAGGCTCGTGGAGGTAATCCGCTACAACGGCAA
CAGGGGGGAGTTCATCGCCGATTTCAACGCGCTCCGCCCCGTCCTCCGCC
TGATGATGCCCGAGAAGGAGCTTGAAGAGTGGCTCGTTGGGACGAGGAAC
GGGTTCAGGATAAGGCCGTTCATAGAGGTTGATTGGAAGTTCGCAAAGCT
CCTCGGCTACTACGTGAGCGAGGGGAGCGCCGGGAAGTGGAAAAACCGGA
CCGGGGGCTGGAGCTACTCGGTGAGGCTTTACAACGAGGACGGGAGCGTT
CTCGACGACATGGAGAGACTCGCGAGGAGTTCTTTGGGGGCGTGAGCGCG

FIG. 4C

GGGGGAACTACGTCGAGATTTCAAAGAAGATGGCCTACATAATCTTCGAG
GGGCTCTGCGGTTCACCGGCCGAGAACAAGAGGGTTCCGTGGCTTATCTT
CACGTCCCCTGAGGAGGTCCGCTGGGCCTTCCTTGAGGGGTACTTCATCG Intein 1 (continued)
GCGACGGCGACGTTCACCCGAGCAAGATGGTTCGGCTCTCCACCAAGAGC
GAGCTTCTGGCTAACGGCCTCGTCCTGCTCCTGAACTCGCTGGGCGTCTC
AGCGATAAACGTCCGCCACGACAGCGGGGTTTACAGGGTCTACGTGAACG
AGGAACTGCCCTTTACAGAGTACCGGAAGCGGAAGAACGCCTCACTTACT
CCCACGTCATACCGAGGGAAGTGCTGGAGGAGACTTCGGCCGGGCCTTCC
AGAAGAACATGAGTCACGGGAAATTCAGGGAGCTGGTGGAAAGCGGGGAG
CTCGACGCGGAAAGGGCCGGTAGGATAGGCTGGCTCCTCGACGGGGATAT
AGTCCTCGACAGGGTCTCGGAAGTCAGGAAGGAAAGCTACGAGGGGTACG
TCTACGACCTGAGCGTTGAGGAGGACGAGAACTTCTGGCGGCTTTGGGT
TCCTCTACGCGCACAACNN AGCTACTACGGCTACTACGGCTATGCCAGGG
CAAGATGGTACTGCAGGGAGTGCGCCGAGAGCGTTACGGCATGGGGAAGG
GAGTACATCGAAATGGTCATCAGAGAGCTTGAGGAAAAGTTCGGTTTTAA
AGTCCTCTATGCAGACACAGACGGTCTCCATGCCACCATTCCTGGAGCGG
ACGCTGAAACAGTCAAGAAAAAGGCAATGGAGTTCTTAAACTATATCAAT
CCCAAACTGCCCGGCCTTCTCGAACTCGAATACGAGGGCTTCTACGTCAG
GGGCTTCTTCGTCACGAAGAAAAAGTACGCGGTCATCGACGAGGAGGGCA
AGATAACCACGCGCGGGCTTGAGATAGTCAGGCGCGACTGGAGCGAGATA
GCGAAGGAGACGCAGGCGAGGGTTTTGGAGGCGATACTCAGGCACGGTGA Extein 2
CGTTGAAGAGGCCGTCAGAATTGTCAGGGAAGTCACCGAAAAGCTGAGCA
AGTACGAGGTTCCGCCGGAGAAGCTGGTTATCCACGAGCAGATAACGCGC
GAGCTCAAGGACTACAAGGCCACCGGCCCGCACGTAGCCATAGCGAAGCG

FIG. 4D

TTTGGCCGCCAGAGGTGTTAAAATCCGGCCCGGAACTGTGATAAGCTACA
TCGTTCTGAAGGGCTCCGGAAGGATAGGCGACAGGGCGATTCCCTTCGAC
GAGTTCGACCCGACGAAGCACAAGTACGATGCGGACTACTACATCGAGAA
CCAGGTTCTGCCGGCAGTTGAGAGAATCCTCAGGGCCTTCGGCTACCGCA
AGGAAGACCTGCGCTACCAGAAGACGAGGCAGGTCGGGCTTGGCGCGTGG
CTGAAGCCGAAGGGGAAGAAGAAGTGA

GGAATTATCTGGTTTCTTTTCCC
AGCATTAAATGCTTCCGACATTGCCTTATTTATGAAACTCCTGTTGTGCC
TGAGTTTGTGCCAGAAAACAGCCTGTTCTGACGGCGCTTTTTCTTGCCAG
GTCTCTTGAGTTTCGCAAGGGTCTTCTCGACCAGCTCAATGGTCTTGTCG
TCATTGTTNNNNNNNNNNNNNNNNNNNNNNCCCGGGGACTTCATACTGGC
GGTAATAGACAGGGATTCCTTCCTCAAGGACTTCCCGGGAGGCATTGGAG
TTTTTTGGTGGGGCTTTCACAGGATTTGCTCATCTTGTGGATTTCTCGTT
CGATTGAATCTGTCCACTTGAGGGTGTAGGTCGAGACGGTGGAGCGCGTA
TTCCGGGAGCGGGTCTTGAGGCTCCATTTTTCAGTCCTCCTCCGGCGAAG 3' Untranslated sequence
AAGTGGAACTCAAGCCGGGTGTTAGCTTATGTTATGTTCCCAACTCCTCC
AGCACCTCCAGGATCCCCTCAATCCCGGAACCTCGAAGCCCCTCTCGTGG
ATCTTTCTAACTTCCTCTGCCTCCGGGTTTATCCAGACCGCCCACATGCC
GGCTCTCAGCGCACCCTCGAAATCCTCCGCGTAGGTGTCGCCGATGTGGA
TTGCCTCGTCCGGCTCGACCCCGAAGCATCGAGCGGTTTTCTGAACATCT
CGGGCATCGGCTTATACGCCAGAACCTCGTCGGCGAAGAAGGTTCCCTCA
ATGTAGTCCATCAGGCCGAACCTCTCGAGGGGGGGCCCGGTACCCAATTC
GCCCTATAGTGAGTCGATTACAATTCACTGGCCGTCGTTTTACAACGTCG
TGACTGGGAAAACCCTGGCGTTACCCAACTTAAGTCGCTTTGCAGCACAT
CCCCC

FIG. 4E

Preliminary Qualification of Mutants

Sequencing with Purified Mutants

Sequencing with the P410L, A485T Double Mutant and $\alpha$-$^{33}$P Dideoxynucleotides

FIG. 14

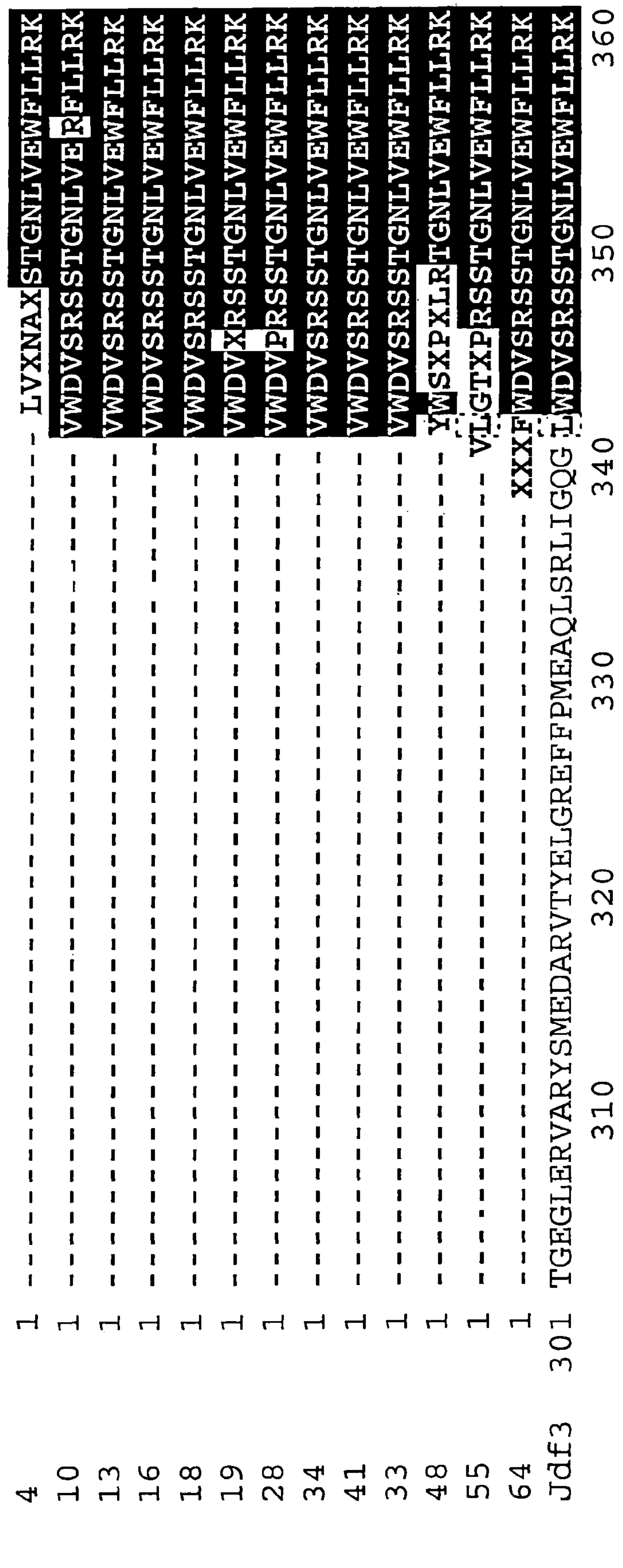

FIG. 14A

| | | | |
|---|---|---|---|
| 4 | 1 | ----------------------------------- | LVXNAXSTGNLVEWFLLRK |
| 10 | 1 | ----------------------------------- | VWDVSRSSTGNLVERFLLRK |
| 13 | 1 | ----------------------------------- | VWDVSRSSTGNLVEWFLLRK |
| 16 | 1 | ----------------------------------- | VWDVSRSSTGNLVEWFLLRK |
| 18 | 1 | ----------------------------------- | VWDVSRSSTGNLVEWFLLRK |
| 19 | 1 | ----------------------------------- | VWDVXRSSTGNLVEWFLLRK |
| 28 | 1 | ----------------------------------- | VWDVPRSSTGNLVEWFLLRK |
| 34 | 1 | ----------------------------------- | VWDVSRSSTGNLVEWFLLRK |
| 41 | 1 | ----------------------------------- | VWDVSRSSTGNLVEWFLLRK |
| 33 | 1 | ----------------------------------- | VWDVSRSSTGNLVEWFLLRK |
| 48 | 1 | --------------------------------YWSXPXLRTGNLVEWFLLRK |
| 55 | 1 | -------------------------------VLGTXPRSSTGNLVEWFLLRK |
| 64 | 1 | ---------------------------XXXFWDVSRSSTGNLVEWFLLRK |
| Jdf3 | 301 | TGEGLERVARYSMEDARVTYELGREFFPMEAQLSRLIGQG LWDVSRSSTGNLVEWFLLRK |
| | | 310      320      330      340 | 350       360 |

| | | |
|---|---|---|
| 4 | 20 | AYERNELAPNKPDERELARRRGGYAGGYVKEPERGLWDNIVYLDFRSLYPSIIITHNVSP |
| 10 | 21 | AYERNELAPNKPDERELARRRGGYAGGYVKEPERGLWDNIVYLDFRSLYPSIIITHSVSP |
| 13 | 21 | AYERNELAPNKPDERELARRRGGYAGGYVKEPERGLWDNIVYLDFRSLYPSIIITHNVSP |
| 16 | 21 | AYERNELAPNKPDERELARRRGGYAGGYVKEPERGLWDNIVYLDFRSLYPSIIITHNVSP |
| 18 | 21 | AYERNELAPNKPDERELARRRGGYAGGYVKEPERGLWDNIVYLDFRSLYPSIIITHNVSP |
| 19 | 21 | AYERNELAPNKPDERELARRRGGYAGGYVKEPERGQWDNIAYLDFRSLYPSIIITHNVSP |
| 28 | 21 | AYERNELAPNKPDERELARRRGGYAGGYVKEPERGLWDNIVYLDFRSLYPSIIITHNVSP |
| 34 | 21 | AYERNELAPNKPDERELARRRGGYAGGYVKEPERGLWDNIVYLDFRSLYPSIIITHNVSP |
| 41 | 21 | AYERNELAPNKPDERELARRRGGYAGGYVKEPERGPWDNIVYLDFRSLYPSIIITHNVSP |
| 33 | 21 | AYERNKLAPNKPDERELARRRGGYAGGYVKEPERGLWDNIVYLDFRSLYPSIIITHNVSP |
| 48 | 21 | AYERNELAPNKPDERELARRRGGYAGGYVKEPERGLWDNIVYLDFRSLYPSIIITHNVSP |
| 55 | 22 | AYERNELAPNKPDERELARRRGGYAGGYVKEPERGLWDNIVYLDFRSHYPSIIITHNVSP |
| 64 | 24 | AYERNELAPNKPDERELARRRGGYAGGYVKEPERGLWDNIVYLDFRSLYPSIIITHNVSP |
| Jdf3 | 361 | AYERNELAPNKPDERELARRRGGYAGGYVKEPERGLWDNIVYLDFRSLYPSIIITHNVSP |

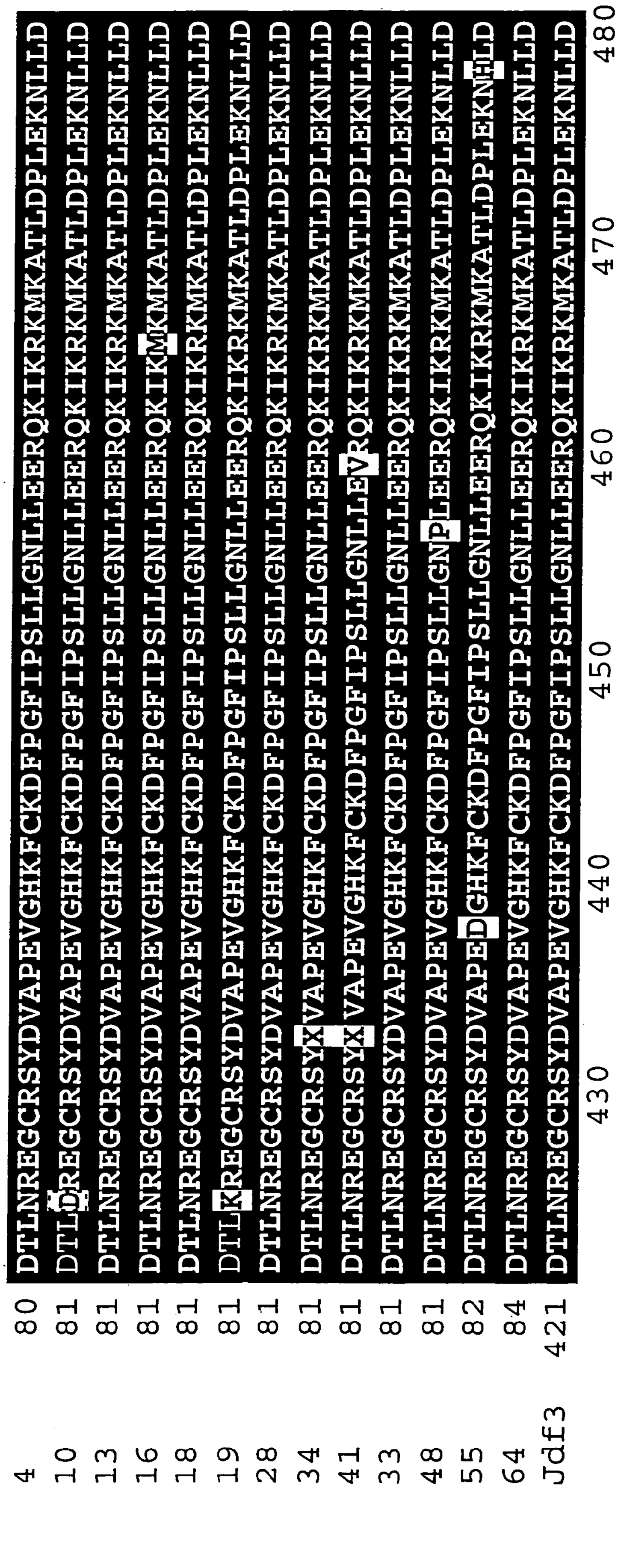

FIG. 14C

| | | |
|---|---|---|
| 4 | 80 | DTLNREGCRSYDVAPEVGHKFCKDFPGFIPSLLGNLLEERQKIKRKMKATLDPLEKNLLD |
| 10 | 81 | DTLDREGCRSYDVAPEVGHKFCKDFPGFIPSLLGNLLEERQKIKRKMKATLDPLEKNLLD |
| 13 | 81 | DTLNREGCRSYDVAPEVGHKFCKDFPGFIPSLLGNLLEERQKIKRKMKATLDPLEKNLLD |
| 16 | 81 | DTLNREGCRSYDVAPEVGHKFCKDFPGFIPSLLGNLLEERQKIKRKMKATLDPLEKNLLD |
| 18 | 81 | DTLNREGCRSYDVAPEVGHKFCKDFPGFIPSLLGNLLEERQKIKRKMKATLDPLEKNLLD |
| 19 | 81 | DTLKREGCRSYDVAPEVGHKFCKDFPGFIPSLLGNLLEERQKIKRKMKATLDPLEKNLLD |
| 28 | 81 | DTLNREGCRSYDVAPEVGHKFCKDFPGFIPSLLGNLLEERQKIKRKMKATLDPLEKNLLD |
| 34 | 81 | DTLNREGCRSYXVAPEVGHKFCKDFPGFIPSLLGNLLEERQKIKRKMKATLDPLEKNLLD |
| 41 | 81 | DTLNREGCRSYXVAPEVGHKFCKDFPGFIPSLLGNLLEVRQKIKRKMKATLDPLEKNLLD |
| 33 | 81 | DTLNREGCRSYDVAPEVGHKFCKDFPGFIPSLLGNLLEERQKIKRKMKATLDPLEKNLLD |
| 48 | 81 | DTLNREGCRSYDVAPEDGHKFCKDFPGFIPSLLGNLLEERQKIKRKMKATLDPLEKNLLD |
| 55 | 82 | DTLNREGCRSYDVAPEDGHKFCKDFPGFIPSLLGNPLEERQKIKRKMKATLDPLEKNLLD |
| 64 | 84 | DTLNREGCRSYDVAPEVGHKFCKDFPGFIPSLLGNLLEERQKIKRKMKATLDPLEKNLLD |
| Jdf3 | 421 | DTLNREGCRSYDVAPEVGHKFCKDFPGFIPSLLGNLLEERQKIKRKMKATLDPLEKNLLD |
| | | 430   440   450   460   470   480 |

| | | |
|---|---|---|
| 4 | 140 | YRQRAIKILANSYYGYCGYARARWYCRECAESVTAWGREYIEMVIRELEEKFGFKVLYAD |
| 10 | 141 | YRQRAIKILANSYYGYYGYARARWYCRECAESVTAWGREYIEMVIRELEEKFGFKVLYAD |
| 13 | 141 | YRQRAIKILANSYYGYYGYARARWYCRECAESVTAWGREYIEMVIRELEEKFGFKVLYAD |
| 16 | 141 | YRQRAIKILANSYYGYYGYARARWYCRECAESVTAWGREYIEMVIRELEEKFGFKVLYAD |
| 18 | 141 | YRQRAIKILANNYYGYYGYARARWYCRECAESVTAWGREYIEMVIRELEEKFGFKVLYAD |
| 19 | 141 | YRQRAIKILANSYYGYYGYARARWYCRECAESVTAWGREYIEMVIRELEEKFGFKVLYAD |
| 28 | 141 | YRQRAIKILANSYYGYYGYARARWYCRECAESVTAWGREYIEMVIRELEEKFGFKVLYAD |
| 34 | 141 | YRQRAIKILANSYYGYYGYARARWYCRECAESVTAWGREYIEMVIRELEEKFGFKVLYAD |
| 41 | 141 | YRQRAIKILANSYYGYYGYARARWYCRECAESVTAWGREYIEMVIRELEEKFGFKVLYAD |
| 33 | 141 | YRQRAIKILANSYYGYYGYARARWYCRECAESVTAWGREYIEMVIRELEEKFGFKVLYAD |
| 48 | 141 | YRQRAIKILANSYYGYYGYARARWYCRECAESVTAWGREYIEMVIRELEEKFGFKVLYAD |
| 55 | 142 | YRQRAIKILANSYYGYYGYARARWYCRECAESVTAWGREYIEMVIRELEEKFGFKVLYAD |
| 64 | 144 | YRQRAIKILANSYYGNYGYARARWYCRECAESVTAWGREYIEMVIRELEEKFGFKVLYAD |
| Jdf3 | 481 | YRQRAIKILANSYYGYYGYARARWYCRECAESVTAWGREYIEMVIRELEEKFGFKVLYAD |

490 500

| | | |
|---|---|---|
| 4 | 200 | TDGLHATIPGADAETVKKKAMEFLNYINPKLPGLLELEYEGFYVRGFFVTKKKYAVIDEE |
| 10 | 201 | TDGLHATIPGADAETVKKKAMEFLNYINPKLPGLLELEYEGFYVRGFFVTKKKYAVIDEE |
| 13 | 201 | TDGLHATIPGADAETVKKKAMEFLNYINPKLPGLLELEYEGFYVRGFFVTKKKYAVIDEE |
| 16 | 201 | TDGLHATIPGADAETVKKKAMEFLNYINPKLPGLLELKYEGFYVRGFFVTKKKYAVIDEE |
| 18 | 201 | TDGLHATIPGADAETVKKKAMEFLNYINPKLPGLLELEYEGFYVRGFFVTKKKYAVIDEE |
| 19 | 201 | TDGLHATIPGADAETVKKKAMEFLNYINLKLPGLLELEYEGFYVRGFFVTKKKXAVIDEE |
| 28 | 201 | TDGLHATIPGADAETVKKKAMEFLNYINPKLPGLLELEYEGFYVRGFFVTKKKYAVIDEE |
| 34 | 201 | TDGLHATIPGADAETVKKKAMEFLNYINPKLPGLLELEYEGFYVRGFFVTKKKYAVIDEE |
| 41 | 201 | TDGLHATIPGADAETVKKKAMEFLNYINPKLPGLLELEYEGFYVRGFFVTKKKYAVIDEE |
| 33 | 201 | TDGLHATIPGADAETVKKKAMEFLNYINPKLPGLLEPEYEGFYVRGFFVTKKKYAVIDEE |
| 48 | 201 | TDGLHATIPGADAETVKKKAMEFLNYINPKLPGLLELEYEGFYVRGFFVTKKKYAVIDEE |
| 55 | 202 | TDGLHATIPGADAETVKKKAMEFLNYINPKLPGLLELEYEGFYVRGFFVTKKKYAVIDEE |
| 64 | 204 | TDGLHATIPGADAETVKKKAMEFLNYINPKLPGLLELEYEGFYVRGFFVTKKKYAVIDEE |
| Jdf3 | 541 | TDGLHATIPGADAETVKKKAMEFLNYINPKLPGLLELEYEGFYVRGFFVTKKKYAVIDEE |
| | | 550 560 570 580 590 600 |

FIG. 15B

| | | |
|---|---|---|
| 4 | 260 | GKITTRGLEIVRRDWSEIAKETQARVLEAVLRHGDVEEAVRIVREVTEKLSKYEVPPEKL |
| 10 | 261 | GKITTRGLEIVRRDWSEIAKETQARVLEAILRHGDVEEAVRIVREVTEKLSKYEVPPEEL |
| 13 | 261 | GKITTRGLEIVRRDWSEIAKETQARVLEAILRHGDVEEAVRIVRKVTEKLSKYEVPPEKL |
| 16 | 261 | GKITTRGLEIVRRDWSEIAKETQARVLEAILRHGDVEEAVRIVREVTEKLSKYEVPPEKL |
| 18 | 261 | GKITTRGLEIVRRDWSEIAKETQARVLEAILRHDDVEEAVRIVREVTEKLSKYEVPPEKL |
| 19 | 261 | GKITTRGLEIVRRDWSKIAKETQARVLEAILRHGDVEEAIRIVREVTEKLSKYEVPPEKL |
| 28 | 261 | GKIATRGLEIVRRDWSEIAKETQARVLEAILRHGDVEEAVRIVREVTEKLSKYEVPPEKL |
| 34 | 261 | GKITTRGLEIVRRDWSEIAKETQARVLEAILRHGDVEEAVRIVREVTEKLNKYEVPPEKL |
| 41 | 261 | GKITTRGLEIVRRDWSEIAKETQARVLEAILRHGDVEEAVRIVREVTEKLSKYEVPPEKL |
| 33 | 261 | GKITTRGLEIVRRDWSEIAKETQARVLEAILRHGDVEEAVRIVREVTEKLSKYEVPPEKL |
| 48 | 261 | GKITTRGLEIVRRDWSEIAKETQARVLEAILRHGDVEEAVRIVREVTEKLSKYEVPPVKL |
| 55 | 262 | GKITTRGLEIVRRDWSEIAKETQARVLEAILRHGDVEEAVRIVREVTEKLSKYEVPPGEA |
| 64 | 264 | GKITTRGLEIVRRDWSEIAKETQARVLEAILRHGDVEEAVRIVREVTEKLSKYEVPPEKL |
| Jdf3 | 601 | GKITTRGLEIVRRDWSEIAKETQARVLEAILRHGDVEEAVRIVREVTEKLSKYEVPPEKL |

SEQUENCE LISTING

```
<160> NUMBER OF SEQ ID NOS: 72

<210> SEQ ID NO 1
<211> LENGTH: 2331
<212> TYPE: DNA
<213> ORGANISM: Thermococcus sp. JDF-3

<400> SEQUENCE: 1

atgatccttg acgttgatta catcaccgag aatggaaagc ccgtcatcag ggtcttcaag      60

aaggagaacg gcgagttcag gattgaatac gaccgcgagt tcgagcccta cttctacgcg     120

ctcctcaggg acgactctgc catcgaagaa atcaaaaaga taaccgcgga gaggcacggc     180

agggtcgtta aggttaagcg cgcggagaag gtgaagaaaa agttcctcgg caggtctgtg     240

gaggtctggg tcctctactt cacgcacccg caggacgttc cggcaatccg cgacaaaata     300

aggaagcacc ccgcggtcat cgacatctac gagtacgaca tacccttcgc caagcgctac     360

ctcatagaca agggcctaat cccgatggaa ggtgaggaag agcttaaact catgtccttc     420

gacatcgaga cgctctacca cgagggagaa gagtttggaa ccgggccgat tctgatgata     480

agctacgccg atgaaagcga ggcgcgcgtg ataacctgga agaagatcga ccttccttac     540

gttgaggttg tctccaccga gaaggagatg attaagcgct tcttgagggt cgttaaggag     600

aaggacccgg acgtgctgat aacatacaac ggcgacaact tcgacttcgc ctacctgaaa     660

aagcgctgtg agaagcttgg cgtgagcttt accctcggga gggacgggag cgagccgaag     720

atacagcgca tgggggacag gtttgcggtc gaggtgaagg gcagggtaca cttcgacctt     780

tatccagtca taaggcgcac cataaacctc ccgacctaca cccttgaggc tgtatacgag     840

gcggttttcg gcaagcccaa ggagaaggtc tacgccgagg agatagccac cgcctgggag     900

accggcgagg ggcttgagag ggtcgcgcgc tactcgatgg aggacgcgag ggttacctac     960

gagcttggca gggagttctt cccgatggag gcccagcttt ccaggctcat cggccaaggc    1020

ctctgggacg tttcccgctc cagcaccggc aacctcgtcg agtggttcct cctaaggaag    1080

gcctacgaga ggaacgaact cgctcccaac aagcccgacg agagggagct ggcgaggaga    1140

aggggggggct acgccggtgg ctacgtcaag gagccggagc ggggactgtg ggacaatatc    1200

gtgtatctag actttcgtag tctctaccct tcaatcataa tcacccacaa cgtctcgcca    1260

gatacgctca accgcgaggg gtgtaggagc tacgacgttg cccccgaggt cggtcacaag    1320

ttctgcaagg acttccccgg cttcattccg agcctgctcg gaaacctgct ggaggaaagg    1380

cagaagataa agaggaagat gaaggcaact ctcgacccgc tggagaagaa tctcctcgat    1440

tacaggcaac gcgccatcaa gattctcgcc aacagctact acggctacta cggctatgcc    1500
```

-continued agggcaagat ggtactgcag ggagtgcgcc gagagcgtta cggcatgggg aagggagtac 1560
atcgaaatgg tcatcagaga gcttgaggaa aagttcggtt ttaaagtcct ctatgcagac 1620
acagacggtc tccatgccac cattcctgga gcggacgctg aaacagtcaa gaaaaaggca 1680
atggagttct taaactatat caatcccaaa ctgcccggcc ttctcgaact cgaatacgag 1740
ggcttctacg tcaggggctt cttcgtcacg aagaaaaagt acgcggtcat cgacgaggag 1800
ggcaagataa ccacgcgcgg gcttgagata gtcaggcgcg actggagcga gatagcgaag 1860
gagacgcagg cgagggtttt ggaggcgata ctcaggcacg gtgacgttga agaggccgtc 1920
agaattgtca gggaagtcac cgaaaagctg agcaagtacg aggttccgcc ggagaagctg 1980
gttatccacg agcagataac gcgcgagctc aaggactaca aggccaccgg cccgcacgta 2040
gccatagcga agcgtttggc cgccagaggt gttaaaatcc ggcccggaac tgtgataagc 2100
tacatcgttc tgaagggctc cggaaggata ggcgacaggg cgattccctt cgacgagttc 2160
gacccgacga agcacaagta cgatgcggac tactacatcg agaaccaggt tctgccggca 2220
gttgagagaa tcctcagggc cttcggctac cgcaaggaag acctgcgcta ccagaagacg 2280
aggcaggtcg ggcttggcgc gtggctgaag ccgaagggga agaagaagtg a 2331

<210> SEQ ID NO 2
<211> LENGTH: 776
<212> TYPE: PRT
<213> ORGANISM: Thermococcus sp. JDF-3

<400> SEQUENCE: 2

Met Ile Leu Asp Val Asp Tyr Ile Thr Glu Asn Gly Lys Pro Val Ile
1 5 10 15

Arg Val Phe Lys Lys Glu Asn Gly Glu Phe Arg Ile Glu Tyr Asp Arg
20 25 30

Glu Phe Glu Pro Tyr Phe Tyr Ala Leu Leu Arg Asp Asp Ser Ala Ile
35 40 45

Glu Glu Ile Lys Lys Ile Thr Ala Glu Arg His Gly Arg Val Val Lys
50 55 60

Val Lys Arg Ala Glu Lys Val Lys Lys Lys Phe Leu Gly Arg Ser Val
65 70 75 80

Glu Val Trp Val Leu Tyr Phe Thr His Pro Gln Asp Val Pro Ala Ile
85 90 95

Arg Asp Lys Ile Arg Lys His Pro Ala Val Ile Asp Ile Tyr Glu Tyr
100 105 110

Asp Ile Pro Phe Ala Lys Arg Tyr Leu Ile Asp Lys Gly Leu Ile Pro
115 120 125

Met Glu Gly Glu Glu Glu Leu Lys Leu Met Ser Phe Asp Ile Glu Thr
130 135 140

Leu Tyr His Glu Gly Glu Glu Phe Gly Thr Gly Pro Ile Leu Met Ile
145 150 155 160

Ser Tyr Ala Asp Glu Ser Glu Ala Arg Val Ile Thr Trp Lys Lys Ile
165 170 175

Asp Leu Pro Tyr Val Glu Val Val Ser Thr Glu Lys Glu Met Ile Lys
180 185 190

Arg Phe Leu Arg Val Val Lys Glu Lys Asp Pro Asp Val Leu Ile Thr
195 200 205

Tyr Asn Gly Asp Asn Phe Asp Phe Ala Tyr Leu Lys Lys Arg Cys Glu
210 215 220

Lys Leu Gly Val Ser Phe Thr Leu Gly Arg Asp Gly Ser Glu Pro Lys

-continued

```
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655
```

```
Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Gly Lys Lys Lys
    770                 775


<210> SEQ ID NO 3
<211> LENGTH: 1300
<212> TYPE: PRT
<213> ORGANISM: Thermococcus sp. JDF-3
<220> FEATURE:
<221> NAME/KEY: MISC_FEATURE
<222> LOCATION: (1015)..(1015)
<223> OTHER INFORMATION: x = uknown

<400> SEQUENCE: 3

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Leu Met Ser Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220
```

-continued

```
Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Leu Leu Pro Gly
                485                 490                 495

Glu Trp Val Ala Val Ile Glu Gly Gly Lys Leu Arg Pro Val Arg Ile
            500                 505                 510

Gly Glu Leu Val Asp Gly Leu Met Glu Ala Ser Gly Glu Arg Val Lys
        515                 520                 525

Arg Asp Gly Asp Thr Glu Val Leu Glu Val Glu Gly Leu Tyr Ala Ser
    530                 535                 540

Pro Ser Thr Gly Ser Pro Arg Lys Pro Ala Gln Cys Arg Lys Pro Gly
545                 550                 555                 560

Thr Ala Met Pro Gly Lys Phe Thr Glu Leu Ser Thr Pro Glu Gly Gly
                565                 570                 575

Leu Ser Val Thr Arg Gly His Ser Leu Phe Ala Tyr Arg Asp Ala Ser
            580                 585                 590

Leu Trp Arg Arg Gly Arg Arg Arg Phe Lys Pro Gly Asp Leu Leu Ala
        595                 600                 605

Val Pro Ser Gly Pro Ser Arg Arg Gly Gly Arg Gly Ser Thr Ser Leu
    610                 615                 620

Asn Cys Ser Ser Asn Cys Pro Arg Arg Lys Arg Pro Thr Cys His Arg
625                 630                 635                 640

His Ser Gly Lys Gly Arg Lys Asn Phe Phe Arg Gly Met Leu Arg Thr
```

-continued

```
                645                 650                 655

Leu Arg Trp Ile Phe Gly Glu Glu Lys Thr Gly Gly Arg Pro Gly Ala
            660                 665                 670

Thr Trp Ser Thr Leu Arg Gly Leu Gly Tyr Val Lys Leu Arg Lys Ile
        675                 680                 685

Gly Tyr Gly Val Val Asp Arg Glu Gly Leu Gly Lys Val Pro Arg Phe
    690                 695                 700

Tyr Glu Arg Leu Val Glu Val Ile Arg Tyr Asn Gly Asn Arg Gly Glu
705                 710                 715                 720

Phe Ile Ala Asp Phe Asn Ala Leu Arg Pro Val Leu Arg Leu Met Met
                725                 730                 735

Pro Glu Lys Glu Leu Glu Glu Trp Leu Val Gly Thr Arg Asn Gly Phe
            740                 745                 750

Arg Ile Arg Pro Phe Ile Glu Val Asp Trp Lys Phe Ala Lys Leu Leu
        755                 760                 765

Gly Tyr Tyr Val Ser Glu Gly Ser Ala Gly Lys Trp Lys Asn Arg Thr
    770                 775                 780

Gly Gly Trp Ser Tyr Ser Val Arg Leu Tyr Asn Glu Asp Gly Ser Val
785                 790                 795                 800

Leu Asp Asp Met Glu Arg Leu Ala Arg Ser Ser Leu Gly Ala Ala Arg
                805                 810                 815

Gly Glu Leu Arg Arg Asp Phe Lys Glu Asp Gly Leu His Asn Leu Arg
            820                 825                 830

Gly Ala Leu Arg Phe Thr Gly Arg Glu Gln Glu Gly Ser Val Ala Tyr
        835                 840                 845

Leu His Val Pro Gly Gly Pro Leu Gly Leu Pro Gly Val Leu His Arg
    850                 855                 860

Arg Arg Arg Arg Ser Pro Glu Gln Asp Gly Ser Ala Leu His Gln Glu
865                 870                 875                 880

Arg Ala Ser Gly Arg Pro Arg Pro Ala Pro Glu Leu Ala Gly Arg Leu
                885                 890                 895

Ser Asp Lys Arg Pro Pro Arg Gln Arg Gly Leu Gln Gly Leu Arg Glu
            900                 905                 910

Arg Gly Thr Ala Leu Tyr Arg Val Pro Glu Ala Glu Glu Arg Leu Thr
        915                 920                 925

Tyr Ser His Val Ile Pro Arg Glu Val Leu Glu Glu Thr Ser Ala Gly
    930                 935                 940

Pro Ser Arg Arg Thr Val Thr Gly Asn Ser Gly Ser Trp Trp Lys Ala
945                 950                 955                 960

Gly Ser Ser Thr Arg Lys Gly Pro Val Gly Ala Gly Ser Ser Thr Gly
                965                 970                 975

Ile Ser Ser Thr Gly Ser Arg Lys Ser Gly Arg Lys Ala Thr Arg Gly
            980                 985                 990

Thr Ser Thr Thr Ala Leu Arg Arg  Thr Arg Thr Ser Gly  Gly Leu Trp
        995                 1000                1005

Val Pro  Leu Arg Ala Gln Xaa  Ser Tyr Tyr Gly Tyr  Tyr Gly Tyr
    1010                 1015                 1020

Ala Arg  Ala Arg Trp Tyr Cys  Arg Glu Cys Ala Glu  Ser Val Thr
    1025                 1030                 1035

Ala Trp  Gly Arg Glu Tyr Ile  Glu Met Val Ile Arg  Glu Leu Glu
    1040                 1045                 1050

Glu Lys  Phe Gly Phe Lys Val  Leu Tyr Ala Asp Thr  Asp Gly Leu
    1055                 1060                 1065
```

His Ala Thr Ile Pro Gly Ala Asp Ala Glu Thr Val Lys Lys Lys
1070 1075 1080

Ala Met Glu Phe Leu Asn Tyr Ile Asn Pro Lys Leu Pro Gly Leu
1085 1090 1095

Leu Glu Leu Glu Tyr Glu Gly Phe Tyr Val Arg Gly Phe Phe Val
1100 1105 1110

Thr Lys Lys Lys Tyr Ala Val Ile Asp Glu Glu Gly Lys Ile Thr
1115 1120 1125

Thr Arg Gly Leu Glu Ile Val Arg Arg Asp Trp Ser Glu Ile Ala
1130 1135 1140

Lys Glu Thr Gln Ala Arg Val Leu Glu Ala Ile Leu Arg His Gly
1145 1150 1155

Asp Val Glu Glu Ala Val Arg Ile Val Arg Glu Val Thr Glu Lys
1160 1165 1170

Leu Ser Lys Tyr Glu Val Pro Pro Glu Lys Leu Val Ile His Glu
1175 1180 1185

Gln Ile Thr Arg Glu Leu Lys Asp Tyr Lys Ala Thr Gly Pro His
1190 1195 1200

Val Ala Ile Ala Lys Arg Leu Ala Ala Arg Gly Val Lys Ile Arg
1205 1210 1215

Pro Gly Thr Val Ile Ser Tyr Ile Val Leu Lys Gly Ser Gly Arg
1220 1225 1230

Ile Gly Asp Arg Ala Ile Pro Phe Asp Glu Phe Asp Pro Thr Lys
1235 1240 1245

His Lys Tyr Asp Ala Asp Tyr Tyr Ile Glu Asn Gln Val Leu Pro
1250 1255 1260

Ala Val Glu Arg Ile Leu Arg Ala Phe Gly Tyr Arg Lys Glu Asp
1265 1270 1275

Leu Arg Tyr Gln Lys Thr Arg Gln Val Gly Leu Gly Ala Trp Leu
1280 1285 1290

Lys Pro Lys Gly Lys Lys Lys
1295 1300

<210> SEQ ID NO 4
<211> LENGTH: 5255
<212> TYPE: DNA
<213> ORGANISM: Thermococcus sp. JDF-3
<220> FEATURE:
<221> NAME/KEY: misc_feature
<222> LOCATION: (3518)..(3519)
<223> OTHER INFORMATION: n = unknown
<220> FEATURE:
<221> NAME/KEY: misc_feature
<222> LOCATION: (4560)..(4580)
<223> OTHER INFORMATION: n = unknown

<400> SEQUENCE: 4
aattccactg ccgtgtttaa cctttccacc gttgaacttg agggtgattt tctgagcctc 60
ctcaatcact taatcgagac cgcggattac cttgaactgg tacacgttca acgattcggt 120
tcttgtaatg gtcgatactg ggccgtgctg gattttctaa acgtctcaag aacggctttc 180
atcaacggaa actgccacgt ctccgccgtc gtgagggtta aacctgaagt tcaagacttt 240
gcaacggaat ggcgagagaa cggcgactac cccagtggaa gagcttttga aagccaaagc 300
cgagcttcag cgaatgtgcg gtgcccttgt tcaagagttg tgagcccttg attgttgttt 360
tctcctcttt tctgataaca tcgatggcga agtttattag ttctcagttc gataatcagg 420

-continued

```
caggtgttgg tcatgatcct tgacgttgat tacatcaccg agaatggaaa gcccgtcatc    480
agggtcttca agaaggagaa cggcgagttc aggattgaat acgaccgcga gttcgagccc    540
tacttctacg cgctcctcag ggacgactct gccatcgaag aaatcaaaaa gataaccgcg    600
gagaggcacg gcagggtcgt taaggttaag cgcgcggaga aggtgaagaa aaagttcctc    660
ggcaggtctg tggaggtctg ggtcctctac ttcacgcacc cgcaggacgt tccggcaatc    720
cgcgacaaaa taaggaagca ccccgcggtc atcgacatct acgagtacga catacccttc    780
gccaagcgct acctcataga caagggccta atcccgatgg aaggtgagga agagcttaaa    840
ctcatgtcct tcgacatcga gacgctctac cacgagggag aagagtttgg aaccgggccg    900
attctgatga taagctacgc cgatgaaagc gaggcgcgcg tgataacctg gaagaagatc    960
gaccttcctt acgttgaggt tgtctccacc gagaaggaga tgattaagcg cttcttgagg   1020
gtcgttaagg agaaggaccc ggacgtgctg ataacataca acggcgacaa cttcgacttc   1080
gcctacctga aaaagcgctg tgagaagctt ggcgtgagct ttaccctcgg gagggacggg   1140
agcgagccga agatacagcg catgggggac aggtttgcgg tcgaggtgaa gggcagggta   1200
cacttcgacc tttatccagt cataaggcgc accataaacc tcccgaccta cacccttgag   1260
gctgtatacg aggcggtttt cggcaagccc aaggagaagg tctacgccga ggagatagcc   1320
accgcctggg agaccggcga ggggcttgag agggtcgcgc gctactcgat ggaggacgcg   1380
agggttacct acgagcttgg cagggagttc ttcccgatgg aggcccagct ttccaggctc   1440
atcggccaag gcctctggga cgtttcccgc tccagcaccg gcaacctcgt cgagtggttc   1500
ctcctaagga aggcctacga gaggaacgaa ctcgctccca acaagcccga cgagagggag   1560
ctggcgagga gaaggggggg ctacgccggt ggctacgtca aggagccgga gcggggactg   1620
tgggacaata tcgtgtatct agactttcgt agtctctacc cttcaatcat aatcacccac   1680
aacgtctcgc cagatacgct caaccgcgag ggtgtagga gctacgacgt tgccccccgag   1740
gtcggtcaca agttctgcaa ggacttcccc ggcttcattc cgagcctgct cggaaacctg   1800
ctggaggaaa ggcagaagat aaagaggaag atgaaggcaa ctctcgaccc gctggagaag   1860
aatctcctcg attacaggca acgcgccatc aagattctcg ccaacagcct tcttcccggg   1920
gagtgggttg cggtcattga aggggggaaa ctcaggcccg tccgcatcgg cgagctggtt   1980
gatggactga tggaagccag cggggagagg gtgaaaagag acggcgacac cgaggtcctt   2040
gaagtcgagg ggctttacgc ctctccttcg acagggagtc caagaaagcc cgcacaatgc   2100
cggtgaaagc cgtgataagg caccgctatg ccggggaagt ttacagaata gctctcaact   2160
ccggaaggag gattaagcgt gacgcgcggc cacagcctct tcgcgtaccg ggacgcgagc   2220
ttgtggaggt gacgggggag gaggaggttc aagcccggcg acctcctggc ggtgccaagc   2280
ggataaccct cccggagagg agggagaggc tcaacatcgt tgaactgctc ctcgaactgc   2340
ccgaggagga aacggccgac atgtcatcga cattccggca agggtagaaa gaacttcttc   2400
aggggaatgc tcagaaccct ccgctggatt ttcggggagg agaagaccgg agggcggcca   2460
ggcgctacct ggagcacctt gcgtgggctc ggctacgtga agctgaggaa aatcggctac   2520
ggggtggttg atagggaggg actgggaaag gtaccgcgct tctacgagag gctcgtggag   2580
gtaatccgct acaacggcaa caggggggag ttcatcgccg atttcaacgc gctccgcccc   2640
gtcctccgcc tgatgatgcc cgagaaggag cttgaagagt ggctcgttgg gacgaggaac   2700
gggttcagga taaggccgtt catagaggtt gattggaagt tcgcaaagct cctcggctac   2760
tacgtgagcg aggggagcgc cgggaagtgg aaaaaccgga ccgggggctg gagctactcg   2820
```

-continued

```
gtgaggcttt acaacgagga cgggagcgtt ctcgacgaca tggagagact cgcgaggagt   2880
tctttggggg cgtgagcgcg gggggaacta cgtcgagatt tcaaagaaga tggcctacat   2940
aatcttcgag ggctctgcg gttcaccggc cgagaacaag agggttccgt ggcttatctt   3000
cacgtcccct gaggaggtcc gctgggcctt ccttgagggg tacttcatcg gcgacggcga   3060
cgttcacccg agcaagatgg ttcggctctc caccaagagc gagcttctgg ctaacggcct   3120
cgtcctgctc ctgaactcgc tgggcgtctc agcgataaac gtccgccacg acagcggggt   3180
ttacagggtc tacgtgaacg aggaactgcc ctttacagag taccggaagc ggaagaacgc   3240
ctcacttact cccacgtcat accgagggaa gtgctggagg agacttcggc cgggccttcc   3300
agaagaacat gagtcacggg aaattcaggg agctggtgga aagcggggag ctcgacgcgg   3360
aaagggccgg taggataggc tggctcctcg acggggatat agtcctcgac agggtctcgg   3420
aagtcaggaa ggaaagctac gaggggtacg tctacgacct gagcgttgag gaggacgaga   3480
acttctggcg ggctttgggt tcctctacgc gcacaacnna gctactacgg ctactacggc   3540
tatgccaggg caagatggta ctgcagggag tgcgccgaga gcgttacggc atggggaagg   3600
gagtacatcg aaatggtcat cagagagctt gaggaaaagt tcggttttaa agtcctctat   3660
gcagacacag acggtctcca tgccaccatt cctggagcgg acgctgaaac agtcaagaaa   3720
aaggcaatgg agttcttaaa ctatatcaat cccaaactgc ccggccttct cgaactcgaa   3780
tacgagggct tctacgtcag ggcttcttc gtcacgaaga aaaagtacgc ggtcatcgac   3840
gaggagggca agataaccac gcgcgggctt gagatagtca ggcgcgactg gagcgagata   3900
gcgaaggaga cgcaggcgag ggttttggag gcgatactca ggcacggtga cgttgaagag   3960
gccgtcagaa ttgtcaggga agtcaccgaa aagctgagca agtacgaggt tccgccggag   4020
aagctggtta tccacgagca gataacgcgc gagctcaagg actacaaggc caccggcccg   4080
cacgtagcca tagcgaagcg tttggccgcc agaggtgtta aaatccggcc cggaactgtg   4140
ataagctaca tcgttctgaa gggctccgga aggataggcg acagggcgat tcccttcgac   4200
gagttcgacc cgacgaagca caagtacgat gcggactact acatcgagaa ccaggttctg   4260
ccggcagttg agagaatcct cagggccttc ggctaccgca aggaagacct gcgctaccag   4320
aagacgaggc aggtcgggct tggcgcgtgg ctgaagccga aggggaagaa gaagtgagga   4380
attatctggt ttcttttccc agcattaaat gcttccgaca ttgccttatt tatgaaactc   4440
ctgttgtgcc tgagtttgtg ccagaaaaca gcctgttctg acggcgcttt ttcttgccag   4500
gtctcttgag tttcgcaagg gtcttctcga ccagctcaat ggtcttgtcg tcattgtttn   4560
nnnnnnnnnn nnnnnnnnnn cccggggact tcatactggc ggtaatagac agggattcct   4620
tcctcaagga cttcccggga ggcattggag ttttttggtg gggctttcac aggatttgct   4680
catcttgtgg atttctcgtt cgattgaatc tgtccacttg agggtgtagg tcgagacggt   4740
ggagcgcgta ttccgggagc gggtcttgag gctccatttt tcagtcctcc tccggcgaag   4800
aagtggaact caagccgggt gttagcttat gttatgttcc caactcctcc agcacctcca   4860
ggatcccctc aatcccggaa cctcgaagcc cctctcgtgg atctttctaa cttcctctgc   4920
ctccgggttt atccagaccg cccacatgcc ggctctcagc gcaccctcga aatcctccgc   4980
gtaggtgtcg ccgatgtgga ttgcctcgtc cggctcgacc ccgaagcatc gagcggtttt   5040
ctgaacatct cgggcatcgg cttatacgcc agaacctcgt cggcgaagaa ggttccctca   5100
atgtagtcca tcaggccgaa cctctcgagg gggggcccgg tacccaattc gccctatagt   5160
```

```
gagtcgatta caattcactg gccgtcgttt tacaacgtcg tgactgggaa aaccctggcg   5220

ttacccaact taagtcgctt tgcagcacat ccccc                              5255


<210> SEQ ID NO 5
<211> LENGTH: 9
<212> TYPE: PRT
<213> ORGANISM: Thermococcus sp. JDF-3
<220> FEATURE:
<221> NAME/KEY: MISC_FEATURE
<222> LOCATION: (2)..(4)
<223> OTHER INFORMATION: x = uknown
<220> FEATURE:
<221> NAME/KEY: MISC_FEATURE
<222> LOCATION: (7)..(7)
<223> OTHER INFORMATION: x = unkown

<400> SEQUENCE: 5

Lys Xaa Xaa Xaa Asn Ser Xaa Tyr Gly
1               5


<210> SEQ ID NO 6
<211> LENGTH: 10
<212> TYPE: PRT
<213> ORGANISM: Thermococcus sp. JDF-3
<220> FEATURE:
<221> NAME/KEY: MISC_FEATURE
<222> LOCATION: (2)..(4)
<223> OTHER INFORMATION: x =unknown
<220> FEATURE:
<221> NAME/KEY: MISC_FEATURE
<222> LOCATION: (7)..(8)
<223> OTHER INFORMATION: x =unknown
<220> FEATURE:
<221> NAME/KEY: MISC_FEATURE
<222> LOCATION: (5)..(5)
<223> OTHER INFORMATION: x = X or F

<400> SEQUENCE: 6

Lys Xaa Xaa Xaa Xaa Gly Xaa Xaa Tyr Gly
1               5                   10


<210> SEQ ID NO 7
<211> LENGTH: 10
<212> TYPE: PRT
<213> ORGANISM: Thermococcus sp. JDF-3
<220> FEATURE:
<221> NAME/KEY: UNSURE
<222> LOCATION: (2)..(3)
<223> OTHER INFORMATION: X = unknown
<220> FEATURE:
<221> NAME/KEY: MISC_FEATURE
<222> LOCATION: (2)..(3)
<223> OTHER INFORMATION: X = UNKNOWN

<400> SEQUENCE: 7

Asp Xaa Xaa Ser Leu Tyr Pro Ser Ile Ile
1               5                   10


<210> SEQ ID NO 8
<211> LENGTH: 10
<212> TYPE: PRT
<213> ORGANISM: Thermococcus sp. JDF-3

<400> SEQUENCE: 8

Asp Phe Arg Ser Leu Tyr Leu Ser Ile Ile
1               5                   10


<210> SEQ ID NO 9
<211> LENGTH: 10
```

<212> TYPE: PRT
<213> ORGANISM: Thermococcus sp. JDF-3

<400> SEQUENCE: 9

Asp Phe Arg Ser His Tyr Pro Ser Ile Ile
1 5 10

<210> SEQ ID NO 10
<211> LENGTH: 10
<212> TYPE: PRT
<213> ORGANISM: Thermococcus sp. JDF-3

<400> SEQUENCE: 10

Asp Phe Arg Ser Phe Tyr Pro Ser Ile Ile
1 5 10

<210> SEQ ID NO 11
<211> LENGTH: 30
<212> TYPE: DNA
<213> ORGANISM: Artificial Sequence
<220> FEATURE:
<221> NAME/KEY: misc_feature
<223> OTHER INFORMATION: Synthetic oligonucleotide PCR primer

<400> SEQUENCE: 11
gggaaacata tgatccttga cgttgattac 30

<210> SEQ ID NO 12
<211> LENGTH: 31
<212> TYPE: DNA
<213> ORGANISM: Artificial Sequence
<220> FEATURE:
<221> NAME/KEY: misc_feature
<223> OTHER INFORMATION: Synthetic oligonucleotide PCR primer

<400> SEQUENCE: 12
gggaaaggat cctcacttct tcttcccctt c 31

<210> SEQ ID NO 13
<211> LENGTH: 34
<212> TYPE: DNA
<213> ORGANISM: Artificial Sequence
<220> FEATURE:
<221> NAME/KEY: misc_feature
<223> OTHER INFORMATION: Synthetic oligonucleotide primer

<400> SEQUENCE: 13
tcagatgaat tcgatgatcc ttgacgttga ttac 34

<210> SEQ ID NO 14
<211> LENGTH: 54
<212> TYPE: DNA
<213> ORGANISM: Artificial Sequence
<220> FEATURE:
<221> NAME/KEY: misc_feature
<223> OTHER INFORMATION: Synthetic oligonucleotide primer

<400> SEQUENCE: 14
gagagaattc ataatgataa ggaggaaaaa attatgatcc ttgacgttga ttac 54

<210> SEQ ID NO 15
<211> LENGTH: 31
<212> TYPE: DNA
<213> ORGANISM: Artificial Sequence
<220> FEATURE:
<221> NAME/KEY: misc_feature
<223> OTHER INFORMATION: Synthetic oligonucleotide primer

<400> SEQUENCE: 15
tcagatctcg agtcacttct tcttcccctt c 31

<210> SEQ ID NO 16
<211> LENGTH: 29
<212> TYPE: DNA
<213> ORGANISM: Artificial Sequence
<220> FEATURE:
<221> NAME/KEY: misc_feature
<223> OTHER INFORMATION: Synthetic oligonucleotide sequencing primer

<400> SEQUENCE: 16
ccagctttcc agactagtcg gccaaggcc 29

<210> SEQ ID NO 17
<211> LENGTH: 16
<212> TYPE: DNA
<213> ORGANISM: Artificial Sequence
<220> FEATURE:
<221> NAME/KEY: misc_feature
<223> OTHER INFORMATION: Synthetic oligonucleotide sequencing primer

<400> SEQUENCE: 17
aactctcgac ccgctg 16

<210> SEQ ID NO 18
<211> LENGTH: 37
<212> TYPE: DNA
<213> ORGANISM: Artificial Sequence
<220> FEATURE:
<221> NAME/KEY: misc_feature
<223> OTHER INFORMATION: Synthetic oligonucleotide primer

<400> SEQUENCE: 18
ggtttcccag tcacgacgtt gtaaaacgac ggccagt 37

<210> SEQ ID NO 19
<211> LENGTH: 18
<212> TYPE: DNA
<213> ORGANISM: Artificial Sequence
<220> FEATURE:
<221> NAME/KEY: misc_feature
<223> OTHER INFORMATION: First strand of synthetic oligonucleotide duplex

<400> SEQUENCE: 19
taacgttggg ggggggca 18

<210> SEQ ID NO 20
<211> LENGTH: 18
<212> TYPE: DNA
<213> ORGANISM: Artificial Sequence
<220> FEATURE:
<221> NAME/KEY: misc_feature
<223> OTHER INFORMATION: Second strand of synthetic oligonucleotide duplex

<400> SEQUENCE: 20
tgcaaccccc ccccgtat 18

<210> SEQ ID NO 21
<211> LENGTH: 139
<212> TYPE: PRT
<213> ORGANISM: Thermococcus sp. JDF-3
<220> FEATURE:
<221> NAME/KEY: MISC_FEATURE
<222> LOCATION: (6)..(6)
<223> OTHER INFORMATION: X = UNKNOWN
<220> FEATURE:
<221> NAME/KEY: MISC_FEATURE
<222> LOCATION: (3)..(3)
<223> OTHER INFORMATION: X = unknown

<400> SEQUENCE: 21

```
Leu Val Xaa Asn Ala Xaa Ser Thr Gly Asn Leu Val Glu Trp Phe Leu
1               5                   10                  15

Leu Arg Lys Ala Tyr Glu Arg Asn Glu Leu Ala Pro Asn Lys Pro Asp
            20                  25                  30

Glu Arg Glu Leu Ala Arg Arg Arg Gly Gly Tyr Ala Gly Gly Tyr Val
        35                  40                  45

Lys Glu Pro Glu Arg Gly Leu Trp Asp Asn Ile Val Tyr Leu Asp Phe
    50                  55                  60

Arg Ser Leu Tyr Pro Ser Ile Ile Ile Thr His Asn Val Ser Pro Asp
65                  70                  75                  80

Thr Leu Asn Arg Glu Gly Cys Arg Ser Tyr Asp Val Ala Pro Glu Val
                85                  90                  95

Gly His Lys Phe Cys Lys Asp Phe Pro Gly Phe Ile Pro Ser Leu Leu
            100                 105                 110

Gly Asn Leu Leu Glu Glu Arg Gln Lys Ile Lys Arg Lys Met Lys Ala
        115                 120                 125

Thr Leu Asp Pro Leu Glu Lys Asn Leu Leu Asp
    130                 135
```

<210> SEQ ID NO 22
<211> LENGTH: 140
<212> TYPE: PRT
<213> ORGANISM: Thermococcus sp. JDF-3

<400> SEQUENCE: 22

```
Val Trp Asp Val Ser Arg Ser Ser Thr Gly Asn Leu Val Glu Arg Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Ser Val Ser Pro
65                  70                  75                  80

Asp Thr Leu Asp Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140
```

<210> SEQ ID NO 23
<211> LENGTH: 140
<212> TYPE: PRT
<213> ORGANISM: Thermococcus sp. JDF-3

<400> SEQUENCE: 23

Val Trp Asp Val Ser Arg Ser Ser Thr Gly Asn Leu Val Glu Trp Phe
1 5 10 15

Leu Leu Arg Lys Ala Tyr Glu Arg Asn Glu Leu Ala Pro Asn Lys Pro
20 25 30

Asp Glu Arg Glu Leu Ala Arg Arg Arg Gly Gly Tyr Ala Gly Gly Tyr
35 40 45

Val Lys Glu Pro Glu Arg Gly Leu Trp Asp Asn Ile Val Tyr Leu Asp
50 55 60

Phe Arg Ser Leu Tyr Pro Ser Ile Ile Ile Thr His Asn Val Ser Pro
65 70 75 80

Asp Thr Leu Asn Arg Glu Gly Cys Arg Ser Tyr Asp Val Ala Pro Glu
85 90 95

Val Gly His Lys Phe Cys Lys Asp Phe Pro Gly Phe Ile Pro Ser Leu
100 105 110

Leu Gly Asn Leu Leu Glu Glu Arg Gln Lys Ile Lys Arg Lys Met Lys
115 120 125

Ala Thr Leu Asp Pro Leu Glu Lys Asn Leu Leu Asp
130 135 140

<210> SEQ ID NO 24
<211> LENGTH: 140
<212> TYPE: PRT
<213> ORGANISM: Thermococcus sp. JDF-3

<400> SEQUENCE: 24

Val Trp Asp Val Ser Arg Ser Ser Thr Gly Asn Leu Val Glu Trp Phe
1 5 10 15

Leu Leu Arg Lys Ala Tyr Glu Arg Asn Glu Leu Ala Pro Asn Lys Pro
20 25 30

Asp Glu Arg Glu Leu Ala Arg Arg Arg Gly Gly Tyr Ala Gly Gly Tyr
35 40 45

Val Lys Glu Pro Glu Arg Gly Leu Trp Asp Asn Ile Val Tyr Leu Asp
50 55 60

Phe Arg Ser Leu Tyr Pro Ser Ile Ile Ile Thr His Asn Val Ser Pro
65 70 75 80

Asp Thr Leu Asn Arg Glu Gly Cys Arg Ser Tyr Asp Val Ala Pro Glu
85 90 95

Val Gly His Lys Phe Cys Lys Asp Phe Pro Gly Phe Ile Pro Ser Leu
100 105 110

Leu Gly Asn Leu Leu Glu Glu Arg Gln Lys Ile Lys Met Lys Met Lys
115 120 125

Ala Thr Leu Asp Pro Leu Glu Lys Asn Leu Leu Asp
130 135 140

<210> SEQ ID NO 25
<211> LENGTH: 140
<212> TYPE: PRT
<213> ORGANISM: Thermococcus sp. JDF-3

<400> SEQUENCE: 25

Val Trp Asp Val Ser Arg Ser Ser Thr Gly Asn Leu Val Glu Trp Phe
1 5 10 15

Leu Leu Arg Lys Ala Tyr Glu Arg Asn Glu Leu Ala Pro Asn Lys Pro
20 25 30

Asp Glu Arg Glu Leu Ala Arg Arg Arg Gly Gly Tyr Ala Gly Gly Tyr
35 40 45

```
Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140


<210> SEQ ID NO 26
<211> LENGTH: 140
<212> TYPE: PRT
<213> ORGANISM: Thermococcus sp. JDF-3
<220> FEATURE:
<221> NAME/KEY: UNSURE
<222> LOCATION: (5)..(5)
<223> OTHER INFORMATION: X = unknown
<220> FEATURE:
<221> NAME/KEY: MISC_FEATURE
<222> LOCATION: (5)..(5)
<223> OTHER INFORMATION: X = UKNOWN

<400> SEQUENCE: 26

Val Trp Asp Val Xaa Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Arg Gly Gly Tyr Ala Gly Gly Tyr
        35                  40                  45

Val Lys Glu Pro Glu Arg Gly Gln Trp Asp Asn Ile Ala Tyr Leu Asp
    50                  55                  60

Phe Arg Ser Leu Tyr Pro Ser Ile Ile Ile Thr His Asn Val Ser Pro
65                  70                  75                  80

Asp Thr Leu Lys Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140


<210> SEQ ID NO 27
<211> LENGTH: 140
<212> TYPE: PRT
<213> ORGANISM: Thermococcus sp. JDF-3

<400> SEQUENCE: 27

Val Trp Asp Val Pro Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Arg Gly Gly Tyr Ala Gly Gly Tyr
        35                  40                  45

Val Lys Glu Pro Glu Arg Gly Leu Trp Asp Asn Ile Val Tyr Leu Asp
```

```
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140


<210> SEQ ID NO 28
<211> LENGTH: 140
<212> TYPE: PRT
<213> ORGANISM: Thermococcus sp. JDF-3
<220> FEATURE:
<221> NAME/KEY: MISC_FEATURE
<222> LOCATION: (92)..(92)
<223> OTHER INFORMATION: X = unknown

<400> SEQUENCE: 28

Val Trp Asp Val Ser Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Xaa Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140


<210> SEQ ID NO 29
<211> LENGTH: 140
<212> TYPE: PRT
<213> ORGANISM: Thermococcus sp. JDF-3
<220> FEATURE:
<221> NAME/KEY: UNSURE
<222> LOCATION: (92)..(92)
<223> OTHER INFORMATION: X = Unknown
<220> FEATURE:
<221> NAME/KEY: MISC_FEATURE
<222> LOCATION: (92)..(92)
<223> OTHER INFORMATION: X = Unknown

<400> SEQUENCE: 29

Val Trp Asp Val Ser Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Arg Gly Gly Tyr Ala Gly Gly Tyr
```

```
        35                  40                  45

Val Lys Glu Pro Glu Arg Gly Pro Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Xaa Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Val Arg Gln Lys Ile Lys Arg Lys Met Lys
        115                 120                 125

Ala Thr Leu Asp Pro Leu Glu Lys Asn Leu Leu Asp
    130                 135                 140


<210> SEQ ID NO 30
<211> LENGTH: 140
<212> TYPE: PRT
<213> ORGANISM: Thermococcus sp. JDF-3

<400> SEQUENCE: 30

Val Trp Asp Val Ser Arg Ser Ser Thr Gly Asn Leu Val Glu Trp Phe
1               5                   10                  15

Leu Leu Arg Lys Ala Tyr Glu Arg Asn Lys Leu Ala Pro Asn Lys Pro
            20                  25                  30

Asp Glu Arg Glu Leu Ala Arg Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140


<210> SEQ ID NO 31
<211> LENGTH: 140
<212> TYPE: PRT
<213> ORGANISM: Thermococcus sp. JDF-3
<220> FEATURE:
<221> NAME/KEY: MISC_FEATURE
<222> LOCATION: (4)..(4)
<223> OTHER INFORMATION: X = unknown
<220> FEATURE:
<221> NAME/KEY: MISC_FEATURE
<222> LOCATION: (6)..(6)
<223> OTHER INFORMATION: X = unknown

<400> SEQUENCE: 31

Tyr Trp Ser Xaa Pro Xaa Leu Arg Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Arg Gly Gly Tyr Ala Gly Gly Tyr
        35                  40                  45
```

Val Lys Glu Pro Glu Arg Gly Leu Trp Asp Asn Ile Val Tyr Leu Asp
50 55 60

Phe Arg Ser Leu Tyr Pro Ser Ile Ile Ile Thr His Asn Val Ser Pro
65 70 75 80

Asp Thr Leu Asn Arg Glu Gly Cys Arg Ser Tyr Asp Val Ala Pro Glu
85 90 95

Val Gly His Lys Phe Cys Lys Asp Phe Pro Gly Phe Ile Pro Ser Leu
100 105 110

Leu Gly Asn Pro Leu Glu Glu Arg Gln Lys Ile Lys Arg Lys Met Lys
115 120 125

Ala Thr Leu Asp Pro Leu Glu Lys Asn Leu Leu Asp
130 135 140

<210> SEQ ID NO 32
<211> LENGTH: 141
<212> TYPE: PRT
<213> ORGANISM: Thermococcus sp. JDF-3
<220> FEATURE:
<221> NAME/KEY: MISC_FEATURE
<222> LOCATION: (5)..(5)
<223> OTHER INFORMATION: X = unknown

<400> SEQUENCE: 32

Val Asp Gly Thr Xaa Pro Arg Ser Ser Thr Gly Asn Leu Val Glu Trp
1 5 10 15

Phe Leu Leu Arg Lys Ala Tyr Glu Arg Asn Glu Leu Ala Pro Asn Lys
20 25 30

Pro Asp Glu Arg Glu Leu Ala Arg Arg Arg Gly Gly Tyr Ala Gly Gly
35 40 45

Tyr Val Lys Glu Pro Glu Arg Gly Leu Trp Asp Asn Ile Val Tyr Leu
50 55 60

Asp Phe Arg Ser His Tyr Pro Ser Ile Ile Ile Thr His Asn Val Ser
65 70 75 80

Pro Asp Thr Leu Asn Arg Glu Gly Cys Arg Ser Tyr Asp Val Ala Pro
85 90 95

Glu Asp Gly His Lys Phe Cys Lys Asp Phe Pro Gly Phe Ile Pro Ser
100 105 110

Leu Leu Gly Asn Leu Leu Glu Glu Arg Gln Lys Ile Lys Arg Lys Met
115 120 125

Lys Ala Thr Leu Asp Pro Leu Glu Lys Asn His Leu Asp
130 135 140

<210> SEQ ID NO 33
<211> LENGTH: 143
<212> TYPE: PRT
<213> ORGANISM: Thermococcus sp. JDF-3
<220> FEATURE:
<221> NAME/KEY: Unsure
<222> LOCATION: (1)..(3)
<223> OTHER INFORMATION: X = unknown
<220> FEATURE:
<221> NAME/KEY: MISC_FEATURE
<222> LOCATION: (1)..(3)
<223> OTHER INFORMATION: X = unknown

<400> SEQUENCE: 33

Xaa Xaa Xaa Phe Trp Asp Val Ser Arg Ser Ser Thr Gly Asn Leu Val
1 5 10 15

Glu Trp Phe Leu Leu Arg Lys Ala Tyr Glu Arg Asn Glu Leu Ala Pro
20 25 30

```
Asn Lys Pro Asp Glu Arg Glu Leu Ala Arg Arg Arg Gly Gly Tyr Ala
        35                  40                  45

Gly Gly Tyr Val Lys Glu Pro Glu Arg Gly Leu Trp Asp Asn Ile Val
    50                  55                  60

Tyr Leu Asp Phe Arg Ser Leu Tyr Pro Ser Ile Ile Ile Thr His Asn
65                  70                  75                  80

Val Ser Pro Asp Thr Leu Asn Arg Glu Gly Cys Arg Ser Tyr Asp Val
                85                  90                  95

Ala Pro Glu Val Gly His Lys Phe Cys Lys Asp Phe Pro Gly Phe Ile
            100                 105                 110

Pro Ser Leu Leu Gly Asn Leu Leu Glu Glu Arg Gln Lys Ile Lys Arg
        115                 120                 125

Lys Met Lys Ala Thr Leu Asp Pro Leu Glu Lys Asn Leu Leu Asp
    130                 135                 140


<210> SEQ ID NO 34
<211> LENGTH: 180
<212> TYPE: PRT
<213> ORGANISM: Thermococcus sp. JDF-3

<400> SEQUENCE: 34

Thr Gly Glu Gly Leu Glu Arg Val Ala Arg Tyr Ser Met Glu Asp Ala
1               5                   10                  15

Arg Val Thr Tyr Glu Leu Gly Arg Glu Phe Phe Pro Met Glu Ala Gln
            20                  25                  30

Leu Ser Arg Leu Ile Gly Gln Gly Asp Trp Asp Val Ser Arg Ser Ser
        35                  40                  45

Thr Gly Asn Leu Val Glu Trp Phe Leu Leu Arg Lys Ala Tyr Glu Arg
    50                  55                  60

Asn Glu Leu Ala Pro Asn Lys Pro Asp Glu Arg Glu Leu Ala Arg Arg
65                  70                  75                  80

Arg Gly Gly Tyr Ala Gly Gly Tyr Val Lys Glu Pro Glu Arg Gly Leu
                85                  90                  95

Trp Asp Asn Ile Val Tyr Leu Asp Phe Arg Ser Leu Tyr Pro Ser Ile
            100                 105                 110

Ile Ile Thr His Asn Val Ser Pro Asp Thr Leu Asn Arg Glu Gly Cys
        115                 120                 125

Arg Ser Tyr Asp Val Ala Pro Glu Val Gly His Lys Phe Cys Lys Asp
    130                 135                 140

Phe Pro Gly Phe Ile Pro Ser Leu Leu Gly Asn Leu Leu Glu Glu Arg
145                 150                 155                 160

Gln Lys Ile Lys Arg Lys Met Lys Ala Thr Leu Asp Pro Leu Glu Lys
                165                 170                 175

Asn Leu Leu Asp
            180


<210> SEQ ID NO 35
<211> LENGTH: 180
<212> TYPE: PRT
<213> ORGANISM: Thermococcus sp. JDF-3

<400> SEQUENCE: 35

Tyr Arg Gln Arg Ala Ile Lys Ile Leu Ala Asn Ser Tyr Tyr Gly Tyr
1               5                   10                  15

Cys Gly Tyr Ala Arg Ala Arg Trp Tyr Cys Arg Glu Cys Ala Glu Ser
            20                  25                  30
```

```
Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Val Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180


<210> SEQ ID NO 36
<211> LENGTH: 180
<212> TYPE: PRT
<213> ORGANISM: Thermococcus sp. JDF-3

<400> SEQUENCE: 36

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Glu Leu
            180


<210> SEQ ID NO 37
<211> LENGTH: 180
<212> TYPE: PRT
```

<213> ORGANISM: Thermococcus sp. JDF-3

<400> SEQUENCE: 37

Tyr Arg Gln Arg Ala Ile Lys Ile Leu Ala Asn Ser Tyr Tyr Gly Tyr
1 5 10 15

Tyr Gly Tyr Ala Arg Ala Arg Trp Tyr Cys Arg Glu Cys Ala Glu Ser
20 25 30

Val Thr Ala Trp Gly Arg Glu Tyr Ile Glu Met Val Ile Arg Glu Leu
35 40 45

Glu Glu Lys Phe Gly Phe Lys Val Leu Tyr Ala Asp Thr Asp Gly Leu
50 55 60

His Ala Thr Ile Pro Gly Ala Asp Ala Glu Thr Val Lys Lys Lys Ala
65 70 75 80

Met Glu Phe Leu Asn Tyr Ile Asn Pro Lys Leu Pro Gly Leu Leu Glu
85 90 95

Leu Glu Tyr Glu Gly Phe Tyr Val Arg Gly Phe Phe Val Thr Lys Lys
100 105 110

Lys Tyr Ala Val Ile Asp Glu Glu Gly Lys Ile Thr Thr Arg Gly Leu
115 120 125

Glu Ile Val Arg Arg Asp Trp Ser Glu Ile Ala Lys Glu Thr Gln Ala
130 135 140

Arg Val Leu Glu Ala Ile Leu Arg His Gly Asp Val Glu Glu Ala Val
145 150 155 160

Arg Ile Val Arg Lys Val Thr Glu Lys Leu Ser Lys Tyr Glu Val Pro
165 170 175

Pro Glu Lys Leu
180

<210> SEQ ID NO 38
<211> LENGTH: 180
<212> TYPE: PRT
<213> ORGANISM: Thermococcus sp. JDF-3

<400> SEQUENCE: 38

Tyr Arg Gln Arg Ala Ile Lys Ile Leu Ala Asn Ser Tyr Tyr Gly Tyr
1 5 10 15

Tyr Gly Tyr Ala Arg Ala Arg Trp Tyr Cys Arg Glu Cys Ala Glu Ser
20 25 30

Val Thr Ala Trp Gly Arg Glu Tyr Ile Glu Met Val Ile Arg Glu Leu
35 40 45

Glu Glu Lys Phe Gly Phe Lys Val Leu Tyr Ala Asp Thr Asp Gly Leu
50 55 60

His Ala Thr Ile Pro Gly Ala Asp Ala Glu Thr Val Lys Lys Lys Ala
65 70 75 80

Met Glu Phe Leu Asn Tyr Ile Asn Pro Lys Leu Pro Gly Leu Leu Glu
85 90 95

Leu Lys Tyr Glu Gly Phe Tyr Val Arg Gly Phe Phe Val Thr Lys Lys
100 105 110

Lys Tyr Ala Val Ile Asp Glu Glu Gly Lys Ile Thr Thr Arg Gly Leu
115 120 125

Glu Ile Val Arg Arg Asp Trp Ser Glu Ile Ala Lys Glu Thr Gln Ala
130 135 140

Arg Val Leu Glu Ala Ile Leu Arg His Gly Asp Val Glu Glu Ala Val
145 150 155 160

Arg Ile Val Arg Glu Val Thr Glu Lys Leu Ser Lys Tyr Glu Val Pro

```
                165                 170                 175

Pro Glu Lys Leu
            180


<210> SEQ ID NO 39
<211> LENGTH: 180
<212> TYPE: PRT
<213> ORGANISM: Thermococcus sp. JDF-3

<400> SEQUENCE: 39

Tyr Arg Gln Arg Ala Ile Lys Ile Leu Ala Asn Asn Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Asp Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180


<210> SEQ ID NO 40
<211> LENGTH: 180
<212> TYPE: PRT
<213> ORGANISM: Thermococcus sp. JDF-3
<220> FEATURE:
<221> NAME/KEY: MISC_FEATURE
<222> LOCATION: (114)..(114)
<223> OTHER INFORMATION: X = Unknown

<400> SEQUENCE: 40

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Leu Lys Leu Pro Gly Leu Leu Glu
                85                  90                  95
```

```
Leu Glu Tyr Glu Gly Phe Tyr Val Arg Gly Phe Phe Val Thr Lys Lys
            100                 105                 110

Lys Xaa Ala Val Ile Asp Glu Glu Gly Lys Ile Thr Thr Arg Gly Leu
        115                 120                 125

Glu Ile Val Arg Arg Asp Trp Ser Lys Ile Ala Lys Glu Thr Gln Ala
    130                 135                 140

Arg Val Leu Glu Ala Ile Leu Arg His Gly Asp Val Glu Glu Ala Ile
145                 150                 155                 160

Arg Ile Val Arg Glu Val Thr Glu Lys Leu Ser Lys Tyr Glu Val Pro
                165                 170                 175

Pro Glu Lys Leu
            180


<210> SEQ ID NO 41
<211> LENGTH: 180
<212> TYPE: PRT
<213> ORGANISM: Thermococcus sp. JDF-3

<400> SEQUENCE: 41

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Ala Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180


<210> SEQ ID NO 42
<211> LENGTH: 180
<212> TYPE: PRT
<213> ORGANISM: Thermococcus sp. JDF-3

<400> SEQUENCE: 42

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45
```

-continued

```
Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Asn Lys Tyr Glu Val Pro
                165                 170                 175

Pro Glu Lys Leu
            180


<210> SEQ ID NO 43
<211> LENGTH: 180
<212> TYPE: PRT
<213> ORGANISM: Thermococcus sp. JDF-3

<400> SEQUENCE: 43

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180


<210> SEQ ID NO 44
<211> LENGTH: 180
<212> TYPE: PRT
<213> ORGANISM: Thermococcus sp. JDF-3

<400> SEQUENCE: 44
```

-continued

```
Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Pro Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180


<210> SEQ ID NO 45
<211> LENGTH: 180
<212> TYPE: PRT
<213> ORGANISM: Thermococcus sp. JDF-3

<400> SEQUENCE: 45

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Val Lys Leu
            180
```

<210> SEQ ID NO 46
<211> LENGTH: 180
<212> TYPE: PRT
<213> ORGANISM: Thermococcus sp. JDF-3

<400> SEQUENCE: 46

```
Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Gly Glu Ala
            180
```

<210> SEQ ID NO 47
<211> LENGTH: 180
<212> TYPE: PRT
<213> ORGANISM: Thermococcus sp. JDF-3

<400> SEQUENCE: 47

```
Tyr Arg Gln Arg Ala Ile Lys Ile Leu Ala Asn Ser Tyr Tyr Gly Asn
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140
```

```
Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180


<210> SEQ ID NO 48
<211> LENGTH: 180
<212> TYPE: PRT
<213> ORGANISM: Thermococcus sp. JDF-3

<400> SEQUENCE: 48

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180


<210> SEQ ID NO 49
<211> LENGTH: 20
<212> TYPE: PRT
<213> ORGANISM: Thermococcus sp. JDF-3

<400> SEQUENCE: 49

Asp Tyr Arg Gln Arg Ala Ile Lys Ile Leu Ala Asn Ser Tyr Tyr Gly
1               5                   10                  15

Tyr Tyr Gly Tyr
            20


<210> SEQ ID NO 50
<211> LENGTH: 12
<212> TYPE: PRT
<213> ORGANISM: Thermococcus sp. JDF-3
<220> FEATURE:
<221> NAME/KEY: MISC_FEATURE
<222> LOCATION: (2)..(4)
<223> OTHER INFORMATION: X = Unknown
<220> FEATURE:
<221> NAME/KEY: MISC_FEATURE
```

<222> LOCATION: (7)..(7)
<223> OTHER INFORMATION: X = Unknown
<220> FEATURE:
<221> NAME/KEY: MISC_FEATURE
<222> LOCATION: (10)..(11)
<223> OTHER INFORMATION: X = Unknown

<400> SEQUENCE: 50

Lys Xaa Xaa Xaa Asn Ser Xaa Tyr Gly Xaa Xaa Gly
1 5 10

<210> SEQ ID NO 51
<211> LENGTH: 30
<212> TYPE: DNA
<213> ORGANISM: Artificial
<220> FEATURE:
<223> OTHER INFORMATION: Synthetic oligonucleotide

<400> SEQUENCE: 51
ctcaacttgg agcgaacgac ctacaccgaa 30

<210> SEQ ID NO 52
<211> LENGTH: 30
<212> TYPE: DNA
<213> ORGANISM: Artificial
<220> FEATURE:
<223> OTHER INFORMATION: Synthetic oligonucleotite

<400> SEQUENCE: 52
ctcatcttgg agcgaacgac ctacaccgaa 30

<210> SEQ ID NO 53
<211> LENGTH: 30
<212> TYPE: DNA
<213> ORGANISM: Artificial
<220> FEATURE:
<223> OTHER INFORMATION: Synthetic Oligonucleotide

<400> SEQUENCE: 53
ctcagcttgg agcgaacgac ctacaccgaa 30

<210> SEQ ID NO 54
<211> LENGTH: 30
<212> TYPE: DNA
<213> ORGANISM: Artificial
<220> FEATURE:
<223> OTHER INFORMATION: Synthetic Oligonucleotide

<400> SEQUENCE: 54
ctcaccttgg agcgaacgac ctacaccgaa 30

<210> SEQ ID NO 55
<211> LENGTH: 25
<212> TYPE: DNA
<213> ORGANISM: Artificial
<220> FEATURE:
<223> OTHER INFORMATION: Synthetic Oligonucleotide

<400> SEQUENCE: 55
ttcggtgtag gtcgttcgct ccaag 25

<210> SEQ ID NO 56
<211> LENGTH: 28
<212> TYPE: DNA
<213> ORGANISM: Artificial
<220> FEATURE:
<223> OTHER INFORMATION: Synthetic oligonucleotide

<400> SEQUENCE: 56
aagtgtaaag cctggggtgc ctaatgag 28

<210> SEQ ID NO 57
<211> LENGTH: 31
<212> TYPE: DNA
<213> ORGANISM: Artificial
<220> FEATURE:
<223> OTHER INFORMATION: Synthetic oligonucleotide

<400> SEQUENCE: 57
ttcagcatct tttactttca ccagcgtttc t 31

<210> SEQ ID NO 58
<211> LENGTH: 34
<212> TYPE: DNA
<213> ORGANISM: Artificial
<220> FEATURE:
<223> OTHER INFORMATION: Synthetic oligonucleotide

<400> SEQUENCE: 58
agctggcgaa agggggatgt gctgcaaggc gatt 34

<210> SEQ ID NO 59
<211> LENGTH: 41
<212> TYPE: DNA
<213> ORGANISM: Artificial
<220> FEATURE:
<223> OTHER INFORMATION: Synthetic oligonucleotide

<400> SEQUENCE: 59
cggtacctcc tggtggatac actggttcct gtaagcagaa g 41

<210> SEQ ID NO 60
<211> LENGTH: 26
<212> TYPE: DNA
<213> ORGANISM: Artificial
<220> FEATURE:
<223> OTHER INFORMATION: Synthetic oligonucleotide

<400> SEQUENCE: 60
gagagcttga ggagagcagg aaaggt 26

<210> SEQ ID NO 61
<211> LENGTH: 37
<212> TYPE: DNA
<213> ORGANISM: Artificial
<220> FEATURE:
<223> OTHER INFORMATION: Synthetic oligonuleotide

<400> SEQUENCE: 61
gatctcccag ggcggcagta agtcttcagc atcaggc 37

<210> SEQ ID NO 62
<211> LENGTH: 29
<212> TYPE: DNA
<213> ORGANISM: Artificial
<220> FEATURE:
<223> OTHER INFORMATION: Synthetic oligonucleotide

<400> SEQUENCE: 62
tcctttggac agggatgagg aataactga 29

<210> SEQ ID NO 63

<211> LENGTH: 33
<212> TYPE: DNA
<213> ORGANISM: Artificial
<220> FEATURE:
<223> OTHER INFORMATION: Degenerate primer
<220> FEATURE:
<221> NAME/KEY: misc_feature
<222> LOCATION: (18)..(18)
<223> OTHER INFORMATION: n = 50% G and T
<220> FEATURE:
<221> NAME/KEY: misc_feature
<222> LOCATION: (16)..(17)
<223> OTHER INFORMATION: n = 25% each G, C, A and T

<400> SEQUENCE: 63
tttcgtagtc tctacnnntc aatcataatc acc 33

<210> SEQ ID NO 64
<211> LENGTH: 20
<212> TYPE: DNA
<213> ORGANISM: Artificial
<220> FEATURE:
<223> OTHER INFORMATION: Synthetic oligonucleotide

<400> SEQUENCE: 64
ggatgtgctg caaggcgatt 20

<210> SEQ ID NO 65
<211> LENGTH: 35
<212> TYPE: DNA
<213> ORGANISM: Artificial
<220> FEATURE:
<223> OTHER INFORMATION: Synthetic oligonucleotide

<400> SEQUENCE: 65
cagctggcga aagggggatg tgctgcaagg cgatt 35

<210> SEQ ID NO 66
<211> LENGTH: 25
<212> TYPE: DNA
<213> ORGANISM: Artificial
<220> FEATURE:
<223> OTHER INFORMATION: Synthetic oligonucleotide

<400> SEQUENCE: 66
ttcggtgtag gtcgttcgct ccaag 25

<210> SEQ ID NO 67
<211> LENGTH: 31
<212> TYPE: DNA
<213> ORGANISM: Artificial
<220> FEATURE:
<223> OTHER INFORMATION: Synthetic oligonucleotide

<400> SEQUENCE: 67
ttcagcatct tttactttca ccagcgtttc t 31

<210> SEQ ID NO 68
<211> LENGTH: 34
<212> TYPE: DNA
<213> ORGANISM: Artificial
<220> FEATURE:
<223> OTHER INFORMATION: Synthetic oligonucleotide

<400> SEQUENCE: 68
agctggcgaa agggggatgt gctgcaaggc gatt 34

-continued

```
<210> SEQ ID NO 69
<211> LENGTH: 29
<212> TYPE: DNA
<213> ORGANISM: Artificial
<220> FEATURE:
<223> OTHER INFORMATION: Synthetic oligonucleotide

<400> SEQUENCE: 69

ccagctttcc agactagtcg gccaaggcc                                        29


<210> SEQ ID NO 70
<211> LENGTH: 16
<212> TYPE: DNA
<213> ORGANISM: Artificial
<220> FEATURE:
<223> OTHER INFORMATION: Synthetic oligonucleotide

<400> SEQUENCE: 70

aactctcgac ccgctg                                                      16


<210> SEQ ID NO 71
<211> LENGTH: 54
<212> TYPE: DNA
<213> ORGANISM: Artificial
<220> FEATURE:
<223> OTHER INFORMATION: Syntheitic oligonucleotide

<400> SEQUENCE: 71

gagagaattc ataatgataa ggaggaaaaa attatgatcc ttgacgttga ttac             54


<210> SEQ ID NO 72
<211> LENGTH: 31
<212> TYPE: DNA
<213> ORGANISM: Artificial
<220> FEATURE:
<223> OTHER INFORMATION: Synthetic oligonucleotide

<400> SEQUENCE: 72

tcagatctcg agtcacttct tcttcccctt c                                     31
```

COMPOSITIONS AND METHODS UTILIZING DNA POLYMERASES

RELATED APPLICATIONS

This application is a continuation of U.S. Ser. No. 10/223,650, filed Aug. 19, 2002, which is a continuation-in-part of U.S. Ser. No. 09/896,923, filed Jun. 29, 2001, which is a continuation-in-part of U.S. Ser. No. 09/698,341, filed Oct. 27, 2000, which claims priority to U.S. Ser. No. 60/162,000, filed Oct. 29, 1999.

FIELD OF THE INVENTION

The present invention relates to compositions and methods utilizing DNA polymerase enzymes with reduced discrimination for non-conventional nucleotides. The enzymes of the invention are useful in many applications calling for the detectable labeling of nucleic acids and are particularly useful in DNA sequencing applications.

BACKGROUND OF THE INVENTION

Detectable labeling of nucleic acids is required for many applications in molecular biology, including applications for research as well as clinical diagnostic techniques. A commonly used method of labeling nucleic acids uses one or more unconventional nucleotides and a polymerase enzyme that catalyzes the template-dependent incorporation of the unconventional nucleotide(s) into the newly synthesized complementary strand.

The ability of a DNA polymerase to incorporate the correct deoxynucleotide is the basis for high fidelity DNA replication in vivo. Amino acids within the active site of polymerases form a specific binding pocket that favors the placement of the correct complementary nucleotide opposite the template nucleotide. If a mismatched nucleotide, ribonucleotide, or nucleotide analog fills that position, the precise alignment of the amino acids contacting the incoming nucleotide may be distorted into a position unfavorable for DNA polymerization. Because of this, the unconventional nucleotides or nucleotide analogs used to label DNA tend to be incorporated into the elongated strand less efficiently than do the standard deoxynucleotide triphosphates (dNTPs; the so-called "standard" dNTPs include deoxyadenosine triphosphate (dATP), deoxycytosine triphosphate (dCTP), deoxyguanosine triphosphate (dGTP), and deoxythymidine triphosphate (dTTP)).

The reduced efficiency with which unconventional nucleotides are incorporated by the polymerase increases the amount of the unconventional nucleotide necessary for DNA labeling. The reduced efficiency of incorporation of a particular nucleotide can also adversely affect the performance of techniques or assays, such as DNA sequencing, that depend upon unbiased incorporation of unconventional nucleotides for homogeneous signal strength.

The identity and exact arrangement of the amino acids of a DNA polymerase that contact an incoming nucleotide triphosphate determine the nature of the nucleotides, both conventional and unconventional, that may be incorporated by that polymerase enzyme. Changes in the exact placement of the amino acids that contact the incoming nucleotide triphosphate at any stage of binding or chain elongation can dramatically alter the polymerase's capacity for utilization of unusual or unconventional nucleotides. Sometimes changes in distant amino acids can influence the incorporation of nucleotide analogs due to indirect global or structural effects. Polymerases with increased capacity to incorporate nucleotide analogs are useful for labeling DNA or RNA strands with nucleotides modified with signal moieties such as dyes, reactive groups or unstable isotopes.

In addition to labeled nucleotides, an extremely important class of modified nucleotides is the dideoxynucleotides. The so-called "Sanger" or "dideoxy" DNA sequencing method (Sanger et al., 1977, Proc. Natl. Acad. Sci. USA 74: 5463, which is incorporated herein by reference) relies upon the template-directed incorporation of nucleotides onto an annealed primer by a DNA polymerase from a mixture containing deoxy- and dideoxynucleotides. The incorporation of a dideoxynucleotide results in chain termination, the inability of the enzyme to catalyze further extension of that strand. Electrophoretic separation of reaction products results in a "ladder" of extension products wherein each extension product ends in a particular dideoxynucleotide complementary to the nucleotide opposite it in the template. The distance of the dideoxynucleotide analog from the primer is indicated by the length of the extension product. When four reactions, each containing one of the four dideoxynucleotide analogs ddA, ddC, ddG, or ddT (ddNTPs) are separated on the same gel, the sequence of the template may be read directly from the ladder patterns. Extension products may be detected in several ways, including for example, the inclusion of isotopically- or fluorescently-labeled primers, deoxynucleotide triphosphates or dideoxynucleotide triphosphates in the reaction.

Fluorescent labeling has the advantages of faster data collection, since detection may be performed while the gel is running, and longer reads of sequence data from a single reaction and gel. Further, fluorescent sequence detection has allowed sequencing to be performed in a single reaction tube containing four differentially-labeled fluorescent dye terminators (the so-called dye-terminator method, Lee et al., 1992, Nucleic Acids Res. 20: 2471, incorporated herein by reference).

A desirable quality of a polymerase useful for DNA sequencing is improved incorporation of dideoxynucleotides. Improved incorporation of dideoxynucleotides can make processes such as DNA sequencing more cost effective by reducing the requirement for expensive radioactive or fluorescent dye-labeled dideoxynucleotides. Moreover, unbiased dideoxynucleotide incorporation provides improved signal uniformity, leading to increased accuracy of base determination. The even signal output further allows subtle sequence differences caused by factors like allelic variation to be detected. Allelic variation, which produces two different half strength signals at the position of relevance, can easily be concealed by the varied signal strengths caused by polymerases with non-uniform ddNTP utilization.

Incorporation of ribonucleotides by the native form of DNA polymerase is a rare event. Mutants that incorporate higher levels of ribonucleotides can be used for applications such as sequencing by partial ribosubstitution. In this system, a mixture of ribonucleotides and deoxynucleotides corresponding to the same base are incorporated by the mutant polymerase (Barnes, 1978 J. Mol. Biol. 119:83-99). When the ribosequencing reactions are exposed to alkaline conditions and heat, fragmentation of the extended strand occurs. If the reactions for all four bases are separated on a denaturing acrylamide gel, they produce a sequencing ladder. there is a need in the art for polymerase mutants with higher utilization of ribonucleotides for this alternative method of sequencing.

Alternatively, the incorporation of ribonucleotides followed by alkaline hydrolysis could be utilized in a system that requires random cleavage of DNA molecules such as DNA shuffling ((Stemmer, 1994, Nature, 370: 389-391) which has also been called molecular breeding, sexual PCR and directed evolution).

Another desirable quality in a DNA labeling enzyme is thermal stability. DNA polymerases exhibiting thermal stability have revolutionized many aspects of molecular biology and clinical diagnostics since the development of the polymerase chain reaction (PCR), which uses cycles of thermal denaturation, primer annealing, and enzymatic primer extension to amplify DNA templates. The prototype thermostable DNA polymerase is Taq polymerase, originally isolated from the thermophilic eubacterium *Thermus aquaticus*. So-called "cycle sequencing" reactions using thermostable DNA polymerases have the advantage of requiring smaller amounts of starting template relative to conventional (i.e., non-cycle) sequencing reactions.

There are three major families of DNA polymerases, termed families A, B and C. The classification of a polymerase into one of these three families is based on structural similarity of a given polymerase to *E. coli* DNA polymerase I (Family A), II (Family B) or III (family C). As examples, Family A DNA polymerases include, but are not limited to Klenow DNA polymerase, *Thermus aquaticus* DNA polymerase I (Taq polymerase) and bacteriophage T7 DNA polymerase; Family B DNA polymerases, formerly known as $\alpha$-family polymerases (Braithwaite and Ito, 1991, Nuc. Acids Res. 19:4045), include, but are not limited to human $\alpha$, $\delta$ and $\epsilon$ DNA polymerases, T4, RB69 and $\phi$29 bacteriophage DNA polymerases, and *Pyrococcus furiosus* DNA polymerase (Pfu polymerase); and family C DNA polymerases include, but are not limited to *Bacillus subtilis* DNA polymerase III, and *E. coli* DNA polymerase III $\alpha$ and $\epsilon$ subunits (listed as products of the dnaE and dnaQ genes, respectively, by Braithwaite and Ito, 1993, Nucleic Acids Res. 21: 787). An alignment of DNA polymerase protein sequences of each family across a broad spectrum of archaeal, bacterial, viral and eukaryotic organisms is presented in Braithwaite and Ito (1993, supra), which is incorporated herein by reference.

The term used to describe the tendency of DNA polymerases to not to carry the incorporation of unnatural nucleotides into the nascent DNA polymer is "discrimination". In Family A DNA polymerases, the effective discrimination against incorporation of dideoxynucleotide analogs is largely associated with a single amino acid residue. The majority of enzymes from the Family A DNA polymerases have a phenylalanine (phe or F) residue at the position equivalent to F762 in *E. coli* Klenow fragment of DNA polymerase and demonstrate a strong discrimination against dideoxynucleotides. A few polymerases (e.g. T7 DNA polymerase) have a tyrosine (tyr or Y) residue at the corresponding position and exhibit relatively weak discrimination against dideoxynucleotides. Family A polymerases with tyrosine at this position readily incorporate dideoxynucleotides at levels equal to or only slightly different from the levels at which they incorporate deoxynucleotides. Conversion of the tyrosine or phenylalanine residues in the site responsible for discrimination reverses the dideoxynucleotide discrimination profile of the Family A enzymes (Tabor and Richardson, 1995, Proc. Natl. Acad. Sci. USA 92:6449).

Among the thermostable DNA polymerases, a mutant form of the Family A DNA polymerase from *Thermus aquaticus*, known as AmpliTaq FS® (Perkin Elmer), contains a F667Y mutation at the position equivalent to F762 of Klenow DNA polymerase and exhibits increased dideoxynucleotide uptake (i.e., reduced discrimination against ddNTPs) relative to the wild-type enzyme. The reduced discrimination for dideoxynucleotide uptake makes it more useful for fluorescent and labeled dideoxynucleotide sequencing than the wild-type enzyme.

The F667Y mutant of Taq DNA polymerase is not suited, however, for use with fluorescein-labeled dideoxynucleotides, necessitating the use of rhodamine dye terminators. Rhodamine dye terminators that are currently utilized with Taq sequencing reactions, however, stabilize DNA secondary structure, causing compression of signal. Efforts to eliminate compression problems have resulted in systems that use high amounts of the nucleotide analog deoxyinosine triphosphate (dITP) in place of deoxyguanosine triphosphate. While incorporation of (dITP) reduces the compression of the signal, the presence of dITP in the reaction produces additional complications including lowered reaction temperatures and increased reaction times. Additionally, the use of rhodamine dyes in sequencing requires undesirable post-reaction purification (Brandis, 1999 Nuc. Acid Res. 27:1912).

Family B DNA polymerases exhibit substantially different structure compared to Family A DNA polymerases, with the exception of the position of acidic residues involved in catalysis in the so-called palm domain (Wang et al., 1997, Cell 89:1087; Hopfner et al., 1999, Proc. Natl. Acad. Sci. USA 96:3600). The unique structure of Family B DNA polymerases may permit a completely different spectrum of interactions with nucleotide analogs, perhaps allowing utilization of analogs which are unsuitable for use with Family A DNA polymerases due to structural constraints. Thermostable Family B DNA polymerases have been identified in hyperthermophilic archaea. These organisms grow at temperatures higher than 90° C. and their enzymes demonstrate greater thermostability (Mathur et al., 1992, Strategies 5:11) than the thermophilic eubacterial Family A DNA polymerases. Family B polymerases from hyperthermophilic archaea may be well suited starting substrates for modification(s) to reduce discrimination against non-conventional nucleotides.

Although the crystal structures of three Family B DNA polymerases have been solved (Wang et al., 1997, supra; Hopfner, K.-P. et al., 1999, Proc. Natl. Acad. Sci. 96: 3600; Zhao, 1999, Structure Fold Des., 7:1189), the structures of DNA-polymerase or dNTP-polymerase co-complexes have not yet been reported. At present, identification of amino acid residues contributing to nucleotide analog discrimination can only be inferred from extrapolation to Family A-dNTP structures or from mutagenesis studies carried out with related Family B DNA polymerases (e.g., human pol$\alpha$, phage T4, phage $\phi$29, *T. litoralis* DNA polymerase).

Sequence comparison of the Family B DNA polymerases indicate six conserved regions numbered I-VI (Braithwaite and Ito, 1993, supra; Wong et al., 1988). Designated conserved regions I-VI of the Human DNA polymerase $\alpha$ and other DNA polymerases are defined as follows: Region I of a Family B DNA polymerase corresponds to amino acids 998-1005 of Human pol $\alpha$; Region II corresponds to amino acids 839-878 of human pol $\alpha$; Region III corresponds to amino acids 943-984 of human pol $\alpha$; Region IV corresponds to amino acids 609-650 of human pol $\alpha$; Region V corresponds to amino acids 1075-1081 of human pol $\alpha$; and Region VI corresponds to amino acids 909-926 of human pol $\alpha$. The crystal structure of bacteriophage RB69 DNA polymerase (Family B) proposed by Wang et al. (Wang et al., 1997, supra) shows that Y416 in region II (which corresponds to Y409 in the Family B DNA polymerase of *Thermococcus* species JDF-3) has the same position as Y115 in HIV reverse transcriptase (RT) and E710 in the Klenow fragment (Family A polymerases). Modeling of the dNTP and primer template complex in RB69 was carried out using the atomic coordinates of the reverse transcriptase-DNA cocrystal. This model predicts the RB69 Y416 packs under the deoxyribose portion of the dNTP. Tyrosine at this position has been implicated in ribose selectivity, contributing to polymerase discrimination between ribonucleotides and deoxyribonucleotides in mammalian reverse transcriptases (Y115) (Gao et al., 1997, Proc. Natl. Acad. Sci. USA 94:407; Joyce, 1994, Proc. Natl. Acad. Sci. USA 94:1619) and in Family A DNA polymerases where modification of the corresponding invariable glutamate residue (E710) reduces discrimination against ribonucleotides (Gelfand et al., 1998, Pat. No. EPO823479; Astatke et al., 1998, Proc. Natl. Acad. Sci. USA 96:3402).

Mutagenesis studies done in Family B DNA polymerases also implicate the region containing the analogous Y in region II in dNTP incorporation and ribose selectivity. Mutations at the corresponding Y865 in human DNA polymerase α affect polymerase fidelity and sensitivity to dNTP nucleotide inhibitors such as AZT-TP, which has a bulky 3'-azido group in place of the 3'-OH group, BuPdGTP, which contains a butylphenyl group attached to the amino group at the C-2 position in the guanine base of dGTP (resulting in a bulkier and more hydrophobic purine base nucleotide) and aphidicolin, a competitive inhibitor of pyrimidine deoxynucleotide triphosphate. Interestingly, the mutants showed no difference in their uptake of ddCTP (Dong et al., 1993, J. Biol. Chem. 268: 26143). Additionally, mutants of bacteriophage T4 DNA polymerase, which have converted L412 to methionine (M) or isoleucine (I) just one amino acid before the analogous Y (Y411), show extreme and mild sensitivity, respectively, to the inorganic pyrophosphate analog phosphonoacetic acid (PAA). Alterations in PAA sensitivity have been shown to predict polymerase interactions with nucleotide analogs. L412 in T4 DNA polymerase corresponds to L410 in *Thermococcus* species JDF-3 DNA polymerase. The L412M T4 DNA polymerase mutant was inhibited with 50-fold less ddGTP than wild-type polymerase while the $K_m$s for dGTP was similar. As stated by the authors in that study, "[d]espite the sensitivity of the L412M DNA polymerase to ddGTP, there was no difference found in the incorporation of ddNTPs by wild-type and L412M DNA polymerase." (Reha-Krantz et al., 1993, J. Virol. 67:60). In bacteriophage ϕ29, mutations in region II (LYP where Y is analogous to *Thermococcus* species JDF3 DNA polymerase Y409) produce mixed results when challenged with PAA; P255S was hypersensitive to PAA while L253V was shown to be less sensitive than the wild-type enzyme (Blasco et al., 1993, J. Biol. Chem. 268: 24106). These data support the role of the LYP region (region II) in polymerase-nucleotide interactions, but improved incorporation of ddNTPs was not achieved in these references.

In another study, extensive mutation of region II in the archaeal Family B DNA polymerase from *Thermococcus litoralis* DNA polymerase (VENT™ polymerase, New England Biolabs) was performed. In that study, 26 different site-directed mutants were made for the sole intent of examining nucleotide analog discrimination (Gardner and Jack, 1999, Nucleic Acids Res. 27: 2545). Site-directed mutagenesis of VENT™ DNA polymerase demonstrated that three mutations at Y412 (which corresponds to JDF-3 DNA polymerase Y409) could alter nucleotide binding (Gardner and Jack, 1999, supra). Y412V was most significant with a 2 fold increase in dideoxynucleotide incorporation and a 200 fold increase in the incorporation of ribonucleotide ATP. The mutation Y412F showed no change in analog incorporation.

Region III of the Family B polymerases (also referred to as motif B) has also been demonstrated to play a role in nucleotide recognition. This region, which corresponds to AA 487 to 495 of JDF-3 Family B DNA polymerase, has a consensus sequence $KX_3NSXYG$ (Jung et al., 1990, supra; Blasco et al., 1992, supra; Dong et al., 1993, J. Biol. Chem. 268:21163; Zhu et al., 1994, Biochem. Biophys. Acta 1219:260; Dong and Wang, 1995, J. Biol. Chem. 270:21563), and is functionally, but not structurally (Wang et al., 1997, supra), analogous to $KX_3(F/Y)GX_2YG$ in helix O of the Family A DNA polymerases. In Family A DNA polymerases, such as the Klenow fragment and Taq DNA polymerases, the O helix contains amino acids that play a major role in dNTP binding (Astatke et al., 1998, J. Mol. Biol. 278:147; Astatke et al., 1995, J. Biol. Chem. 270:1945; Polesky et al., 1992, J. Biol. Chem. 267: 8417; Polesky et al., 1990, J. Biol. Chem. 265:14579; Pandey et al., 1994, J. Biol. Chem. 269:13259; Kaushik et al., 1996, Biochem. 35:7256). Specifically, helix O contains the F (F763 in the Klenow fragment; F667 in Taq) which confers ddNTP discrimination in Family A DNA polymerases ($KX_3$ $\underline{(F/Y)}GX_2YG$) (Tabor and Richardson, 1995, supra).

Directed mutagenesis studies in region III of VENT™ DNA polymerase also targeted an alanine analogous to A485 of the *Thermococcus* species JDF-3 DNA polymerase (Jung et al., 1990, supra). These mutants (A□C, A□S, A□L, A□I, A□F and A□V) exhibited a range of specific activities from 0.12 to 1.2 times the polymerase activity of the progenitor enzyme (Gardner and Jack, 1999, Nucl. Acids Res. 27:2545). The dideoxynucleotide incorporation ranged from 4 to 15 times the unmutated enzyme. Interestingly, the mutant with the highest dideoxynucleotide incorporation (15×) had a specific activity of only 0.12× of the original enzyme.

Site-directed mutagenesis studies on the Family B DNA polymerase from *Thermococcus barossii* modified each residue independently in the sequence ILANSF, which corresponds to AA residues 488-493 of the JDF-3 DNA polymerase, to tyrosine (Reidl et al., U.S. Pat. No. 5,882,904). That study indicated that an L489Y mutant exhibits approximately 3 times greater incorporation of dideoxynucleotides relative to an enzyme bearing the wild-type leucine residue at this site.

One area of active research involves the use of nucleic acid arrays, often referred to as nucleic acid or DNA "chips", in the simultaneous analyses of multiple different nucleic acid sequences. Many of these applications, such as those described in U.S. Pat. No. 5,882,904 (Reidl et al., issued Mar. 16, 1999) will benefit from DNA polymerases exhibiting reduced discrimination against non-conventional nucleotides, particularly fluorescently-labeled non-conventional nucleotides. Applications being addressed in the chip format include DNA sequencing and mutation detection, among others. For example, the "mini-sequencing" methods (e.g., Pastinen et al., 1997, Genome Res. 7: 606; Syvanen, 1999, Human Mutation 13: 1-10) and the arrayed primer extension (APEX) mutation detection method (Shumaker et al., 1996, Hum. Mutat. 7: 346) and methods like them can benefit from DNA polymerases with reduced discrimination against fluorescently-labeled or other non-conventional nucleotides. There is a need in the art for a non-discriminating DNA polymerase for use in chip or gel based mini-sequencing systems. Such a system would advantageously permit detection of multiplexed single nucleotide polymorphisms (SNPs) and allow for quantitative genotyping. Identification of sequence variation permits the diagnosis and treatment of genetic disorders, predisposition to multifactorial diseases, and sensitivity to new or existing pharmaceutical products.

With the completion of the human genome project, considerable attention is now focused on analyzing genetic variations between individuals, and specifically, single nucleotide polymorphisms (SNPs) which have been estimated to occur one in every 1000 bp (Halushka et al., 1999). The importance of SNPs is that they serve as genetic markers that enable identification of disease related loci (Lai et al., 1998). They can also be used to investigate the underlying cause of genetic diseases and could eventually help pave the way to personalized medicine.

Current assays used in SNP detection include hybridization to allele-specific oligonucleotide (ASO) probes (Saiki et al., 1989), oligonucleotide ligation assay (OLA) (Landegren et al., 1988), restriction fragment length polymorphism (RFLP) (Shi et al., 2001), TaqMan assay (Livak et al., 1995), molecular beacon assay (Tyagi et al., 1998), and primer extension assay (Tyagi et al., 1998; Gilles et al., 1999; Fu et al., 1998) on a variety of platforms including gel electrophoresis (Chen et al., 1997), MALDI-TOF mass spectrometry (Fu et al., 1998), solid phase minisequencing (Syvanen et al., 1990), semiconductor microchips (Gilles et al., 1999), and flow cytometric analysis (Taylor et al., 2001).

The principle of minisequencing is to anneal primers immediately adjacent to the SNP positions to be analyzed and to extend these primers with ddNTPs complementary to the SNP (Syvanen et al., 1990, hereby incorporated as reference) using a DNA polymerase that readily incorporates ddNTPs. Minisequencing is unique since it is based on the high accuracy (high specificity) of polymerase mediated nucleotide incorporation reactions rather than the thermostability of matched and mismatched species which affects most other SNP detection methods. Thus, compared to hybridization-based methods, minisequencing is insensitive to small variations in reaction conditions, temperature, and to flanking DNA sequence. Moreover, minisequencing allows discrimination between homozygous and heterozygous genotypes (Chen et al., 1997). These characteristics are important in multiplexing and/or high throughput SNP detection. With the completion of the genome project and considerable interest in high throughput SNP detection, a significant market exists for enzymes that efficiently incorporate ddNTPs and dye labeled-ddNTPs in single base extension assays (mini sequencing).

DNA polymerases constitute a core component of minisequencing protocols. Efficient ddNTP and dye-ddNTP incorporation and high fidelity are essential characteristics of minisequencing enzymes. Commercially available DNA polymerases that are suitable for sequencing and minisequencing have been derived from either Taq (Taq F667Y mutants such as ThermoSequenase and AmpliTaqFS) or bacteriophage T7 DNA polymerase (Sequenase), which are both family A DNA polymerases. A tyrosine (Y) residue in the nucleotide binding pocket of T7 (native) or Taq (engineered F667Y mutant) DNA polymerase confers efficient ddNTP incorporation (Tabor et al., 1995). In two recent mutagenesis studies employing archaeal (family B) DNA polymerases, mutations were identified that reduced ddNTP discrimination; however, the archaeal DNA polymerase mutants incorporated ddNTPs less efficiently than the Taq F667Y mutant (Gardner et al., 1999; Evans et al., 2000).

There is a need in the art for DNA polymerases with reduced discrimination against unconventional nucleotides. There is particularly a need in the art for thermostable DNA polymerases exhibiting reduced discrimination against dideoxynucleotides, and further, for DNA polymerases exhibiting reduced discrimination against fluorescently labeled dideoxynucleotides.

SUMMARY OF THE INVENTION

The present invention relates to compositions and methods utilizing DNA polymerase enzymes exhibiting reduced discrimination against non-conventional nucleotides. Enzymes with this quality are useful in many applications calling for the detectable labeling of nucleic acids and are particularly useful in DNA sequencing applications.

The invention further relates to a Family B DNA polymerase having one or more mutations at a site or sites corresponding to L408, P410, S345, and/or A485 of SEQ ID NO: 2, or a fragment thereof which retains the ability to direct the template-dependent polymerization of nucleic acid. The invention also encompasses mutants and modified versions (e.g., reversibly inactivated versions of a Family B polymerase prepared, for example, by chemical modification or antibody complexing) of a Family B polymerase mutated at sites corresponding to L408, P410 and or A485 of SEQ ID NO: 2.

In one embodiment, the DNA polymerase has a dual mutation comprising comprising a serine to proline mutation at a site corresponding to S345 of SEQ ID NO: 2; and a proline to leucine mutation at a site corresponding to P410 of SEQ ID NO: 2.

The invention encompasses purified thermostable DNA polymerase having an amino acid sequence presented in SEQ ID NO: 2 from residue 1 to 776.

In one embodiment, the thermostable DNA polymerase is isolated from *Thermococcus* species JDF-3.

In another embodiment, the thermostable polymerase is isolated from a recombinant organism transformed with a vector that codes for the expression of *Thermococcus* species JDF-3 DNA polymerase.

The invention encompasses a composition for identifying a nucleotide at a given position of a template DNA molecule, the composition comprising a Family B DNA polymerase having reduced discrimination against non-conventional nucleotides and a first primer, wherein the first primer anneals to the immediate 3' of the nucleotide at the given position of the template DNA molecule.

In one embodiment, the Family B DNA polymerase is a JDF-3 DNA polymerase. In a preferred embodiment, the JDF-3 DNA polymerase has a sequence of SEQ ID NO: 2 and further comprises one or more amino acid mutations at D141, E143, A485, L408 or P410. In a further preferred embodiment, the JDF-3 DNA polymerase has one or more amino acid mutations selected from the group consisting of: D141A or D141T, E143A, L408H or L408F, A485T, and P410L.

In another embodiment, the JDF-3 DNA polymerase is substituted at position P410 with an amino acid having a non polar side chain. It is preferred that the non polar side chain is selected from the group of methionine, glycine, alanine, valine, leucine, isoleucine, phenylalanine and proline.

In another embodiment, the JDF-3 DNA polymerase comprises four amino acid mutations, at D141A, E 143A, P410L and A485T.

It is preferred that the above-described Family B DNA polymerase is deficient in 3' to 5' exonuclease activity.

In another embodiment of the above compositions, the composition further comprises at least one chain-terminating nucleotide analog, wherein the chain-terminating nucleotide analog is incorporated into the first primer by the Family B DNA polymerase in a template-dependent manner. It is preferred that the at least one chain-terminating nucleotide analog is labeled with a first detectable label. In another embodiment, more than one chain-terminating nucleotide analog is labeled, each chain-terminating nucleotide analog being labeled with a different first detectable label. It is preferred that the chain-terminating nucleotide analog is a dideoxynucleotide, preferably one selected from the group consisting of: ddATP, ddTTP, ddCTP and ddGTP.

In another embodiment, the first primer is labeled with a second detectable label. It is preferred that the first and second detectable labels generate a signal for identifying the nucleotide at the given position of the template DNA molecule.

In another embodiment, the composition further comprises a second primer. It is preferred that the first primer is labeled with a second detectable label and the second primer is labeled with a third detectable label, and that the second and third detectable labels generate a signal for identifying the nucleotide at the given position of the template DNA molecule. It is further preferred that the second primer anneals to the immediate 5' of the nucleotide at the given position of the template DNA molecule.

In one embodiment, the above-described composition further comprises a DNA ligase and/or a reaction buffer for the Family B DNA polymerase.

In another embodiment, the template DNA molecule is the product of a polymerase chain reaction or a plasmid DNA.

In any of the preceding embodiments comprising a first, second or third detectable label, the detectable label(s) is/are preferably selected from the group consisting of: a fluorescent label, an isotope, a chemiluminescent label, a quantum dot label, an antigen, or an affinity moiety. It is preferred that the first detectable label is a rhodamine label or a cyanine label.

The invention further encompasses an isolated recombinant Family B DNA polymerase having reduced discrimination against non-conventional nucleotides, wherein the DNA polymerase comprises an amino acid mutation at a position corresponding to P410 of SEQ ID NO:2. In one embodiment, the amino acid mutation is a substitution with an amino acid having a non-polar side chain. It is preferred that the amino acid having a non-polar side chain is selected from the group of methionine, glycine, alanine, valine, leucine, isoleucine, phenylalanine and proline. It is further preferred that the amino acid having a non-polar side chain is selected from the group of glycine, leucine, isoleucine and methionine.

The invention further encompasses an isolated recombinant Family B DNA polymerase having reduced discrimination against non-conventional nucleotides, wherein the DNA polymerase comprises amino acid mutations in the P Helix and at a position corresponding to P410 of SEQ ID NO: 2. In one embodiment, the amino acid mutation in the P Helix is located at a position corresponding to A485 of SEQ ID NO: 2. In another embodiment, the amino acid mutation at a position corresponding to P410 of SEQ ID NO: 2 is a substitution with an amino acid having a non-polar side chain. It is preferred that the amino acid having a non-polar side chain is selected from the group of methionine, glycine, alanine, valine, leucine, isoleucine, phenylalanine and proline. It is further preferred that the amino acid having a non-polar side chain is selected from the group of glycine, leucine, isoleucine and methionine.

The invention further encompasses a kit for identifying a nucleotide at a given position of a template DNA molecule, the kit comprising a Family B DNA polymerase having reduced discrimination against non-conventional nucleotides and a first primer, wherein the first primer anneals to the immediate 3' of the nucleotide at the given position of the template DNA molecule.

In one embodiment, the Family B DNA polymerase is a JDF-3 DNA polymerase. In a preferred embodiment, the JDF-3 DNA polymerase has a sequence of SEQ ID NO: 2 and further comprises one or more amino acid mutations at D141, E143, A485, L408 or P410. In a further embodiment, the JDF-3 DNA polymerase is substituted at a position corresponding to P410 of SEQ ID No: 2 with an amino acid having a non-polar side chain. It is preferred that the amino acid having a non-polar side chain is selected from the group of methionine, glycine, alanine, valine, leucine, isoleucine, phenylalanine and proline. It is further preferred that the amino acid having a non-polar side chain is selected from the group of glycine, leucine, isoleucine and methionine.

In another embodiment of the kit, the JDF-3 DNA polymerase has one or more amino acid mutations selected from the group consisting of: D141A or D141T, E143A, L408H or L408F, A485T, and P410L. In a preferred embodiment, the JDF-3 DNA polymerase comprises four amino acid mutations at D141A, E 143A, P410L and A485T.

In another embodiment of the kit, the Family B DNA polymerase is deficient in 3' to 5' exonuclease activity.

In another embodiment, the kit further comprises at least one chain-terminating nucleotide analog, wherein the chain-terminating nucleotide analog is incorporated into the first primer by the Family B DNA polymerase in a template-dependent manner. In another embodiment, the at least one chain-terminating nucleotide analog is labeled with a first detectable label. In another embodiment, more than one chain-terminating nucleotide analog is labeled, each chain-terminating nucleotide analog being labeled with a different first detectable label. In a preferred embodiment, the chain-terminating nucleotide analog is a dideoxynucleotide. In a further preferred embodiment, the dideoxynucleotide is selected from the group consisting of: ddATP, ddTTP, ddCTP and ddGTP.

In another embodiment of the kit, the first primer is labeled with a second detectable label. It is preferred that the first and second detectable labels generate a signal for identifying the nucleotide at the given position of the template DNA molecule.

Another embodiment of the kit further comprises a second primer. In one embodiment of this version of the kit, the first primer is labeled with a second detectable label and the second primer is labeled with a third detectable label, the second and third detectable labels generate a signal for identifying the nucleotide at the given position of the template DNA molecule. In another embodiment, the second primer anneals to the immediate 5' of the nucleotide at the given position of the template DNA molecule.

Another embodiment of the kit further comprises a DNA ligase and/or a reaction buffer for the Family B DNA polymerase.

In one embodiment of the kit, the template DNA molecule is the product of a polymerase chain reaction or is a plasmid DNA.

In another embodiment of a kit comprising a first, and/or second and/or third detectable label, the label(s) is/are selected from the group consisting of: a fluorescent label, an isotope, a chemiluminescent label, a quantum dot label, an antigen, or an affinity moiety. In a preferred embodiment, the first detectable label is a rhodamine label or a cyanine label.

In another embodiment of the kit, the kit further comprises a control template and/or at least one control primer.

In another embodiment, the kit comprises a control template and four control primers.

The invention further comprises a kit for identifying a nucleotide at a given position of a template DNA molecule, the kit comprising a Family B DNA polymerase having reduced discrimination against non-conventional nucleotides, wherein the DNA polymerase comprises an amino acid mutation at a position corresponding to P410 of SEQ ID NO:2. In one embodiment, the amino acid mutation at a position corresponding to P410 of SEQ ID NO:2 is an amino acid substitution with an amino acid having a non polar side chain. In a preferred embodiment, the amino acid having a non polar side chain is selected from the group of methionine, glycine, alanine, valine, leucine, isoleucine, phenylalanine and proline. It is further preferred that the amino acid having a non polar side chain is selected from the group of methionine, glycine, leucine and isoleucine.

The invention further encompasses a kit for identifying a nucleotide at a given position of a template DNA molecule, the kit comprising a Family B DNA polymerase having reduced discrimination against non-conventional nucleotides, wherein the DNA polymerase comprises an amino acid mutation in the P Helix and at a position corresponding to P410 of SEQ ID NO: 2. In one embodiment, the amino acid mutation in the P Helix is located at a position corresponding to A485 of SEQ ID NO: 2. In a preferred embodiment, the mutation at a position corresponding to P410 of SEQ ID NO: 2 is a substitution with an amino acid with a non-polar side chain. It is further preferred that the amino acid having a non polar side chain is selected from the group of amino acid selected from the group of methionine, glycine, alanine, valine, leucine, isoleucine, phenylalanine and proline. It is further preferred that the amino acid having a non polar side chain is selected from the group of methionine, glycine, leucine and isoleucine.

The invention further encompasses a method of identifying a nucleotide at a given position of a template DNA molecule in a sample, the method comprising: contacting a first primer with the template DNA molecule, wherein the contacting allows the first primer to anneal to the immediate 3' of the nucleotide at the given position of the template DNA molecule, so as to form a duplex between the first primer and the template DNA molecule; incubating the duplex from step (a), in the presence of a Family B DNA polymerase and at least one chain-terminating nucleotide analog, the Family B DNA polymerase having reduced discrimination against non-conventional nucleotides and the terminator is labeled with a first detectable label, wherein the incubating allows the incorporation of a labeled chain-terminating nucleotide analog into the first primer by the DNA polymerase in a template-dependent manner; and determining the presence or identity of the duplex from step (b) by a signal generated from the first detectable label.

In one embodiment, the Family B DNA polymerase is a JDF-3 DNA polymerase. In a preferred embodiment, the JDF-3 DNA polymerase has a sequence of SEQ ID NO: 2 and further comprises one or more amino acid mutations at D141, E143, A485, L408 or P410. In a further preferred embodiment, the JDF-3 DNA polymerase is substituted at position P410 with an amino acid having a non polar side chain. In a further preferred embodiment, the amino acid having a non polar side chain is selected from the group consisting of methionine, glycine, alanine, valine, leucine, isoleucine, phenylalanine and proline.

In another embodiment, the JDF-3 DNA polymerase has one or more amino acid mutations selected from the group consisting of: D141A or D141T, E143A, L408H or L408F, A485T, and P410L. In a preferred embodiment, the JDF-3 DNA polymerase comprises four amino acid mutations: D141A, E 143A, P40L and A485T.

In another embodiment of the method, the Family B DNA polymerase is deficient in 3' to 5' exonuclease activity.

In another embodiment of the method, at least one chain-terminating nucleotide analog is labeled with a first detectable label. In another embodiment of the method, more than one chain-terminating nucleotide analog is labeled, each chain-terminating nucleotide analog being labeled with a different first detectable label. It is preferred that the chain-terminating nucleotide analog is a dideoxynucleotide. It is preferred that the dideoxynucleotide is selected from the group consisting of: ddATP, ddTTP, ddCTP and ddGTP.

In another embodiment of the method, the first primer is labeled with a second detectable label.

In another embodiment of the method, first and second detectable labels generate a signal for identifying the nucleotide at the given position of the template DNA molecule.

In another embodiment of the method, the template DNA molecule is the product of a polymerase chain reaction or a plasmid. In another embodiment, the method further comprises removing PCR primers and dNTPs from the PCR product before step (a).

The invention further encompasses a method of identifying a nucleotide at a given position of a template DNA molecule in a sample, the method comprising: contacting a first primer and s second primer with the template DNA molecule, wherein the contacting allows the first primer to anneal to the immediate 3' of the nucleotide at the given position of the template DNA molecule and the second primer to anneal to the immediate 5' of the nucleotide at the given position of the template DNA molecule, so as to form a complex between the template DNA molecule and the first and second primers, the first primer being labeled with a second detectable label and the second primer being labeled with a third detectable label; incubating the complex from step (a), in the presence of a DNA ligase, wherein the incubating allows the ligation between the first and second primers so as to form a single molecule; and determining the presence or identity of the single molecule from step (b) by a signal generated from the second and third detectable labels.

In one embodiment of the method comprising a first and/or second and/or third detectable label, the first or second or third detectable label is/are selected from the group consisting of: a radiolabel, a fluorescent label, a chemiluminescent label, a colorimetric label and an enzymatic label. In a preferred embodiment, the first detectable label is a rhodamine label or a cyanine label.

The invention further encompasses a method of identifying a nucleotide at a given position of a template DNA molecule in a sample, the method comprising: contacting a first primer with the template DNA molecule, wherein the contacting allows the first primer to anneal to the immediate 3' of the nucleotide at the given position of the template DNA molecule, so as to form a duplex between the first primer and the template DNA molecule; incubating the duplex from step (a), in the presence of a Family B DNA polymerase and at least one chain-terminating nucleotide analog, the Family B DNA polymerase having reduced discrimination against non-conventional nucleotides, wherein the DNA polymerase comprises an amino acid mutation in a position corresponding to P410 of SEQ ID NO:2 and the terminator is labeled with a first detectable label, wherein the incubating allows the incorporation of a labeled chain-terminating nucleotide analog into the first primer by the DNA polymerase in a template-dependent manner; and determining the presence or identity of the duplex from step (b) by a signal generated from the first detectable label.

In one embodiment, the amino acid mutation at a position corresponding to P410 of SEQ ID NO:2 is an amino acid substitution with an amino acid having a non polar side chain. In a preferred embodiment, the amino acid having a non polar side chain is selected from the group of methionine, glycine, alanine, valine, leucine, isoleucine, phenylalanine and proline. In a further preferred embodiment, the amino acid having a non polar side chain is selected from the group of methionine, glycine, leucine and isoleucine.

The invention further encompasses a method of identifying a nucleotide at a given position of a template DNA molecule in a sample, the method comprising: contacting a first primer with the template DNA molecule, wherein the contacting allows the first primer to anneal to the immediate 3' of the nucleotide at the given position of the template DNA molecule, so as to form a duplex between the first primer and the template DNA molecule; incubating the duplex from step (a), in the presence of a Family B DNA polymerase and at least one chain-terminating nucleotide analog, the Family B DNA polymerase having reduced discrimination against non-conventional nucleotides, wherein the DNA polymerase comprises amino acid mutations in the P Helix and at a position corresponding to P410 of SEQ ID NO:2 and the terminator is labeled with a first detectable label, wherein the incubating allows the incorporation of a labeled chain-terminating nucleotide analog into the first primer by the DNA polymerase in a template-dependent manner; and determining the presence or identity of the duplex from step (b) by a signal generated from the first detectable label.

In one embodiment, the amino acid mutation in the P Helix is located at a position corresponding to position A485 of SEQ ID NO: 2.

In another embodiment, the amino acid mutation at a position corresponding to position P410 of SEQ ID NO: 2 is an amino acid substitution with an amino acid having a non polar side chain. In one embodiment, the amino acid having a non polar side chain is selected from the group of methionine, glycine, alanine, valine, leucine, isoleucine, phenylalanine and proline. In a preferred embodiment, the amino acid having a non polar side chain is selected from the group of methionine, glycine, leucine and isoleucine.

As used herein, "discrimination" refers to the tendency of DNA polymerase to not incorporate non-conventional nucleotides into a nascent DNA polymer. DNA polymerase has the ability to sense nucleotide structure, including but not limited to nucleotide base complementarity, and structural features of the sugar and heterocyclic base, thereby allowing DNA polymerase to preferentially utilize conventional deoxynucleotides rather than non-conventional nucleotides for incorporation into a nascent polymer. DNA polymerase strongly prefers to incorporate the conventional deoxynucleotides dATP, dCTP, dGTP and dTTP into DNA polymers; the polymerase is unlikely to progress with an unconventional nucleotide in its binding pocket.

As used herein, "reduced discrimination" refers to a reduction of at least 50% in the tendency of a DNA polymerase to exclude a non-conventional nucleotide from (that is, to not incorporate non-conventional nucleotides into) a nascent DNA polymer, relative to a parental or wild type DNA polymerase which does not exhibit reduced discrimination. The preference of DNA polymerase to incorporate the conventional deoxynucleotides dATP, dCTP, dGTP and TTP rather than non-conventional nucleotides into DNA polymers is thereby reduced compared to the natural level of preference, such that non-conventional nucleotides are more readily incorporated into DNA polymers by DNA polymerase. According to the invention, a polymerase exhibiting reduced discrimination will exhibit reduced discrimination against at least one non-conventional nucleotides, but may not exhibit reduced discrimination against all non-conventional nucleotides.

According to the invention, discrimination is quantitated by measuring the concentration of a non-conventional nucleotide required to inhibit the incorporation of the corresponding conventional nucleotide by 50%. This concentration is referred to herein as the "$I_{50\%}$" for a non-conventional nucleotide. Discrimination against a given non-conventional nucleotide is "reduced" if the $I_{50\%}$ for that non-conventional nucleotide is reduced by at least two fold (50%) relative to an identical assay containing, in place of the mutant DNA polymerase, a parental DNA polymerase.

Alternatively, reduced discrimination may be quantitated by determining the amount of a non-conventional nucleotide (for example, a dideoxynucleotide, ribonucleotide, or cordycepin) required in a reaction with a mutant polymerase having reduced discrimination to generate a sequencing ladder identical to a sequencing ladder produced using the wild-type or parental enzyme. The sequencing ladder can be examined, for example, in the range of 1 to 400 bases from the primer terminus, and the ladders will be identical in the number of extension products generated as well as the lengths of extension products generated in the sequencing reaction. For this type of assay, a constant amount of dNTPs and varying amounts of non-conventional nucleotides are used to generate a sequencing ladder with both the wild-type (or parental) enzyme and the mutant polymerase (for ribonucleotides, a sequencing ladder is generated by alkali cleavage of the polymerization products). See Gardner & Jack, 1999, supra. A mutant exhibits reduced discrimination if it requires at least two-fold (50%) less, five-fold (80%) less, ten-fold (100%) less, etc. of the amount of the non-conventional nucleotide used by the wild-type or parental polymerase to produce a sequencing ladder identical (with respect to the number and length of extension products generated) to that generated by the wild-type or parental enzyme.

As used herein, the term "parental" or "progenitor" refers to a polymerase used as the starting material in generating a mutant polymerase having reduced discrimination. The term "parental" is meant to encompass not only a so-called "wild-type" enzyme as it occurs in nature, but also intermediate forms, for example, an exonuclease deficient enzyme that is used as the starting material for generating an enzyme with reduced discrimination against non-conventional nucleotides.

As used herein, "non-conventional nucleotide" refers to a) a nucleotide structure that is not one of the four conventional deoxynucleotides dATP, dCTP, dGTP, and dTTP recognized by and incorporated by a DNA polymerase, b) a synthetic nucleotide that is not one of the four conventional deoxynucleotides in (a), c) a modified conventional nucleotide, or d) a ribonucleotide (since they are not normally recognized or incorporated by DNA polymerases) and modified forms of a ribonucleotide. Non-conventional nucleotides include but are not limited to those listed in Table III, which are commercially available, for example, from New England Nuclear. Any one of the above non-conventional nucleotides may be a "conjugated nucleotide", which as used herein refers to nucleotides bearing a detectable label, including but not limited to a fluorescent label, isotope, chemiluminescent label, quantum dot label, antigen, or affinity moiety.

As used herein, the term "cell", "cell line" and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

As used herein, the term "organism transformed with a vector" refers to an organism carrying a recombinant gene construct.

As used herein, "thermostable" refers to a property of a DNA polymerase, such that the enzyme active at elevated temperatures and is resistant to DNA duplex-denaturing temperatures in the range of about 93° C. to about 97° C. "Active" means the enzyme retains the ability to effect primer extension reactions when subjected to elevated or denaturing temperatures for the time necessary to effect denaturation of double-stranded nucleic acids. Elevated temperatures as used herein refer to the range of about 70° C. to about 75° C., whereas non-elevated temperatures as used herein refer to the range of about 35° C. to about 50° C.

As used herein, "archaeal" refers to an organism or to a DNA polymerase from an organism of the kingdom Archaea.

As used herein, "primer" refers to an oligonucleotide, whether natural or synthetic, which is substantially complementary (i.e., at least 7 out of 10, preferably 9 out of 10, more preferably 9 out of 10 bases are fully complementary) and can anneal to a complementary template DNA to form a duplex between the primer and the template DNA. A primer may serve as a point of initiation of nucleic acid synthesis by a polymerase following annealing to a DNA strand to be sequenced. A primer is typically a single-stranded oligodeoxyribonucleotide. The appropriate length of a primer depends on the intended use of the primer, but for DNA sequencing applications typically ranges from about 15 to about 40 nucleotides in length.

As used herein, "Family B DNA polymerase" refers to any DNA polymerase that is classified as a member of the Family B DNA polymerases, where the Family B classification is based on structural similarity to *E. coli* DNA polymerase II. The Family B DNA polymerases, formerly known as α-family polymerases, include, but are not limited to those listed as such in Table I.

Conserved regions I-VI of the Human DNA polymerase α and other DNA polymerases are defined as follows: Region I of a Family B DNA polymerase corresponds to amino acids 998-1005 of Human pol α; Region II corresponds to amino acids 839-878 of human pol α; Region III corresponds to amino acids 943-984 of human pol α; Region IV corresponds to amino acids 609-650 of human pol α; Region V corresponds to amino acids 1075-1081 of human pol α; and Region VI corresponds to amino acids 909-926 of human pol α. Based on the Family B DNA polymerase sequence alignments available in the art (e.g., Braithwaite and Ito, 1991, supra; Braithwaite and Ito, 1993, supra; Wang et al., 1997, Cell 89:1087) or created by one of skill in the art using available software (e.g., the Needleman-Wunsch algorithm), one skilled in the art can readily determine the limits of Regions I-VI of any given Family B DNA polymerase.

As used herein, "Family A DNA polymerase" refers to any DNA polymerase that is classified as a member of the Family A DNA polymerases, where the Family A classification is based on structural similarity to *E. coli* DNA polymerase I. Family A DNA polymerases include, but are not limited to those listed as such in Table I.

As used herein, "3' to 5' exonuclease deficient" or "3' to 5' exo$^-$" refers to an enzyme that substantially lacks the ability to remove incorporated nucleotides from the 3' end of a DNA polymer. DNA polymerase exonuclease activities, such as the 3' to 5' exonuclease activity exemplified by members of the Family B polymerases, can be lost through mutation, yielding an exonuclease-deficient polymerase. As used herein, a DNA polymerase that is deficient in 3' to 5' exonuclease activity substantially lacks 3' to 5' exonuclease activity. "Substantially lacks" encompasses a complete lack of activity, or a "substantial" lack of activity. "Substantial" lack of activity means that the 3' exonuclease activity of the mutant polymerase relative to the parental polymerase is 0.03%, and also may be 0.05%, 0.1%, 1%, 5%, 10%, or 20%, but is not higher than 50% of the 3' exonuclease activity of the parental or wild type polymerase.

As used herein, "mutation" refers to a change introduced into a starting parental DNA sequence that changes the amino acid sequence encoded by the DNA. The consequences of a mutation include but are not limited to the creation of a new character, property, function, or trait not found in the protein encoded by the parental DNA.

As used herein, "wild-type" refers to the typical state of an organism, strain, gene, protein or characteristic as it occurs in nature. The wild-type is therefore the natural state that is distinguished from a mutant, which was derived from the wild type by introduction of change(s) to the wild-type.

As used herein, "corresponding" refers to sequence similarity in a comparison of two or more nucleic acids or polypeptides, where functionally equivalent domains or sub-sequences are identified; such functionally equivalent domains or sub-sequences or amino acids within such a domain or sub-sequence are said to "correspond". That is, two or more sequences are compared through a comparative alignment analysis in which an entire sequence is examined for regions of sequence that are similar or identical, and thus regions likely to be functionally equivalent to regions from the other sequence(s) are identified.

As used herein in reference to comparisons of an amino acid, amino acid sequence, or protein domain, the term "similar" refers to amino acids or domains that although not identical, represent "conservative" differences. By "conservative" is meant that the differing amino acid has like characteristics with the amino acid in the corresponding or reference sequence. Typical conservative substitutions are among Ala, Val, Leu and Ile; among Ser and Thr; among the acidic residues Asp and Glu; among Asn and Gln; and among the basic residues Lys and Arg; or aromatic residues Phe and Tyr. In calculating the degree (most often as a percentage) of similarity between two polypeptide sequences, one considers the number of positions at which identity or similarity is observed between corresponding amino acid residues in the two polypeptide sequences in relation to the entire lengths of the two molecules being compared.

As used herein, the term "functionally equivalent" means that a given motif, region, or amino acid within a motif or region performs the same function with regard to the overall function of the enzyme as a motif, region or amino acid within a motif or region performs in another enzyme.

As used herein, "chain terminating nucleotide analog" refers to a nucleotide analog that once incorporated cannot serve as a substrate for subsequent extension by a DNA polymerase, thereby terminating the elongation of a DNA polymer by a DNA polymerase. Such a nucleotide analog typically lacks a hydroxyl group on its sugar moiety to which DNA polymerase can synthesize a phosphodiester bond with an incoming nucleotide. Chain terminating nucleotide analogs are a subset of non-conventional nucleotides, and include but are not limited to dideoxynucleotides.

As used herein, "detectably labeled" refers to a structural modification that incorporates a functional group (label) that can be readily detected by various means. Compounds that can be detectably labeled include but are not limited to nucleotide analogs. Detectable nucleotide analog labels include but are not limited to fluorescent compounds, isotopic compounds, chemiluminescent compound, quantum dot labels, biotin, enzymes, electron-dense reagents, and haptens or proteins for which antisera or monoclonal antibodies are available. The various means of detection include but are not limited to spectroscopic, photochemical, biochemical, immunochemical, or chemical means.

As used herein in reference to a polynucleotide or polypeptide, the term "isolated" means that a naturally occurring sequence has been removed from its normal cellular environment or is synthesized in a non-natural environment (e.g., artificially synthesized). Thus, the sequence may be in a cell-free solution or placed in a different cellular environment. The term does not imply that the sequence is the only nucleotide or polypeptide chain present, but that it is essentially free (about 90-95% pure at least) of non-nucleotide or non-polypeptide material, respectively, naturally associated with it.

As used herein, the term "recombinant" refers to a polynucleotide or polypeptide that is altered by genetic engineering (i.e., by modification or manipulation of the genetic material encoding that polynucleotide or polypeptide).

The invention encompasses full length mutant DNA polymerases, as described herein, as well as a functional fragment of a mutant polymerase, that is, a fragment of a DNA polymerase that is less than the entire amino acid sequence of the mutant polymerase and retains the ability, under at least one set of conditions, to catalyze the polymerization of a polynucleotide. Such a functional fragment may exist as a separate entity, or it may be a constituent of a larger polypeptide, such as a fusion protein.

As used herein, the term "complementary DNA strand" refers to that DNA molecule synthesized from a template DNA molecule by a DNA polymerase in a primer extension reaction.

As used herein, the term "template DNA molecule" refers to that strand of a nucleic acid from which a complementary nucleic acid strand is synthesized by a DNA polymerase, for example, in a primer extension reaction. A "template DNA molecule", also refers to a template DNA strand whose sequence needs to be identified. The sequence may need to be identified for a single nucleotide at a given position of the template DNA molecule (i.e., by mini-sequencing) or for a fragment of or the whole DNA molecule (i.e., by sequencing). The term "sequence", according to the present invention, refers to the identification of a nucleotide at a given position or at more than one position of a template DNA molecule.

As used herein, the term "non polar amino acid" refers to amino acids with non charged, aliphatic side chains. In a preferred embodiment, "non polar amino acid" refers to the amino acids alanine, glycine, valine, leucine or isoleucine.

As used herein, "P Helix" refers to the domain of archaeal Family B DNA polymerases residing at the end of the "fingers" domain. As the term is used herein, the P Helix of a Family B DNA polymerase corresponds to amino acids 480 to 499 of the JDF-3 Family B DNA polymerase disclosed herein. The sequence of the JDF-3 Family B DNA polymerase P Helix is as follows:

$^{480}$DYRQRAIKILANSYYGYYGY$^{499}$

The P Helix, along with the "palm" and "thumb" domains make up the polymerase unit of the archaeal DNA polymerase. The P Helix of archaeal DNA polymerases is described in Hopfner et al., (1999) Proc. Natl. Acad. Sci. U.S.A. 96: 3600-3605, incorporated herein by reference, which details the crystal structure of *Thermococcus gorgonarius* (Tgo) DNA polymerase and provides an alignment of nine Family B DNA polymerases. The "fingers" domain of the Tgo DNA polymerase is located at amino acids 450 to 499 of the Tgo DNA polymerase (the palm domain is located at amino acids 369 to 449 and 500 to 585 of the Tgo DNA polymerase, and the thumb domain is located at amino acids 586 to 773), and emerges from the palm domain as an α-helix-rich insertion. The 50 residues of the "fingers" domain are folded into two antiparallel coiled α-helices of approximately equal size. One of these helices, Helix P, consists of amino acids 480 to 499 of the Tgo DNA polymerase (numbered as in Hopfner et al.) and corresponds to amino acids 480 to 499 of the JDF-3 Family B DNA polymerase. That is, the "P Helix" of JDF-3 Family B DNA polymerase consists of amino acids 480 to 499 as numbered herein. The D480 to Y499 P Helix sequence of JDF-3 Family B DNA polymerase differs only at amino acid Y493 from the P helix sequence of the Tgo DNA polymerase, which has phenylalanine at position 493. A key feature of the P Helix is the highly conserved $KX_3NSXYGX_2G$ motif of B type polymerases located at amino acids 487 to 498 of both the JDF-3 and Tgo Family B DNA polymerases. The P Helix is also structurally related to the O helix of Family A DNA polymerases.

The term "corresponds to," when used in the context of similarity or homology between protein sequences or domains means that an amino acid at a particular position in a first polypeptide is identical or similar to a corresponding amino acid in a second polypeptide that is in an optimal global sequence alignment with the first polypeptide. An optimal global alignment is achieved using, for example, the Needleman-Wunsch algorithm (Needleman and Wunsch, 1970, J. Mol. Biol. 48:443-453). "Identity" means that an amino acid at a particular position in a first polypeptide is identical to a corresponding amino acid or nucleotide in a second polypeptide that is in an optimal global alignment with the first polypeptide or polynucleotide. In contrast to identity, "similarity" encompasses amino acids that are conservative substitutions. A "conservative" substitution is any substitution that has a positive score in the blosum62 substitution matrix (Hentikoff and Hentikoff, 1992, Proc. Natl. Acad. Sci. USA 89: 10915-10919). Typical conservative substitutions are among Met, Val, Leu and Ile; among Ser and Thr; among the residues Asp, Glu and Asn; among the residues Gln, Lys and Arg; or aromatic residues Phe and Tyr.

An example of the parameters for optimal global sequence alignment using the Needleman-Wunsch alignment algorithm for polypeptide alignment useful to determine "corresponding" sequences or domains are as follows: Substitution matrix: blosum62; Gap scoring function: -A-B*LG, where A=11 (the gap penalty), B=1 (the gap length penalty) and LG is the length of the gap. Using the Needleman-Wunsch algorithm and these parameters, or using other alignment software known in the art, one of skill in the art can readily determine whether a given amino acid, sequence of amino acids, or region of sequence in a given Family B DNA polymerase "corresponds to" an amino acid, sequence of amino acids or region of sequence in the JDF-3 Family B DNA polymerase disclosed herein. Further features and advantages of the invention will become more fully apparent in the following description of the embodiments and drawings thereof, and from the claims.

BRIEF DESCRIPTION OF THE DRAWINGS

FIG. 1 shows the DNA sequence encoding *Thermococcus* species JDF-3 DNA polymerase (intein removed) (SEQ ID NO: 1).

FIG. 2 shows the amino sequence of *Thermococcus* species JDF-3 DNA polymerase (intein removed) (SEQ ID NO: 2).

FIG. 3 shows the amino acid sequence of the genomic clone encoding *Thermococcus* species JDF-3 DNA polymerase (SEQ ID NO: 3). The position of an intein, removed by post-translational processing, is shown.

FIG. 4 shows the DNA sequence of the genomic clone encoding *Thermococcus* species JDF-3 DNA polymerase (SEQ ID NO: 4). DNA sequences are shown which correspond to 5' and 3' untranslated regions, polymerase-coding regions (exteins), and an intein-coding region.

FIG. 14 shows the sequence alignment of dye-dideoxynucleotide selected JDF-3 mutants (amino acids 301-480). Nucleic acid residues highlighted by white boxes indicate the location of a mutation. The mutation S345P is one of two mutations present in mutant 28.

FIG. 15 shows the sequence alignment of dye-dideoxynucleotide selected JDF-3 (amino acids 481-660). Nucleic acid residues highlighted by white boxes indicate the location of a mutation.

FIG. 23 A: Polymerase activity was expressed as corrected cpms of 3H-TTP incorporated into activated calf thymus DNA in 30 minutes in the presence of 100 μM each dNTP.

DESCRIPTION

Figure 5:
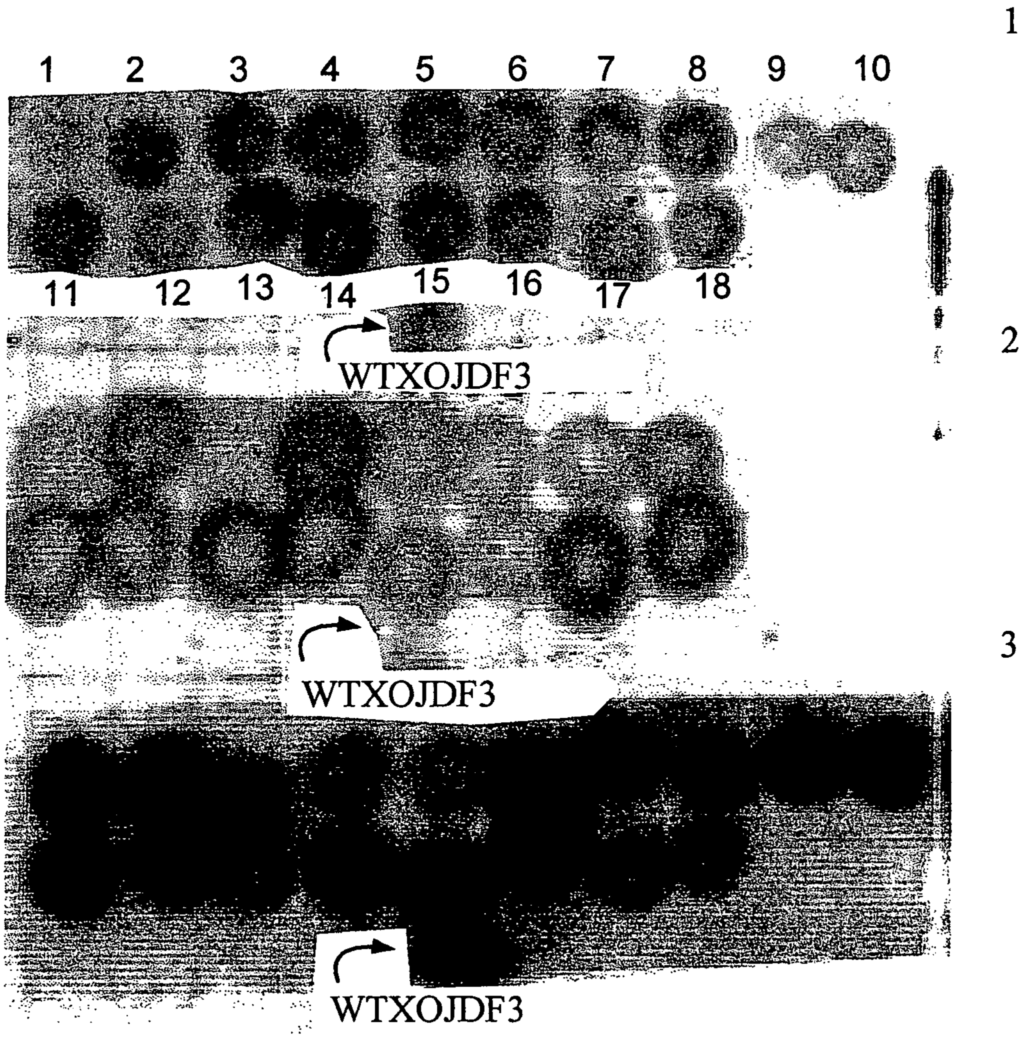
FIG. 5 shows nucleotide incorporation by JDF-3 mutants. Lambda phage clones which incorporated $^{33}$P-labeled ddNTPs in the primary library screen were rescreened to assess $^{33}$P-ddNTP incorporation in the presence of: (panel 1) 0.5 mM $MnCl_2$ or (panel 2) 1.5 mM $MgCl_2$. Polymerase activity was measured using $^{33}$P-dNTPs in the presence of 1.5 mM $MgCl_2$ (panel 3). Nucleotide utilization is shown for clones 1-18 and for the parental #550 clone.

The invention is based on the discovery of Family B DNA polymerases that bear one or more genetic alterations resulting in reduced discrimination against non-conventional nucleotides relative to their unmodified wild-type forms. All references described herein are incorporated by reference herein in their entirety.

Family B DNA Polymerase Exhibiting Reduced Discrimination Against Non-Conventional Nucleotides:

A. DNA Polymerases Useful According to the Invention

According to the invention, DNA polymerases of Family B may be mutated to generate enzymes exhibiting reduced discrimination against non-conventional nucleotides. Table I includes a non-limiting list of known DNA polymerases categorized by family.

TABLE I

| DNA POLYMERASES BY FAMILY | Reference |
|---|---|
| **FAMILY A DNA POLYMERASES** | |
| Bacterial DNA Polymerases | |
| a) *E. coli* DNA polymerase I | (1) |
| b) *Streptococcus pneumoniae* DNA polymerase I | (2) |
| c) *Thermus aquaticus* DNA polymerase I | (3) |
| d) *Thermus flavus* DNA polymerase I | (4) |
| e) *Thermotoga maritima* DNA polymerase I | |
| Bacteriophage DNA Polymerases | |
| a) T5 DNA polymerase | (5) |
| b) T7 DNA polymerase | (6) |
| c) Spo1 DNA polymerase | (7) |
| d) Spo2 DNA polymerase | (8) |
| Mitochondrial DNA polymerase | (9, 10, 11) |
| Yeast Mitochondrial DNA polymerase II | |
| **FAMILY B DNA POLYMERASES** | |
| Bacterial DNA polymerase | |
| *E. coli* DNA polymerase II | (15) |
| Bacteriophage DNA polymerase | |
| a) PRD1 DNA polymerase | (16, 17) |
| b) φ29 DNA polymerase | (18) |
| c) M2 DNA polymerase | (19) |
| d) T4 DNA polymerase | (20) |
| Archaeal DNA polymerase | |
| a) *Thermococcus litoralis* DNA polymerase (Vent) | (21) |
| b) *Pyrococcus furiosus* DNA polymerase | (22) |
| c) *Sulfolobus solfataricus* DNA polymerase | (23) |
| d) *Thermococcus gorgonarius* DNA polymerase | (64) |
| e) *Thermococcus* species TY | (65) |
| f) *Pyrococcus* species strain KODI | (66) |
| g) *Sulfolobus* acidocaldarius | (67) |
| h) *Thermococcus* species 9°N-7 | (68) |
| i) *Pyrodictium occultum* | (69) |
| j) *Methanococcus voltae* | (70) |
| k) *Desulfurococcus* strain TOK (D. Tok Pol) | (71) |
| Eukaryotic Cell DNA polymerase | |
| (1) DNA polymerase alpha | |
| a) Human DNA polymerase (alpha) | (24) |
| b) *S. cerevisiae* DNA polymerase (alpha) | (25) |

TABLE I-continued

| DNA POLYMERASES BY FAMILY | Reference |
|---|---|
| c) *S. pombe* DNA polymerase I (alpha) | (26) |
| d) *Drosophila melanogaster* DNA polymerase (alpha) | (27) |
| e) *Trypanosoma brucei* DNA polymerase (alpha) | (28) |
| (2) DNA polymerase delta | |
| a) Human DNA polymerase (delta) | (29, 30) |
| b) Bovine DNA polymerase (delta) | (31) |
| c) *S. cerevisiae* DNA polymerase III (delta) | (32) |
| d) *S. pombe* DNA polymerase III (delta) | (33) |
| e) *Plasmodiun falciparum* DNA polymerase (delta) | (34) |
| (3) DNA polymerase epsilon | |
| *S. cerevisiae* DNA polymerase II (epsilon) | (35) |
| (4) Other eukaryotic DNA polymerase | |
| *S. cerevisiae* DNA polymerase Rev3 | (36) |
| Viral DNA polymerases | |
| a) Herpes Simplex virus type 1 DNA polymerase | (37) |
| b) Equine herpes virus type 1 DNA polymerase | (38) |
| c) Varicella-Zoster virus DNA polymerase | (39) |
| d) Epstein-Barr virus DNA polymerase | (40) |
| e) Herpesvirus saimiri DNA polymerase | (41) |
| f) Human cytomegalovirus DNA polymerase | (42) |
| g) Murine cytomegalovirus DNA polymerase | (43) |
| h) Human herpes virus type 6 DNA polymerase | (44) |
| i) Channel Catfish virus DNA polymerase | (45) |
| j) Chlorella virus DNA polymerase | (46) |
| k) Fowlpox virus DNA polymerase | (47) |
| l) Vaccinia virus DNA polymerase | (48) |
| m) Choristoneura biennis DNA polymerase | (49) |
| n) Autographa california nuclear polymerase virus (AcMNPV) DNA polymerase | (50) |
| o) *Lymantria dispar* nuclear polyhedrosis virus DNA polymerase | (51) |
| p) Adenovirus-2 DNA polymerase | (52) |
| q) Adenovirus-7 DNA polymerase | (53) |
| r) Adenovirus-12 DNA polymerase | (54) |
| Eukaryotic linear DNA plasmid encoded DNA polymerases | |
| a) S-1 Maize DNA polymerase | (55) |
| b) kalilo neurospora intermedia DNA polymerase | (56) |
| c) pA12 ascobolus immersus DNA polymerase | (57) |
| d) pCLK1 *Claviceps purpurea* DNA polymerase | (58) |
| e) maranhar *neurospora crassa* DNA polymerase | (59) |
| f) pEM *Agaricus bitorquis* DNA polymerase | (60) |
| g) pGKL1 *Kluyveromyces lactis* DNA polymerase | (61) |
| h) pGKL2 *Kluyveromyces lactis* DNA polymerase | (62) |
| i) pSKL *Saccharomyces kluyveri* DNA polymerase | (63) |

B. Plasmids

The starting sequences for the generation of Family B DNA polymerases according to the invention may be contained in a plasmid vector. A non-limiting list of cloned Family B DNA polymerases and their GenBank Accession numbers are listed in Table II.

TABLE II

| Accession Information for Cloned Family B Polymerases | |
|---|---|
| Vent *Thermococcus litoralis* | |
| ACCESSION | AAA72101 |
| PID | g348689 |
| VERSION | AAA72101.1 GI: 348689 |
| DBSOURCE | locus THCVDPE accession M74198.1 |
| THEST *THERMOCOCCUS* SP. (STRAIN TY) | |
| ACCESSION | O33845 |
| PID | g3913524 |
| VERSION | O33845 GI: 3913524 |
| DBSOURCE | swissprot: locus DPOL_THEST, accession O33845 |
| Pab *Pyrococcus abyssi* | |
| ACCESSION | P77916 |
| PID | g3913529 |
| VERSION | P77916 GI: 3913529 |
| DBSOURCE | swissprot: locus DPOL_PYRAB, accession P77916 |
| PYRHO *Pyrococcus horikoshii* | |
| ACCESSION | O59610 |
| PID | g3913526 |
| VERSION | O59610 GI: 3913526 |
| DBSOURCE | swissprot: locus DPOL_PYRHO, accession O59610 |
| PYRSE *PYROCOCCUS* SP. (STRAIN GE23) | |
| ACCESSION | P77932 |
| PID | g3913530 |
| VERSION | P77932 GI: 3913530 |
| DBSOURCE | swissprot: locus DPOL_PYRSE, accession P77932 |
| DeepVent *Pyrococcus* sp. | |
| ACCESSION | AAA67131 |
| PID | g436495 |
| VERSION | AAA67131.1 GI: 436495 |
| DBSOURCE | locus PSU00707 accession U00707.1 |
| Pfu *Pyrococcus furiosus* | |
| ACCESSION | P80061 |
| PID | g399403 |
| VERSION | P80061 GI: 399403 |
| DBSOURCE | swissprot: locus DPOL_PYRFU, accession P80061 |
| JDF-3 *Thermococcus* sp. Unpublished Baross gi\|2097756\|pat\|US\|5602011\|12 Sequence 12 from patent U.S. Pat. No. 5602011 | |
| 9degN THERMOCOCCUS SP. (STRAIN 9ON-7). | |
| ACCESSION | Q56366 |
| PID | g3913540 |
| VERSION | Q56366 GI: 3913540 |
| DBSOURCE | swissprot: locus DPOL_THES9, accession Q56366 |
| KOD *Pyrococcus* sp. | |
| ACCESSION | BAA06142 |
| PID | g1620911 |
| VERSION | BAA06142.1 GI: 1620911 |
| DBSOURCE | locus PYWKODPOL accession D29671.1 |
| Tgo *Thermococcus gorgonarius.* | |
| ACCESSION | 4699806 |
| PID | g4699806 |
| VERSION | GI: 4699806 |
| DBSOURCE | pdb: chain 65, release Feb. 23, 1999 |
| THEFM *Thermococcus fumicolans* | |
| ACCESSION | P74918 |
| PID | g3913528 |
| VERSION | P74918 GI: 3913528 |
| DBSOURCE | swissprot: locus DPOL_THEFM, accession P74918 |
| METTH *Methanobacterium thermoautotrophicum* | |
| ACCESSION | O27276 |
| PID | g3913522 |
| VERSION | O27276 GI: 3913522 |
| DBSOURCE | swissprot: locus DPOL_METTH, accession O27276 |
| Metja *Methanococcus jannaschii* | |
| ACCESSION | Q58295 |
| PID | g3915679 |
| VERSION | Q58295 GI: 3915679 |
| DBSOURCE | swissprot: locus DPOL_METJA, accession Q58295 |

TABLE II-continued

| Accession Information for Cloned Family B Polymerases | |
|---|---|
| POC *Pyrodictium occultum* | |
| ACCESSION | B56277 |
| PID | g1363344 |
| VERSION | B56277 GI: 1363344 |
| DBSOURCE | pir: locus B56277 |
| ApeI *Aeropyrum pernix* | |
| ACCESSION | BAA81109 |
| PID | g5105797 |
| VERSION | BAA81109.1 GI: 5105797 |
| DBSOURCE | locus AP000063 accession AP000063.1 |
| ARCFU *Archaeoglobus fulgidus* | |
| ACCESSION | O29753 |
| PID | g3122019 |
| VERSION | O29753 GI: 3122019 |
| DBSOURCE | swissprot: locus DPOL__ARCFU, accession O29753 |
| *Desulfurococcus* sp. Tok. | |
| ACCESSION | 6435708 |
| PID | g64357089 |
| VERSION | GT: 6435708 |
| DBSOURCE | pdb. chain 65, release Jun. 2, 1999 |

Plasmids acceptable for the expression of modified forms of Family B DNA polymerases may be selected from a large number known in the art by one of skill in the art. A plasmid vector for expression of a modified DNA polymerase according to the invention will preferably comprise sequences directing high level expression of a DNA polymerase, and will more preferably comprise sequences directing inducible, high level expression of a DNA polymerase. As one example of an inducible high level expression system, plasmids placing a modified DNA polymerase coding sequence according to the invention under the control of a bacteriophage T7 promoter may be introduced to bacteria containing an inducible T7 RNA polymerase gene within their chromosome. Induction of the T7 RNA polymerase gene subsequently induces high level expression of the T7 promoter-driven modified DNA polymerase gene (see for example, Gardner & Jack, Nucleic Acids Res. 27: 2545).

C. Mutagenesis

The cloned wild-type form of a Family B DNA polymerase may be mutated to generate forms exhibiting reduced discrimination against non-conventional nucleotides by a number of methods.

First, methods of random mutagenesis which will result in a panel of mutants bearing one or more randomly-situated mutations exist in the art. Such a panel of mutants may then be screened for those exhibiting reduced discrimination relative to the wild-type polymerase (see "Methods of Evaluating Mutants for Reduced Discrimination", below). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Second, there are a number of site-directed mutagenesis methods known in the art which allow one to mutate a particular site or region in a straightforward manner. There are a number of kits available commercially for the performance of site-directed mutagenesis, including both conventional and PCR-based methods. Examples include the EXSITE™ PCR-Based Site-directed Mutagenesis Kit available from Stratagene (Catalog No. 200502; PCR based) and the QUIKCHANGE™ Site-directed mutagenesis Kit from Stratagene (Catalog No. 200518; non-PCR-based), and the CHAMELEON® double-stranded Site-directed mutagenesis kit, also from Stratagene (Catalog No. 200509).

Older methods of site-directed mutagenesis known in the art relied upon sub-cloning of the sequence to be mutated into a vector, such as an M13 bacteriophage vector, that allows the isolation of single-stranded DNA template. In these methods one annealed a mutagenic primer (i.e., a primer capable of annealing to the site to be mutated but bearing one or mismatched nucleotides at the site to be mutated) to the single-stranded template and then polymerized the complement of the template starting from the 3' end of the mutagenic primer. The resulting duplexes were then transformed into host bacteria and plaques were screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease DpnI (recognition target sequence: 5-Gm6ATC-3, where the A residue is methylated) is used to select against parental DNA, since most common strains of *E. Coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

The method is described in detail as follows:

PCR-based Site Directed Mutagenesis of the 3'-5' Exonuclease Domain

Plasmid template DNA (approximately 0.5 pmole) is added to a PCR cocktail containing: 1× mutagenesis buffer (20 mM Tris HCl, pH 7.5; 8 mM MgCl2; 40 ug/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other)

must contain a 5' phosphate to facilitate later ligation), 250 uM each dNTP, 2.5 U Taq DNA polymerase, and 2.5 U of Taq Extender (Available from Stratagene; See Nielson et al. (1994) Strategies 7: 27, and U.S. Pat. No. 5,556,772). The PCR cycling is performed as follows: 1 cycle of 4 min at 94° C., 2 min at 50° C. and 2 min at 72° C.; followed by 5-10 cycles of 1 min at 94° C., 2 min at 54° C. and 1 min at 72° C. The parental template DNA and the linear, PCR-generated DNA incorporating the mutagenic primer are treated with DpnI (10 U) and Pfu DNA polymerase (2.5 U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent *E. coli* according to standard methods.

D. Non-Conventional Nucleotides Useful According to the Invention.

There is a wide variety of non-conventional nucleotides available in the art. Any or all of them are contemplated for use with a DNA polymerase of the invention. A non-limiting list of such non-conventional nucleotides is presented in Table III.

TABLE III

| Non-Conventional Nucleotides | |
|---|---|
| DIDEOXYNUCLEOTIDE ANALOGS | |
| Fluorescein Labeled | Fluorophore Labeled |
| Fluorescein-12-ddCTP | Eosin-6-ddCTP |
| Fluorescein-12-ddUTP | Coumarin-5-ddUTP |
| Fluorescein-12-ddATP | Tetramethylrhodamine-6-ddUTP |
| Fluorescein-12-ddGTP | Texas Red-5-ddATP |
| Fluorescein-N6-ddATP | LISSAMINE ™-rhodamine-5-ddGTP |
| FAM Labeled | TAMRA Labeled |
| FAM-ddUTP | TAMRA-ddUTP |
| FAM-ddCTP | TAMRA-ddCTP |
| FAM-ddATP | TAMRA-ddATP |
| FAM-ddGTP | TAMRA-ddGTP |
| ROX Labeled | JOE Labeled |
| ROX-ddUTP | JOE-ddUTP |
| ROX-ddCTP | JOE-ddCTP |
| ROX-ddATP | JOE-ddATP |
| ROX-ddGTP | JOE-ddGTP |
| R6G Labeled | R110 Labeled |
| R6G-ddUTP | R110-ddUTP |
| R6G-ddCTP | R110-ddCTP |
| R6G-ddATP | R110-ddATP |
| R6G-ddGTP | R110-ddGTP |
| BIOTIN Labeled | DNP Labeled |
| Biotin-N6-ATP | DNP-N6-ddATP |

TABLE III-continued

| Non-Conventional Nucleotides | |
|---|---|
| DEOXYNUCLEOTIDE ANALOGS | |
| TTP Analogs | dATP-Analogs |
| Fluorescein-12-dUTP | Coumarin-5-dATP |
| Coumarin-5-dUTP | Diethylaminocoumarin-5-dATP |
| Tetramethylrhodamine-6-dUTP | Fluorescein-12-dATP |
| Tetraethylrhodamine-6-dUTP | Fluorescein Chlorotriazinyl-4-dATP |
| Texas Red-5-dUTP | LISSAMINE ™-rhodamine-5-dATP |
| LISSAMINE ™-rhodamine-5-dUTP | Naphthofluorescein-5-dATP |
| Naphthofluorescein-5-dUTP | Pyrene-8-dATP |
| Fluorescein Chlorotriazinyl-4-dUTP | Tetramethylrhodamine-6-dATP |
| Pyrene-8-dUTP | Texas Red-5-dATP |
| Diethylaminocoumarin-5-dUTP | DNA-N6-dATP |
| | Biotin-N6-dATP |
| dCTP Analogs | dGTP Analogs |
| Coumarin-5-dCTP | Coumarin-5-dGTP |
| Fluorescein-12-dCTP | Fluorescein-12-dGTP |
| Tetramethylrhodamine-6-dCTP | Tetramethylrhodamine-6-dGTP |
| Texas Red-5-dCTP | Texas Red-5-dGTP |
| LISSAMINE ™-rhodamine-5-dCTP | LISSAMINE ™-rhodamine-5-dGTP |
| Naphthofluorescein-5-dCTP | Diethylaminocoumarin-5-dCTP |
| Fluorescein Chlorotriazinyl-4-dCTP | |
| Pyrene-8-dCTP | |
| Fluorescein-N4-dCTP | |
| Biotin-N4-dCTP | |
| DNP-N4-dCTP | |
| RIBONUCLEOTIDE ANALOGS | |
| CTP Analogs | UTP Analogs |
| Coumarin-5-CTP | Fluorescein-12-UTP |
| Fluorescein-12-CTP | Coumarin-5-UTP |
| Tetrainethylrhodainine-6-CTP | Tetramethylrhodamine-6-UTP |
| Texas Red-5-CTP | Texas Red-5-UTP |
| LISSAMINE ™-rhodamine-5-CTP | LISSAMINE ™-5-UTP |
| Naphthofluorescein-5-CTP | Naphthofluorescein-5-UTP |
| Fluorescein Chlorotriazinyl-4-CTP | Fluorescein Chlorotriazinyl-4-UTP |
| Pyrene-8-CTP | Pyrene-8-UTP |
| Fluorescein-N4-CTP | |
| Biotin-N4-CTP | |
| ATP Analogs | |
| Coumarin-5-ATP | |
| Fluorescein-12-ATP | |
| Tetramethylrhodamine-6-ATP | |
| Texas Red-5-ATP | |
| LISSAMINE ™-rhodamine-5-ATP | |
| Fluorescein-N6-ATP | |
| Biotin-N6-ATP | |
| DNP-N6-ATP | |

Additional non-conventional nucleotides useful according to the invention include, but are not limited to 7-deaza-dATP, 7-deaza-dGTP, 5'-methyl-2'-deoxycytidine-5'-triphosphate. Further non-conventional nucleotides or variations on those listed above are discussed by Wright & Brown, 1990, Pharmacol. Ther. 47: 447. It is specifically noted that ribonucleotides qualify as non-conventional nucleotides, since ribonucleotides are not generally incorporated by DNA polymerases. Modifications of Family B DNA polymerases that result in the ability, or enhanced ability, of the polymerase to incorporate labeled or unlabeled ribonucleotides are specifically contemplated herein.

E. Methods of Evaluating Mutants for Reduced Discrimination

Random or site-directed mutants generated as known in the art or as described herein and expressed in bacteria may be screened for reduced discrimination against non-conventional nucleotides by several different assays. In one method, Family B DNA polymerase proteins expressed in lytic lambda phage plaques generated by infection of host bacteria with expression vectors based on, for example, Lambda ZapII®, are transferred to a membrane support. The immobilized proteins are then assayed for polymerase activity on the membrane by immersing the membranes in a buffer containing a DNA template and the unconventional nucleotides to be monitored for incorporation.

Mutant polymerase libraries may be screened using a variation of the technique used by Sagner et al (Sagner, G., Ruger, R., and Kessler, C. (1991) *Gene* 97:119-123). For this approach, lambda phage clones are plated at a density of 10-20 plaques per square centimeter. Proteins present in the plaques are transferred to filters and moistened with polymerase screening buffer (50 mM Tris (pH 8.0), 7 mM $MgCl_2$, 3 mM β-ME). The filters are kept between layers of plastic wrap and glass while the host cell proteins are heat-inactivated by incubation at 65° C. for 30 minutes. The heat-treated filters are then transferred to fresh plastic wrap and approximately 35 ⊠ l of polymerase assay cocktail are added for every square centimeter of filter. The assay cocktail consists of 1× cloned Pfu (cPfu) magnesium free buffer (1× buffer is 20 mM Tris-HCl (pH 8.8), 10 mM KCl, 10 mM $(NH4)_2SO_4$, 100 ug/ml bovine serum albumin (BSA), and 0.1% Triton X-100; Pfu Magnesium-free buffer may be obtained from Stratagene (Catalog No. 200534)), 125 ng/ml activated calf thymus or salmon sperm DNA, 1.29 ⊠ Ci/ml α-$^{33}$P ddNTP or dideoxynucleotides (at a dNTP:dye-ddNTP ratio of 1:15). Initial screening was done in the presence of $MnCl_2$, but the preferred method was to screen in 1× Taq Polymerase buffer (1.5 mM $MgCl_2$) The filters are placed between plastic wrap and a glass plate and then incubated at 65° C. for one hour, and then at 70° C. for one hour and fifteen minutes. Filters are then washed three times in 2×SSC for five minutes per wash before rinsing twice in 100% ethanol and vacuum drying. Filters are then exposed to X-ray film (approximately 16 hours), and plaques that incorporate label are identified by aligning the filters with the original plate bearing the phage clones. Plaques identified in this way are re-plated at more dilute concentrations and assayed under similar conditions to allow the isolation of purified plaques.

In assays such as the one described above, the signal generated by the label is a direct measure of the activity of the polymerase with regard to that particular unconventional nucleotide or combination of unconventional nucleotides used in the assay. Unconventional nucleotides corresponding to all four conventional nucleotides may be included in the reactions, or, alternatively, only one unconventional nucleotide may be included to assess the effect of the mutation(s) on utilization of a given unconventional nucleotide. One approach is to use unconventional nucleotides corresponding to all four nucleotides in a first screen to identify clones that incorporate more than a reference wild-type clone, and then to monitor the incorporation of individual unconventional nucleotides in a subsequent screen. In the preferred screening mode, only the dideoxynucleotides and dideoxynucleotide analogs of ddATP, ddCTP, and ddTTP would be used since ddGTP is not discriminated against by some DNA polymerases and increases the background signal of any screen.

In order to screen for clones with enhanced ability to incorporate dideoxynucleotides, clones identified in first screens utilizing only dideoxynucleotides may then be characterized by their sensitivity to low levels of each of the four dideoxynucleotides in a DNA polymerase nucleotide incorporation assay employing all four dNTPs, a $^3$H-TTP tracer, and a low level of each ddNTP. Since incorporation of dideoxynucleotides stops DNA chain elongation, superior ability to incorporate dideoxynucleotides diminishes the incorporation of tritium labeled deoxynucleotides relative to wild-type DNA polymerase. Comparisons of ddNTP concentrations that bring about 50% inhibition of nucleotide incorporation ($I_{50\%}$) can be used to compare ddNTP incorporation efficiency of different polymerases or polymerase mutants. Comparisons of $I_{50\%}$ values for ddATP, ddCTP, ddGTP, and ddTTP can be used to identify mutants with reduced selectivity for particular bases. Such mutants would be expected to produce more uniform DNA sequencing ladders.

In order to measure incorporation of individual ddNTPs, cocktails are prepared which consist of varying concentrations of the ddNTP of interest, and a total of 200 μM of each nucleotide triphosphate. For example, the incorporation of ddATP by wild type JDF-3 polymerase may be measured at 0, 40, 80, 120 and 160 μM ddATP. In these reactions, dATP concentrations would be adjusted to 200, 160, 120, 80, and 40 μM, respectively, so that the total amount of adenine nucleotide triphosphate is 200 μM. In comparison, mutants may be assayed using ddATP concentrations of 0, 5, 10, and 20 μM ddATP, and adjusted dATP concentrations of 200, 195, 190, and 180 μM, respectively (dATP+ddATP=200 μM). Additional cocktails are prepared to similarly measure ddCTP, ddGTP, and ddTTP incorporation.

Incorporation of nucleotides under the concentration parameters described above may be measured in extension reactions by adding, for example, 1 μl of appropriately diluted bacterial extract (i.e., heat-treated and clarified extract of bacterial cells (see Example 1, part M) expressing a cloned polymerase or mutated cloned polymerase) to 10 μl of each nucleotide cocktail, followed by incubation at 72° C. for 30 minutes. Extension reactions are quenched on ice, and then 5 μl aliquots are spotted immediately onto DE81 ion-exchange filters (2.3 cm; Whatman #3658323). Unincorporated label is removed by 6 washes with 2×SSC (0.3M NaCl, 30 mM sodium citrate, pH 7.0), followed by a brief wash with 100% ethanol. Incorporated radioactivity is then measured by scintillation counting. Reactions that lack enzyme are also set up along with sample incubations to determine “total cpms” (omit filter wash steps) and “minimum cpms” (wash filters as above).

Cpms bound is proportional to the amount of polymerase activity present per volume of bacterial extract. The volume of bacterial extract (generally about 0.25-1 μl) which brings about incorporation of approximately 10,000 cpms is determined for use in subsequent nucleotide analog incorporation testing.

Genes for mutant DNA polymerases generated by random mutagenesis may be sequenced to identify the sites and number of mutations. For those mutants comprising more than one mutation, the effect of a given mutation may be evaluated by introduction of the identified mutation to the exo$^-$ progenitor gene by site-directed mutagenesis in isolation from the other mutations borne by the particular mutant. Screening assays of the single mutant thus produced will then allow the determination of the effect of that mutation alone.

F. Expression of Mutated Family B DNA Polymerase According to the Invention

Methods known in the art may be applied to express and isolate the mutated forms of Family B DNA polymerase according to the invention. Many bacterial expression vectors contain sequence elements or combinations of sequence elements allowing high level inducible expression of the protein encoded by a foreign sequence. For example, as mentioned above, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter (see Gardner & Jack, 1999, supra).

Appropriate host strains of bacteria may be selected from those available in the art by one of skill in the art. As a non-limiting example, *E. coli* strain BL-21 is commonly used for expression of exogenous proteins since it is protease deficient relative to other strains of *E. coli*. BL-21 strains bearing an inducible T7 RNA polymerase gene include WJ56 and ER2566 (Gardner & Jack, 1999, supra). For situations in which codon usage for the particular polymerase gene differs from that normally seen in *E. coli* genes, there are strains of BL-21 that are modified to carry tRNA genes encoding tRNAs with rarer anticodons (for example, argU, ileY, leuW, and proL tRNA genes), allowing high efficiency expression of cloned protein genes, for example, cloned archaeal enzyme genes (several BL21-CODON PLUS™ cell strains carrying rare-codon tRNAs are available from Stratagene, for example).

There are many methods known to those of skill in the art that are suitable for the purification of a modified DNA polymerase of the invention. For example, the method of Lawyer et al. (1993, PCR Meth. & App. 2: 275) is well suited for the isolation of thermostable DNA polymerases expressed in *E. coli*, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure thermostable DNA polymerase. Further, as detailed in Example 1, part N, below, DNA polymerase mutants may be isolated by an ammonium sulfate fractionation, followed by Q Sepharose and DNA cellulose columns, or by adsorption of contaminants on a HiTrap Q column, followed by gradient elution from a HiTrap heparin column.

G. Preparation of *Thermococcus* species JDF-3 Thermostable DNA Polymerase With Reduced Discrimination To prepare thermostable Family B polymerases which exhibit reduced discrimination for dideoxynucleotide triphosphates (ddNTPs), the DNA sequence encoding a 3' to 5' exonuclease-deficient (D141A) Family B polymerase from the hyperthermophilic archaeon *Thermococcus* species JDF-3 was subjected to random mutagenesis using "error-prone PCR" as described herein, and cloned into the bacteriophage lambda Zap®II. The polymerase from JDF-3 was chosen due to superior processivity, polymerization rate and ddNTP incorporation relative to the Family B DNA polymerase from *Pyrococcus furiosus* (Pfu) (see Table IV, below). The library of mutants was plated on *E. coli* hosts and the proteins present in the lytic plaques were transferred to a solid support that was then immersed in a buffer containing DNA template and all four α-$^{33}$P labeled dideoxynucleotides. Mutants that incorporated the labeled dideoxynucleotide produced signals that corresponded to their ability to incorporate the α-$^{33}$P ddNTPs. Isolated clones were then characterized by their sensitivity to low levels of each of the four dideoxynucleotides in a DNA polymerase nucleotide incorporation assay employing all four dNTPs and a $^{3}$H-TTP tracer. Since incorporation of dideoxynucleotides stops DNA chain elongation, superior ability to incorporate dideoxynucleotides diminishes the incorporation of tritium labeled deoxynucleotides. The unmutated progenitor DNA polymerase rarely incorporates dideoxynucleotides and is only 50% inhibited at high ddNTP levels (100-160 micromolar each ddNTP). The mutant enzymes show 50% inhibition at 5 to 40 micromolar concentrations of ddNTP and improved incorporation was observed for all four ddNTPs (ddATP, ddCTP, ddTTP and ddGTP; see Tables V and VI in Example 1, below).

The incorporation of non-conventional nucleotides was also evaluated through use of purified mutant polymerases in cycle sequencing, with α-$^{33}$P labeled ddNTPs present at 0.021 μM and dNTPs present at 2.1 μM each. The mutants readily utilized all four dideoxynucleotides and produced sequencing ladders that compared favorably to Thermo Sequenase®, which uses an F667Y Taq DNA polymerase mutant (VanderHorn et al., 1997, BioTechniques 22: 758).

The domains of relevance in 17 of the 40 purified mutants were sequenced. Most randomly mutated clones contained more than one mutation in the regions sequenced but all mutants contained mutations at one of three sites. Mutations predicted to confer an enhanced ddNTP uptake phenotype were introduced into the progenitor exonuclease deficient DNA polymerase sequence by site-directed mutagenesis to eliminate ancillary mutations which were not expected to contribute to the improved dideoxynucleotide uptake phenotype.

Sixteen of the seventeen JDF-3 DNA polymerase mutations were found in region II (motif A) on either side of the tyrosine in the consensus sequence 404 DxxSLYPSII 413. These mutations consisted of DFRSLYLSII (P410L), DFRSHYPSII (L408H) and DFRSFYPSII (L408F). Therefore, the LYP motif of region II appears to be important in ddNTP discrimination in the JDF-3 Family B polymerase.

The prior art modification of the tyrosine corresponding to Y409 in JDF3 Family B DNA polymerase is recognized for its positioning in the nucleotide binding pocket. As shown herein, however, modification of the residues neighboring Y409 (L408H or L408F or P410L) had the unexpected effect of profoundly altering nucleotide binding, particularly with respect to ddNTP incorporation.

The only JDF-3 DNA polymerase mutation leading to enhanced incorporation of non-conventional nucleotides occurring outside of region II is an alanine (ala or A) to threonine (thr or T) conversion at position 485 in region III (A485T). This site is two residues upstream of $KX_3NSXYG$ (Jung et al., 1990, supra; Blasco et al., 1992, supra; Dong et al., 1993, J. Biol. Chem. 268:21163; Zhu et al., 1994, Biochem. Biophys. Acta 1219:260; Dong and Wang, 1995, J. Biol. Chem. 270:21563) (referred to as region III or motif B) which is functionally, but not structurally (Wang et al., 1997, supra), analogous to $KX_3$(F/Y)$GX_2YG$ in helix O of the Family A DNA polymerases. In Family A DNA polymerases, such as the Klenow fragment and Taq DNA polymerases, the O helix contains amino acids that play a major role in dNTP binding (Astatke et al., 1998, J. Mol. Biol. 278:147; Astatke et al., 1995, J. Biol. Chem. 270:1945; Polesky et al., 1992, J. Biol. Chem. 267:8417; Polesky et al., 1990, J. Biol. Chem. 265:14579; Pandey et al., 1994, J. Biol. Chem. 269:13259; Kaushik et al., 1996, Biochem. 35:7256). Specifically, helix O contains the F (F762 in the Klenow fragment; F667 in Taq) which confers ddNTP discrimination in Family A DNA polymerases ($KX_3$(F/Y)$GX_2YG$) (Tabor and Richardson, 1995, supra).

The effect of the A485T mutation on ddNTP incorporation in the JDF-3 DNA polymerase is surprising since the RB69 and *Thermococcus gorgonarius* crystal structures (Hopfner et al., 1999, supra) show it facing away from the proposed active site of the nucleotide binding surface. Moreover, the type of side chain conferring ribose selectivity in archaeal Family B DNA polymerases (A: small, non-polar) is different from that of the bulky, aromatic Y and F residues that dictate ddNTP discrimination in Family A DNA polymerases (Tabor and Richardson, 1995, supra). Additionally, this position (A485) is not well conserved among either DNA polymerase family and is not included in the consensus sequence for this domain (Braithwaite and Ito, 1993, supra), implying a lack of critical importance in dNTP recognition.

A JDF-3 double mutant was constructed that contains mutations P410L and A485T. In dideoxynucleotide cycle sequencing, the banding pattern intensity demonstrated by the double mutant was extremely uniform, suggesting little if any preference for any dNTP over its corresponding ddNTP (See FIG. 8 and Example 1Q). This polymerase characteristic improves the accuracy of base calling in automated sequencing. We presume that combinations of P410L and A485 mutations, L408H and A485 mutations, and L408F and A485 mutations would result in enzymes that exhibit improved ddNTP incorporation. The efficiency of dideoxynucleotide incorporation by such double mutant enzymes may also be characterized or quantitated by measurement of the $I_{50\%}$ as described herein to determine the relative degree of improvement in incorporation.

EXAMPLES

The following examples are offered by way of illustration only and are by no means intended to limit the scope of the claimed invention.

Example 1

A. Cloning a DNA Polymerase Gene from *Thermococcus* Species JDF-3 DNA Polymerase A *Thermococcus* species was cultured from submarine samples taken from the Juan de Fuca ridge. Genomic DNA was isolated and used to prepare a genomic DNA library in ZAP II (Stratagene) using standard procedures. The lambda library was plated on XL1-Blue MRF' *E. coli* and screened for clones with DNA polymerase activity using a variation of the method described by Sagner et al. (Sagner, G., Ruger, R., and Kessler, C. (1991) *Gene* 97:119-123). Plaques containing active polymerase were cored and stored in SM buffer. Positive primary plaques were re-plated and re-assayed to allow purification of isolated clones. Secondary clones were excised according to the instructions provided with the ZAP II system (Stratagene), and the DNA sequence of the insert determined (FIG. 1).

The translated amino acid sequence of the JDF-3 DNA polymerase is shown in FIG. 2. Amino acid sequence alignments show that JDF-3 DNA polymerase exhibits homology to the class of DNA polymerases referred to as Family B.

Recombinant JDF-3 DNA polymerase was purified as described below (see "Purification of JDF-3" (method 1)). The biochemical properties of JDF-3 DNA polymerase have been compared to those of other commercially available archaeal DNA polymerases. The results shown in Table IV and V indicated that, compared to other enzymes, JDF-3 exhibits higher processivity, a faster polymerization rate ($K_{cat}$), and a greater tendency to utilize ddNTPs. JDF-3 DNA polymerase was therefore chosen for development of a DNA sequencing enzyme.

TABLE IV

Polymerase Activities of Archaeal Family B DNA Polymerases

| Polymerase | Specific Activity (U/mg) × $10^4$ Activated DNA | | Primed M13 | DNA (nm) | dNTP (μM each) |
|---|---|---|---|---|---|
| Pfu | 2.6 ± .07 | 4.1 ± .07 | 2.0 ± .02 | 0.7 | 16 ± 2 |
| exo⁻ Pfu | | | 2.3 | 0.5 | 12 |
| JDF-3 | 1.2 + .07 | | 5.2 | 2.0 | 16 ± 2 |
| Vent | 1.8[a] | | 0.7[a] | 0.1[a] | 57[a] |

[a]H. Kong, R. B. Kucera, and W. E Jack, J. Biol. Chem. 268, 1965 (1993).

B. Intein Removal from the Gene Encoding JDF-3 DNA Polymerase

By alignment to Family B DNA polymerase sequences, the JDF-3 DNA polymerase clone was found to contain an intein sequence (FIGS. 3 and 4). To improve expression of recombinant JDF-3 polymerase, the intein was removed by inverse PCR. PCR primers were designed to prime immediately upstream and downstream to the sequence coding for the intein termini, and were oriented such that the 3' ends of the primers were pointed away from the intein. The primers were also modified with 5'-phosphate groups to facilitate ligation. The plasmid/insert sequence was PCR amplified and circularized by standard methods.

C. Construction of a JDF-3 DNA Polymerase Mutant with Diminished 3'-5' Exonuclease Activity DNA polymerases lacking 3'-5' exonuclease (proofreading) activity are preferred for applications requiring nucleotide analog incorporation (e.g., DNA sequencing) to prevent removal of nucleotide analogs after incorporation. The 3'-5' exonuclease activity associated with proofreading DNA polymerases can be reduced or abolished by mutagenesis. Sequence comparisons have identified three conserved motifs (exo I, II, III) in the 3'-5' exonuclease domain of DNA polymerases (reviewed V. Derbyshire, J. K. Pinsonneault, and C. M. Joyce, *Methods Enzymol.* 262, 363 (1995)). Replacement of any of the conserved aspartic or glutamic acid residues with alanine has been shown to abolish the exonuclease activity of numerous DNA polymerases, including archaeal DNA polymerases such as Vent (H. Kong, R. B. Kucera, and W. E. Jack, *J. Biol. Chem.* 268 1965 (1993)) and Pfu (Stratagene, unpublished). Conservative substitutions lead to reduced exonuclease activity, as shown for mutants of the archaeal 9° N-7 DNA polymerase (M. W. Southworth, H. Kong, R. B. Kucera, J. Ware, H. Jannasch, and F. B. Perler, *Proc. Natl. Acad. Sci.* 93, 5281 (1996)).

JDF-3 DNA polymerase mutants exhibiting substantially reduced 3'-5' exonuclease activity were prepared by introducing amino acid substitutions at the conserved 141D or 143E residues in the exo I domain. Using the CHAMELEON® Double-Stranded, Site-Directed Mutagenesis Kit (Stratagene), the following JDF-3 mutants were constructed: D141A, D141N, D141S, D141T, D141E and E143A.

To analyze JDF-3 mutant proteins, the DNA sequence encoding JDF-3 DNA polymerase was PCR amplified using primers GGG AAA CAT ATG ATC CTT GAC GTT GAT TAC (where NdeI site in bold and start codon underlined) and GGG AAA GGA TCC TCA CTT CTT CTT CCC CTT C (where BamHI site shown in bold type). The PCR products were digested, purified, and ligated into a high expression level vector using standard methods. Plasmid clones were transformed into BL21 (DE3). Recombinant bacterial clones were grown using standard procedures and JDF-3 polymerase mutants were expressed in the absence of induction. The exonuclease and polymerase activities of recombinant clones were assayed using bacterial lysates. Typically, crude extracts were heated at 70° C. for 15-30 minutes and then centrifuged to obtain a cleared lysate.

There are several methods of measuring 3' to 5' exonuclease activity known in the art, including that of Kong et al. (Kong et al., 1993, J. Biol. Chem. 268: 1965) and that of Southworth et al. (Southworth et al., 1996, Proc. Natl. Acad. Sci. U.S.A. 93: 5281), the full contents of both of which are hereby incorporated by reference. The exonuclease activity of wild type and active mutant polymerases as measured by the Kong et al. method were as follows:

Exo Activity (U/mg):

wt 915

D141A7

D141N953

D141S 954

D141T 0.5

D141E 940

E143A 0.3

The combination exonuclease mutant D141A+E143A was made as described in section L.

The E143A JDF-3 mutant (clone #550) exhibited significantly reduced 3'-5' exo activity and was chosen for further mutagenesis to improve incorporation of ddNTP and other nucleotide analogs. Other JDF-3 mutants with substantially reduced exonuclease activity could have been used for this purpose, such as the JDF-3 D141T mutant. for experiment or applications requiring the absolute elimination of 3' to 5' exonuclease activity, the double mutant D141A+E143A was preferred.

D. Error-Prone PCR Amplification of the JDF-3 DNA Polymerase Gene

Random mutations were introduced into exo$^-$ JDF-3 by amplifying the entire gene (clone #550) under conditions which did not support high fidelity replication. To broaden the spectrum of potential mutations, three different PCR enzymes were used under error-prone conditions.

In the preferred mode, ten reactions of 100 µl each were amplified with each PCR enzyme.

i. Amplification with Taq DNA Polymerase:

| Reaction Mixture | | |
|---|---|---|
| 1x | | magnesium free Taq Buffer (Stratagene catalog #200530) |
| 1 | mM | each TTP and dCTP |
| 0.2 | mM | each dGTP and dATP |
| 2 | ng/µl | Primer 923 (also called 490) |
| 2 | ng/µl | Primer 721 |
| 0.05 | u/µl | Taq2000 (Stratagene catalog #600195) |
| 1.5 | mM | $MgCl_2$ |
| 0.5 | mM | $MnCl_2$ |
| 0.1 | pM | plasmid DNA (clone #550) |

Cycling Parameters

PCRs were carried out using Stratagene's ROBOCYCLER™40 Temperature Cycler with a Hot Top assembly. The following cycling conditions were used:

1) 95° C. for 1 minute
2) 95° C. for 1 minute
3) 54° C. for 1 minute
4) 72° C. for 2.5 minutes
5) Repeat steps 2 to 4 thirty times.

ii. Amplification with Exo$^-$ JDF-3 DNA Polymerase

| Reaction Mixture | | |
|---|---|---|
| 1x | | magnesium free Taq Buffer (Stratagene catalog #200530) |
| 450 | µM | each deoxynucleotide (dGTP, dATP, TTP and dCTP) |
| 2 | ng/µl | Primer 923 (also called 490) |
| 2 | ng/µl | Primer 721 |
| 0.1 | u/µl | exo$^-$ JDF-3 DNA polymerase |
| 0.5 | mM | $MnCl_2$ |
| 0.1 | pM | plasmid DNA (clone #550) |

Cycling Parameters

PCRs were carried out using Stratagene's ROBOCYCLER™40 Temperature Cycler with a Hot Top assembly. The following cycling conditions were used:

1) 95° C. for 1 minute
2) 95° C. for 1 minute
3) 54° C. for 1 minute
4) 72° C. for 2.5 minutes
5) Repeat steps 2 through 4 thirty times.

iii. Amplification with Exo$^-$ Pfu DNA Polymerase

| Reaction Mixture | | |
|---|---|---|
| 1x | | TAQPLUS ® Precision Buffer (Stratagene catalog #600210) |
| 200 | µM | each deoxynucleotide (dGTP, dATP, TTP, dCTP) |
| 2 | ng/µl | Primer 923 (also called 490) |
| 2 | ng/µl | Primer 721 |
| 0.05 | u/µl | exo$^-$ Pfu DNA polymerase (Stratagene catalog number 600163) |
| 0.1 | pM | plasmid DNA (clone #550) |

Cycling Parameters

PCRs were carried out using Perkin-Elmer's 9600 Temperature Cycler. The following cycling conditions were used:

1) 95° C. for 1 minute
2) 95° C. for 1 minute
3) 53° C. for 1 minute
4) 72° C. for 5 minutes
5) Repeat steps 2 through 4 thirty times.

Forward Primers

Earlier versions of the mutant libraries were made with the forward primer 461, which contains an EcoR I site. When products amplified with primers 461 and 923 were restriction digested and cloned into the lambda vector as described in the following section, JDF-3 DNA polymerase was synthesized as a fusion protein with the first 39 amino acids of the vector-encoded β-galactosidase (lacZ) protein.

```
Primer 461
5' TCAGATGAATTCGATGATCCTTGACGTTGATTAC 3'
        EcoR I    JDF-3 specific sequence
```

The clones isolated using primer 461 were designed as p#.

The preferred mode of amplification and cloning utilizes the forward primer 721, which also contains an EcoR I site followed by three consecutive in-frame stop codons and a ribosome binding site. This arrangement allows the JDF-3 DNA polymerase to be translated without any vector-derived residues at the amino terminus. The clones isolated from libraries constructed with the forward primer 721 were designated as 1-# to differentiate them from the p# series of clones.

```
Primer 721
5' GAGAGAATTCATAATGATAAGGAGGAAAAAATTATGATCCTTGACGT
TGATTAC 3'
       EcoRI    3xSTOP     JDF-3 specific sequence

Reverse Primers
Primer 923 (490)
5' TCAGATCTCGAGTCACTTCTTCTTCCCCTTC 3'
          Xho I     JDF-3 specific sequence
```

E. Preparing PCR Products for Cloning

PCR products were purified and concentrated with the STRATAPREP™ PCR Purification kit (Stratagene catalog number 400771). The PCR products were then digested with 50 units of Xho I and 50 units of EcoR I in 1.5× Universal buffer (10× Universal Buffer: 1M KOAc, 250 mM Tris-Acetate (pH 7.6), 100 mM MgOAc, 5 mM β-mercaptoethanol and 100 μg/ml BSA) for one hour at 37° C. The digested samples were run on a 1% agarose, 1×TBE gel and visualized with ethidium bromide staining. The 2.3 kb amplification product was gel isolated and purified with the STRATAPREP™ DNA Gel Extraction Kit (Stratagene catalog number 400766).

F. Cloning PCR Inserts into the Uni-Zap®XR Lambda Vector 200 ng of purified amplification product was ligated with 1 μg of UNI-ZAP®XR Lambda Vector (Stratagene catalog #239213), which had been predigested with EcoR I and Xho I and then dephosphorylated with alkaline phosphatase (Stratagene catalog number 237211). The DNAs were ligated using 2 units of T4 DNA ligase (Stratagene catalog number 600011) and 0.5 mM ATP in 1× ligase buffer (50 mM Tris-HCL (pH 7.5), 7 mM $MgCl_2$, 1 mM DTT) in reaction volumes of 10 to 15 μl. Ligations were carried out at 16° C. for a minimum of 16 hours.

G. Lambda Packaging and Bacterial Infection

Two microliters of each ligation reaction were packaged with GIGAPACK® III Gold Packaging extract (Stratagene catalog #200201) for 90 minutes at room temperature before being stopped with 500 μl SM buffer (50 mM Tris pH 7.5, 10 mM NaCl, 8 mM $MgSO_4$ and 0.01% gelatin) and 20 μl of chloroform. The packaged lambda vectors were plated on *E. coli* XL 1-Blue MRF' host cells.

H. Dideoxynucleotide Screening

Mutant polymerase libraries were screened using a variation of the technique used by Sagner et al (Sagner, G., Ruger, R., and Kessler, C. (1991) *Gene* 97:119-123). Lambda phage clones were plated at a density of 10-20 plaques per square centimeter. Proteins present in the plaques were transferred to filters and moistened with polymerase screening buffer (50 mM Tris (pH 8.0), 7 mM $MgCl_2$, 3 mM b-ME). The filters were kept between layers of plastic wrap and glass while the host cell proteins were heat-inactivated by incubation at 65° C. for 30 minutes. The heat-treated filters were transferred to fresh plastic wrap and approximately 35 μl of the polymerase assay cocktail was added for every square centimeter of filter. Polymerase assay cocktail consisted of 1× cloned Pfu magnesium-free buffer (Stratagene catalog #200534), 125 ng/ml activated calf thymus or salmon sperm DNA, 1.29 μCi/ml α-$^{33}$P ddNTP (Amersham), and 0.5 mM $MnCl_2$. Initial screening was done in the presence of $MnCl_2$, but the preferred method was to screen in 1× Taq Polymerase buffer (1.5 mM $MgCl_2$). The filters were sandwiched between plastic wrap and glass again and incubated at 65° C. for one hour, and then at 70° C. for one hour and 15 minutes. The filters were washed three times in 2×SSC for five minutes each time before being rinsed twice in 100% ethanol and dried on a vacuum dryer. The filters were exposed to X-ray film for approximately 16 hours. Plaques corresponding to strong signals were cored and placed in SM buffer. The positive primary plaques were replated at more dilute concentrations and assayed under essentially similar conditions to allow the purification of isolated plaques.

Dye-Dideoxynucleotide Screening

To detect mutant polymerases with improved capacity for dye-deoxynucleotide and dye-dideoxynucleotide utilization, the JDF-3 mutant DNA polymerase library was screened as described previously with the following exceptions:

Polymerase Assay Cocktail for Flu-12-dUTP Screening:

0.9× Taq Buffer (Stratagene Catalog #200435), 65 μM dATP, 65 μM dCTP, 65 μM dGTP, 65 μMdTTP, 0.3 μM Fluoroesceine-12-dUTP (Stratagene in-house production), 0.75 μg/μl activated calf thymus DNA.

Polymerase Assay Cocktail for ROX ddNTP

1× Taq Buffer, 0.9 μM dATP, 0.9 μM dCTP, 0.9 μM dGTP, 0.9 μl TTP, 0.6 μM ROX ddATP (New England Nuclear (NEN) NEN478), 0.06 μM ROX ddGTP (NEN NEL479), 0.06 μM ROX ddCTP (NEN NEL477), 0.06 μM ROX ddUTP (NEN NEL476), 0.84 μg/μl activated calf thymus DNA. (Note: A screening system without ROX ddGTP is the preferred method since DNA polymerases do not discriminate against ddGTP).

Polymerase Assay Cocktail for Fluoroesceine ddUTP

1× Taq Buffer, 70 μM dATP, 70 μM dTTP, 70 μM dCTP, 15 μM dTTP, 1 μM Fluoroesceine-12-ddUTP (NEN NEL40), 0.84 μg/μl activated calf thymus DNA.

Antibody Binding to Fluoroesceine

The filters were blocked overnight with 1% non-fat dry milk dissolved in TBST (50 mM Tris pH 8.0, 150 mM NaCl, 0.05% Tween-20) at 4° C. The filters were washed briefly in TBST before alkaline phosphatase conjugated anti-fluoroesceine antibody from the Illuminator kit (Stratagene catalog #300360) was added at a 1/10,000 dilution in 50 ml TBST. The antibody was detected with NBT/BCIP at concentrations of 0.3 mg/ml and 0.15 mg/ml respectively in a buffer composed of 100 mM Tris pH 9.5, 100 mM NaCl, and 5 mM $MgCl_2$.

Antibody Binding to Rhodamine

Anti-ROX antibody (Zymed cat. no. 71-3600 rabbit Rhodamine (5-ROX polyclonal, 1 mg/ml)) was diluted to 1:1000 in TBST. The blocked filters were blotted briefly to remove excess moisture then laid on plastic wrap and covered with 2.5 ml of the diluted antibody solution. An additional sheet of plastic wrap was laid over the filters before incubation at room temperature for 1 hour. The filters were washed briefly three times with TBST, then washed three times with gentle agitation for 15 minutes each time. The washed filters were incubated with alkaline phosphatase conjugated goat anti-rabbit antibodies diluted 1:5000 in TBST. The filters were incubated with the antibody for one hour then detected with NBT/BCIP as described previously.

I. Dideoxynucleotide Qualification

Lambda phage clones which incorporated $^{33}$P-labeled ddNTPs in the primary library screen were re-screened to verify polymerase activity and to assess the contribution of the divalent metal ion to $^{33}P$-ddNTP incorporation. The clones selected during this round of screening were designated as p#. These clones all contained an amino-terminal tag, as discussed in the section entitled "Forward Primers". FIG. 5 shows that clones p1, p2, p3, p6, p7, p8, p9, p10, p11, p12, p14, p15, and p16 exhibited wild type levels of DNA polymerase activity, based upon similarity in signal strength to the parental #550 clone (FIG. 5, panel 3). Although initial screening was carried out in the presence of 0.5 mM $MnCl_2$, all of the clones except p9 and p10 were able to incorporate $^{33}P$-labeled ddNTPs to at least some extent in the presence of 1.5 mM $MgCl_2$ (panel 2), with clones p2, p4, p8, p11, p12, p13, p14, p15, p17, and p18 producing the highest signals.

Eighteen mutants were chosen for evaluation. One microliter of phage isolated from each purified plaque was placed on each of three *E. coli* XL1-Blue MRF' lawns. Phage containing a parental copy of exo$^-$ JDF3 DNA (#550 clone) were also spotted on the grid. The plaques formed by the phage were transferred to filters and treated as described in the preceding screening section with the exception of the final buffer composition. The buffers used for each filter (filters 1-3) are as follows:

| Filter 1: Dideoxynucleotide screen with manganese chloride | |
|---|---|
| 1x | Taq DNA polymerase magnesium-free buffer |
| 1.28 μCi/ml | $^{33}P$ ddNTPs |
| 0.5 μg/μl | Activated Calf Thymus DNA (Sigma) |
| 0.5 mM | $MnCl_2$ |

| Filter 2: Dideoxynucleotide screen with magnesium chloride | |
|---|---|
| 1x | Taq DNA polymerase buffer (containing 1.5 mM $MgCl_2$, catalog #200435) |
| 1.28 μCi/ml | $^{33}P$ ddNTP |
| 0.5 μg/μl | Activated Calf Thymus DNA (Sigma) |

| Filter 3: Deoxynucleotide screen with magnesium chloride | |
|---|---|
| 1x | Taq DNA polymerase buffer |
| 0.072 mM | dGTP, dCTP and TTP |
| 40 μM | dATP |
| 0.5 μg/ml | Activated Calf Thymus DNA (Sigma) |
| 0.01 μCi | α-$^{33}P$ dATP. |

Results are shown in FIG. 5.

Dye-Dideoxynucleotide Qualification

As described in the previous segments, primary lambda clones were spotted on an *E. coli* lawn and re-screened with the appropriate antibody or antibodies.

J. Excision of Lambda Clones

When incubated with helper phage under suitable conditions, Lambda Zap™ vectors are designed to produce phagemid copies of the part of the vector containing pBluescript (SK−) and the insert. This process yields a plasmid (pBluescript SK−) vector carrying the same insert that was contained in the lambda clone. Excision of clones with the desired phenotype was carried out according to the instructions in the EXASSIST™ system (Stratagene catalog #200253).

K. Sequence Analysis of Mutants

The mutants were sequenced by Sequetech Corporation (Mountain View, Calif.) using the following primers:

```
Primer 3 (or primer G)
5' CCAGCTTTCCAGACTAGTCGGCCAAGGCC 3'

Primer 5 (or JDF3-1128)
5' AACTCTCGACCCGCTG 3'
```

L. Dideoxynucleotide Mutagenesis

To conclusively identify the amino acids contributing to reduced ddNTP discrimination, individual point mutations were introduced into the exo$^-$ JDF-3 #550 clone using the QUIKCHANGE™ Site-Directed Mutagenesis Kit (Stratagene catalog #200518). The following mutants were prepared: L408H, L408F, P410L, A485T, S345P, D373Y, A619V, and L631V. In addition, a double mutant (P410L/A485T) was constructed by introducing the A485T mutation into the exo$^-$ JDF-3 P410L mutant clone. To completely eliminate all 3' to 5' exonuclease activity, the mutation D141A was added to all clones. A pre-existing 5' to 3' exonuclease mutation (E143A) was present in the parental template JDF-3 550.

Dye-Dideoxynucleotide Mutagenesis

To conclusively identify amino acids responsible for contributing to reduced discrimination of dye nucleotides, the mutation S345P was generated alone and in combination with the P410L and P410L+A485T.

M. Preparation of Heat-Treated Bacterial Extracts

*E. coli* SOLR cells containing the excised plasmid were grown overnight at 37° C. The cells contained in 500 μl of culture were collected by microcentrifugation. The cell pellets were resuspended in 50 μl of 50 mM Tris (pH 8.0). Lysozyme was added to a final concentration of 1 μg/μl, and the cells were lysed during a 10 minute incubation at 37° C., followed by 10 minutes at 65° C. The heat-inactivated cell material was collected by microcentrifugation and the supernatants were assayed for dNTP and ddNTP incorporation as described below.

N. Purification of JDF-3 and JDF-3 Polymerase Mutants

One method for purifying exo$^-$ JDF-3 DNA polymerase involves ammonium sulfate fractionation, followed by Q Sepharose and DNA cellulose columns. A second method has been developed to allow rapid purification of JDF-3 polymerase mutants, and entails adsorption of contaminants on a HiTrap Q column, followed by gradient elution from a HiTrap heparin column (section iii).

i. Preparation of Bacterial Lysate.

Frozen cell paste (3-14 grams) was resuspended with 3× volume of lysis buffer, consisting of 50 mM Tris-HCl (pH 8.0), 1 mM EDTA, and 10 mM β-mercaptoethanol. Lysozyme was added to 0.2 mg/ml and PMSF was added to 1 mM final concentration. The cells were lysed on ice over a period of 1 hour. The lysate was then sonicated for 2 minutes (90% duty, level of 2×2.5, 1×3.0). Following sonication, the lysate was heated at 65□C. for 15 minutes to denature bacterial proteins. The heated lysate was then centrifuged for 30 minutes at 14.5K rpm in a Sorvall RC-2B centrifuge using a Sorvall SS-34 rotor, and the supernatant was recovered.

ii. Ammonium Sulfate Fractionation and Q Sepharose/DNA Cellulose Chromatography (Method 1)

Ammonium sulfate was added to the bacterial lysate to a final concentration of 45%. The ammonium sulfate was added over a period of 15 minutes, and the mixture was stirred for an additional 30 minutes. The mixture was centrifuged as described above, and the supernatant was recovered. Additional ammonium sulfate was then added to bring the final concentration to 65%. The mixture was centrifuged as described above, and the supernatant removed. The pellet was resuspended in 10 ml of buffer A consisting of 50 mM Tris-HCl (pH 7.5), 1 mM EDTA, 10 mM β-mercaptoethanol, 0.1% (v/v) Tween 20, and 10% (v/v) glycerol. The supernatant was dialyzed overnight against 2 changes of buffer A (3 liters each).

The dialysate was loaded onto a 2.6×9.4 cm Q-Sepharose Fast Flow column (50 mls), pre-equilibrated in buffer A. The column was washed with buffer A until the absorbence ($OD_{280}$) approached baseline. The column was then eluted with a gradient from 0 to 1M NaCl/buffer A. Fractions were collected, and analyzed by SDS-PAGE and DNA polymerase activity assays (see below). Active protein typically eluted between 130 and 240 mM NaCl. Active fractions were pooled and dialyzed overnight against 2 changes of buffer B (3 liters each), consisting of 50 mM Tris-HCl (pH 7.5), 1 mM EDTA, 10 mM β-mercaptoethanol, 0.1% (v/v) Tween 20, 10% (v/v) glycerol, and 50 mM NaCl.

The Q-Sepharose eluate was then loaded onto a 1.6×4.9 cm (10 mls) DNA cellulose column, equilibrated in buffer B. The column was washed with buffer B until the absorbence ($OD_{280}$) approached baseline. The column was then eluted with a gradient from 50 to 1000 mM NaCl/buffer A. Fractions were collected, and analyzed by SDS-PAGE and DNA polymerase activity assays. Active protein typically eluted between 280 and 360 mM NaCl. Active fractions were pooled and dialyzed overnight against JDF-3 final dialysis buffer, consisting of 25 mM Tris-HCl (pH 7.5), 100 mM KCl, 0.1 mM EDTA, 1 mM DTT, 0.1% (v/v) Tween 20, 0.1% (v/v) Igepal 630, 10⊠g/ml BSA, and 50% (v/v) glycerol.

iii. HiTrap Q/HiTrap Heparin Chromatography (Method 2)

The preferable method for rapid purification of multiple mutants is as follows. Bacterial cell lysates were prepared as described for method 1, except that Tween 20 and Igepal CA 630 were added to a final concentration of 0.01% (v/v) just prior to the heat denaturation step, and a heat denaturation temperature of 72° C. was used.

The lysate was loaded onto a 1.6×2.5 cm (5 mls) HiTrap Q column (pre-packed column from Pharmacia), pre-equilibrated in buffer C consisting of 50 mM Tris-HCl (pH 8.2), 1 mM EDTA, 10 mM β-mercaptoethanol, 0.1% (v/v) Tween 20, and 0.1% (v/v) Igepal CA 630. The column was washed with buffer C until the absorbence ($OD_{280}$) approached baseline. The flow through fractions ($OD_{280}$ absorbence above background) were collected and then loaded onto a 1.6×2.5 cm (5 mls) HiTrap heparin column (pre-packed column from Pharmacia), pre-equilibrated in buffer D consisting of 50 mM Tris-HCl (pH 8.2), 1 mM EDTA, 1 mM DTT, 0.1% (v/v) Tween 20, 0.1% (v/v) Igepal CA 630, and 10% glycerol (v/v). The column was washed with buffer D until the absorbence ($OD_{280}$) approached baseline. The column was then eluted with a gradient from 0 to 1M KCl/buffer D. Fractions were collected, and analyzed by SDS-PAGE and DNA polymerase activity assays. Active protein typically eluted between 390 and 560 mM NaCl. Active fractions were pooled and dialyzed overnight against JDF-3 final dialysis buffer (see above). Purified polymerases were stored at −20° C.

iv. Analysis of Purified Proteins

The concentrations of JDF-3 and mutant DNA polymerases were determined relative to a BSA standard (Pierce), using Pierce's Coumassie Blue Protein assay reagent. In addition, the purity and relative protein concentrations of different polymerase preparations were verified by SDS-PAGE. Polymerase samples were electrophoresed on 4-20% Tris-glycine gels (Novex), and the gels were silver-stained using standard procedures.

O. Nucleotide Incorporation Assay

DNA polymerase activity was measured using purified JDF-3 polymerase mutants or heat-treated bacterial extracts prepared from various mutant clones. DNA polymerase activity was measured by monitoring the incorporation of $^{3}$H-TTP into activated calf thymus DNA. A typical DNA polymerase reaction cocktail contained:

10 mM Tris-HCl, pH 8.8

1.5 mM $MgCl_2$ 50 mM KCl 0.001% gelatin

200 μM each dATP, dCTP, dGTP

195 μM TTP

5 μM [$^{3}$H]TTP (NEN #NET-221H, 20.5 Ci/mmole; partially evaporated to remove EtOH).

250 μg/ml of activated calf thymus DNA (e.g., Pharmacia #27-4575-01)

Incorporation was measured by adding 1 μl of polymerase samples to 10 μl aliquots of polymerase cocktail. DNA polymerase samples were diluted in a suitable storage buffer (e.g., 25 mM Tris-HCl (pH 7.5), 100 mM KCl, 0.1 mM EDTA, 1 mM DTT, 0.1% (v/v) Tween 20, 0.1% (v/v) Igepal 630, 10 ⊠g/ml BSA, and 50% (v/v) glycerol). Polymerization reactions were conducted for 30 minutes at 72□C. Extension reactions were quenched on ice, and then 5 μl aliquots were spotted immediately onto DE81 ion-exchange filters (2.3 cm; Whatman #3658323). Unincorporated [$^{3}$H]TTP was removed by 6 washes with 2×SSC (0.3M NaCl, 30 mM sodium citrate, pH 7.0), followed by a brief wash with 100% ethanol. Incorporated radioactivity was measured by scintillation counting. Reactions that lacked enzyme were also set up along with sample incubations to determine "total cpms" (omit filter wash steps) and "minimum cpms" (wash filters as above).

Cpms bound is proportional to amount of polymerase activity present per volume of bacterial extract. The volume of bacterial extract (0.25-1 μl) which brought about incorporation of approximately 10,000 cpms was determined for use in subsequent nucleotide analog incorporation testing.

P. Quantitating ddNTP Incorporation Efficiency

JDF-3 polymerase mutants were evaluated to assess relative ddNTP incorporation efficiency. Nucleotide incorporation was measured in the presence of varying concentrations of each ddNTP terminator (ddATP, ddCTP, ddGTP, and ddTTP). Since ddNTP incorporation produces non-extendable termini, polymerization is strongly inhibited for polymerases that incorporate ddNTPs efficiently. Comparisons of ddNTP concentrations that bring about 50% inhibition of nucleotide incorporation ($I_{50\%}$) can be used to compare ddNTP incorporation efficiency of different polymerases or polymerase mutants. Comparisons of $I_{50\%}$ values for ddATP, ddCTP, ddGTP, and ddTTP can be used to identify mutants with reduced selectivity for particular bases. Such mutants would be expected to produce more uniform DNA sequencing ladders.

To measure incorporation of individual ddNTPs, cocktails were prepared which consisted of varying concentrations of the ddNTP of interest, and a total of 200 μM of each nucleotide triphosphate. For example, the incorporation of ddATP by wild type JDF-3 polymerase was measured at 0, 40, 80, 120 and 160 μM ddATP. In these reactions, dATP concentrations were adjusted to 200, 160, 120, 80, and 40 μM, respectively, so that the total amount of adenine nucleotide triphosphate was 200 μM. In comparison, mutants were assayed using ddATP concentrations of 0, 5, 10, and 20 μM ddATP, and adjusted dATP concentrations of 200, 195, 190, and 180 μM, respectively (dATP+ddATP=200 μM). Additional cocktails were prepared to measure ddCTP, ddGTP, and ddTTP incorporation. To assess ddNTP incorporation by JDF-3 mutants at 3 different ddNTP concentrations, 12 reaction cocktails were prepared consisting of:

10 mM Tris-HCl, pH 8.8

1.5 mM $MgCl_2$ 50 mM KCl 0.001% gelatin

5 μM [$^3$H]TTP (NEN #NET-221H, 20.5 Ci/mmole; partially evaporated to remove EtOH)

250 μg/ml of activated calf thymus DNA (e.g., Pharmacia #27-4575-01)

To each of 12 reaction cocktails was added the appropriate amounts of dNTPs and ddNTPs as summarized below:

| Cocktail | DGTP | dDATP | dCTP | TTP | ddGTP | ddATP | ddCTP | ddTTP |
|---|---|---|---|---|---|---|---|---|
| G-0 | 200 μM | 200 μM | 200 μM | 195 μM | 0 | 0 | 0 | 0 |
| G-5 | 195 μM | 200 μM | 200 μM | 195 μM | 5 | 0 | 0 | 0 |
| G-10 | 190 μM | 200 μM | 200 μM | 195 μM | 10 | 0 | 0 | 0 |
| G-20 | 180 μM | 200 μM | 200 μM | 195 μM | 20 | 0 | 0 | 0 |
| A-0 | 200 μM | 200 μM | 200 μM | 195 μM | 0 | 0 | 0 | 0 |
| A-5 | 200 μM | 195 μM | 200 μM | 195 μM | 0 | 5 | 0 | 0 |
| A-10 | 200 μM | 190 μM | 200 μM | 195 μM | 0 | 10 | 0 | 0 |
| A-20 | 200 μM | 180 μM | 200 μM | 195 μM | 0 | 20 | 0 | 0 |
| C-0 | 200 μM | 200 μM | 200 μM | 195 μM | 0 | 0 | 0 | 0 |
| C-5 | 200 μM | 200 μM | 195 μM | 195 μM | 0 | 0 | 5 | 0 |
| C-10 | 200 μM | 200 μM | 190 μM | 195 μM | 0 | 0 | 10 | 0 |
| C-20 | 200 μM | 200 μM | 180 μM | 195 μM | 0 | 0 | 20 | 0 |
| T-0 | 200 μM | 200 μM | 200 μM | 195 μM | 0 | 0 | 0 | 0 |
| T-5 | 200 μM | 200 μM | 200 μM | 190 μM | 0 | 0 | 0 | 5 |
| T-10 | 200 μM | 200 μM | 200 μM | 185 μM | 0 | 0 | 0 | 10 |
| T-20 | 200⊠M | 200⊠M | 200⊠M | 175⊠M | 0 | 0 | 0 | 20 |

Incorporation was measured by adding 1 μl of appropriately diluted bacterial extract (10,000 cpms) to 10 μl of each polymerase cocktail. Polymerization reactions were conducted for 30 minutes at 72° C. The extension reactions were counted as described above.

Reactions that lacked enzyme were also set up along with sample incubations to determine "minimum cpms" (wash filters as above). To determine % activity as a function of ddNTP concentration, background ("minimum cpms" value) was first subtracted from each of the sample cpms. "Total cpms", which are equivalent to 100% activity (0 ddNTPs), are determined by averaging the corrected cpms for the 4 reactions lacking ddNTPs (A-0, G-0, C-0, and T-0). Percent remaining activity was then calculated by dividing corrected sample cpms (with ddNTPs) by the corrected total cpms (average 0 ddNTPs).

Percent activity was plotted as a function of ddNTP concentration. $I_{50\%}$ values for each ddNTP (ddNTP concentration which inhibits nucleotide incorporation by 50%) were determined for each mutant. Comparisons allowed the identification of mutants with improved ddNTP incorporation relative to wild type JDF-3.

Initial studies used purified enzymes, and $I_{50\%}$ values were determined from inhibition plots employing 40-160 μM ddNTPs. The results in Table V show that mutants p8 (P410L), p11 (P410L), and p12 (A485T) are inhibited by lower concentrations of ddNTPs than the parental exo$^-$ JDF-3 polymerase. Greater sensitivity indicates that the mutants incorporate all four ddNTPs more efficiently than the original JDF-3 polymerase.

For enzymes which preferentially incorporate TTP over ddTTP (exo$^-$ JDF-3, exo$^-$ Pfu), the use of increasingly higher concentrations of ddTTP (80-160 μM) and correspondingly lower concentrations of TTP (115-35 μM), in combination with a constant amount of [$^3$H]TTP (5 μM), leads to an increase in cpms incorporated with increasing ddNTP concentration. Therefore, in these initial experiments (where ddTTP>120 μM), $I_{50\%}$ values for TTP are artificially high. While they can be used to compare ddTTP incorporation among different polymerase mutants, they can not be used to assess reduced/enhanced preference for ddTTP relative to ddCTP, ddGTP, or ddATP.

TABLE V $I_{50\%}$ Values for Purified JDF-3 and JDF-3 Mutants.

| Purified Polymerase | Primary Mutation | $I_{50\%}$ Values (⊠M) ddATP | ddGTP | ddCTP | ddTTP |
|---|---|---|---|---|---|
| Exo$^-$ JDF-3 | — | 160 | 110 | >160 | >>160 |
| Exo$^-$ Pfu | — | >160 | >160 | >160 | >>160 |
| JDF-3 mutant p8 | P410L | 30 | 25 | 40 | 40 |
| JDF-3 mutant p11 | P410L | 30 | 30 | 60 | >160 |
| JDF-3 mutant p12 | A485T | 40 | 25 | 25 | 150 |

To allow a larger number of mutant clones to be screened, subsequent experiments employed bacterial extracts containing JDF-3 polymerase mutants. In addition, sensitivity was improved by using lower concentrations of each ddNTP inhibitor (5-20 μM). The results in Table VI demonstrate that all of the mutants selected from the primary filter screen exhibited improved incorporation of ddNTPs. Improvements in ddNTP incorporation were as high as >20-fold. All of the mutants containing a mutation at amino acid 408 (L408H/F), 410 (P410L), or 485 (A485T) (referred to as the “primary mutation”) exhibited reduced discrimination against all four ddNTPs. Most, but not all, mutants with the L408H/F primary mutation produced very similar $I_{50\%}$ values (<2-fold difference) for all four ddNTPs, indicating that base selectivity is diminished or absent.

TABLE VI $I_{50\%}$ Values for JDF-3 Mutants (Bacterial Extracts).

| JDF-3 mutant clones | Primary mutation | $I_{50\%}$ Values (μM) ddATP | ddGTP | ddCTP | ddTTP |
|---|---|---|---|---|---|
| Exo⁻ JDF-3 | — | >80 | >80 | >80 | >80 |
| 1-1, 1-4, 1-18 | L408H | 8 to >20 | 4 to 5 | 6 to 13 | 5.5. to 10 |
| 1-25, 1-28, 1-29, 1-17 | L408F | 4.5 to >20 | 3.5 to 10 | 4 to 6.5 | 4 to 8 |
| p8 | P410L | 18.5 | 12 | 9.5 | >20 |
| 1-5, 1-6, 1-17 | P410L | 10 to >20 | 3.5 to 9 | 16.5 to >20 | 11 to >20 |
| 1-41, 1-38, 1-37, 1-3, 1-19, 1-30, 1-27, 1, 20 1-26, 1-32, 1-16, 1-12 | Not determined | 7 to >20 | 3.5 to 12 | 4 to >20 | 5 to >20 |

Q. Sequencing with Purified JDF-3 Polymerase Mutants i. Sequencing with Radioactively Labeled Dideoxynucleotides 1 to 2 μl of purified enzyme was substituted into the Thermo Sequenase radiolabeled terminator cycle sequencing kit (Amersham-Pharmacia #US79750). The samples were processed according to the manufacturer’s instructions using the control primer and template provided with the kit. Three microliters of each sequencing reaction were loaded onto a 6% acylamide-7M urea, 1×TBE CASTAWAY™ Precast gel (Stratagene catalog #s 401090 and 401094). When the bromophenol blue indicator dye reached the end of the gel, the gel was fixed, dried and exposed to film for 24-72 hours (FIG. 6).

Figure 6:
FIG. 6 shows $^{33}$P-ddNTP cycle sequencing reactions performed using JDF-3 polymerase mutants. Purified JDF-3 mutants were substituted into the Thermo Sequenase radiolabeled terminator cycle sequencing kit. DNA sequencing ladders were generated as per the kit's instructions using the following polymerases: (A) Thermo Sequenase (B) JDF-3 #550 clone (parental) (C) JDF-3 A485T mutant (clone p12) (D) JDF-3 P410L mutant (clone p11) (E) JDF-3 P410L mutant (clone p8). The top of the original sequencing gel is shown on the side. The lanes are: (bottom) ddGTP, ddATP, ddTTP, ddCTP (top). Clones p8, p11, and p21 contain ancillary mutations and an amino-terminal tag.

The results in FIG. 6 show that clones p11 (panel D) and p8 (panel E) exhibit a dramatic improvement in the incorporation of all four ddNTPs compared to the parental #550 clone (panel B). Mutants p11 and p8 both contain the primary P410L mutation and an amino tag, but differ with respect to the number and types of ancillary mutations. Mutant p12 (panel C) produced a faint sequencing ladder, presumably due to the use of an insufficient amount of enzyme or the presence of ancillary mutations which reduce thermal stability. There is evidence of termination products in all lanes, suggesting an improvement in the incorporation of all four ddNTPs relative to the parental clone. Mutant p12 contains the primary mutation A485T in addition to ancillary mutations. In contrast to JDF-3 mutants identified here, the parental clone shows a strong preference to incorporate ddGTP, as evidenced both in primer extension (FIG. 6) and ddNTP inhibition assays (Tables V and VI).

ii. Sequencing with a Radioactively Labeled Primer and Fluorescent Dideoxynucleotides Different DNA polymerases and polymerase mutants will exhibit varying degrees of discrimination against the dye moieties on the dideoxynucleotide analogs. An assessment of usage of dye-labeled dideoxynucleotide analogs by the JDF-3 polymerase mutants was carried out. The procedure used was as follows:

a. Primer Labeling

The sequencing primer SK was radioactively labeled with the KINACE-IT™ Kinasing Kit (Stratagene catalog #200390). The incubation reaction (40 μl) contained the following components:

| | | |
|---|---|---|
| 1x | | kinase buffer #1 |
| 0.75 | μCi/μl | γ-$^{33}$P ATP |
| 0.375 | u/μl | T4 polynucleotide kinase |
| 2.5 | pmol/μl | SK primer |

The reaction was incubated at 37° C. for 45 minutes. The primer was purified away from free nucleotides with a size exclusion matrix (NUC TRAP® Stratagene catalog number 400701).

b. Dye Labeled-Dideoxynucleotide:dNTP Ratios

Fluorescent dideoxynucleotides were purchased from New England Nuclear (NEN):

| | |
|---|---|
| R6G-ddATP | NEN catalog number NEL-490 |
| R110-ddTP | NEN catalog number NEL-495 |
| TAMRA-ddUTP | NEN catalog number NEL-472 |
| ROX-ddCTP | NEN catalog number NEL-477 |

Incorporation was measured using 3 different concentrations of dye labeled dideoxynucleotides (ddNTPs) and a constant amount of deoxynucleotides (dNTPs; 2.14 μM):

| | |
|---|---|
| Condition 3) 1:1 | (2-14 ⊠ M each dNTP:2.14 μM dye-labeled ddNTP) |
| Condition 2) 1:0.1 | (2.14 μM each dNTP:0.214 μM dye-labeled ddNTP) |
| Condition 1) 1:0.01 | (2.14 μM each dNTP:0.0214 μM dye-labeled ddNTP) |

c. Preparation of the DNA Sequencing Reaction Mixtures

Four polymerases were tested for utilization of dye-labeled ddNTPs, exo⁻ JDF-3 (#550 clone), Thermo Sequenase (4 u/μl), JDF-3 P410L (clone p8 with ancillary mutations and an amino-terminal tag) and JDF-3 L408H (clone 1-1). A mixture containing the following reagents was assembled:

| | | |
|---|---|---|
| 13.7 | μl | $H_2O$ |
| 1 | μl | labeled SK primer (2 pmol/μl) |
| 1 | μl | pBluescript KS (0.2 μg/μl) |
| 1 | μl | polymerase (~1.5 u/μl) |
| 2 | μl | 10X buffer (reaction buffer 1 for all but L408H which uses 1.5 mM $MgCl_2$, buffer (see below) |

10× Reaction Buffer 1

260 mM Tris pH 9.5

65 mM $MgCl_2$ $10\times1.5$ mM $MgCl_2$ buffer
24 mM $MgCl_2$
260 mM Tris pH 9.5
2.5 μl of each dye-labeled ddNTP terminator (ddGTP, ddATP, ddTTP and ddGTP was aliquotted separately into one of four tubes. 4.5 μl of each polymerase reaction was added to each of the four tubes, to give a final reaction volume of 7 μl.

d. Cycle Sequencing Reactions

The samples were cycled in a RoboCycler®96 Temperature Cycler with a Hot Top Assembly (Stratagene Catalog #400870 and #400894) using the following conditions:

1) 1 minute at 95° C.
2) 1 minute at 95° C.
3) 1 minute at 50° C.
4) 2 minutes at 72° C.
5) Repeat steps 2-4 thirty times.

4 μl of stop solution (95% formamide, 20 mM EDTA, 0.05% bromophenol blue, 0.05% xylene cyanol FF) was added to each of the amplified reactions before heating them to 99° C. for five minutes. The samples were electrophoresed on a 6% CASTAWAY™ gel as described above. The gels were dried and then exposed to film for 72 hours (FIG. 7).

Figure 7:
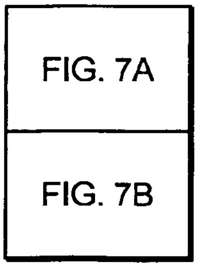
FIG. 7 shows cycle sequencing reactions performed using dye-labeled ddNTPs and JDF-3 polymerase mutants. DNA sequencing ladders were generated using (1) 2.14 μM dNTP: 0.0214 μM ddNTP; (2) 2.14 μM dNTP: 0.214 μM ddNTP; or (3) 2.14 μM dNTP: 2.14 μM ddNTP. The following purified DNA polymerases were used: (A) JDF-3 #550 clone (parental) (B) Thermo Sequenase (C) JDF-3 P410L mutant (clone p8, contains ancillary mutations and an amino tag) (E) JDF-3 L408H mutant (clone 1-1). The top of the original sequencing gel is shown on the right hand side.
Figure 7A:
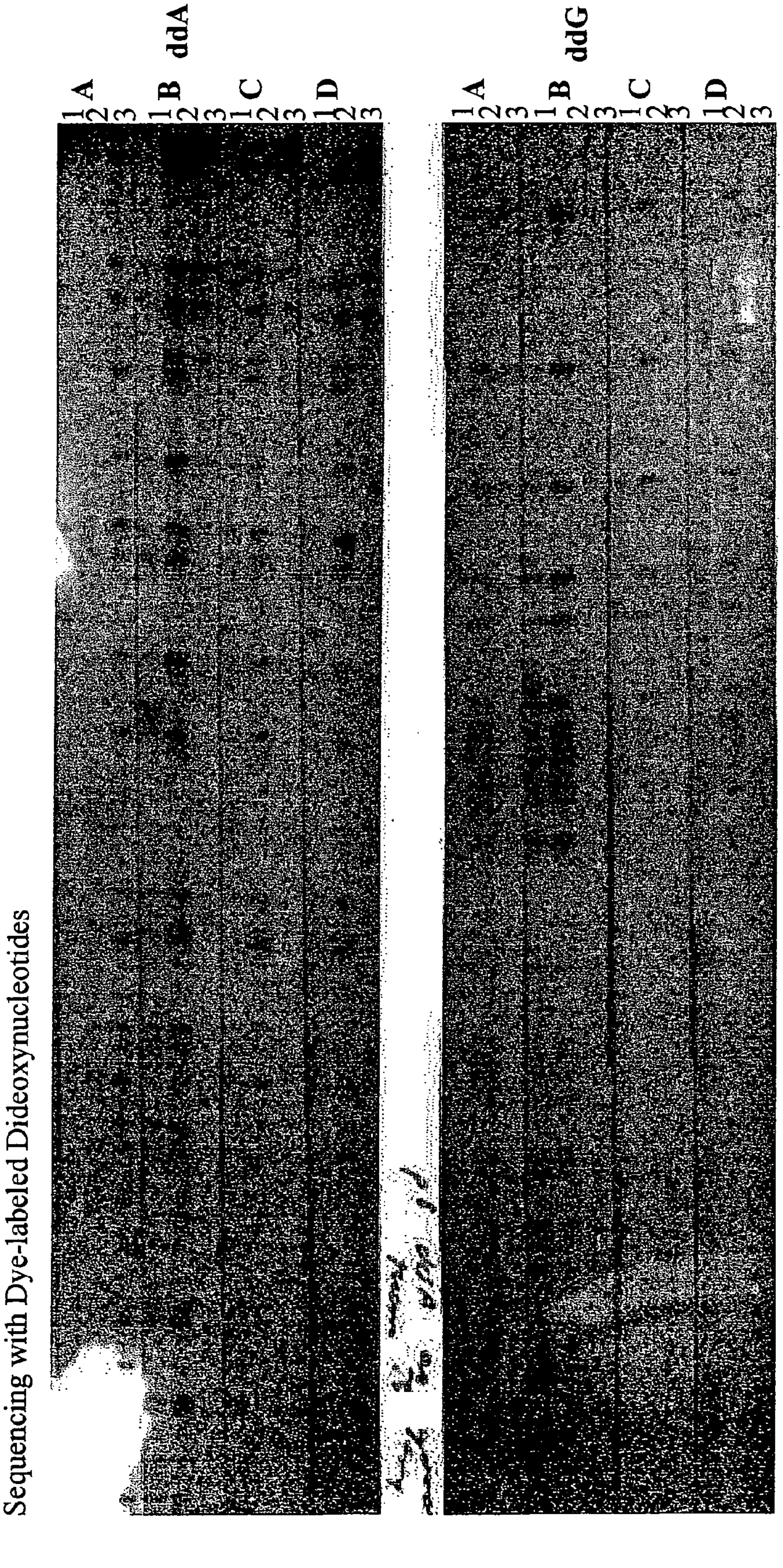
Figure 7B:
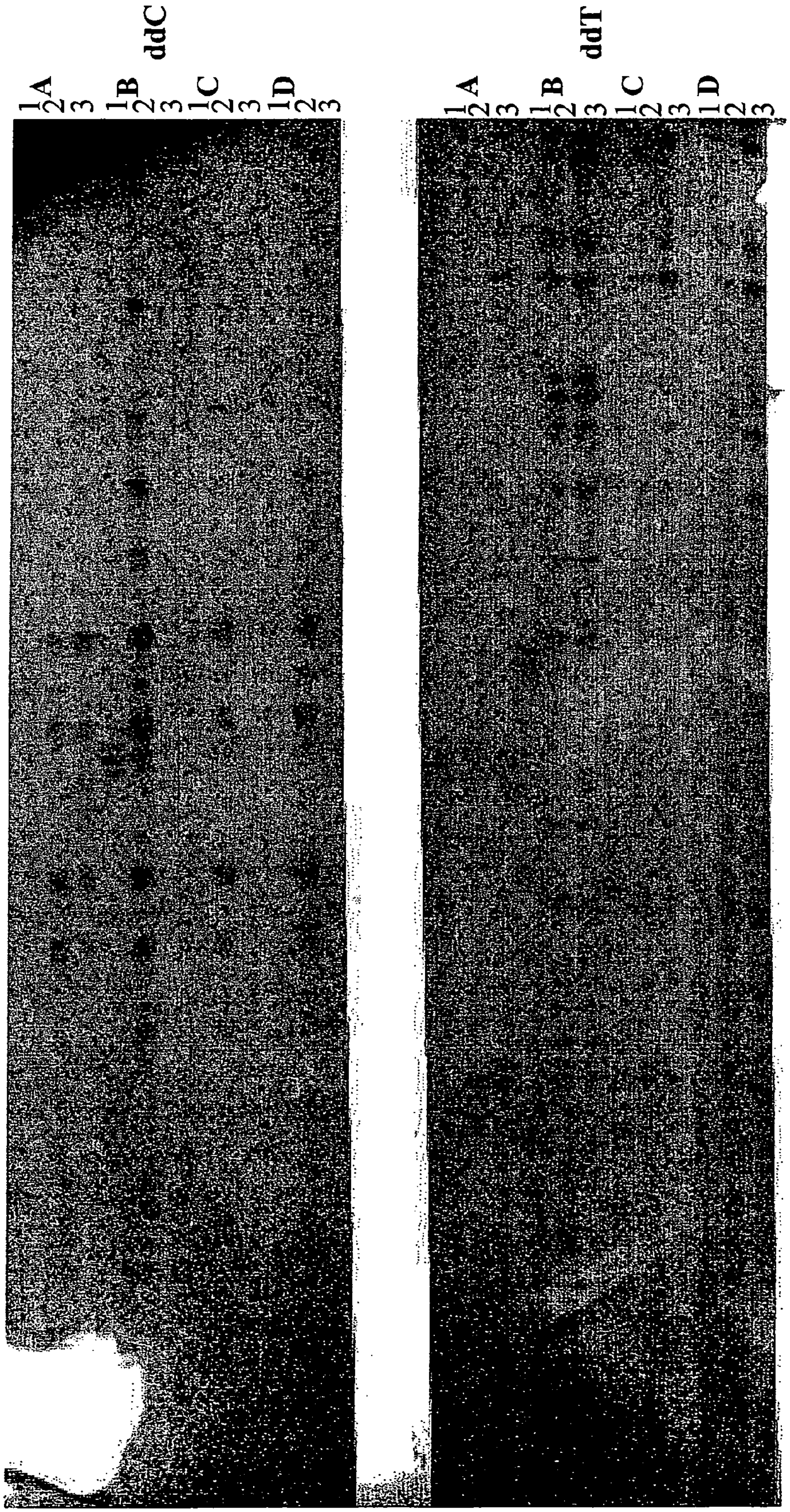

The results of studies designed to assess utilization of dye-labeled ddNTPs by the different polymerase clones are shown in FIG. 7. Clones p8 (panel C) and 1-1 (panel D) exhibited significantly improved incorporation of R6G-ddATP and R110-ddGTP, compared to the parental clone (panel A). Improvement was evidenced by the synthesis of sequencing ladders at 0.01× (1) and 0.1× (2) dye-ddNTP/dNTP ratios. Optimization of reaction conditions and/or dye moieties may be performed to realize improvements in the incorporation of ddTTP and ddCTP.

iii. Sequencing with Double-Mutant $exo^-$ JDF-3 DNA Polymerase.

To verify that changes at residues 408, 410, and 485 were sufficient to improve ddNTP incorporation, individual mutations were introduced into the parental 550 (JDF-3 $exo^-$ DNA polymerase) clone by site-directed mutagenesis. In addition, point mutations were combined to examine whether they resulted in further improvements in dideoxynucleotide incorporation over polymerases bearing single mutations.

DNA sequencing reactions consisting of 1× reaction buffer, 0.15 pmol/μl long −20 primer, and 10 ng/μg pBluescript KS were prepared as follows:

| | |
|---|---|
| 81 μl | $H_20$ |
| 9 μl | −20 long primer (2 pmol/μl) |
| 6 μl | pBluescript KS (0.2 μg/μl) |
| **μl | polymerase |
| 12 μl | 10X buffer (260 mM Tris pH 9.5, 65 mM $MgCl_2$) |

18 μl of the cocktail listed above was aliquotted into the appropriate number of tubes (one per polymerase). Each polymerase (2 μl) was added to an aliquot of cocktail and the tubes were mixed well. Each resulting polymerase mixture (4.5 μl) was then added to each of four tubes, already containing 0.06 mM of one of the four -$^{33}$P-dideoxynucleotides (ddATP, ddTTP, ddGTP or ddTTP; 1500 Ci/mmol; 450 μCi/ml) and 6 mM each deoxynucleotide in a volume of 2.5 μl.

The sequencing reactions were cycled in a ROBOCYCLER®96 temperature cycler with a Hot Top Assembly using the following conditions:

1) 1 minute at 95° C.
2) 45 seconds at 95° C.
3) 45 seconds at 60° C.
4) 1.5 minutes at 72° C.
5) Repeat steps 2-4 thirty times.

Stop solution (μl; 95% formamide, 20 mM EDTA, 0.05% bromophenol blue, 0.05% xylene cyanol FF) was added to each reaction before heating to 99° C. for five minutes. Each sample (4 μl) was loaded onto a 6% acrylamide denaturing CastAway gel. The gel was run and treated as described previously.

Figure 8:
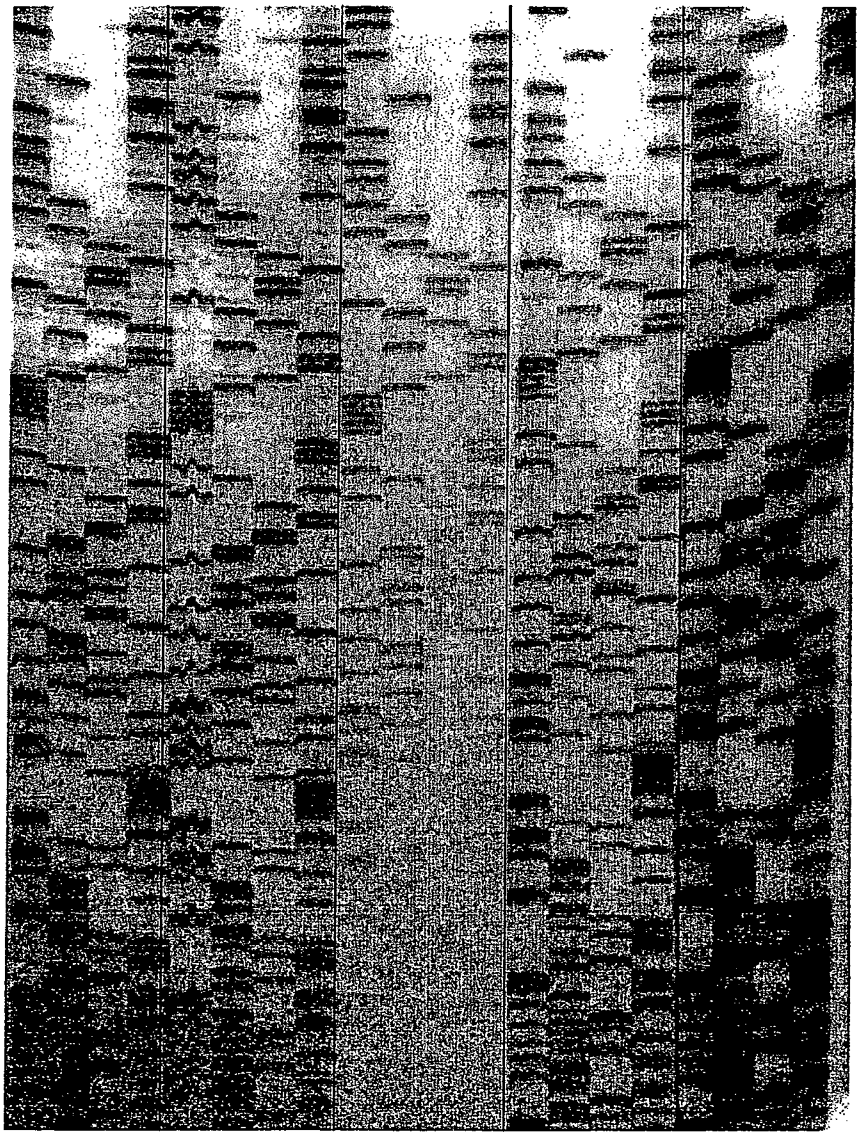
FIG. 8 shows cycle sequencing reactions performed using the JDF-3 P410L/A485T double mutant and α-$^{33}$P Dideoxynucleotides. DNA sequencing ladders were generated using the JDF-3 P410L/A485T double mutant at (A) 2 μl (B) 1 μl (C) 0.5 μl, the JDF-3 P410L mutant (clone p8, contains ancillary mutations and an amino-terminal tag) (D), or Thermo Sequenase (E). The top of the original sequencing gel is shown on the left side. The lanes are: (bottom) ddGTP, ddATP, ddTTP, ddCTP (top).

FIG. 8 shows that the P410L/A485T double mutant exhibits exceptionally even signals. Band uniformity was improved compared to mutant p8 (P410L mutation plus ancillary mutations that do not include A485T) and mutant A485T (data not shown). Mutant p8 exhibited a tendency to preferentially incorporate ddGTP and ddCTP in a sequence-dependent fashion. The optimal amount of enzyme may be higher than the quantity tested in this experiment. Sequence produced by the commercially available Family A DNA polymerase mutant, Thermo Sequenase, is shown in panel E.

iv. Ribonucleotide Incorporation by JDF-3 Polymerase Mutants.

A primer annealed to single stranded DNA template was extended in a mixture containing all ribonucleotides or all deoxynucleotides with the mutant and progenitor polymerases.

M13 mp18+ single stranded DNA was annealed to 95× molar excess of the 38mer primer by heating the mixture to 95° C. and cooling slowly at room temperature.

```
38mer primer:
5' GGTTTTCCCAGTCACGACGTTGTAAAACGACGGCCAGT 3'
```

Preliminary assays were carried out to determine what dilutions of enzyme would be necessary to examine the incorporation activity at non-maximal levels. The final assay solutions were composed as described below:

| Ribonucleotide mixture | |
|---|---|
| 20 ng/μl | annealed primer/template |
| 1x | Cloned Pfu buffer (Stratagene catalog #200532) |
| 200 μM each | GTP, UTP, ATP |
| 50 μM | CTP |
| 1 μM | 5-$^3$H CTP 20.2 Ci/mmole |
| 0.05-0.3 units | JDF-3 polymerase* |
| Deoxyribonucleotide mixture | |
| 20 ng/μl | annealed primer template |
| 1x | Cloned Pfu buffer |
| 200 μM each | dGTP, dATP, dCTP |
| 50 μM | TTP (deoxyribonucleotide) |
| 1 μM | Thymidine 5'-triphosphate, [methyl-$^3$H] 20.5 Ci/mmole |
| 0.05-0.3 units | JDF-3 polymerase* |

*Added separately

Nine microliters of the polymerase-free mixtures were placed in 0.2 ml tubes before the polymerases were added. The samples were incubated at 72° C. in a ROBOCYCLER®96 temperature cycler with Hot Top Assembly (Stratagene Catalog Nos. 400870 and 400894). The deoxyribonucleotide mixture was removed at 2 minutes and placed at approximately 2° C. The ribonucleotide mixture was incubated for 30 minutes. Seven microliters of the assay mixture were spotted onto DE81 filter circles (Whatmann) and dried prior to being washed three times in 2×SSC (0.3M NaCl, 0.03M sodium citrate) for five minutes each wash. The filters were rinsed twice in ethanol and allowed to dry before being quantified with a scintillation counter.

Figure 9:
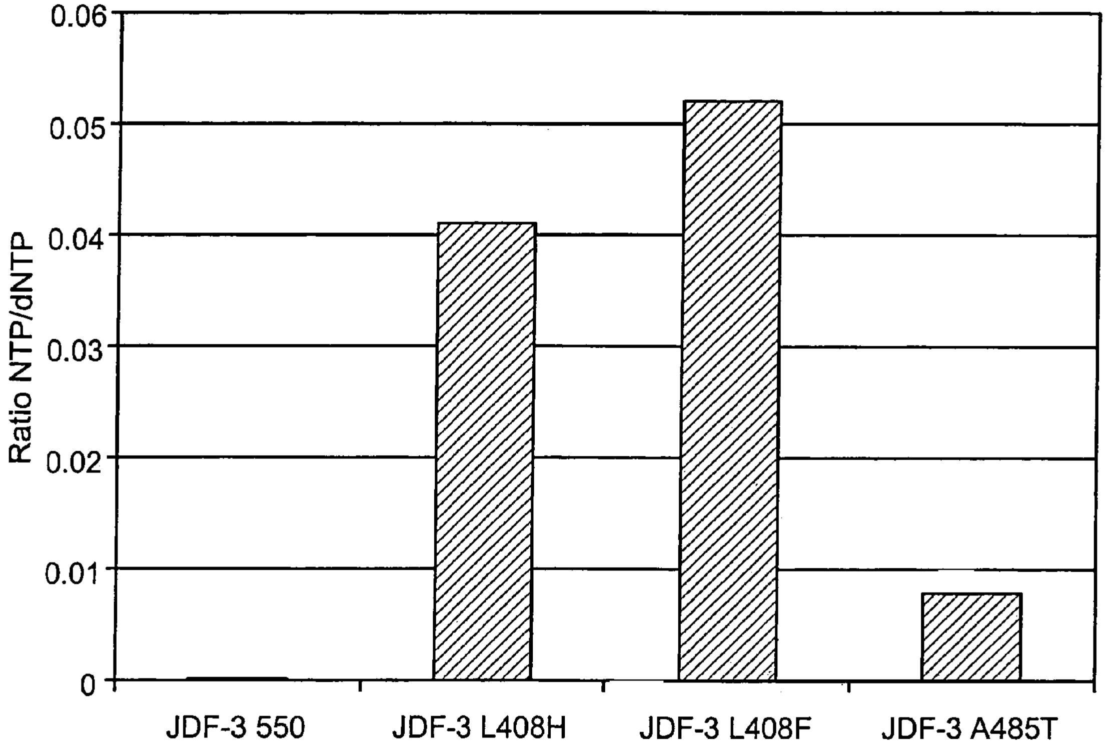
FIG. 9 shows the result of ribonucleotide incorporation assays using exo JDF-3 (550) and mutants of this progenitor clone. The ratios of ribonucleotide versus deoxynucleotide incorporation are plotted for JDF-3 550, JDF-3 L408H, JDF-3 L408F and JDF-3 A485T.
Figure 10:
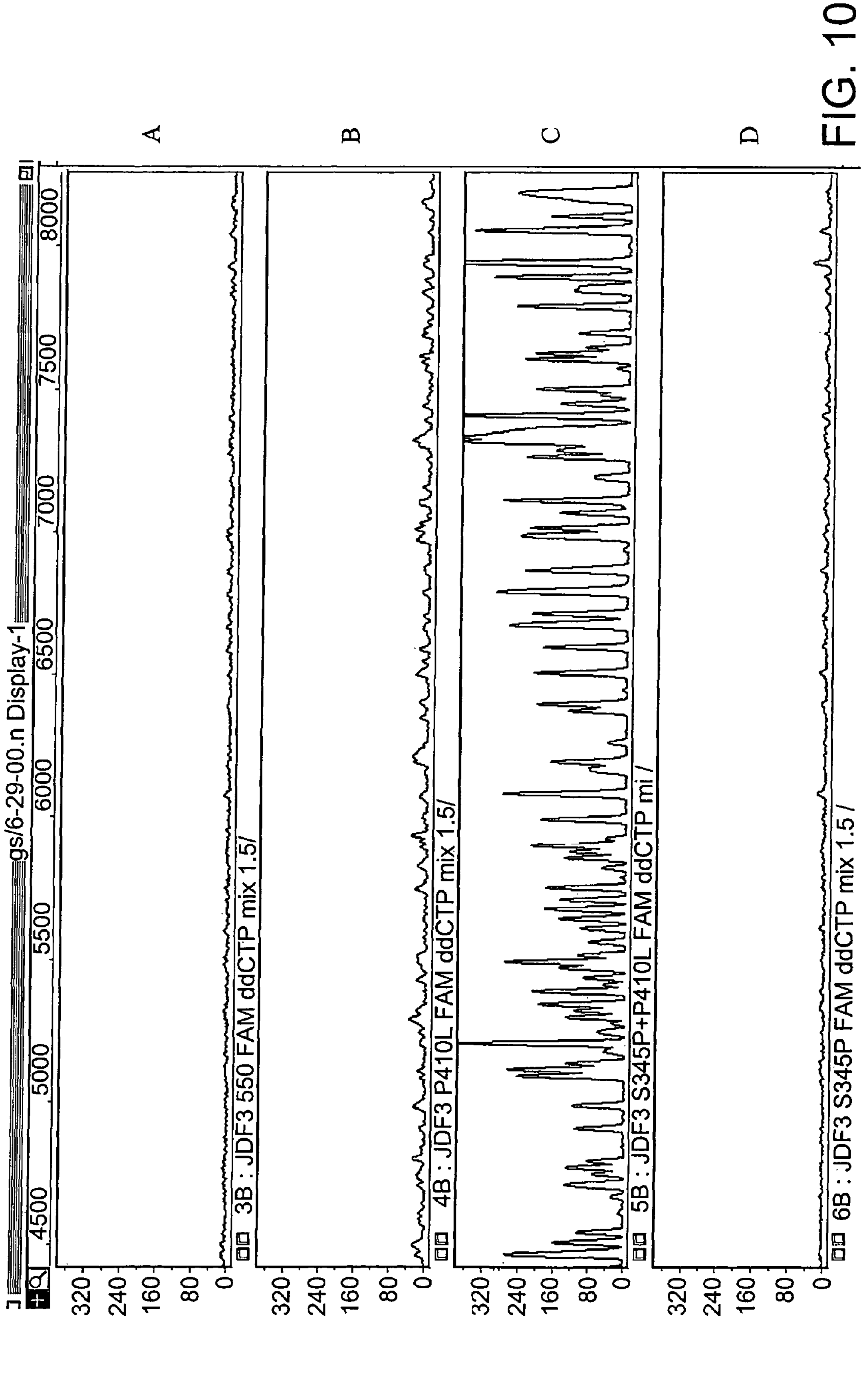
FIG. 10 shows the traces of the sequence generated by four versions of JDF-3 DNA polymerase and FAM ddCTP. Panel A shows the minimal trace produced by the progenitor polymerase JDF-3 550, Panel B demonstrates the slightly improved trace made by JDF-3 P410L, Panel C shows the sequence generated by the double mutant S345P and P410L, and Panel D shows the trace created by JDF-3 S345P.
Figure 11:
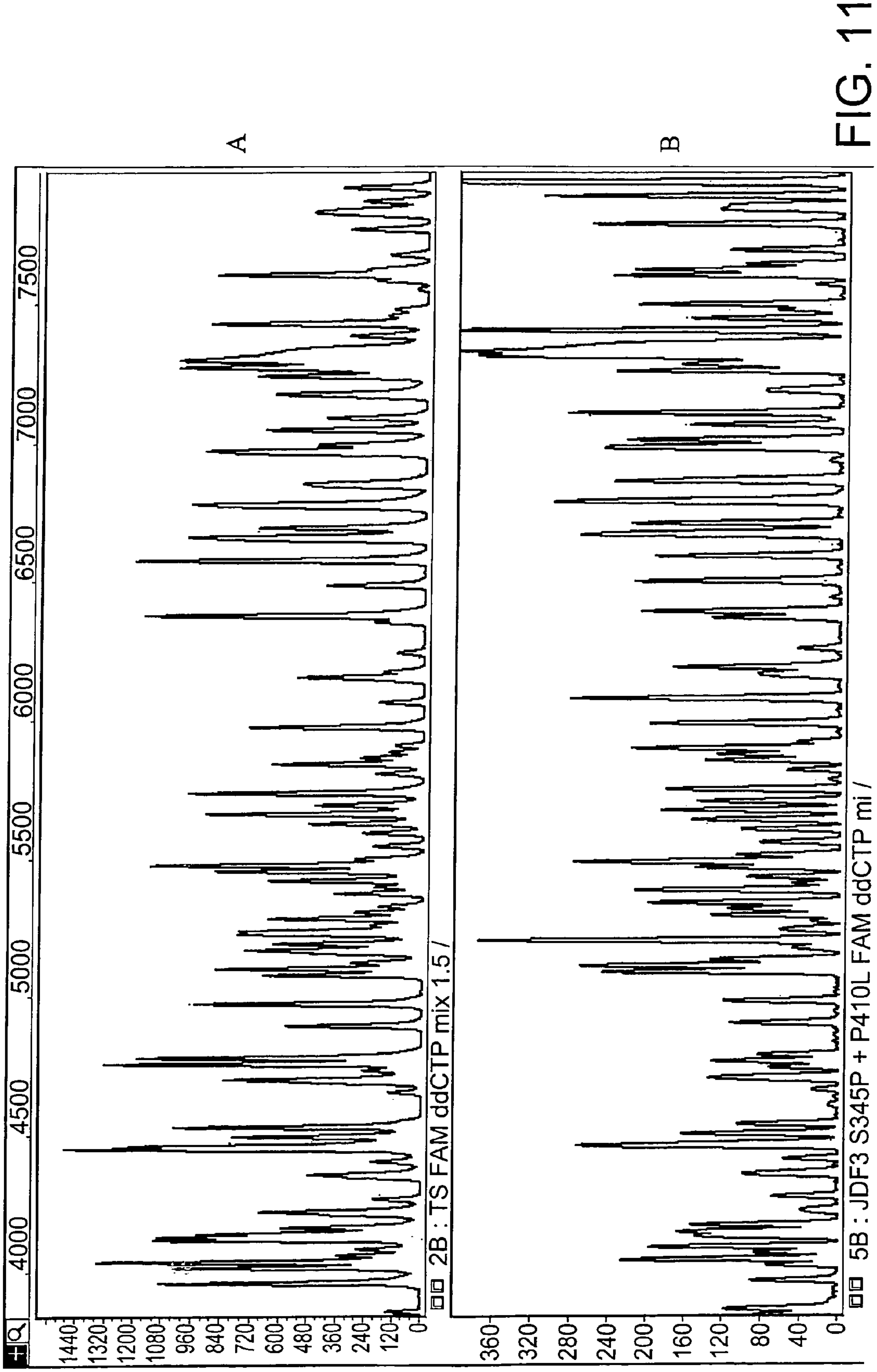
FIG. 11 shows the difference in peak uniformity demonstrated by Thermo Sequenase in Panel A and the double mutant JDF-3 S345P+P410L in Panel B.
Figure 12:
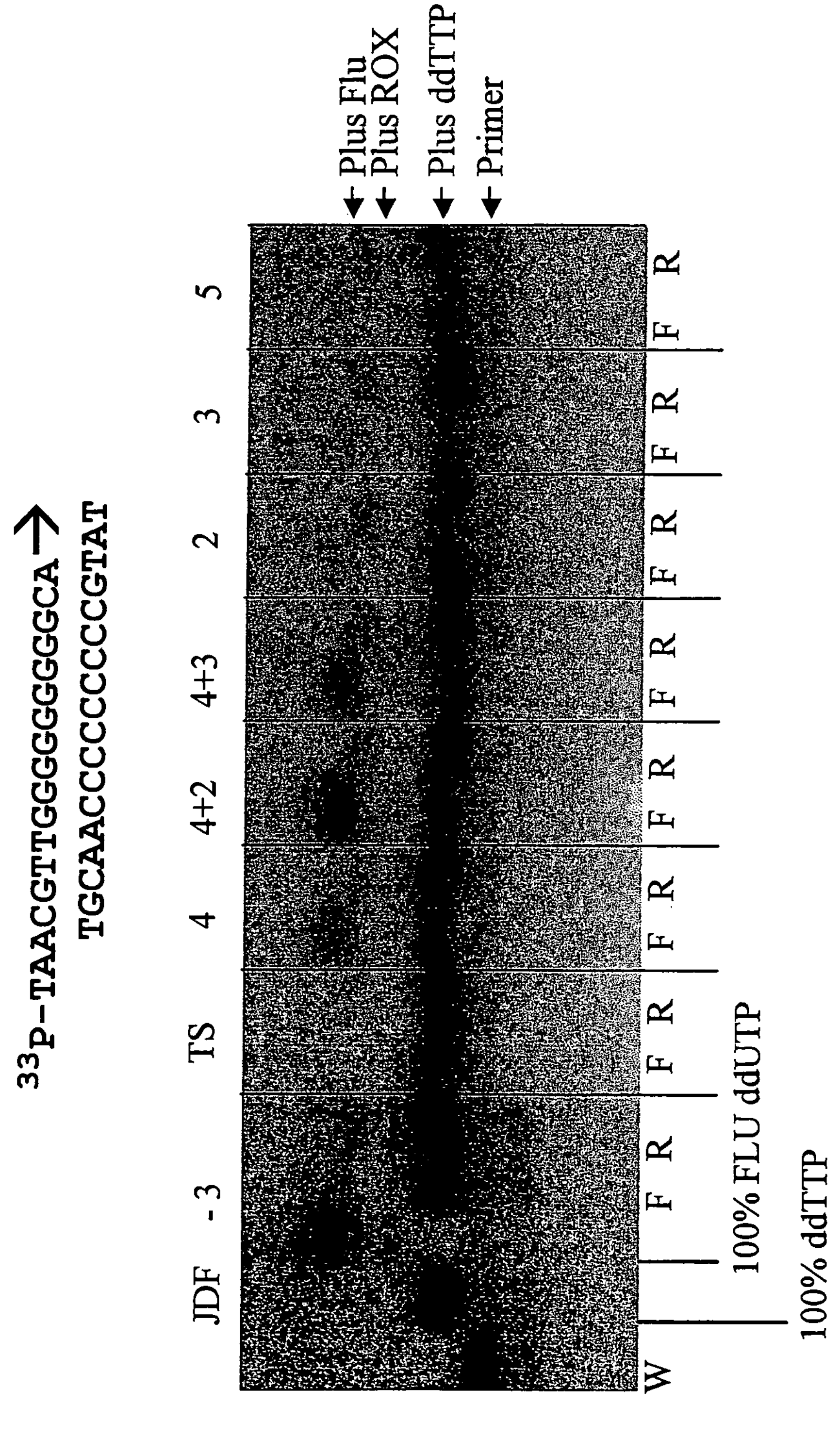
FIG. 12 shows the separated products of 3' extension of a labeled oligonucleotide with the dideoxynucleotide thymidine triphosphate of ROX-ddUTP (New England Nuclear (NEN) NEL476) or Fluorescein-12-ddUTP (NEN NEL401). Mutant 4 is JDF-3 S345P, Mutant 2 is JDF-3 P410L, Mutant 3 is JDF-3 A485T and Mutant 5 is Y496N. F indicates FLU ddUTP and R indicates ROX ddUTP.
Figure 13:
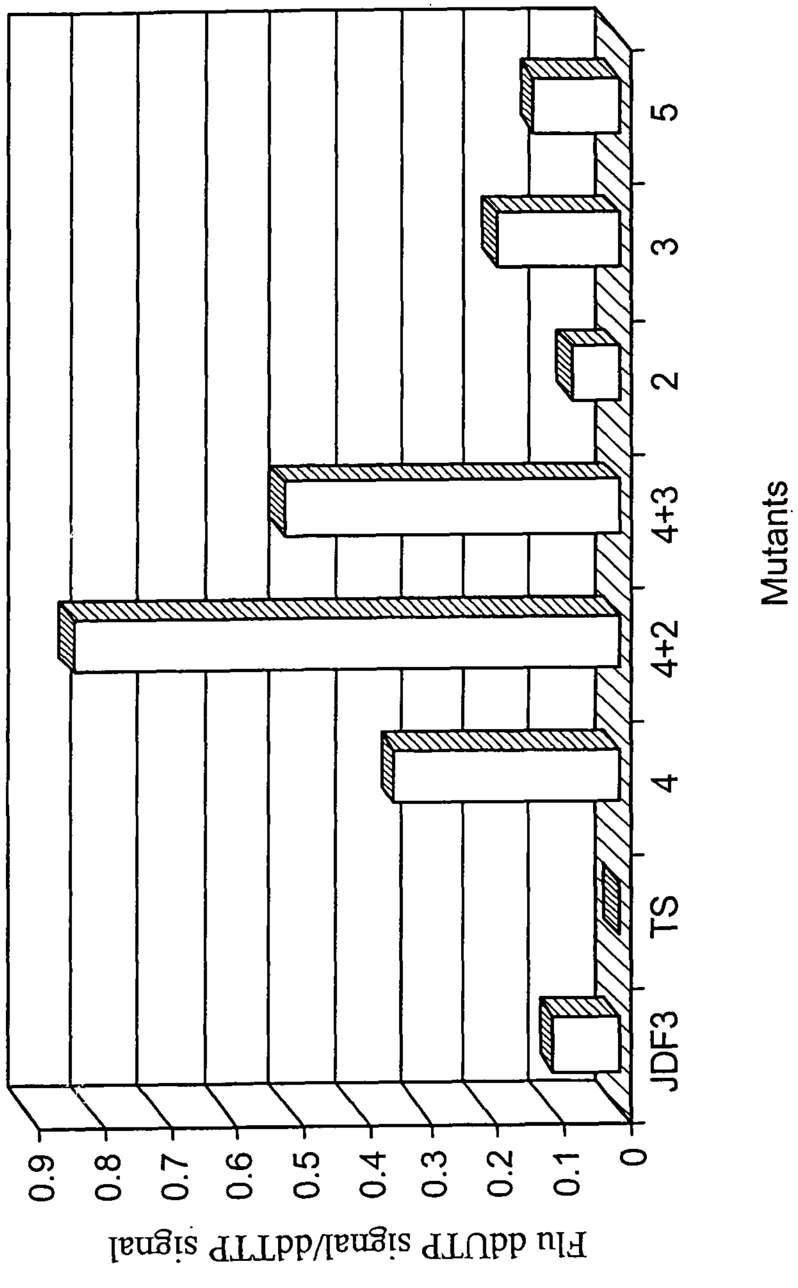
FIG. 13 shows a graphic representation of the relative band intensities form FIG. 12. The numerical values are generated by dividing the intensity value of the ddTTP band into the intensity value for the Fluoroescein-12-ddUTP bands.

Background counts per minute (CPM) for the deoxyribonucleotide and the ribonucleotide reactions were subtracted from the respective averaged CPM value of duplicate samples for each enzyme. The background-corrected ribonucleotide CPM value was divided by the background-corrected deoxyribonucleotide CPM value (FIG. 9).

| Polymerase | Ratio NTP/dNTP | Relative to JDF-3 550 |
|---|---|---|
| JDF-3 550 | 0.000165162 | 1 |
| JDF-3 L408H | 0.041087258 | 249 |
| JDF-3 L408F | 0.051703924 | 313 |
| JDF-3 A485T | 0.007628583 | 46 |

v. Ribonucleotide Sequencing with JDF-3 Polymerase Mutants.

Ribonucleotides incorporated into a deoxyribonucleotide polymer are susceptible to alkali hydrolysis which can produce a sub-population of polymer lengths. When labeled primer is extended in the presence of a particular ribonucleotide base (for example ATP) and the four deoxyribonucleotide bases, the fragments resulting from alkali hydrolysis create a population of different lengths, which correspond to all the possible positions where ATP was incorporated. When those fragments are size separated, their migration pattern, with respect to other ribonucleotide base (CTP, UTP and GTP) hydrolysis products allows the template sequence to be read. As described previously, most DNA polymerases discriminate against non-conventional deoxynucleotides. A subset of the JDF-3 DNA polymerase mutants which allow improved uptake of the unconventional dideoxynucleotides also show improved tolerance for ribonucleotide incorporation.

100 ng of the 38mer primer was kinased with $\alpha$-$^{33}$P according to the instructions in the KINACE-IT™ Kinasing Kit (Stratagene catalog #300390).

```
38mer primer:
5' GGTTTTCCCAGTCACGACGTTGTAAAACGACGGCCAGT 3'
```

The labeled oligonucleotide was purified from contaminating free nucleotides with a NUC TRAP® Probe Purification Column (Statagene catalog #400701) in 10T.1E (10 mM Tris pH 8.0, 0.1 mM EDTA). Labeled oligonucleotide (~7 picomoles) was annealed to 0.09 pmoles M13 mp18+ by heating to 95° C. then cooling to room temperature in the presence of 0.32 mM $MgCl_2$.

| Extension components | |
|---|---|
| 0.054 pM | annealed primer/template |
| 200 μM | each dNTP |
| 1x cPfu | DNA polymerase buffer (Stratagene catalog #200532) |
| 4-200 | ATP* |
| 0.1-5 Units | JDF-3 polymerase* |

*Added separately

Eight microliters of a cocktail containing the first three components listed above were aliquoted into a 0.2 ml tube. 1 μl of polymerase and 1 μl of 2 mM, 0.2 mM or 0.4 mM ATP were added and the reaction was incubated at 72° C. for 15 minutes. The reaction volume was brought to 100 μl with 1xcPfu polymerase buffer and transferred to a 1.5 ml tube. After heating the reactions in the presence of 70 mM NaOH for 15 minutes at 100° C., the reaction was neutralized with 70 mM HCl and precipitated through the addition of 10 μl 3M sodium acetate and 327.5 μl of ethanol. The samples were microcentrifuged for 30 minutes at 14 krpm before the supernatant was removed and the pellet washed in 80% ethanol. After vacuum drying, the samples were resuspended in 5 μl of sequencing stop solution (95% formamide, 20 mM EDTA, 0.05% bromophenol blue, 0.05% xylene cyanol FF) and 2.5 μl was loaded on a 6% acylamide-7M urea, 1×TBE CAST-AWAY™ Precast gel (Stratagene catalog numbers 401090 and 401094). The gels were run at 50 watts until the bromophenol blue dye migrated past the bottom of the gel after which the gel was fixed, dried and exposed to film for 72 hours.

Sequencing ladders for JDF-3 550 (wild-type nucleotide incorporation) and all the mutants tested were visible at the 200⊠M and 20⊠M ATP level. At the 4⊠M level, only the L408H and L408F mutants produced ladders (data not shown).

vi. Sequencing with Dye-Dideoxynucleotide Terminators

Primer was extended in the presence of FAM ddCTP (NENNEL481). The sequence reactions were purified and run on an ABI 370.

Reaction conditions for cycle-sequencing were as described below:

1× cPFU buffer, 200 ng pBluescript II KS plasmid, 3 pmole T7 primer, 0.23 mM dCTP, 0.23 mM dATP, 0.23 mM dTTP, 0.23 mM dGTP with 0.046 mM FAM ddCTP. The samples were cycled in a Perkin-Elmer cycler in 10 ⊠l volumes for 25 cycles of the temperatures and times described below:

| | |
|---|---|
| 95° C. | 30 s |
| 55° C. | 30 s |
| 72° C. | 2 min |

The samples were purified using CentriSep columns according to the manufacturer's instructions. After drying, the samples were resuspended in 3 ⊠l of a loading dye comprised of 66.7% deionized formamide, 16.7 mg/ml Blue Dextran, and 8.3 mM EDTA. Samples were heated at 95° C. for three minutes and loaded on a 5% LongRangen gel in an ABI PRISM 377 DNA sequencer.

Data was processed in Gene Scan 2.1.

Example 2

Labeling of DNA

The modified DNA polymerases of the invention are applicable to labeling of DNA. It is known to those skilled in the art that there are several means by which to label DNA, including the incorporation of radiolabeled nucleotides. One such common means is by random priming, which enables one of skill in the art to generate labeled DNA fragments, typically about 50 to about 1000 bases long. The procedure described herein are adapted from F. Ausubel et al., Short Protocols in Molecular Biology, Third Edition, John Wiley and Sons, Inc., 1995.

As a first step toward random priming DNA, a reaction mix containing 2.5 microliters 0.5 mM 3dNTP (dCTP, dGTP, TTP, each at 0.5 mM), 50 ⊠ Ci [-$^{32}$P]dATP, 1 microliter of 3 to 8 units/microliter DNA polymerase in 50 mM Tris-HCl, pH 7.5, 10 mM $MgCl_2$, 1 mM dithiothreitol, 0.05 mg/ml bovine serum albumin is prepared in a total volume of 11 microliters and incubated on ice. Next, about 30 to about 100 ng of DNA is mixed with about with 1 to 5 ⊠ g of random hexanucleotides in 14 microliters and boiled for 2 to 3 minutes and then placed on ice. The 11 microliter reaction mix is then added to the DNA/random hexamer mix, and the random priming reaction is incubated over 10 minutes to as much as 4 hours at room temperature. To stop the reaction, 1 microliter 0.5 M EDTA, 3 microliters 10 mg/ml tRNA, and 100 microliters 10 mM Tris-HCl, pH 7.4 is added and the mixture is extracted with phenol. The labeled DNA is then separated from unincorporated radioactive precursors by chromatography.

R. Gel Assay for Dye-Dideoxynucleotide Incorporation

A labeled oligonucleotide duplex was extended with a mixture of dideoxynucleotides and dye-dideoxynucleotides. When the duplex was separated on a denaturing 20% Acrylamide/7 M urea gel, labeled oligonucleotides terminated with a dideoxynucleotide could be resolved from oligonucleotides terminated with dye-deoxynucleotides.

Oligonucleotides:

| | |
|---|---|
| 259C | $^{32}$P-TAACGTTGGGGGGGGGCAI |
| 258C | TGCAACCCCCCCCCGTAT |

The 5' end of 259 C was labeled and purified as described in Section Q.ii.a except that $^{32}$Pβ-ATP was used. The labeled oligonucleotide 259 C was at a concentration of approximately 0.7 ng/⊠l. The complimentary oligonucleotide (258 C) was added as an equal concentration, heated to 95° C. for three minutes, 50° C. for 5 minutes and room temperature for 20 minutes. Heat killed lysates of the relevant mutants were prepared as described in Example section C. The reactions were incubated in a 5 ⊠l volume composed of 30 mM Tris pH 8.0 and 3 mM $MgCl_2$ with a nucleotide mixture totaling 0.1 mM. The ratio of ddTTP to FLU ddUTP or ROXddUTP was 10:1. The dimer was present at a concentration of 1.2 picomoles and 0.5 ⊠l of enzyme or crude lysate or purified enzyme was added to the reaction before incubation at 50° C. in the RobeCycler® Gradient 96 Temperature Cycler with Hot Top. The samples were incubated for 20 s before 3 ⊠l of a formamide based loading dye was added and the samples were heat-denatured at 95° C. for 3 minutes then loaded onto a 20% acrylamide/7 M urea gel and subjected to electrophoresis at a constant 60 watts. The gel was exposed to X-ray film and the film was analyzed in the EagleEye® Eagle Sight software package.

Example 3

The modified DNA polymerases of the invention are also applicable to identify a nucleotide at a given position of a template DNA molecule, i.e., by mini-sequencing. For example, the JDF-3 DNA polymerase P410L/A485T mutant (JDF-3 D141A/E143A/P410L/A485T) generates the longest and most uniform radioactive DNA sequencing ladders using low ddNTP/dNTP ratios (1/100), indicating efficient ddNTP incorporation, minimal base selectivity, and high polymerase activity. This example describe the properties of this JDF-3 DNA polymerase P410L/A485T mutant and a procedure for optimizing the conditions for mini-sequencing using the mutant polymerase.

A. Experimental Protocol i. Materials

StrataPrep PCR columns, StrataPrep DNA gel extraction columns, cold ddNTPs, calf alkaline phosphatase and pBluescript II were from Stratagene. Rhodamine labeled-ddNTPs were purchased from NEN. EDTA/blue dextran, rhodamine dye-matrix standards, and the SNaPshot ddNTP primer extension kit were purchased from Applied Biosystems. ThermoSequenase (Taq F667Y mutant) was from Amersham Pharmacia Biotech. Long Ranger polyacrylamide gels (6%) were purchased from BMA. Shrimp alkaline phosphatase and exonuclease I were from USB corporation. CENTRI-SEP spin columns were purchased from Princeton Separations. Deionized formamide was from Sigma. Oligonucleotides (PAGE purified) whose sequences are listed in Table VII, were purchased from Genset oligos. All other reagents were molecular biology grade.

ii. Primer:Template Formation:

Duplex primer template pairs were formed by annealing the template with 10 fold excess of the appropriate primer in a solution containing 10 mM Tris-HCl (pH 8) and 0.1 mM EDTA using the following temperature regimen: 5 min at 95° C. and then cool slowly to room temperature. Concentrations of the primer:templates are expressed as moles of single stranded templates.

iii. Product Analysis:

The dye labeled products were resolved on 6% polyacrylamide/urea gels and visualized on a Applied Biosystems model 377 DNA sequencer using 3.1.2 GeneScan fragment analysis software for peak identification and fluorescence measurements. A rhodamine dye-matrix was installed on the ABI 377 sequencer according to the manufacturer's protocol.

TABLE VII

| Synthetic oligonucleotides | |
|---|---|
| Temp-A | 5'-CTCAACTTGGAGCGAACGACCTACACCGAA |
| Temp-T | 5'-CTCATCTTGGAGCGAACGACCTACACCGAA |
| Temp-G | 5'-CTCAGCTTGGAGCGAACGACCTACACCGAA |
| Temp-C | 5'-CTCACCTTGGAGCGAACGACCTACACCGAA |
| *pBL25C | 5'-TTCGGTGTAGGTCGTTCGCTCCAAG |
| *pBL28T | 5'-AAGTGTAAAGCCTGGGGTGCCTAATGAG |
| *pBL31G | 5'-TTCAGCATCTTTTACTTTCACCAGCGTTTCT |
| *pBL34A | 5'-AGCTGGCGAAAGGGGGATGTGCTGCAAGGCGATT |
| *pPC41T | 5'-CGGTACCTCCTGGTGGATACACTGGTTCCTGTAAGCAGA AG |
| *pPC26G | 5'-GAGAGCTTGAGGAGAGCAGGAAAGGT |
| *pPC37A | 5'-GATCTCCCAGGGCGGCAGTAAGTCTTCAGCATCAGGC |
| *pPC29C | 5'-TCCTTTGGACAGGGATGAGGAATAACTGA |

*The numbers indicate the length of the primer before extension by one ddNTP and the succeeding letters show the ddNTP that is incorporated.

iv. Purification and Optimal Reaction Buffer of JDF-3 P410L/A485T DNA Polymerase:

JDF-3 P410L/A485T was expressed in XL-10 Gold and purified as described in the "Purification of JDF-3 P410L/A485T mutant" Product Transfer Document by Brad Scott. One unit of enzyme is defined as the amount that will catalyze the incorporation of 10 nmol of total nucleotide into acid insoluble form in 30 minutes at 72° C. The 10× reaction buffer for JDF-3 P410L/A485T contains: 200 mM Tris-HCl (pH 8.8), 100 mM KCl, 100 mM $(NH4)_2SO_4$, 20 mM $MgSO_4$.

v. Enzyme Assays:

a. Kinetic Analysis of Rhodamine Labeled-ddNTP Incorporation and Misincorporation:

$K_m$ and $V_{max}$ values for rhodamine labeled-ddNTP incorporation were measured by incubating 50 nM primer: template with limiting amounts of polymerase (0.1 units or 5 nM) and varying concentrations of rhodamine labeled-ddNTP ranging from 0.1 nM to 500 nM. Samples were incubated at 60° C. for 10 minutes. The reactions were then quenched with ice-cold 0.2 M EDTA (final concentration). Unincorporated rhodamine labeled ddNTPs were removed by purifying the extended primer:templates on CENTRI-SEP spin columns. Reactions were then dried, and the pellets dissolved in 3:1 formamide:EDTA/blue dextran and analyzed by 6% denaturing PAGE on an ABI 377 sequencer. All peak area quantitations were performed using 3.1.2 GeneScan software and $K_m$ and $V_{max}$ values were calculated using Lineweaver-Burk plots.

$K_m$ and $V_{max}$ values for primer:template were measured with limiting amounts of enzyme (0.1 units or 5 nM) in the presence of 0 nM of R110-ddGTP and varying concentrations of primer:template (pBL31G:pBluescript II) ranging from 0.5 to 100 nM. Samples were incubated for 10 minutes at 60° C. The reactions were then quenched, purified from unincorporated rhodamine labeled-ddNTPs, and analyzed as described above.

To determine the kinetics of misinsertion, the steady state Michaelis-Menten $K_m$ and $V_{max}$ parameters were calculated by incubations of limiting amounts of enzyme (0.1 units or 5 nM) in presence of 50 nM primer:template and varying concentrations of non-complementary rhodamine labeled ddNTP (1 nM to 10,000 nM) for 10 minutes at 60° C. Analysis and quantitations were performed as above.

b. Screen for Fidelity:

Reactions (10 μl) contained 1 unit of enzyme in 1× reaction buffer, 15 nM primer template, 25 nM of unlabeled complementary ddNTP, and 25, 100, 500, or 1000 nM of rhodamine labeled non-complementary ddNTP in four separate reactions. The reactions were incubated in a Perkin-Elmer 9600 for 25 cycles as follows: 96° C. for 10 s, 50° C. for 5 s, and 60° C. for 30 s. The reactions were then quenched with ice-cold 0.2 M EDTA (final concentration) and the products were purified from unincorporated rhodamine labeled ddNTPs and analyzed as described above.

c. Assays for Rhodamine Labeled ddNTP Incorporation:

These experiments were performed using 1 unit of enzyme, 15 nM primer:template (pBL25C and Temp-A, Temp-T, Temp-C, or Temp-G in four separate reactions), and 50 nM dye-ddNTP (TAMRA- or R110-labeled). The reactions were incubated at 60° C. for 10 minutes and then quenched with ice-cold 0.2 M EDTA (final concentration). The products were purified from unincorporated dye-labeled ddNTPs and analyzed as described above.

B. Optimization Procedures:

i. Preparation of DNA Templates for Minisequencing:

Fragments containing the SNP(s) of interest are amplified from genomic DNA using standard PCR conditions. In this study, PCR reactions were carried out using 2.5 units of TaqPlus Precision DNA polymerase blend. A 4 kb fragment of the human alpha-1-antitrypsin gene was amplified from 100 ng human genomic DNA using 10 pmol of the pPC26G and pPC29C primers (Table VII). The following program was used in a Robocycler: 1 cycle of 95° C. for 2 min, 30 cycles of 95° C. for 1 min, 58° C. for 1 min, and 72° C. for 4 min, followed by one cycle at 72° for 7 min.

In order to purify the resulting 4 kb fragment from PCR primers and unincorporated dNTPs, the fragment can be: (1) purified using the StrataPrep DNA gel extraction kit; (2) treated with exoI/SAP; or (3) incubated on StrataPrep columns with SAP or CIAP. To treat the PCR fragment with exoI/SAP, 2 units of each enzyme was added to 4 μl of PCR product, and the mixture was incubated for 1 hour at 37° C., followed by 15 minutes at 72° C. to inactivate the enzymes. To purify the PCR amplified fragment using StrataPrep columns, a 50 μl PCR reaction was loaded on a StrataPrep column and processed as described in the StrataPrep column manual, except that before elution, 1 unit of CIAP in 50 μl 1× corresponding reaction buffer was added to the column. The column was incubated at room temperature for 5 minutes, washed, and the PCR fragment was eluted as described in the manual. The eluate was incubated at 72° C. for 15 minutes to inactivate any remaining CIAP. All of these clean up methods produced DNA templates that were pure enough for subsequent minisequencing.

ii. Minisequencing Protocol Using Plasmids or PCR Amplified Fragments:

Minisequencing of pBluescript (0.25 pmol) was carried out using 0.15 pmol of each primer (e.g. pBL25C), 1 unit enzyme, 0.04 μM of R6G-ddA, R110-ddG, and ROX-ddC, and 0.2 μM of TAMRA-ddU. When using PCR amplified fragments, template concentrations as low as 0.02 pmol/rxn were used. All reactions were performed in 10 μl volumes. The thermal cycling program consisted of 25 cycles of 96° C. for 10 s, 50° C. for 5 s, and 60° C. for 30 s in a Perkin-Elmer 9600 or 25 cycles of 96° C. for 50 s, 50° C. for 50 s, and 60° C. for 50 s in a Robocycler.

In order to purify the labeled primers from unincorporated dye-ddNTPs, samples were either treated with SAP or CIAP, or purified using CENTRI-SEP columns according to manufacturers's recommendations. 1 unit of CIAP or 0.5 unit of SAP was added to each 10 μl reaction and incubated at 37° C. for 60 min, followed by 15 minutes at 72° C. to inactivate alkaline phosphatase. Reactions were then dried and pellets were dissolved in 10 μl of 3:1 formamide:EDTA/blue dextran. 1 μl of each reaction was resolved by 6% denaturing PAGE on an ABI 377 sequencer and analyzed using GeneScan 3.1.2 (Applied Biosystems).

Figure 16A:
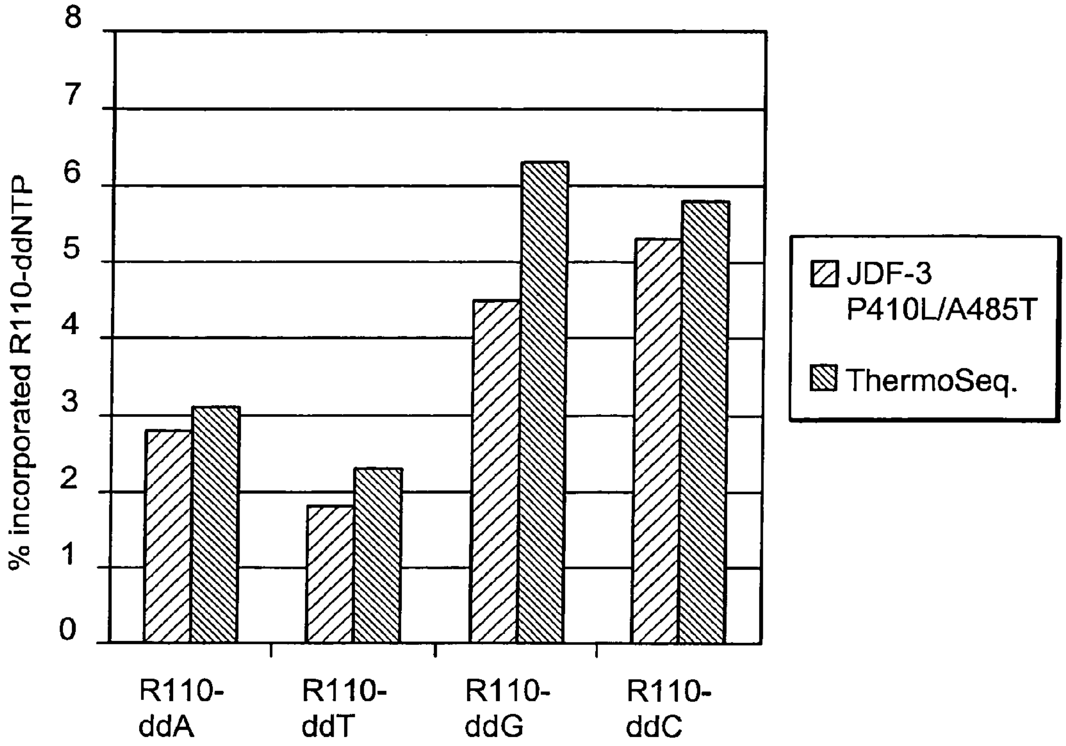
FIG. 16. Incorporation of rhodamine labeled-ddNTPs by JDF-3 P410L/A485T and ThermoSequenase (Taq F667Y). The JDF-3 P410L/A485T and Taq F667Y mutants show slightly different incorporation rates for each of the rhodamine-labeled-ddNTPs. Reactions in panels A and B contained 0.05 μM of either TAMRA- or R110-labeled-ddNTPs, 15 nM primer:template, and 1 unit of enzyme. Reactions were incubated as described in the Experimental Protocol.
Figure 16B:
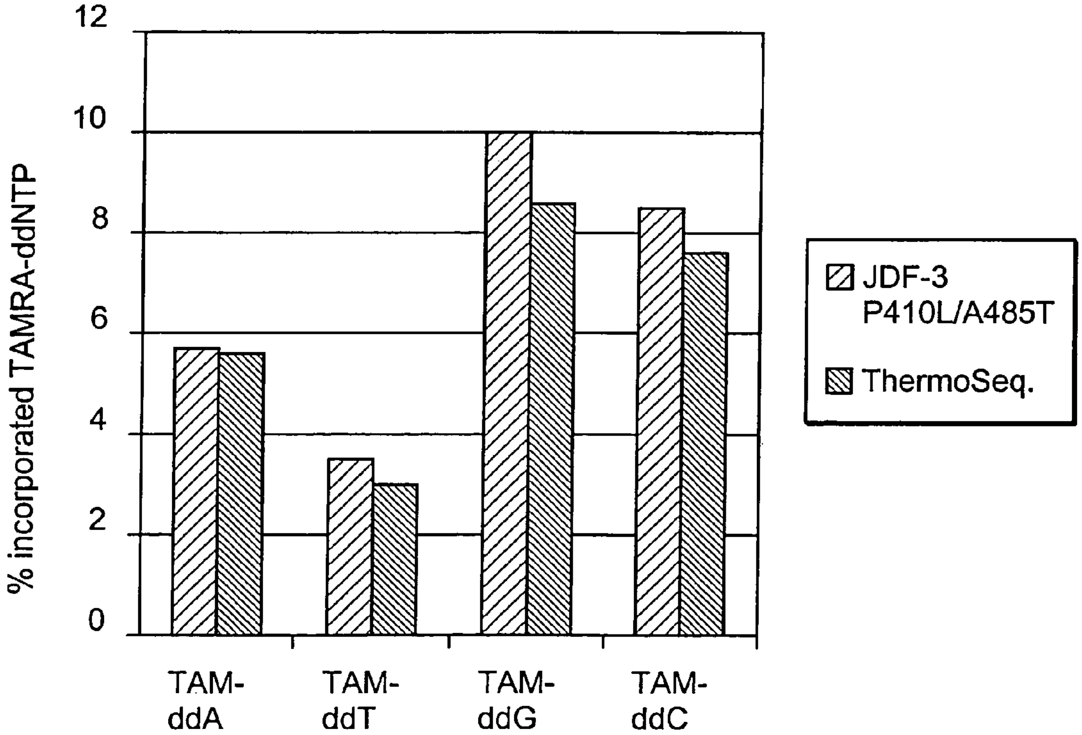
Figure 17A:
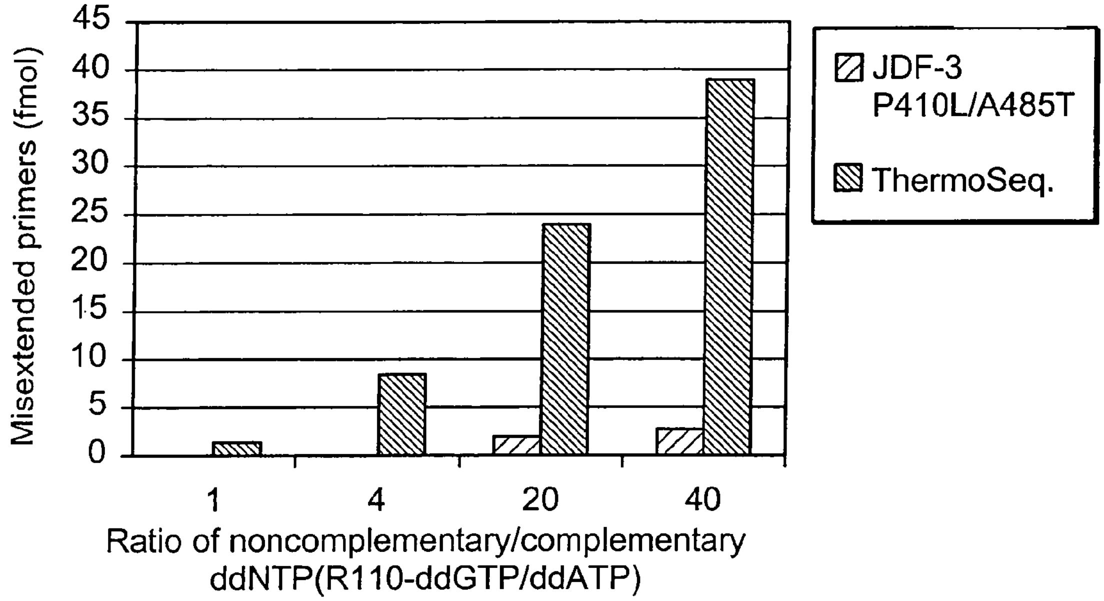
FIG. 17. Misinsertion of rhodamine labeled-ddNTPs by JDF-3 P410L/A485T and ThermoSequenase (Taq F667Y). JDF-3 P410L/A485T shows higher fidelity compared to Taq F667Y when incorporating certain ddNTPs. Reactions in panels A and B contained 1 unit of either JDF-3 P410L/A485T or ThermoSequenase, 15 nM primer:template (panel A: pBluescript:pBL34A; panel B: pBluescript:pBL31G), and 25 nM of unlabeled complementary ddNTP (panelA: ddATP; panel B: ddGTP) and either 25, 100, 500, or 1000 nM of dye-labeled non-complementary ddNTP (panel A: R110-ddGTP; panel B: R110-ddUTP) in four separate reactions. Reactions were incubated and analyzed as described in the Experimental Protocol. Panel C shows the sequencing gel from which the data in panel A was derived.
Figure 17B:
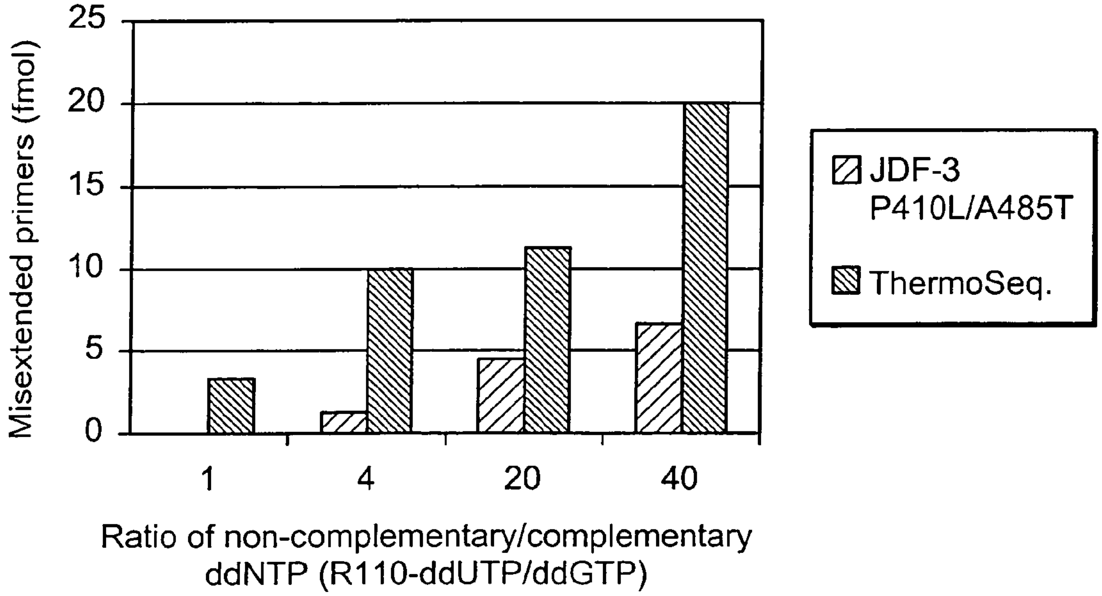
Figure 17C:
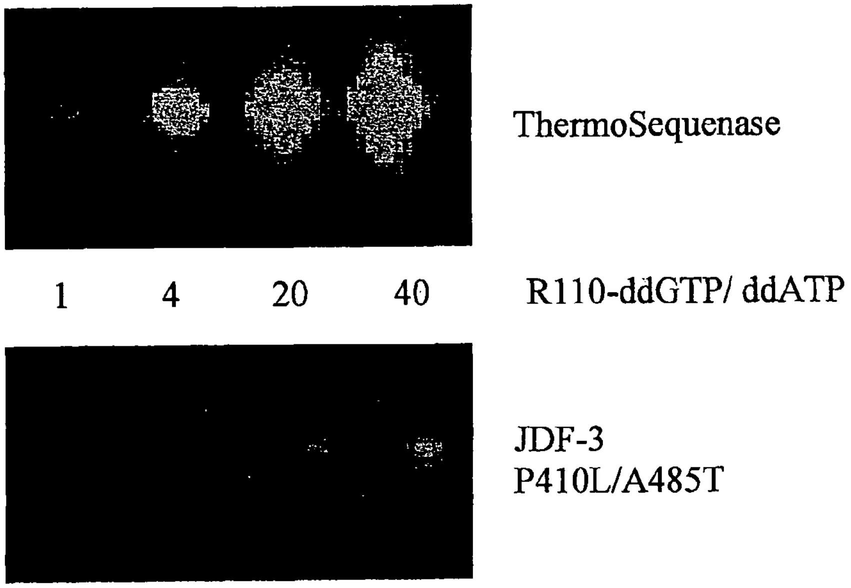

C. Results i. Buffer and Reaction Temperature Optimizations:

Since *Thermococcus* sp. JDF-3 DNA polymerase is closely related to archaeal *P. furiosus* DNA polymerase (Pfu), cloned Pfu buffer (10× buffer: 200 mM Tris-HCl (pH 8.8), 100 mM KCl, 100 mM $(NH4)_2SO_4$, 20 mM $MgSO_4$, 1% Triton X100, and 1 mg/ml BSA) was used as a starting point for buffer optimization. Changes in enzyme activity due to buffer and reaction temperature alterations were determined by measuring R6G-ddATP incorporation using the pBL34A:pBluescript primer:template system. The presence of Triton X-100 and BSA in this buffer was found to create an artifact (double band effect) in sequencing gels (data not shown). Enzyme activity was measured at pH 8.4 and 9.5, in the presence of varying concentrations of KCl (20, 40 or 80 mM), $(NH_4)_2SO_4$ (5 or 20 mM), and $MgSO_4$ (4 or 8 mM), respectively. None of these changes had a noticeable effect on the activity of JDF-3 P410L/A485T. Therefore, cloned Pfu buffer lacking BSA and Triton was identified as the optimal reaction buffer for minisequencing. Furthermore, the activity vs. temperature profile of JDF-3 P410L/A485T showed that nucleotide incorporation did not increase significantly between 60° C. and 72° C. (data not shown). To keep the extension temperature below the melting temperatures of minisequencing primers, all subsequent experiments were performed at 60° C.

ii. Incorporation of Rhodamine-Dideoxyribonucleotides:

Relative incorporation of rhodamine labeled-ddNTPs by the JDF-3 P410L/A485T and Taq F667Y mutants was determined. We used both TAMRA- and R110-labeled ddNTPs, and the amount of incorporated dye-ddNTPs was measured in fluorescence units. These experiments were performed using pBL25C as the primer, and Temp-A, Temp-T, Temp-C, or Temp-G as the complementary template in four separate reactions. The only difference between these four primer:template systems is the SNP site, thereby eliminating the possibility that primer:template sequence has an effect on dye-ddNTP incorporation. FIG. 16 panel B shows that JDF-3 P410L/A485T incorporates TAMRA-ddGTP and TAMRA-ddCTP slightly more efficiently compared to TAMRA-ddATP and TAMRA-ddUTP. ddCTP and ddGTP are also incorporated more efficiently than ddATP and ddUTP when R110 labeled ddNTPs are employed (FIG. 16 panel A). Gardner and Jack had also observed variation in the incorporation of ribonucleotides by the A488L mutant (equivalent to JDF-3 A485) of Vent DNA polymerase (from archaeon *Thermococcus litoralis*)[15]. In fact, the Vent A488L mutant incorporated UMP 10 fold less efficiently than CMP, GMP, and AMP, and the wild type Vent DNA polymerase showed similar bias against dUMP incorporation.

We performed similar rhodamine labeled-ddNTP incorporation experiments using the same number of units of Taq F667Y. As panels A and B in FIG. 16 indicate, the JDF-3 P410L/A485T and Taq F667Y mutants exhibit similar TAMRA- and R110-ddNTP incorporation efficiencies and limited (<3-fold) base selectivity, with the preference order of: G>C>A>T.

iii. Kinetic Parameters for Polymerization Reaction:

$K_m$ and $V_{max}$ values for primer:template and rhodamine-ddNTPs were determined as described in the Experimental Protocol. These values are reported in Table VIII, which compares the kinetic properties of JDF-3 P410L/A485T and Taq F667Y. This comparison establishes that the JDF-3 P410L/A485T and Taq F667 mutants exhibit similar steady-state kinetic parameters, and therefore, have similar affinities for both primer:template and rhodamine-ddNTP substrates.

Furthermore, kinetic parameters in Table VIII were used to determine incorporation efficiency of TAMRA-ddCTP ($V_{max}/K_m$=3.3/1=3.3) in comparison to TAMRA-ddATP ($V_{max}/K_m$=1.9/0.9=2.1). Incorporation efficiency of TAMRA-ddCTP is 1.5 fold more than TAMRA-ddATP, suggesting that JDF-3 P410L/A485T mutant incorporates different ddNTPs at slightly different rates, confirming the results obtained in FIG. 16.

TABLE VIII

Steady-state kinetic parameters[a] for rhodamine labeled ddNTPs and primer:template.

| | JDF-3 P410L/A485T mutant | | ThermoSeq. (Taq F667Y mutant) | |
|---|---|---|---|---|
| Substrate | $K_m$(nM) | $V_{max}$(fmol/min) | $K_m$(nM) | $V_{max}$(fmol/min) |
| Primer:template[d] | 10 | 7.4 | 8 | 7.4 |
| R6G-ddATP[c] | 0.33 | 6 | 0.35 | 9 |
| TAMRA-ddATP[c] | 0.9 | 1.9 | 0.6 | 1.9 |
| TAMRA-ddCTP[b] | 1 | 3.3 | 0.3 | 2.3 |

Figure 18:
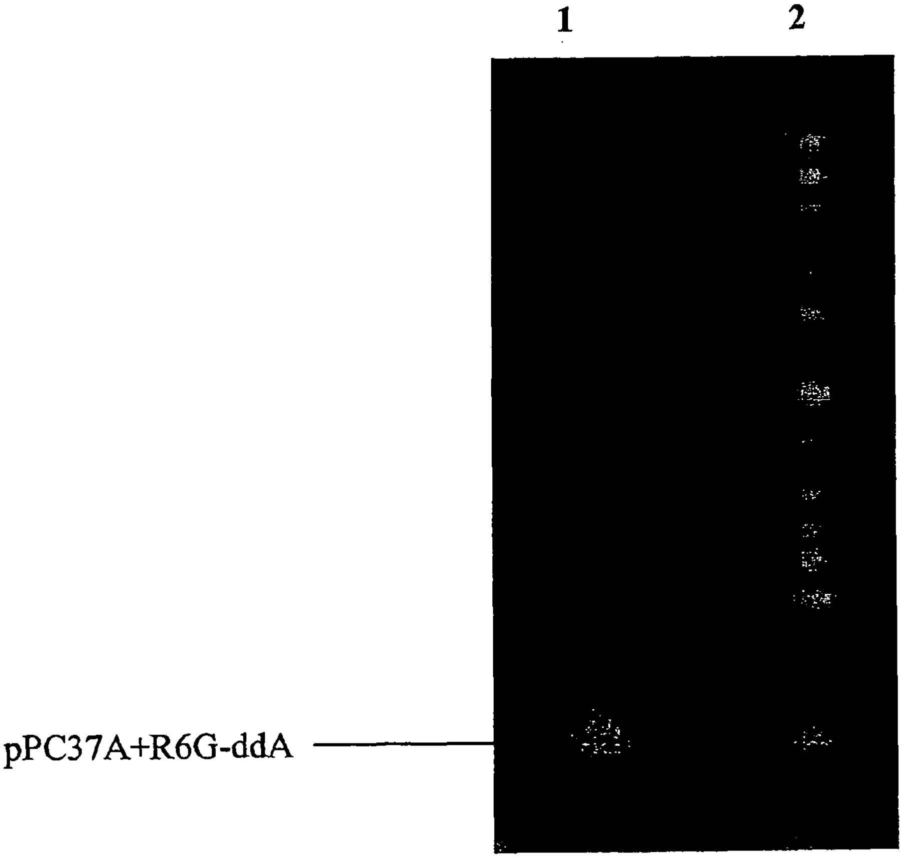
FIG. 18. Incubation of PCR amplified fragments on Strataprep columns with CIAP helps purify fragments prior to minisequencing. 1 unit of JDF-3 P410L/A485T was incubated in presence of 0.05 μM R6G-ddATP, 0.15 pmol pPC37A, and 0.02 pmol of a 4 kb PCR fragment amplified from human genomic DNA. The PCR product was purified on a StrataPrep column, either with (1) or without (2) CIAP treatment, as described in the Experimental Protocol.

[a]All values have ±<30% error and are obtained from at least two independent experiments.
[b]pBL25C:pBluescript
[c]BL34A:pBluescript
[d]pBL31G:pBluescript iii. Fidelity:

Fidelity was determined as the tendency of a DNA polymerase to incorporate the correct nucleotide in the presence of increasing amounts of a non-complementary nucleotide. These assays employed constant amounts of primer:template, an unlabeled complementary ddNTP and DNA polymerase, and various concentrations of a rhodamine-labeled non-complementary ddNTP, as described in the Experimental Protocol. The amount of misextended primers is plotted against the ratio of rhodamine-labeled incorrect ddNTP/unlabeled correct ddNTP (FIG. 18 panels A and B). We performed similar assays for all possible mispairs (Table IX).

TABLE IX

All possible mispairs.

| | | | |
|---|---|---|---|
| ddG:dT | ddT:dC | **ddC:dA** | **ddA:dG** |
| **ddT:dT** | **ddC:dC** | **ddA:dA** | **ddG:dG** |

The two mispairs indicated in bold are formed more efficiently by Taq F667Y DNA polymerase compared to JDF-3 P410L/A485T mutant.

The two mispairs, ddT:dC and ddG:dT, are formed at a significantly higher frequency (3 or 20 fold) by Taq F667Y mutants (ThermoSequenase and AmpliTaq FS) compared to JDF-3 P410L/A485T (FIG. 18 panels A and B). The other mispairs are formed less frequently and at a similar rate for JDF-3 P410L/A485T and Taq F667Y.

Similar rates of ddG:dT mispair formation were obtained using AmpliTaqFS (Taq F667Y mutant; ABI). AmpliTaqFS is only available in a mixture containing dye-ddNTPs and reaction buffer (SNaPshot kit; ABI). In order to test AmpliTaqFS, we removed dye-ddNTPs by adding 0.5 unit of SAP to 5 μl of the SnaPshot kit mix, followed by incubations at 37° C. for 30 minutes and at 72° C. for 15 minutes. The resulting mix, free of dye-ddNTPs, was then used in fidelity assays.

In order to establish that this difference in fidelity is not sequence specific, we performed similar experiments with two other primer:template systems (pBL25C:Temp-T and pPC34A:4 kb PCR amplified fragment) and obtained similar misincorporation rates for both enzymes (data not shown). We also obtained similar misincorporation rates using TAMRA-labeled ddNTPs as the incorrect ddNTP (data not shown). Therefore, the lower fidelity exhibited by Taq F667Y DNA polymerase is neither sequence specific nor due to increased misincorporation of R110 dyes.

To gain more insight into the mechanism of lower fidelity, we determined the misinsertion frequency for the mispair ddG:dT, which was evaluated in terms of relative $K_m$ and $V_{max}$ values for the wrong versus correct dye-ddNTP. Efficiency of nucleotide misinsertion was determined opposite a DNA template dT, primed with a 34-nucleotide oligomer (pBL34A). Apparent Michaelis constant ($K_m$) and maximum velocity ($V_{max}$) and relative insertion frequencies were measured for ddATP and ddGTP (Table X).

TABLE X

Kinetic Parameters[a] of TAMRA-ddATP insertion versus TAMRA-ddGTP misinsertion.

| DNA polymerase | I.E.[b] ($V_{max}/K_m$) | M.E.[b] ($V_{max}/K_m$) | M.F.[b] (M.E./I.E.) |
|---|---|---|---|
| JDF-3 P410L/A485T | 1.9/0.9 = 2.1 | 4.7/700 = 0.0067 | 0.003 |
| ThermoSequenase (Taq F667Y) | 1.9/0.6 = 3.2 | 16.9/100 = 0.169 | 0.053 |

[a]All values have ±<30% error and are obtained from 3 independent experiments.
[b]I.E., M.E. and M.F. are insertion efficiency, misinsertion efficiency and misinsertion frequency, respectively.

As shown in Table X, the misinsertion frequency of Taq F667Y for ddG:dT is significantly (~17 fold) higher than that exhibited by JDF-3 P410L/A485T. This difference is mostly due to differences in $K_m$ for the wrong dye-ddNTP•primer: template ternary complex. The Taq F667Y mutant exhibits a 7-fold lower $K_m$ (higher binding affinity) for wrong nucleotide (ddGTP) opposite dT, compared to the JDF-3 P410L/A485T mutant.

iv. Development of a Minisequencing Kit:

There are five major steps involved in SNP detection by minisequencing and gel electrophoresis: (i) extraction of DNA from blood or tissue samples; (ii) PCR amplification of specific fragments of genomic DNA containing SNPs; (iii) treatment of PCR products prior to minisequencing to remove unreacted PCR primers and dNTPs; (iv) minisequencing of PCR products and purification of extended primers; (v) analysis of fluorescent labeled primers using gel electrophoresis and GeneScan software (ABI). Here, we have optimized steps (iii) and (iv), and developed a minisequencing kit containing enzyme, reaction buffer, rhodamine labeled-ddNTPs, and a control primer:template system.

To optimize step iii, we used three different approaches to purify PCR products from unreacted PCR primers and dNTPs prior to minisequencing as described in the Experimental Protocol. We found that DNA templates purified using StrataPrep columns without CIAP treatment were contaminated with enough residual dNTPs to interfere with subsequent minisequencing. In the presence of trace amounts of contaminating dNTPs, sequencing ladders were produced instead of a single extended primer (FIG. 18, lane 2). The same problem was also observed using Qiagen's QIAquick PCR purification columns (data not shown). However, adding CIAP directly to PCR products, bound to StrataPrep columns, effectively removed residual dNTPs, and the eluted DNA after heat treatment (15 minutes at 72° C.) was suitable for minisequencing applications (FIG. 18, lane 1).

Figure 19:
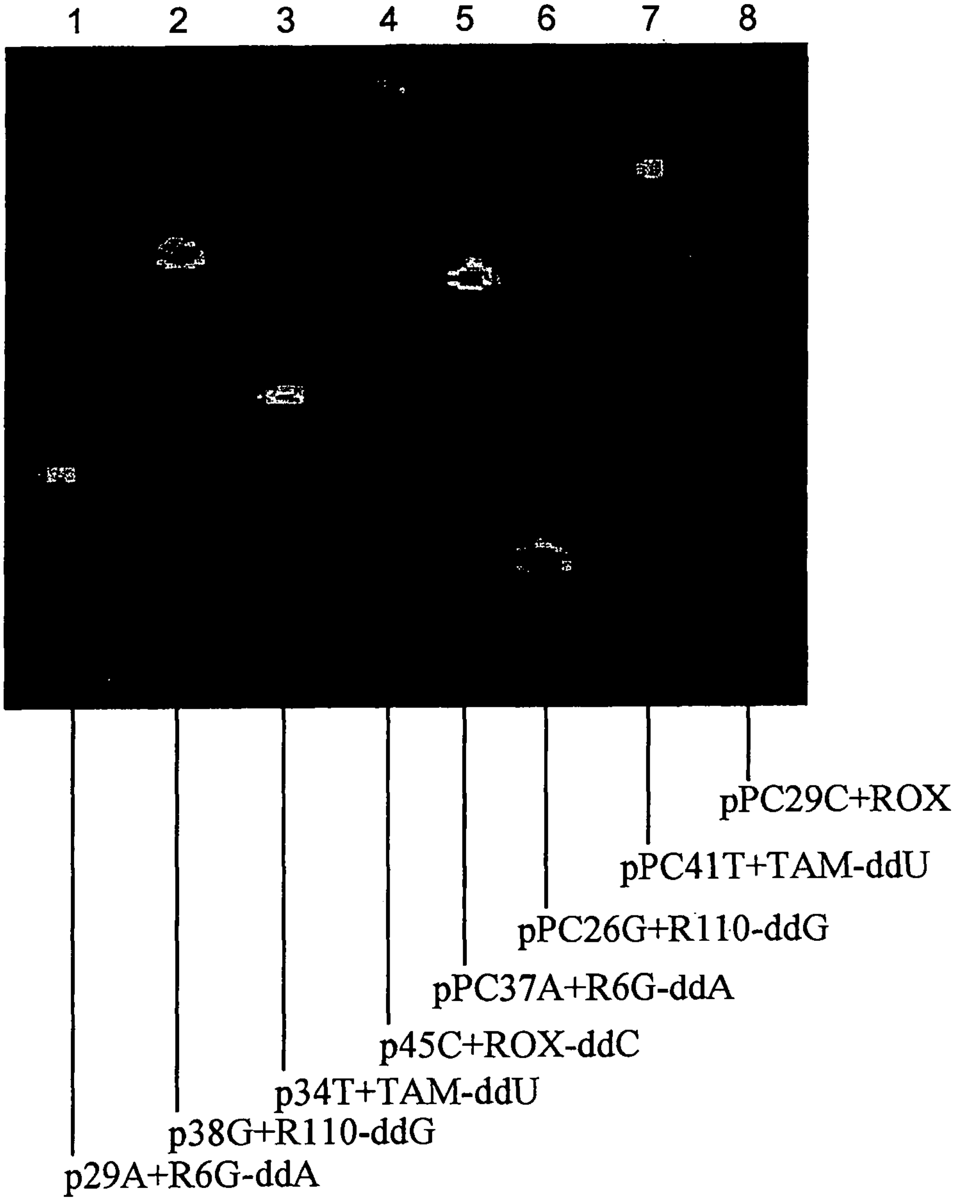
FIG. 19. Minisequencing using JDF-3 P410L/A485T and two different primer:template systems. All reactions contained 1 unit of JDF-3 P410L/A485T, 0.04 μM R6G-ddA, R110-ddG, ROX-ddC, and 0.2 μM TAM-ddU in 1× reaction buffer. Reactions 1 through 4 also contained 0.4 pmol pGEM and 1 μl of p29A, p38G, p34T, and p45C (ABI #4312166), respectively. Reactions 5 through 8 contained 0.02 pmol of 4 kb PCR product and 0.15 pmol pPC37A, pPC26G, pPC41T, and pPC29C, respectively. Reactions were incubated as described in the Experimental Protocol.

Three different primer:template systems were used to optimize the JDF-3 P410L/A485T minisequencing kit, including pBluescript with primers pBL34A, pBL31G, pBL28T, and pBL25C (Table VII) which will be used as the kit controls (FIG. 22); a 4 kb PCR fragment with primers pPC37A, pPC41T, pPC26G, and pPC29C; and pGEM with four control primers (ABI #4312166) (FIG. 19). Our kit protocol employs four rhodamine-labeled ddNTPs in one reaction (see Experimental Protocol section), although it could be adapted in the future for customers interested in performing four separate reactions, each with a different rhodamine labeled-ddNTP (plus three unlabeled ddNTPs).

The concentrations of JDF-3 P410L/A485T, dye-ddNTPs, primer, and template were optimized for minisequencing and fluorescence detection by ABI 377 sequencer (see Experimental protocol for optimized conditions). Higher concentrations of enzyme, dye-ddNTPs, and primer:template will increase the fluorescent signal. However, such increases in signal saturate the ABI 377 detector and result in dye bleed-through (more than one color showing in one spot).

Figure 20:
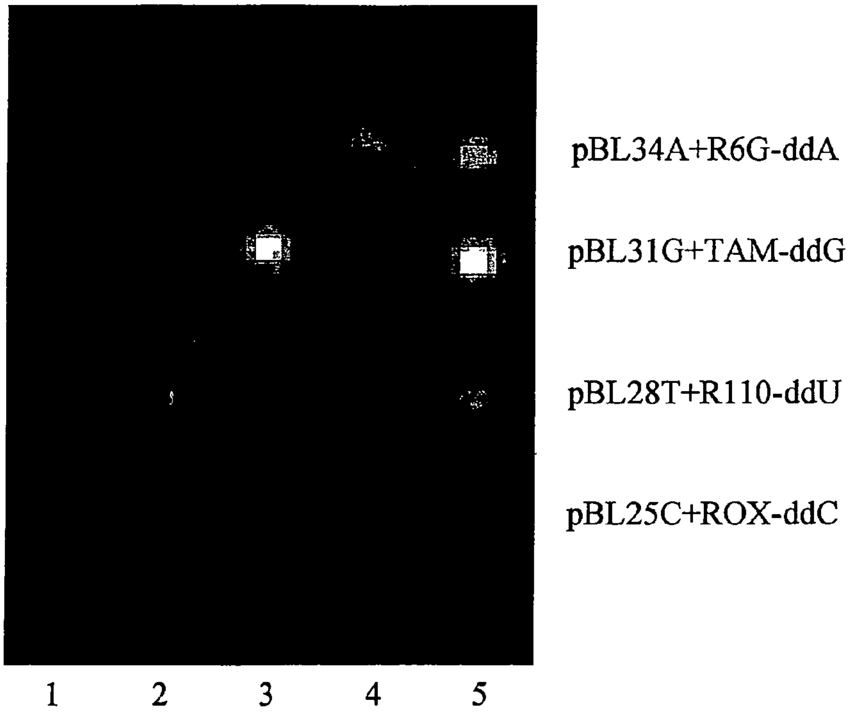
FIG. 20. Multiplexing does not affect the signal strength generated by JDF-3 P410L/A485T. All reactions contained 1 unit of JDF-3 P410L/A485T, 0.25 pmol pBluescript, 0.04 μM R6G-ddA, TAM-ddG, ROX-ddC, and 0.2 μM R110-ddU in 1× reaction buffer. Reactions 1, 2, 3, 4, contained 0.15 pmol pBL25C, pBL28T, pBL31G, and pBL34A, respectively. Reaction 5 contained 0.15 pmol of all four primers. Reactions were incubated as described in the Experimental Protocol.

Different rhodamine dye/ddNTP combinations can be used with JDF-3 P410L/A485T (FIG. 20; TAM-ddG and R110-ddU instead of R110-ddG and TAM-ddUTP). However, the dye/base combination proposed in the Experimental Protocol (R6G-ddATP, R110-ddGTP, ROX-ddCTP, and TAMRA-ddUTP) exhibited the greatest signal uniformity with three different sets of primer:templates. Since JDF-3 P410L/A485T slightly discriminates against incorporation of ddUTP (FIG. 16 panels A and B), ddUTP is used at 5 times the concentration of other ddNTPs. Moreover, preliminary data shows that JDF-3 P410L/A485T can incorporate dyes other than rhodamine (e.g., cyanine dyes). It is imperative to point out that primer:template sequence could also affect the efficiency of dye-ddNTP incorporation and therefore the signal uniformity.

β-testing of JDF-3 P410L/A485T at Stanford genome technology center was performed using Cy3-ddATP and Cy5-ddCTP, and immobilized primers on Zyomyx aldehyde slides.

The following protocol (Applied Biosystems) should be used in designing primers for minisequencing: (1) Since SNP validation by minisequencing is not flexible with respect to the location of the primer, the negative strand (−) of DNA can be used for primer design if positive strand (+) is difficult to assay; (2) Design primers of 18 nucleotides in length or greater with melting temperatures of 45° C. or greater; (3) Check primers for extendable hairpin structures and primer dimer formation; (4) Primers should be PAGE purified; (5) A negative control (lacking DNA template) should be run when evaluating a new primer.

We also tested whether JDF-3 P410L/A485 could be used for multiplexing (several primers with one template in a single reaction) without the signal strength being affected. FIG. 20 indicates that the signal strength remained unaltered when four primers were used to detect four SNPs in the same template DNA. It should be pointed out that we did not optimize the kit for multiplexing, but this application may be further developed in future generations of the kit.

We then determined the amount of SAP or CIAP that can be used to purify minisequencing products from unincorporated rhodamine labeled-ddNTPs. 0.5 unit of SAP or 1 unit of CIAP in 10 μl minisequencing reactions degrades all unincorporated dye-ddNTPs. Using suboptimal units of alkaline phosphatase could result in fluorescent signal from unincorporated dye-ddNTPs, thereby masking the SNP signal.

Figure 21:
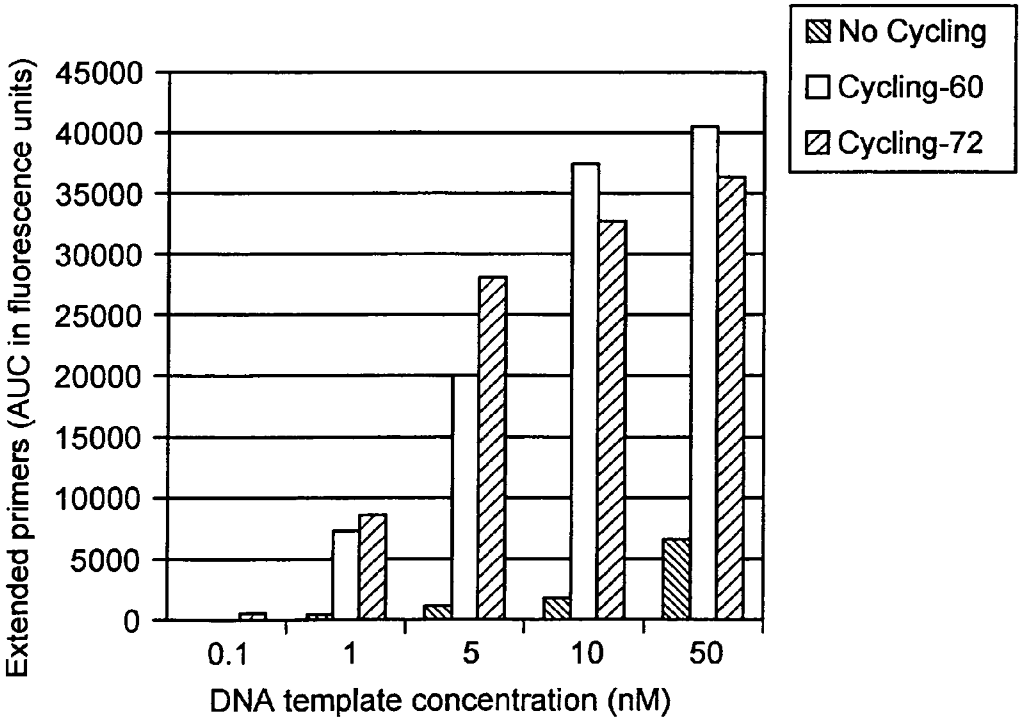
FIG. 21. Thermal cycling improves minisequencing signal significantly. 1 unit of JDF-3 P410L/A485T was incubated in presence of 15 nM pBL25C, 100 nM ROX-ddCTP, and 0.1, 1, 5, 10, or 50 nM pBluescript in five separate reactions. Incubations were performed using a Perkin-Elmer 9600 for one cycle of 96° C. for 2 min, 50° C. for 1 min, and 60° C. for 10 min, or 25 cycles of 96° C. for 10 s, 50° C. for 5 s, and 60° C. or 72° C. for 30 s. Reactions were purified from unincorporated ROX-ddCTP using SAP treatment and the products were analyzed and quantitated as described in the Experimental Protocol.

In optimizing the kit cycling conditions, we evaluated whether thermal cycling improved product yield. As FIG. 21 indicates, cycling with extension temperatures of 60° C. or 72° C. did not significantly alter enzyme activity. However, thermal cycling did improve the minisequencing signal compared to a single incubation at 60° C. for 10 minutes. The improved signal is expected when the concentration of DNA template is much lower than minisequencing primer. However, as FIG. 21 indicates, even when the minisequencing primer is saturated with DNA template, thermal cycling seems to improve signal, presumably because the minisequencing primer competes with the complementary strand of double-stranded DNA when annealing to the DNA template.

Figure 22A:
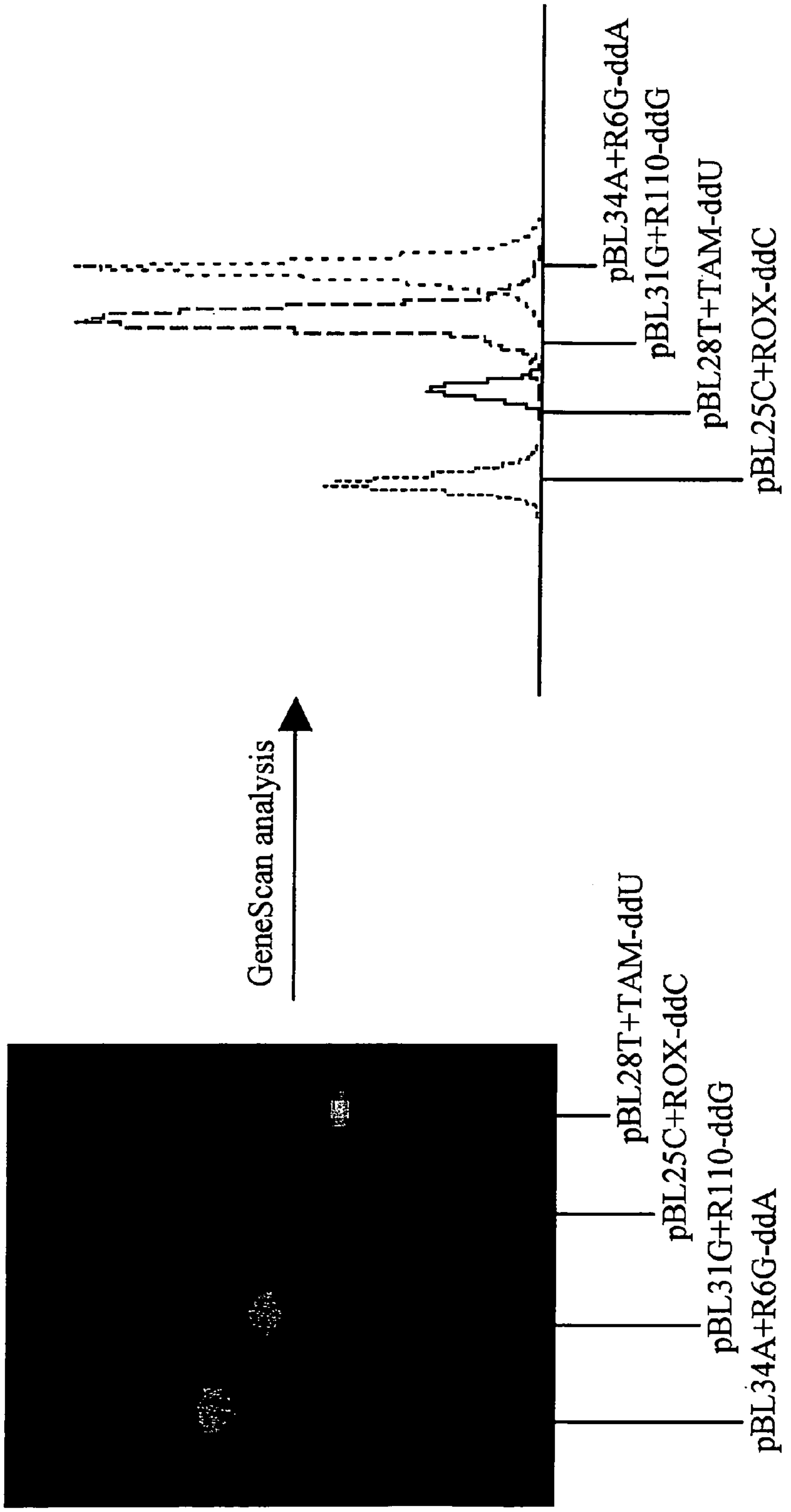
FIG. 22. Performance comparison of our minisequencing kit containing JDF-3 P410L/A485T to the SNaPshot kit from Applied Biosystems. (A) Minisequencing reactions contained 1 unit of JDF-3 P410L/A485T, 0.25 pmol pBluescript, 0.04 μM R6G-ddA, R110-ddG, and ROX-ddC, 0.2 μM TAMRA-ddU, and 0.15 pmol pBL34A, pBL31G, pBL25C, or pBL28T, in four separate reactions respectively. Reactions were incubated, purified and analyzed (using a rhodamine matrix) as described in the Experimental Protocol. (B) The SNaPshot kit was used with the same amount of primer:template as above. Since this kit utilizes dichloro-rhodamine labeled ddNTPs, a dichloro-rhodamine matrix was installed for analysis of the corresponding bands.
Figure 22B:
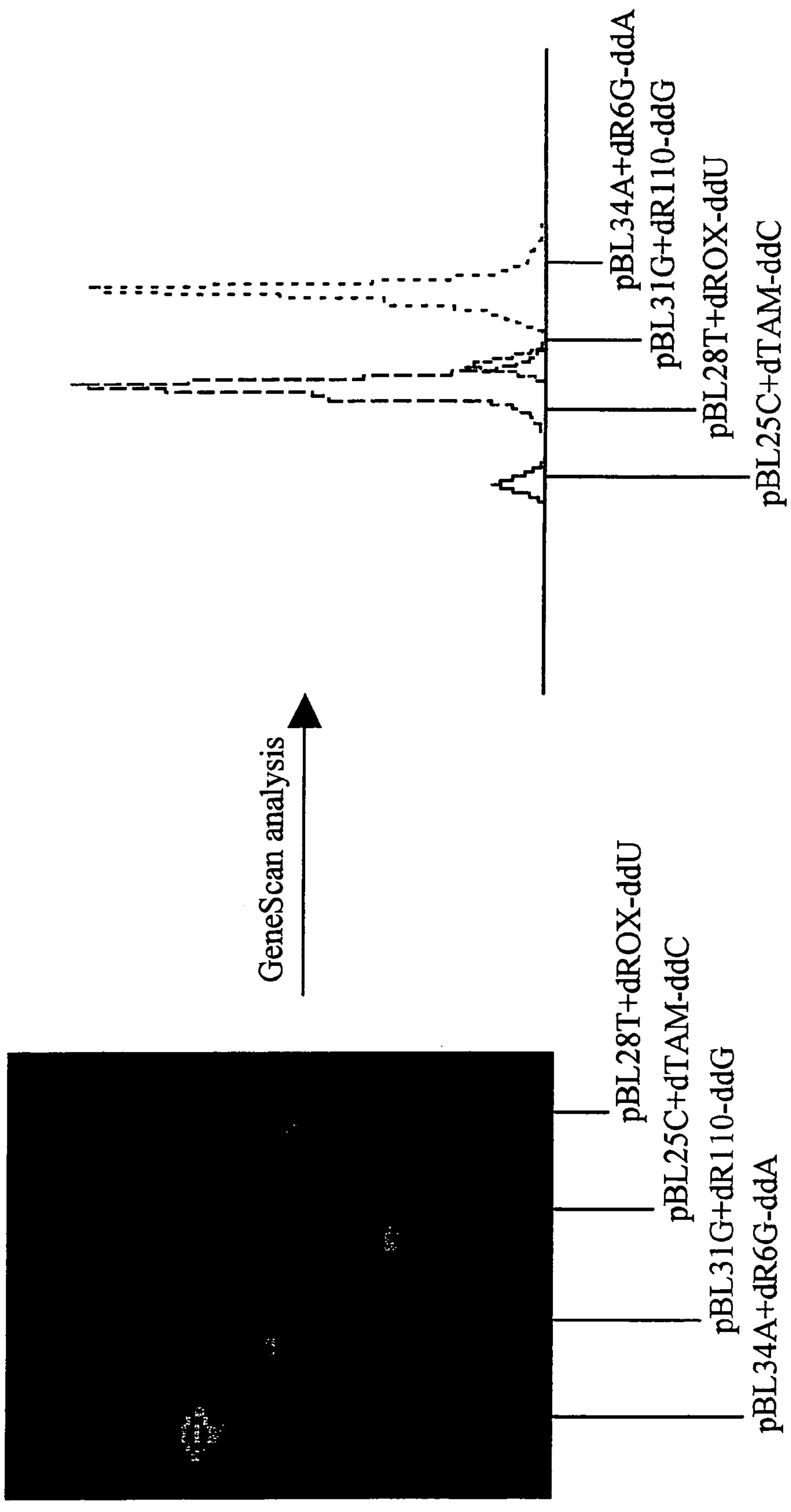

FIG. 22 shows the performance of our minisequencing kit compared to ABI's SNaPshot kit. Since our minisequencing kit employs rhodamine-labeled ddNTPs, a rhodamine dye matrix had to be installed on the ABI 377 sequencer to analyze product bands. In contrast, the SNaPshot kit utilizes dichloro-rhodamine labeled ddNTPs and a dichloro-rhodamine matrix was installed to analyze the products generated with the SNaPshot kit. As discussed above, our kit employs ROX-ddC and TAMRA-ddU instead of TAMRA-ddC and ROX-ddU (SNaPshot dye-ddNTPs) to improve ddU incorporation by JDF-3 P410L/A485T. ABI does not disclose the concentrations of AmpliTaq FS or dichloro-rhodamine labeled ddNTPs employed in the SNaPshot reaction mixture, so comparisons were simply carried out using the same primer:template amounts and each kit's recommended protocol. As shown in FIG. 22, our kit produces more uniform signals compared to the SnaPshot kit, which generated relatively low signals for ddC and ddG compared to ddA and ddU.

Example 4

This example shows the identification of alternative side chain substitutions at P410 that improve ddNTP incorporation.

Methods:

Mutagenesis.

Site directed mutagenesis of JDF-3 DNA polymerase P410 was carried out using JDF-3 141A/143A/pET plasmid DNA and the QuikChange Multi Kit (Stratagene). Amino acid P410 was randomized by incorporating the degenerate primer: 5' pTTT-CGT-AGT-CTC-TAC-NNX-TCA-ATC-ATA-ATC-ACC (SEQ ID NO:), where N=25% each G, C, A, and T and X=50% G and T. Thirty-two clones were randomly selected and plasmid DNA was prepared. The clones were sequenced using JDF-3 primer #3 to identify the amino acid substitution at 410. The following mutants were represented among the 32 random clones: 2 Met (ATG), 2 His (CAT), 2 Gln (CAG), 3 Gly (GGT), 1 Leu (CTG), 1 Trp (TGG), 1 Ser (TCT), 1 Thr (ACT), 1 Arg (CGT), and 1 Ile (ATT).

Polymerase Mutant Preparation:

Transformants were grown overnight in 1.5 ml LB plus 100 μg/ml ampicillin. The cells were collected by centrifugation and the pellets were resuspended in 50 μl of 50 mM Tris (pH 8.0). Lysozyme was added to a final concentration of 1 μg/ml, and the cells were lysed during a 10 minute incubation at 37° C., followed by 65° C. The heat-inactivated cell material was removed by centrifugation and the supernatants were assayed for dNTP and ddNTP incorporation.

ddNTP Incorporation Assay:

Reaction cocktails were prepared containing 1× cloned Pfu buffer, 250 μg/ml activated calf thymus DNA, 2.5 μM 3H-TTP, and 100 μM TTP. Four reaction cocktails were prepared with different ddNTP concentrations (0, 20, 40, and 80 μM each ddG, ddC, ddA) as follows:

| | 0 | 20 | 40 | 80 |
|---|---|---|---|---|
| dGTP, dCTP, dATP | 100 μM | 80 μM | 60 μM | 20 μM |
| ddGTP, ddCTP, ddATP | 0 | 20 μM | 40 μM | 80 μM |

Figure 23A:
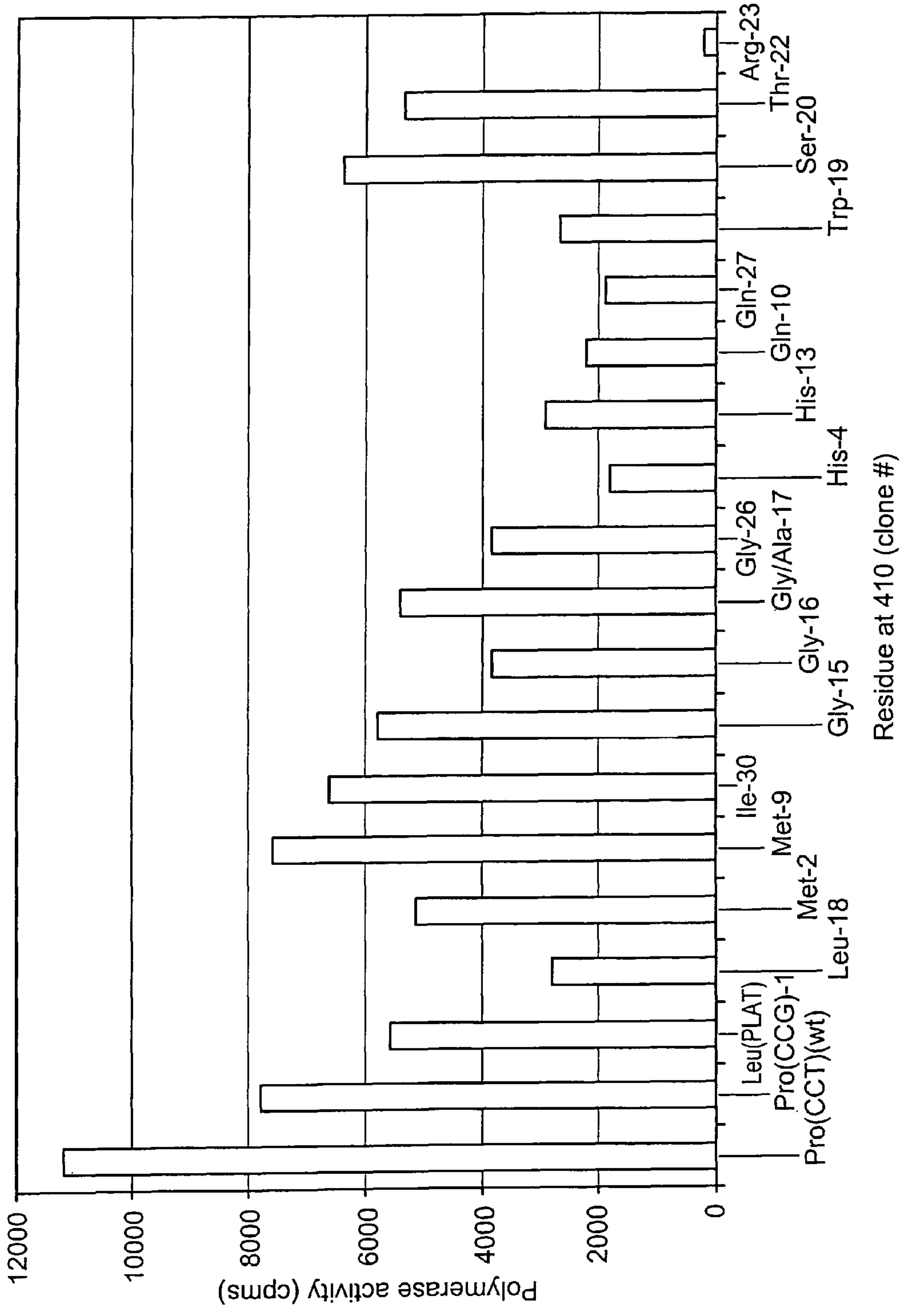
FIG. 23 shows the activity of JDF-3 DNA polymerase containing amino acid substitutions at position P410.
FIG. 23B: ddNTP incorporation was determined as percent activity in the presence of 20 μM each ddA, ddG, and ddC ("20"), as follows: (corrected cpms at 20 μM ddNTP)/(corrected cpms at 0 μM ddNTP).
Figure 23B:
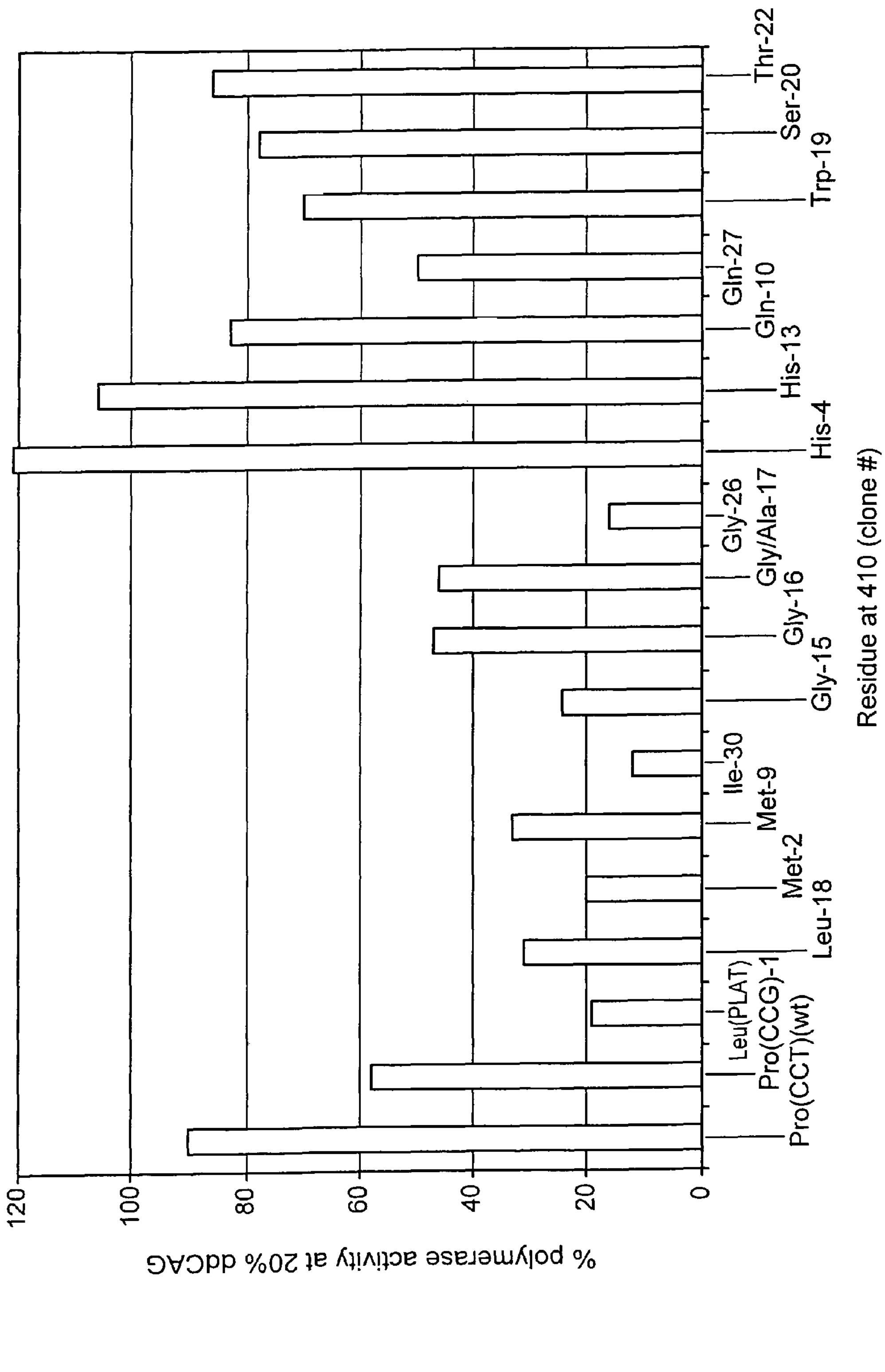

JDF-3 mutant extracts were diluted 1:1 in 1× cloned Pfu buffer, and then 10 μl aliquots of each sample were added to 20 μl of each reaction cocktail (0, 20, 40, and 80). The reactions were incubated at 72° C. for 30 minutes. Incorporated cpms were determined as described herein. Polymerase activity was expressed as corrected cpms of 3H-TTP incorporated into activated calf thymus DNA in 30 minutes in the presence of 100 μM each dNTP ("0"; FIG. 23A). ddNTP incorporation was determined as percent activity in the presence of 20 μM each ddA, ddG, and ddC ("20"), as follows: (corrected cpms at 20 μM ddNTP)/(corrected cpms at 0 μM ddNTP) (FIG. 23B).

Results:

Substituting P410 with Leu, Met, Ile, Gly, His, Gln, Trp, Ser, and Thr produced mutants that retained at least some detectable DNA polymerase activity. In contrast, replacing P410 with Arg appeared to completely inactivate JDF-3 (FIG. 23).

The mutants that incorporate ddNTPs more efficiently than the wild type JDF-3 D141A/E143A enzyme were P410L, P410M, P410I, and P410G. The P410L mutation was identified, as previously described herein, by random mutagenesis and plaque lift screening with $^{33}$P-ddNTPs. There was little-to-no improvement in ddNTP incorporation when P410 was replaced by His, Gln, Trp, Ser, or Thr.

In general, replacing P410 with non-polar side chains (M, G, L, I) improves ddNTP incorporation, while replacing P410 with polar, uncharged (W, Q, S, T, C) has no affect whereas replacing P410 with charged polar side chains inactivates the DNA polymerase (R) or reduces ddNTP incorporation (H).

Example 5

Generation and Analysis of JDF-3 DNA Polymerase Double Mutants

The entire gene encoding JDF-3 DNA polymerase was amplified using primers 721 and 923 (Table 1) and subjected to random mutagenesis as described herein. A 3'-5' exonuclease deficient mutant (E143A) of JDF-3 DNA polymerase was used in these studies to prevent removal of nucleotide analogs after incorporation. A lambda phage library of JDF-3 DNA polymerase mutants was screened for improved incorporation of $\alpha^{33}$P-ddNTPs, and the most active clones were isolated and sequenced. DNA sequence analysis showed that the most active clones contained either a P410L or A485T mutation, in addition to other mutations.

Partially-purified JDF-3 mutants were then analyzed with respect to relative sensitivity ($I_{50\%}$) to low levels of each of the four ddNTPs in a nucleotide incorporation assay employing dNTPs (3H-TTP tracer). $I_{50\%}$ values were determined as the concentration of each ddNTP that inhibits DNA polymerase activity by 50%. $I_{50\%}$ values for wild type (3'-5' exo$^-$) JDF-3 DNA polymerase were 160 μM, 110 μM, and >160 μM for ddA, ddG, and ddC, respectively (ddT data omitted due to interference from selective uptake of $^3$H-TTP tracer in the presence of ddTTP inhibitor). In comparison, $I_{50\%}$ values for ddA, ddG, and ddC were 30 μM, 25 μM, and 40 μM for a P410L mutant and 40 μM, 25 μM, and 25 μM for an A485T mutant, respectively. Therefore, preliminary data indicated that separate mutations at either P410 or A485 produces a modest (≥4- to 6-fold) reduction in discrimination against all four ddNTPs.

Since the JDF-3 mutants isolated from the random library contained mutations other than P410L and A485T, that could affect activity, stability, or ddNTP incorporation, each mutation was introduced separately into a 3'-5' exonuclease minus (D141A/E143A) version of JDF-3 DNA polymerase by site-directed mutagenesis. A double mutant containing the P410L and A485T mutations was also constructed. Preliminary testing ($I_{50\%}$) of partially purified mutants confirmed that the P410L and A485T mutations were responsible for reduced ddNTP discrimination. No improvement in ddNTP incorporation was observed using other JDF-3 DNA polymerase point mutants (data not shown).

Figure 24:
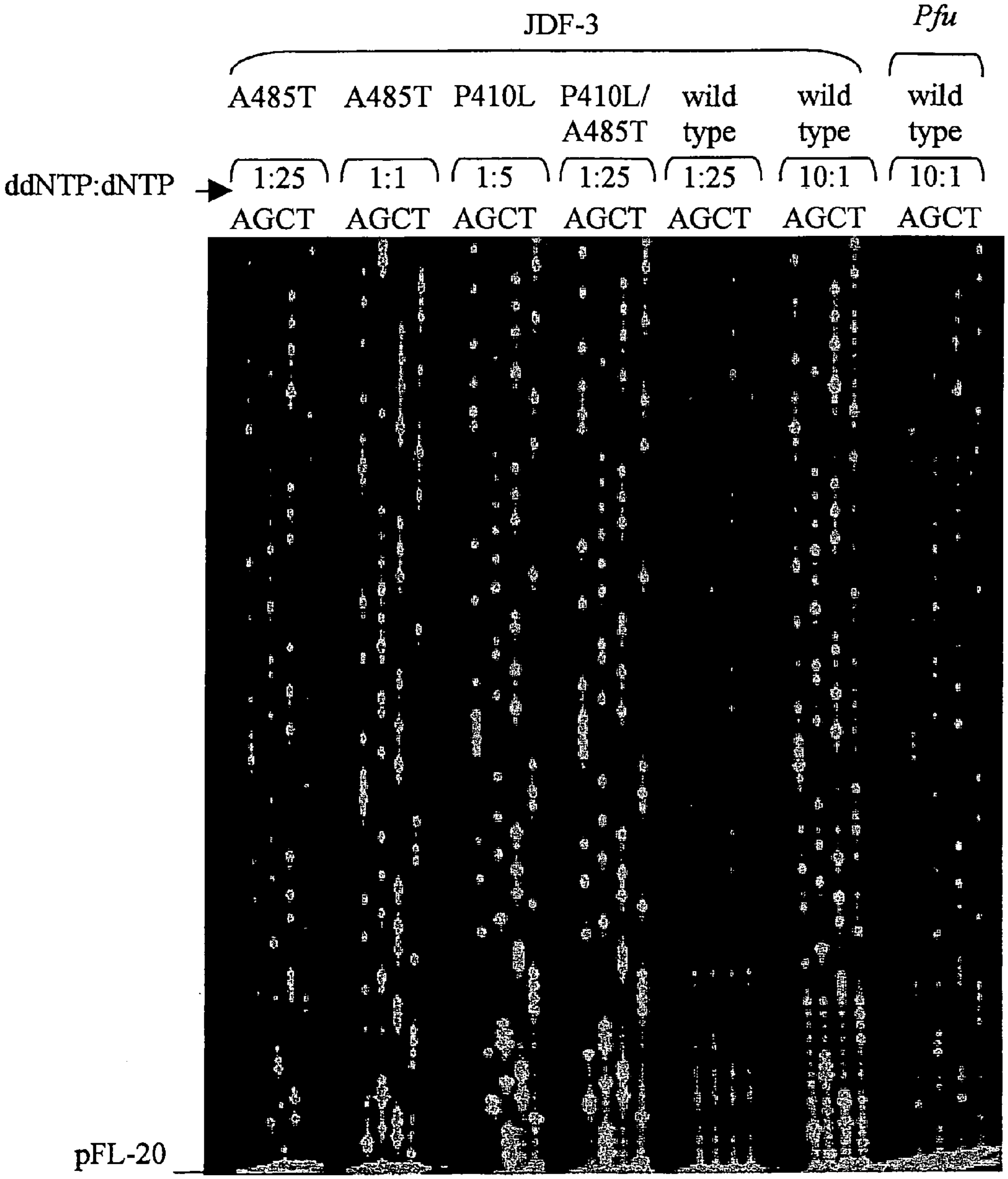
FIG. 24. Sequencing patterns generated with exonuclease minus versions of wild type JDF-3 DNA polymerase, JDF-3 DNA polymerase mutants, and Pfu DNA polymerase at the indicated ddNTP:dNTP ratios. Dideoxy sequencing reactions were performed as described in the Example 5.

Relative Improvement in ddNTP Uptake by P410 and A485 Mutations:

Single (P410L, A485T) and double (P410/A485T) mutants were purified (as described in Hansen, C. J. et al. (2001). Compositions and methods utilizing DNA polymerases; WO 0132887 and relative improvement in ddNTP incorporation was quantified in dye-primer sequencing reactions. Relative ddNTP incorporation efficiencies were determined by comparing sequencing ladders produced at varying ddNTPs: dNTPs ratios, ranging from 10:1 to 1:25 (FIG. 24). The ddNTP:dNTP ratios that give an equivalent banding pattern (in terms of product length, signal strength, and lack of non-specific termination) were compared between wild type and mutant enzymes.

For the JDF-3 P410L/A485T mutant, sequencing ladders produced at 1:25 ddNTP:dNTP are of similar pattern compared to those generated with the JDF-3 P410L mutant at 1:5 ddNTP:dNTP and the JDF-3 A485T mutant at 1:1 ddNTP: dNTP (FIG. 24). Therefore, the double mutant incorporates ddNTPs 5- and 25-fold more efficiently than the single P410L and A485T mutants, respectively, indicating that the combination of mutations produces an additive effect. Wild type ($exo^-$) JDF-3 DNA polymerase and the P410L/A485T mutant produced comparable sequencing patterns at 10:1 and 1:25 ddNTP:dNTP ratios, respectively, indicating that the double mutant exhibits a 250-fold improvement in ddNTP incorporation compared to wild type. Moreover, little non-specific termination was observed in ladders produced with the JDF-3 P410L/A485T mutant. Additional experiments showed that 3'-5' $exo^-$ Pfu DNA polymerase required a ddNTP:dNTP ratio of >50:1 to produce comparable sequencing ladders to $exo^-$ JDF-3 DNA polymerase at a 10:1 ddNTP:dNTP ratio. These results indicate that wild type JDF-3 DNA polymerase is inherently more efficient at incorporating ddNTPs compared to Pfu DNA polymerase.

Figure 26B:
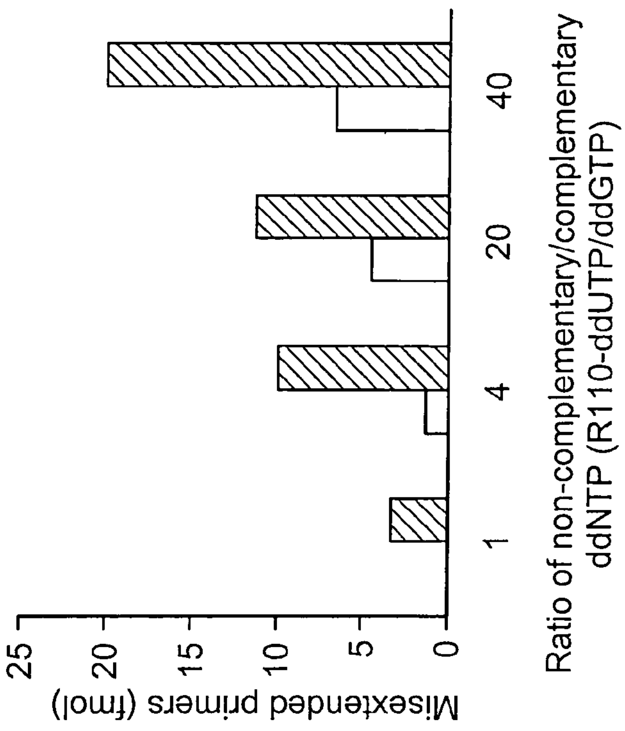
FIG. 26. Misinsertion of rhodamine labeled-ddNTPs by JDF-3 P410L/A485T and Taq F667Y (Thermo Sequenase) DNA polymerases. Reactions in panels A and B contained 1 unit of JDF-3 P410L/A485T or Taq F667Y, 15 nM primer:template (panel A: pBL34A:pBluescript II; panel B: pBL31G:pBluescript II), 25 nM of unlabeled complementary ddNTP (panelA: ddATP; panel B: ddGTP), and either 25, 100, 500, or 1000 nM of dye-labeled non-complementary ddNTP (panel A: R110-ddGTP; panel B: R110-ddUTP) in four separate reactions. Reactions were incubated and analyzed as described in the Example 5. Panel C shows the sequencing gel from which the data in panel A was derived.
Figure 26A:
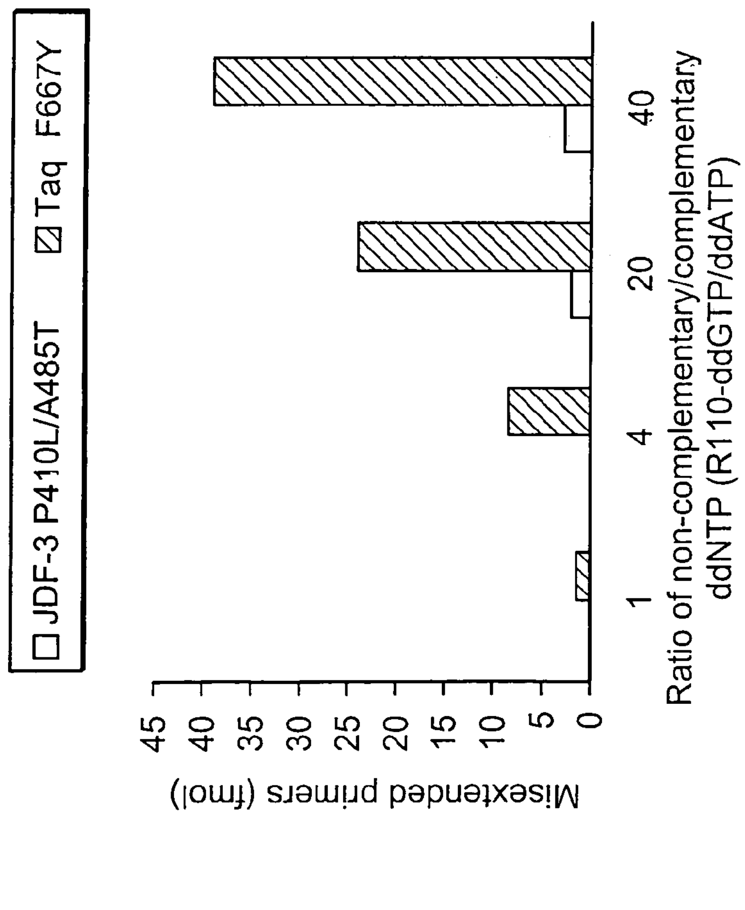
Figure 26C:
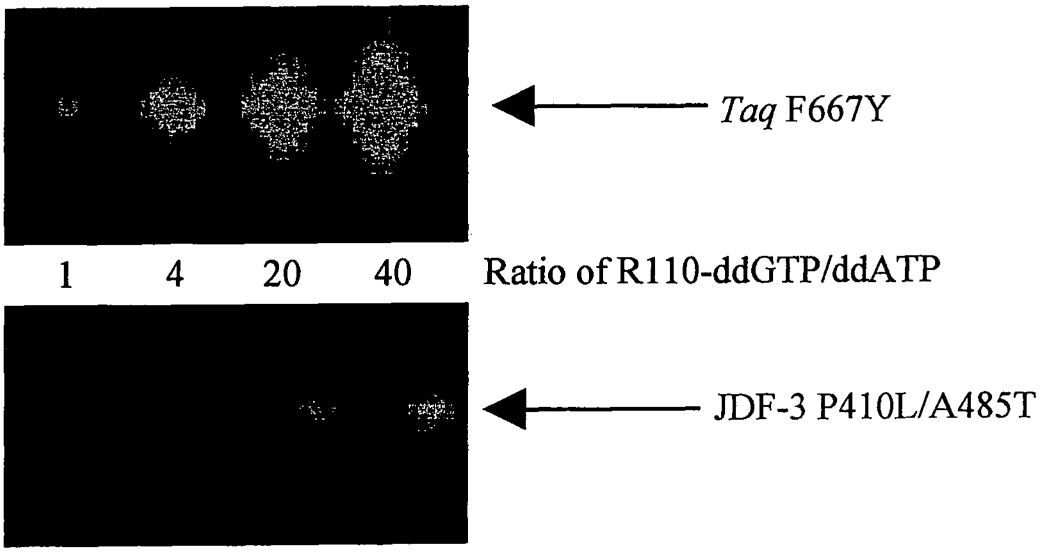

Kinetic Parameters for Dye-ddNTP Incorporation:

Vent A488[7] and Pfu A486 mutations (Evans, S. J. et al. (2000). Nucleic Acids Res. 28, 1059-66) provided moderate improvements (15- and 150-fold, respectively, relative to wild type) in ddNTP incorporation compared to the F667Y mutation in Taq (3000-8000-fold improvement relative to wild type; Tabor, S. et al. Proc. Natl. Acad. Sci. USA 92, 6339-43). However, in the absence of direct side-by-side comparisons, it was difficult to assess relative affinities of Taq and archaeal DNA polymerase mutants for ddNTPs. Moreover, the Vent and Pfu studies did not address potential improvements in dye-labeled ddNTP incorporation, which is relevant for fluorescent DNA sequencing applications. The kinetic parameters of the Taq F667Y mutant were therefore compared with those of the JDF-3 P410L/A485T in single-base extension assays (FIG. 26 and Table 2).

$K_m$ and $V_{max}$ values were determined for primer:template and rhodamine-ddNTPs as described previously for dNTPs by Patel, P. H. et al. (2001). J. Biol. Chem. 276, 5044-51. Incorporation was monitored at 60° C. (~$T_m$ of primers used in primer extension reactions) due to practical limitations imposed by primer-template stability. Reaction time (10 min.) and enzyme amount (0.1 U) were selected to ensure that reactions were in the linear range over the range of primer:template and dye-terminator concentrations tested (data not shown). FIG. 26 (panels A and B) shows the incorporation of R6G- and TAMRA-ddATP by 0.1 units of JDF-3P410L/A485T and Taq F667Y mutants, respectively, while Table 2 compares the kinetic properties of the two enzymes in single-base extension assays. $K_m$ values for rhodamine-labeled ddNTPs ranged from 0.3 to 1 nM for the JDF-3 P410L/A485T mutant and from 0.3 to 0.6 nM for the Taq F667Y mutants, depending on the dye (R6G, TAMRA) or base (ddATP, ddCTP) tested. This comparison establishes that the JDF-3 P410L/A485T and Taq F667 mutants exhibit similar steady-state kinetic parameters for both primer:template and rhodamine-ddNTP substrates.

Fidelity of ddNTP and Dye-ddNTP Incorporation:

Archaeal Family B DNA polymerases, such as Pfu and JDF-3, are known to have higher replication fidelity than non-proofreading eubacterial DNA polymerases such as Taq due the presence of an associated 3'-5' exonuclease-dependent proofreading activity (Cline, J. et al. (1996). Nucleic Acids Res. 24, 3546-51). However, 3'-5' exonuclease minus versions of Pfu and JDF-3 DNA polymerase exhibit higher error rates than Taq DNA polymerase (Cline, J. et al. (1996). Nucleic Acids Res. 24, 3546-51), suggesting that misincorporation and/or mispair extension rates may be higher in archaeal DNA polymerases, but compensated for by the associated editing function. In addition to exhibiting potentially higher misincorporation rates, mutations near the active site of $exo^-$ JDF-3 DNA polymerase (P410L, A485T) could reduce insertion fidelity with respect to unlabeled and/or dye-labeled ddNTPs.

Figure 27A:
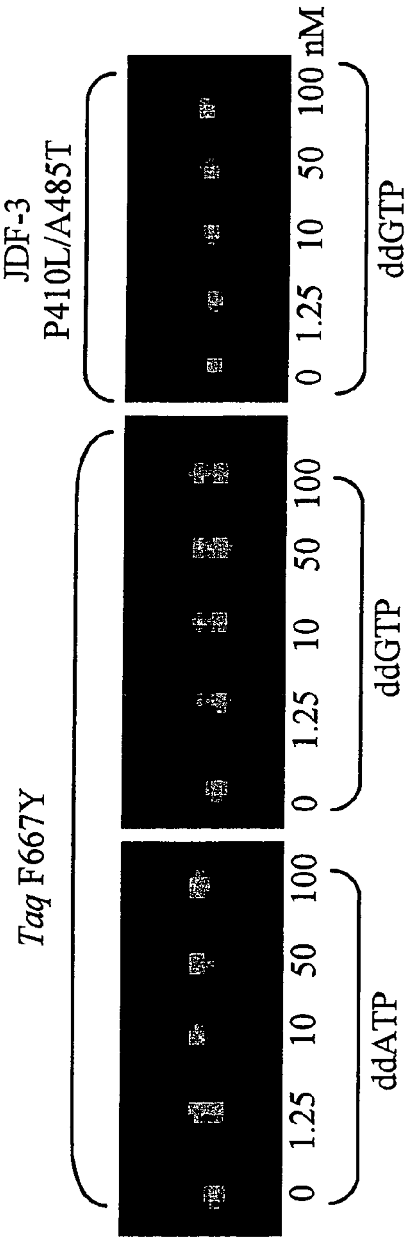
FIG. 27. Misinsertion of unlabeled ddNTPs by JDF-3 P410L/A485T and Taq F667Y (Thermo Sequenase) DNA polymerases. Reactions in panel A contained 1 unit of either Taq F667Y or JDF-3 P410L/A485T, 2.5 nM primer-template (pFL35:pBluescript), and a complementary (A) or non-complementary (G) ddNTP at concentrations of 0, 1.25, 10, 50 or 100 nM. Reactions in panel B contained 1 unit of either Taq F667Y or JDF-3 P410L/A485T, 2.5 nM primer-template (pFL35:pBluescript A562G), and a complementary (G) or non-complementary (T) ddNTP at concentrations of 0, 1.25, 10, 50, or 100 nM. Reactions were incubated and analyzed as described in Example 5.
Figure 27B:
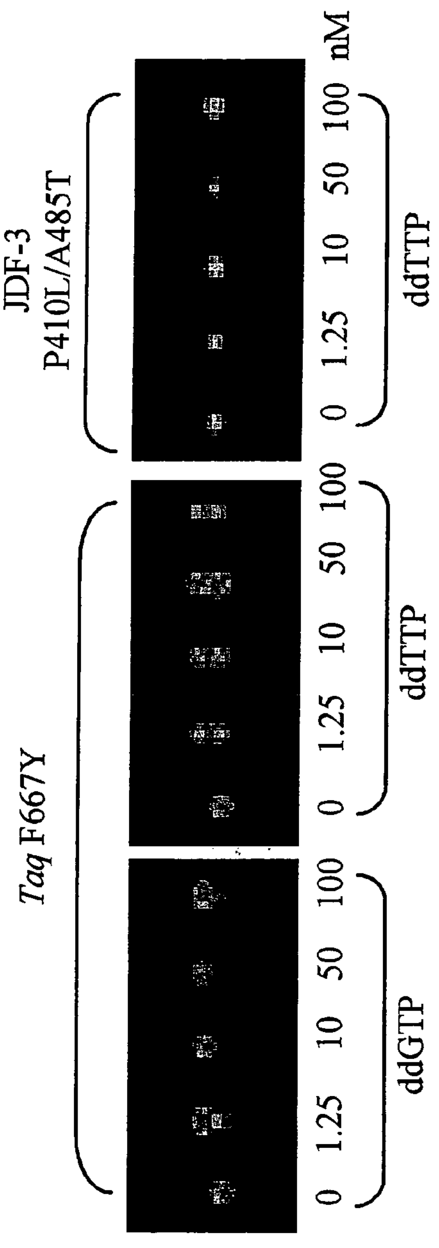

To address these concerns, the insertion fidelity of the JDF-3 P410L/A485T and Taq F667Y mutants was compared. In the first set of fidelity assays, a constant amount of primer:template, an unlabeled complementary ddNTP, and increasing concentrations of R110-labeled non-complementary ddNTP was used (Materials and Methods). The amount (1 U) of JDF3 P410L/A485T and Taq F667Y DNA polymerases used in these misincorporation assays gave equal rates of incorporation for correct ddNTPs (data not shown), indicating that misincorporation of incorrect ddNTPs is due to infidelity. The amount of misextended primers was determined and plotted against the ratio of R110-labeled incorrect ddNTP/unlabeled correct ddNTP (FIG. 27, panels A and B). Similar assays for all 12 possible mispairs was performed (ddG:dT, ddT:dG, ddT:dC, ddC:dT, ddC:dA, ddA:dC, ddA:dG, ddG:dA, ddT:dT, ddC:dC, ddA:dA, ddG:dG). Two mispairs, ddT:dC and ddG:dT, are formed at a significantly higher frequency (3- and 20-fold, respectively) by Taq F667Y compared to JDF-3 P410L/A485T (FIG. 27, panels A and B). The other mispairs are formed less frequently, and at similar rates for the JDF-3 P410L/A485T and Taq F667Y mutants (data not shown).

In order to establish that this difference in fidelity is not sequence specific, similar experiments with two other primer:template systems (pBL25C:Temp-T and pBL25C:Temp-C) were performed. In both cases, Taq exhibited a significantly greater tendency to generate ddG:dT and ddT:dC mispairs compared to JDF-3 P410L/A485T (data not shown). Moreover, similar misincorporation rates using TAMRA-labeled ddNTPs were obtained, instead of R110-labeled ddNTPs as the incorrect ddNTP (data not shown), indicating that misinsertion rates are unrelated to selective misincorporation of R110 dye and/or R110-T/C combinations.

A second set of fidelity assays was conducted to address the contribution of rhodamine dye to high ddG:dT and ddT:dC misinsertion frequency. A fluorescently labeled primer (2.5 nM pFL35) opposite dT in the template strand was extended, in reactions containing either correct (ddA) or incorrect (ddG) unlabeled ddNTPs (at concentrations of 1.25 nM to 10 nM) (FIG. 4 panel A). Similar experiments were performed in which primer extension occurred opposite dC in the template strand, in the presence of correct (ddG) or incorrect (ddT) unlabeled ddNTPs (FIG. 28 panel B). Incorporation of ddNMP at the 3'-end of the primer was detected as a shift in primer mobility. The amount (1 U) of JDF3 P410L/A485T and Taq F667Y DNA polymerases used in these misincorporation assays gave equal rates of incorporation for correct ddNTPs (data not shown), indicating that observed misincorporation of incorrect ddNTPs can be attributed to infidelity. As shown previously with R110-labeled ddGTP and ddUTP (FIG. 27), Taq F667Y exhibits a greater tendency to misincorporate unlabeled ddG opposite dT, and unlabeled ddT opposite dC, compared to JDF-3 P410L/A485T (FIG. 28). These results indicate that the relatively high ddG:dT misinsertion rate (and ddT:dC to a lower extent) exhibited by Taq F667Y DNA polymerase is unrelated to selective misincorporation of rhodamine-labeled ddG or ddT, but rather reflects the enzyme's greater inherent tendency to misincorporate ddGTP opposite dT and ddT opposite dC.

Figure 25A:
FIG. 25. Insertion and misinsertion assays employing JDF3 P410L/A485T and Taq F667Y (Thermo Sequenase) DNA polymerases. Assays were carried out as described under the Materials and Methods. In panel A, the correct nucleotide (R6G-ddAMP) was incorporated in the presence of R6G-ddATP at 0.0001, 0.001, 0.005, 0.01, 0.05, 0.1, 0.5 μM, respectively, by JDF3 P410L/A485T (lanes 1-7) and Taq F667Y (lanes 8-14). In panel B, the correct nucleotide (TAMRA-ddAMP) was inserted at TAMRA-ddATP concentrations of 0.001, 0.005, 0.01, 0.05, 0.1, 0.5 μM, respectively, by JDF3 P410L/A485T (lanes 1-6) and Taq F667Y (lanes 7-12). In panel C, incorrect TAMRA-ddGMP was incorporated into standing start primer-template by incubating JDF3 P410L/A485T (lanes 1-8) or Taq F667Y (lanes 9-16) DNA polymerases with TAMRA-ddGTP at concentrations of 0.005, 0.01, 0.05, 0.1, 1, 5, 10 μM, respectively.
Figure 25B:
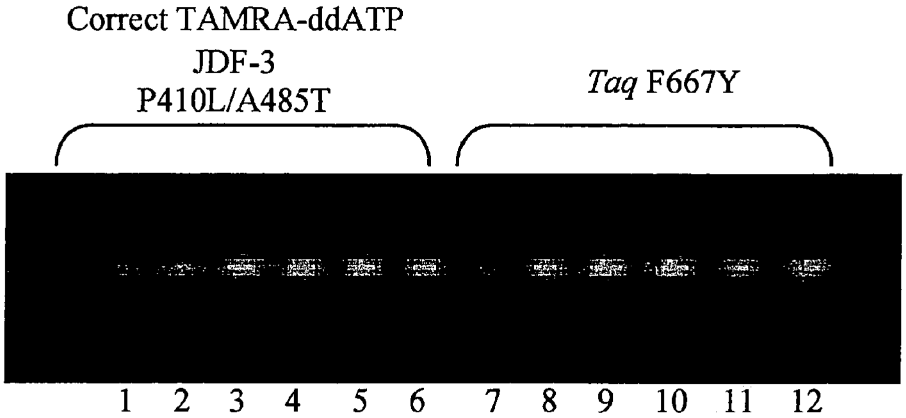
Figure 25C:
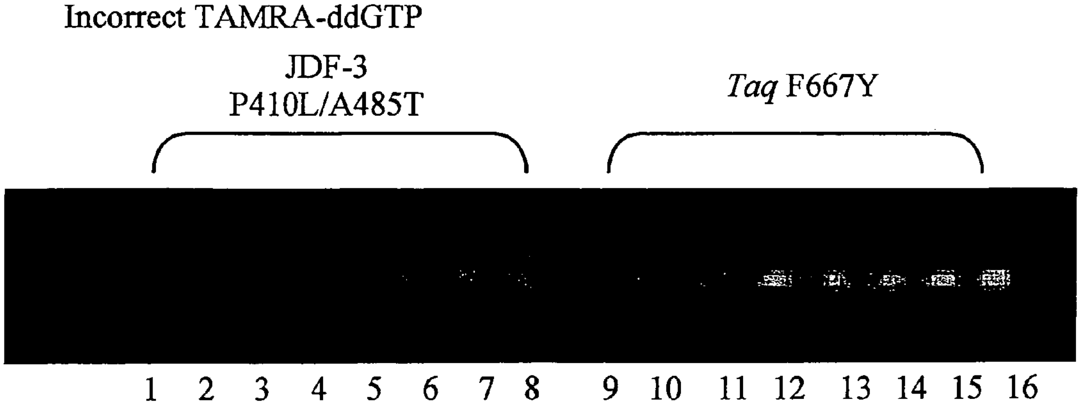

In further studies, the misinsertion frequency for the ddG:dT mispair was determined in terms of relative $K_m$ and $V_{max}$ values for incorporation of wrong versus correct dye-ddNTP. Extension from the pBL34A primer was measured opposite dT in the template strand. FIG. 25 panels B and C compare the incorporation of correct (TAMRA-ddA) and incorrect (TAMRA-ddG) nucleotides by 0.1 units of JDF-3 P410L/A485T and Taq F667Y mutants, respectively. Apparent Michaelis constant ($K_m$), maximum velocity ($V_{max}$), and relative insertion frequencies were measured for TAMRA-ddATP and TAMRA-ddGTP (Table 3). The misinsertion frequency for the ddGTP:dT mispair is approximately 17-fold higher for the Taq F667Y mutant compared to the JDF-3 P410L/A485T mutant. Differences in ddGTP:dT misinsertion frequency are attributed primarily to differences in $K_m$ for the wrong dye-ddNTP (ddGTP)•primer:template ternary complex.

Materials and Methods

Rhodamine labeled-ddNTPs were purchased from NEN. EDTA/blue dextran and rhodamine dye-matrix standards were purchased from Applied Biosystems. Thermo Sequenase™ was from Amersham Pharmacia Biotech. Long Ranger® polyacrylamide gels (6%) were purchased from BMA. CENTRI-SEP spin columns were from Princeton Separations. pBluescript® II was from Stratagene. Oligonucleotides (PAGE purified) were purchased from Genset oligos (Table 1). All other reagents were molecular biology grade. The sequence of *Thermococcus* JDF-3 DNA polymerase has GenBank accession no. AX135459].

Mutagenesis and Purification of JDF-3 DNA Polymerase:

Random mutations were introduced into a 3'-5' exonuclease deficient JDF-3 (E143A) DNA polymerase mutant by amplifying the entire gene (GenBank accession no. AX135459) with primers 721 and 923 (Table 1) using the GeneMorph PCR mutagenesis kit (Stratagene) or Taq as described in Cadwell, R. C. & Joyce, G. F. (1994) PCR Methods Appl. 3, S136-40, except that 1.5 mM $MgCl_2$ was used. The purified PCR products were ligated into the UNI-ZAP®XR vector (Stratagene), and the lambda DNA was packaged with Gigapak®III Gold packaging extract and plated on *E. coli* XL1-Blue MRF' cells, as recommended by the manufacturer. The mutant library was screened for clones with enhanced ddNTP incorporation using the technique of Sagner et al. (1991) Gene 97, 119-23 with minor modifications. Plaque lifts were incubated in polymerase assay cocktail containing 125 ng/ml activated calf thymus DNA (Sigma), 1.29 μCi/ml $\alpha^{33}$PddNTP (Amersham), 10 mM Tris (pH 8.8), 50 mM KCl, 1.5 mM $MgCl_2$, and 0.001% gelatin. Plaques producing the strongest signals were cored, and lambda phage clones were excised (pBluescript®II $SK^-$) using ExAssist® Interference-Resistant helper phage (Stratagene), according to the manufacturer's recommendations. Mutants were sequenced using primers 3 and 5 (Table 1). Site-directed mutants were constructed using the QuikChange™ Site-Directed Mutagenesis Kit (Stratagene).

DNA polymerase mutants were expressed in XL10-Gold® ultracompetent cells (Stratagene). Partially-purified protein samples were prepared by heating (15 minutes @ 72° C.) and centrifuging (14,000 rpm, 5 minutes) resuspended bacterial cells. JDF-3 DNA polymerase mutants were purified to >90% homogeneity as described previously Hansen, et al. (2001) WO 0132887). DNA polymerase activity was measured as described Hogrefe, H. H. et al. (2001) In Methods Enzymol. (Adams, M. W. W. & Kelly, R. M., eds.), pp. 334, Academic Press, San Diego, where one unit of polymerase activity is defined as the amount of enzyme that catalyzes the incorporation of 10 mmoles of total nucleotide into DE81 filter-bound form in 30 minutes at 72° C.

$I_{50\%}$ Assays:

ddNTP incorporation was expressed ($I_{50\%}$) as the ddNTP concentration that reduces dNTP incorporation by 50%. Polymerase assays were performed with activated calf thymus DNA as described by Hogrefe, H. H. et al. (2001). (Adams, M. W. W. & Kelly, R. M., eds.), pp. 334, Academic Press, San Diego, except that each reaction contained 0-20 μM (mutants) or 160 μM ($exo^-$ JDF-3) of one ddNTP (e.g., ddGTP), plus the amount of corresponding dNTP that gives 200 μM total nucleotide (e.g. [ddGTP]+[dGTP]=200 μM). The other three dNTPs were present at 200 μM each (e.g., dCTP, dATP, TTP). Reactions were carried out at 72° C. using DNA polymerase amounts that exhibited the same unit activity under standard conditions (Hogrefe, H. H. et al. (2001). In Methods Enzymol. (Adams, M. W. W. & Kelly, R. M., eds.), pp. 334, Academic Press, San Diego). $I_{50\%}$ values were extrapolated from plots of % activity (background-corrected cpms incorporated in the presence of ddNTP/background-corrected cpms incorporated in the absence of ddNTPs) vs. ddNTP concentration.

Sequencing Assays:

Sequencing reactions (20 μl) consisted of 0.5 pmol fluorescein-labeled primer pFl-20 (Table 1), 1 pmol pBluescript II, 5 U DNA polymerase, all four dNTPs (each at 50 μM) and varying concentrations of only one ddNTP in 20 mM Tris pH 8.8, 10 mM $(NH_4)_2SO_4$, and 2 mM $MgSO_4$. Reactions were incubated in a Perkin-Elmer 9600 for 25 cycles as follows: 95° C. for 20 s, 50° C. for 20 s and 72° C. for 4 min. The reactions were quenched with ice-cold 0.2 M EDTA (final concentration), dried, and the pellets dissolved in 3:1 formamide:EDTA/blue dextran. Reactions were then analyzed by 6% denaturing PAGE on an ABI 377 sequencer.

Kinetic Analysis of Rhodamine-ddNTP Incorporation and Misincorporation:

Primer:template duplexes were formed by annealing templates with a 10-fold excess of primer in 10 mM Tris-HCl (pH 8)/0.1 mM EDTA using the following temperature regimen: 5 min at 95° C., followed by slow cooling to room temperature. Primer:template concentrations are expressed as moles of single-stranded template.

$K_m$ and $V_{max}$ values for rhodamine-ddNTP incorporation were measured as described Patel, P. H. et al. (2001). J. Biol. Chem. 276, 5044-51 by incubating 50 nM primer:template with limiting amounts of DNA polymerase (0.1 units, 5 nM) and varying concentrations of rhodamine labeled-ddNTP (0.1 nM to 500 nM). All single nucleotide incorporations with R6G-ddATP and TAMRA-ddATP employed pBL34A:pBluescript II, while reactions with TAMRA-ddCTP were performed with pBL25C:pBluescript II. The 10× reaction buffer used for JDF-3 DNA polymerase contained 200 mM Tris-HCl (pH 8.8), 100 mM KCl, 100 mM $(NH4)_2SO_4$, and 20 mM $MgSO_4$, while the 10× reaction buffer employed with the Taq F667Y mutant consisted of 260 mM Tris-HCl (pH 9.5) and 65 mM $MgCl_2$. Samples were incubated at 60° C. for 10 minutes, and the reactions were quenched with ice-cold 0.2 M EDTA (final concentration). Unincorporated rhodamine-ddNTPs were removed with CENTRI-SEP spin columns according to the manufacturer's manual. Reactions were dried, and the pellets were dissolved in 3:1 formamide:EDTA/blue dextran and analyzed by 6% denaturing PAGE on an ABI 377 sequencer. Peak area quantitations were performed using 3.1.2 GeneScan® software and $K_m$ and $V_{max}$ values were calculated using Lineweaver-Burk plots.

$K_m$ and $V_{max}$ values for primer:template were measured with limiting amounts of enzyme (0.1 units, 5 nM) in the presence of 100 nM dye-ddNTP and varying concentrations of primer:template (0.5-100 nM). Single nucleotide incorporations with R110-ddGTP employed pBL31G:pBluescript II, while reactions with ROX-ddCTP were carried out with pBL25C:pBluescript II. Samples were incubated and analyzed as described above.

To determine the kinetics of misinsertion, $K_m$ and $V_{max}$ values were calculated by incubating limiting amounts of enzyme (0.1 units, 5 nM) in presence of 50 mM primer: template (pBL34A:pBluescript II) and varying concentrations of non-complementary rhodamine-ddGTP (1-10,000 nM) for 10 minutes at 60° C. Analysis and quantitation were performed as above.

ddNTP Misincorporation Assays:

Fidelity assays using labeled ddNTPs (10 μl) contained 1 unit DNA polymerase in 1× reaction buffer, 15 nM primer: template, 25 nM of unlabeled complementary ddNTP, and 25, 100, 500, or 1000 nM of rhodamine-labeled non-complementary ddNTP in four separate reactions. The reactions were incubated in a Perkin-Elmer 9600 for 25 cycles as follows: 96° C. for 10 s, 50° C. for 5 s, and 60° C. for 30 s. The reactions were quenched and analyzed as above.

Fidelity assays using unlabeled ddNTPs (10 μl) contained 2.5 nM primer:template (pFL-35:pBluescript), 1 U DNA polymerase, and 1× reaction buffer. Complementary or non-complementary ddNTP was added to the reaction at concentrations of 0, 1.25, 10, 50, or 100 nM. The reactions were incubated in a Perkin-Elmer 9600 for 25 cycles as follows: 96° C. for 10 s, 50° C. for 5 s, and 60° C. for 30 s, and then analyzed as described above.

TABLE 1

Synthetic oligonucleotides

| | |
|---|---|
| Temp-T | 5'-CTCATCTTGGAGCGAACGACCTACACCGAA |
| Temp-C | 5'-CTCACCTTGGAGCGAACGACCTACACCGAA |
| *pFL20 | 5'-(Fl)GGATGTGCTGCAAGGCGATT |
| *pFL35 | 5'-(Fl)CAGCTGGCGAAAGGGGGATGTGCTGCAAGGCG ATT |
| pBL2SC | 5'-TTCGGTGTAGGTCGTTCGCTCCAAG |
| pBL31G | 5'-TTCAGCATCTTTTACTTTCACCAGCGTTTCT |
| pBL34A | 5'-AGCTGGCGAAAGGGGGATGTGCTGCAAGGCGATT |
| Primer 3 | 5'-CCAGCTTTCCAGACTAGTCGGCCAAGGCC |
| Primer 5 | 5'-AACTCTCGACCCGCTG |
| Primer 721 | 5'-GAGAGAATTCATAATGATAAGGAGGAAAAAATTAT GATCCTTGACGTTGATTAC |
| Primer 923 | 5'-TCAGATCTCGAGTCACTTCTTCTTCCCCTTC |

*pFl-20 and pFL-35 are labeled with fluorescein at their 5'-ends.

TABLE 2

Steady-state kinetic parameters* for rhodamine-labeled ddNTPs and primer:template.

| Substrate | JDF-3 P410L/A485T $K_m$ (nM) | JDF-3 P410L/A485T $V_{max}$ (fmol/min) | Taq F667Y $K_m$ (nM) | Taq F667Y $V_{max}$ (fmol/min) |
|---|---|---|---|---|
| Primer:template†,‡ | 10 | 7.4 | 8 | 7.4 |
| R6G-ddATP‡ | 0.33 | 6 | 0.35 | 9 |
| TAMIRA-ddATP‡ | 0.9 | 1.9 | 0.6 | 1.9 |
| TAMRA-ddCTP‡ | 1 | 3.3 | 0.3 | 2.3 |

*All values have ±<30% error and were obtained from three independent experiments.
†Nmoles of template, in the presence of 10-fold excess of annealed primer.
‡Primer:template used for each experiment is defined in the Materials and Methods section.

TABLE 3

Kinetic Parameters* for TAMRA-ddATP† insertion versus TAMRA-ddGTP‡ misinsertion.

| DNA polymerase | I.E.‡ ($V_{max}/K_m$) | M.E.‡ ($V_{max}/K_m$) | M.F.‡ (M.E./I.E.) |
|---|---|---|---|
| JDF-3 P410L/A485T | 1.9/0.9 = 2.1 | 4.7/700 = 0.0067 | 0.003 |
| Taq F667Y | 1.9/0.6 = 3.2 | 16.9/100 = 0.169 | 0.053 |

*All values have ±<30% error and were obtained from 3 independent experiments.
†Primer:template used for each experiment is defined in the Materials and Methods section.
‡I.E., M.E. and M.F. are insertion efficiency, misinsertion efficiency and misinsertion frequency, respectively.

REFERENCES

1. Joyce, C. M., Kelley, W. S. and Grindley N. D. F. (1982) J. Biol. Chem. 257, 1958-1964.
2. Lopes, P. Martinez, S., Diaz, A. Espinosa, M. And Lacks, S. A. (1989) J. Biol. Chem. 264, 4255-4263.
3. Lawyer, F. C., Stoffel, S., Saiki, R. K., Myambo, K. Drummond, R. and Gelfand, D. H. (1989) J. Biol. Chem. 264, 6427-6437.
4. Akhmetzjanov, A. A. and Vakhitov, V. A. (1992) Nucl. Acids Res. 20, 5839.
5. Leavitt, M. C. and Ito, J. (1989) Proc. Acad. Sci. U.S.A. 86, 4465-4469.
6. Dunn, J. J. and Studier, F. W. (1983) J. Mol. Biol. 166, 477-535.
7. Scarlato, V. And Gargano, S. (1992) Gene 118, 109-113.
8. Ràdén, B. And Rutberg, L. (1984) J. Virol. 52, 9-15.
9. Foury, F. (1989) J. Biol. Chem. 264, 20552-20560.
10. Ito, J. And Braithwaite, D. K. (1990) Nucl. Acids Res. 18, 6716.
11. Blanco, L. Bernad, A. And Salas, M. (1991) Nucl. Acids res. 19, 955.
12. Hahn, S. And Rüger, W, (1989) Nucl. Acids Res. 17, 6729.
13. Hollingsworth, H. C. and Nossal, N. G. (1991) J. Biol. Chem. 266, 1888-1897.
14. Kaliman, A. V., Krutilina, A. I., Kryukov, V. M. and Bayev, A. A. (1986) FEBS Lett. 195, 61-64.
15. Iwasaki, H. Ishino, Y., Toh, H. Nakata, A. and Shinagawa, H. (1991) Mol. Gen. Genet. 226, 24-33.
16. Jung, G., Leavitt, M. C., Hsieh, J.-C. and Ito, J. (1987) Proc. Natl. Acad. Sci. U.S.A. 84, 8287-8291.
17. Savilahti, H. And Bamford D. H. (1987) Gene 57, 121-130.
18. Yoshikawa, H. And Ito, J. (1982) Gene 17, 323-335.
19. Matsumoto, K., Takano, H., Kim, C. I. and Hirokawa, H. (1989) Gene 84, 247-255.
20. Spicer, E. K., Rush, J. Fung, C., Reha-Krantz, L. J., Karam, J. D. and Konigsberg, W. H. (1988) J. Biol. Chem. 263, 7478-7486.
21. Perler, F. B., Comb, D. G., Jack, W. E., Moran, L. S., Qiang, B., Kucera, R. B., Benner, J., Slatko, B. E., Nwankwo, D. O., Hempstead, S. K., Carlow, C. K. S. and Jannasch, H. (1992) Proc. Natl. Acad. Sci. USA 89, 5577-5581.
22. Mathur, E. J., Adams, M. W., Callen, W. N. and Cline, J. M. (1991) Nucleic. Acids Res. 19, 6952.
23. Pisani, F. W., De Martino, C. and Rossi, M. (1992) Nucl. Acids Res. 20, 2711-2716.
24. Wong S., W. Wahl, A. F., Yuan, P.-M., Arai, N., Pearson, B. E., Arai, K, -i., Korn, D., Hunkapiller, M. W. and Wang, T. S.-F. (1988) EMBO J. 7, 37-47.
25. Pizzagalli, A., Valsasnini, P., Plevani, P. and Lucchini, G. (1988) Proc. Natl. Acad. Sci. U.S.A. 85, 3772-3776.

26. Damagnez, V., Tillit, J., deRecondo, A.-M. and Baldacci, G. (1991) Mol. Gen. Genet. 226, 182-189.

27. Hirose, F., Yamaguchi, M. Nishida, Y., Masutani, M., Miyazawa, H., Hanaoka, F. and Matsukage, A. (1991) Nucl. Acids Res. 19, 4991-4998.

28. Leegwater, P. A. J., Strating, M., Murphy, N. B., Kooy, R. F., van der Vliet, P. C. and Overdulve, J. P. (1991) Nucl. Acids Res. 19, 6441-6447.

29. Chung, D. W., Zhang, J., Tan C.-K., Davie, E. W., So, A. G. and Downey, K. M. (1991) Proc. Natl. Acad. Sci. USA 88, 11197-11201.

30. Yang, C.-L., Chang, L. S., Zhang, P., Hao, H., Zhu, L., Tommey, N. L. and Lee, M. Y. W. T. ((1992) Nucl. Acids Res. 20, 735-745.

31. Zhang, J. Chung, D. W., Tan, C.-K., Downey, K. M., Davie, E. W. and So, A. G. (1991) Biochemistry 30, 11742-11750.

32. Morrison, A. and Sugino, A. (1992) Nucl. Acids Res. 20, 375.

33. Pignéde, G., Bouvier, D., deRecondo, A.-M. And Baldacci, G. (1991) J. Mol. Biol. 222, 209-218.

34. Ridley, R. G., White, J. H., McAleese, S. M., Gorman, M., Alano, P., deVies, E. and Kilbey, B. J. (1991) Nucl. Acids Res. 19, 6731-6736.

35. Morrison, A., Araki, H., Clark, A. B., Hamatake, R. K. and Sugino, A. (1990) Cell 62, 1143-1151.

36. Morrison, A., Christensen, R. B., Alley, J., Beck, A. K., Bernstine, E. G., Lemontt, J. F. and Lawrence, C. W. (1989) J. Bacteriol. 171, 5659-5667.

37. Gibbs, J. S., Chiou, H. C., Hall, J. D., Mount, D. W., Retondo, M. J., Weller, S. K. and Coen, D. M. (1985) Proc. Natl. Acad. Sci. U.S.A. 82, 7969-7973.

38. Telford, E. A., Watson, M. S., McBride, K. and Davison, A. J. (1992) Virology 189, 304-316.

39. Davison, A. J. and Scott, J. E. (1986) J. Gen. Virol. 67, 1759-1816.

40. Baer, R., Bankier, A. T. Biggin, M. D., Deininger, P. L., Farrell, P. J., Gibson, T. J., Hatfull, G., Hudson, G. S., Satchwell, S. C., Seguin, C., Tuffnell, P. S. and Barrell, B. G. (1984) Nature 310, 207-211.

41. Albrecht, J.-C. and Fleckenstein, B. (1990) Virology 174, 533-542.

42. Kouzarides, T. Bankier, A. T., Satchwell, S. C., Weston, K., Tomlinson, P. and Barrell, B. G. (1987) J. Virol, 61, 125-133.

43. Elliott, R., Clark, C. Jaquish, D. and Spector, D. H. (1991) Virology n185, 169-186.

44. Teo, I. A., Griffin, B. E. and Jones, M. D. (1991) J. Virol. 65, 4670-4680.

45. Davison, A. J. (1992) Virology 186, 9-14.

46. Grabherr, R., Strasser, P. and Van Etten, J. L. (1992) Virology 188, 721-731.

47. Binns, M. M., Stenzier, L. Tomley, F. M., Campbell, J. and Broursnell, M. E. G. (1987) Nucl. Acids Res. 15, 6563-6573.

48. Earl P. L., Jones, E. V. and Moss, B. (1986) Proc. Natl. Acad. Sci. U.S.A. 83, 3659-3663.

49. Mustafa, A. And Yuen, L. (1991) DNA Seq. 2, 39-45.

50. Tomalski, M. D., Wu, J. and Miller, L. K. (1988) Virology 167, 591-600.

51. Bjornson, R. M. and Rohrmann, G. F. (1992) J. Gen. Virol 73, 1499-1504.

52. Gingeras, T. R., Sciaky, D., Gelinas, R. E., Bing-Dong, J., Yen, C. E., Kelly, M. M., Bullock, P. A. Parsons, B. L., O'Neill. K. E. and Roberts, R. J. (1982) J. Biol. Chem., 257, 13475-13491.

53. Engler, J. A., Hoppe, M. S. and van Bree, M. P. (1983) Gene 21, 145-159.

54. Shu, L., Hing, J. S., Wei, Y.-f. and Engler, J. A., (1986) Gene 46, 187-195.

55. Paillard, M., Sederoff, R. R. and Levings, C. S. III (1985) EMBO J. 4, 1125-1128.

56. Chan, B. S.-S., Court, D. A., Vierula, P. J. and Bertrand, H. (1991) Curr. Genet. 20, 225-237.

57. Kempken, F., Meinhardt, F. and Esser, K. (1989) Mol. Gen. Genet, 218, 623-530.

58. Oester, B. And Tudzynski, P. (1989) Mol. Gen. Genet. 217, 132-140.

59. Court D. A. and Bertrand, H. (1992) Curr. Genet. 22, 385-397.

60. Robison, M. M., Royer, J. C. and Horgen, P. A. (1991) Curr. Genet. 19, 495-502.

61. Stark, M. J. R., Mileham, A. J., Romanos, M. A. and Boyd, A. (1994) Nucl. Acids Res. 12, 6011-6030.

62. Tommasino, M. Ricci, S. and Galeotti, C. L. (1988) Nucl. Acids Res. 16, 5863-5878.

63. Hishinuma, F. and Hirai, K. (1991) J. Gen. Genet. 226, 97-106.

64. Hopfner, K. P. et al. (1999) Proc. Natl. Acad. Sci. U.S.A. 96, 3600-3605.

65. Niehaus, F. et al. (1997) Gene 204, 153-158.

66. Tagaki et al. (1997) Appl. Environ. Microbiol. 63, 4504-4510.

67. Datukishvili, N. et al. (1996) Gene 177, 271-273.

68. Southworth, M. W. et al. (1996) Proc. Natl. Acad. Sci. U.S.A. 93, 5281-5285.

69. Uemori, T. et al. (1995) J. Bacteriol. 177, 2164-2177.

70. Konisky, J. et al. (1994) J. Bacteriol. 176, 6402-6403.

71. Zhao (1999) Structure Fold Des. 7, 1189.

72. Lai, E., Riley, J., Purvis, I. & Roses, A. A 4-Mb high-density single nucleotide polymorphism-based map around human APOE. Genomics 54, 31-8. (1998).

73. Saiki, R. K., Walsh, P. S., Levenson, C. H. & Erlich, H. A. Genetic analysis of amplified DNA with immobilized sequence-specific oligonucleotide probes. Proc Natl Acad Sci USA 86, 6230-4. (1989).

74. Landegren, U., Kaiser, R., Caskey, C. T. & Hood, L. DNA diagnostics—molecular techniques and automation. Science 242, 229-37. (1988).

75. Shi, M. M. Enabling large-scale pharmacogenetic studies by high-throughput mutation detection and genotyping technologies. Clin Chem 47, 164-72. (2001).

76. Livak, K. J., Marmaro, J. & Todd, J. A. Towards fully automated genome-wide polymorphism screening. Nat Genet. 9, 341-2. (1995).

77. Tyagi, S., Bratu, D. P. & Kramer, F. R. Multicolor molecular beacons for allele discrimination. Nat Biotechnol 16, 49-53. (1998).

78. Gilles, P. N., Wu, D. J., Foster, C. B., Dillon, P. J. & Chanock, S. J. Single nucleotide polymorphic discrimination by an electronic dot blot assay on semiconductor microchips. Nat Biotechnol 17, 365-70. (1999).

79. Fu, D. J. et al. Sequencing exons 5 to 8 of the p53 gene by MALDI-TOF mass spectrometry. Nat Biotechnol 16, 381-4. (1998).

80. Chen, X. & Kwok, P. Y. Template-directed dye-terminator incorporation (TDI) assay: a homogeneous DNA diagnostic method based on fluorescence resonance energy transfer. Nucleic Acids Res 25, 347-53. (1997).

81. Syvanen, A. C., Aalto-Setala, K., Harju, L., Kontula, K. & Soderlund, H. A primer-guided nucleotide incorporation assay in the genotyping of apolipoprotein E. Genomics 8, 684-92. (1990).

82. Taylor, J. D. et al. Flow cytometric platform for high-throughput single nucleotide polymorphism analysis. Biotechniques 30, 661-6, 668-9. (2001).
83. Chen, X., Zehnbauer, B., Gnirke, A. & Kwok, P. Y. Fluorescence energy transfer detection as a homogeneous DNA diagnostic method. Proc Natl Acad Sci USA 94, 10756-61. (1997).
84. Tabor, S. & Richardson, C. C. A single residue in DNA polymerases of the *Escherichia coli* DNA polymerase I family is critical for distinguishing between deoxy- and dideoxyribonucleotides. Proc Natl Acad Sci USA 92, 6339-43. (1995).
85. Gardner, A. F. & Jack, W. E. Determinants of nucleotide sugar recognition in an archaeon DNA polymerase. Nucleic Acids Res 27, 2545-53. (1999).
86. Evans, S. J. et al. Improving dideoxynucleotide-triphosphate utilisation by the hyperthermophilic DNA polymerase from the archaeon *Pyrococcus furiosus*. Nucleic Acids Res 28, 1059-66. (2000).

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

The invention claimed is:

1. A composition for identifying a nucleotide at a given position of a template DNA molecule, said composition comprising a Family B DNA polymerase having reduced discrimination against non-conventional nucleotides and a first primer, wherein said first primer anneals to the immediate 3' of said nucleotide at the given position of said template DNA molecule, and wherein said Family B DNA polymerase has a substitution at a position corresponding to L408, P410, or both L408 and P410 of SEQ ID NO:2, which result in reduced discrimination by the mutant polymerase as compared to the non-mutant polymerase from which it is derived.

2. The composition of claim 1, wherein said Family B DNA polymerase is a JDF-3 DNA polymerase having a sequence of SEQ ID NO:2 but comprising a substitution at L408, P410, or both L408 and P410, and further comprising a substitution at A485.

3. The composition of claim 2, wherein said JDF-3 DNA polymerase has one or more of the following substitutions: L408H, L408F, A485T, or P410L.

4. The composition of claim 2, wherein said JDF-3 DNA polymerase is substituted at position P410 with an amino acid having a non polar side chain.

5. The composition of claim 4, wherein said amino acid having a non polar side chain is selected from the group of methionine, glycine, alanine, valine, leucine, isoleucine, phenylalanine and proline.

6. The composition of claim 3, wherein said JDF-3 DNA polymerase comprises the following two amino acid mutations: P410L and A485T.

7. The composition of any one of claims 1 and 3-6, wherein said Family B DNA polymerase further comprises a substitution at a position corresponding to D141 or E143 or both D141 and E143 of SEQ ID NO:2, which reduces or abolishes 3' to 5' exonuclease activity.

8. The composition of claim 1, further comprising at least one chain-terminating nucleotide analog, wherein said chain-terminating nucleotide analog is incorporated into said first primer by said Family B DNA polymerase in a template-dependent manner.

9. The composition of claim 8, wherein at least one chain-terminating nucleotide analog is labeled with a first detectable label.

10. The composition of claim 8, wherein more than one chain-terminating nucleotide analog is labeled, each chain-terminating nucleotide analog being labeled with a different first detectable label.

11. The composition of claim 8, wherein said chain-terminating nucleotide analog is a dideoxynucleotide.

12. The composition of claim 11, wherein said dideoxynucleotide is selected from the group consisting of: ddATP, ddTTP, ddCTP and ddGTP.

13. The composition of claim 8, wherein said first primer is labeled with a second detectable label.

14. The composition of claim 13, wherein first and second detectable labels generate a signal for identifying said nucleotide at the given position of the template DNA molecule.

15. The composition of claim 1, further comprising a second primer.

16. The composition of claim 15, wherein said first primer is labeled with a second detectable label and said second primer is labeled with a third detectable label, said second and third detectable labels generate a signal for identifying said nucleotide at the given position of the template DNA molecule.

17. The composition of claim 16, wherein said second primer anneals to the immediate 5' of said nucleotide at the given position of said template DNA molecule.

18. The composition of claim 17, further comprising a DNA ligase.

19. The composition of claim 1, further comprising a reaction buffer for said Family B DNA polymerase.

20. The composition of claim 1, wherein said template DNA molecule is the product of a polymerase chain reaction or a plasmid DNA.

21. The composition of any one of claim 9, 13, or 16, wherein said first or second or third detectable label is one selected from the group consisting of: a fluorescent label, an isotope, a chemiluminescent label, a quantum dot label, an antigen, or an affinity moiety.

22. The composition of claim 21, wherein said first detectable label is a rhodamine label or a cyanine label.

23. An isolated recombinant Family B DNA polymerase having reduced discrimination against non-conventional nucleotides, wherein said DNA polymerase comprises an amino acid substitution at a position corresponding to P410 of SEQ ID NO:2, which reduces discrimination by the mutant polymerase as compared to the non-mutant polymerase from which it is derived.

24. The isolated recombinant Family B DNA polymerase of claim 23, wherein said amino acid substitution is a substitution with an amino acid having a non-polar side chain.

25. The isolated recombinant Family B DNA polymerase of claim 24, wherein said amino acid having a non-polar side chain is selected from the group of methionine, glycine, alanine, valine, leucine, isoleucine, phenylalanine and proline.

26. The isolated recombinant Family B DNA polymerase of claim 23, further comprising an amino acid substitution at a position corresponding to A485 of SEQ ID NO:2.

27. The isolated recombinant Family B DNA polymerase of claim 26, wherein said amino acid substitution at a position corresponding to P410 of SEQ ID NO:2 is a substitution with an amino acid having a non-polar side chain.

28. The isolated recombinant Family B DNA polymerase of claim 27, wherein said amino acid having a non-polar side chain is selected from the group of methionine, glycine, alanine, valine, leucine, isoleucine, phenylalanine and proline.

29. A kit for identifying a nucleotide at a given position of a template DNA molecule, said kit comprising a Family B DNA polymerase having reduced discrimination against non-conventional nucleotides and a first primer, wherein said first primer anneals to the immediate 3' of said nucleotide at the given position of said template DNA molecule, and wherein said Family B DNA polymerase has a substitution at a position corresponding to L408, P410, or both L408 and P410 of SEQ ID NO:2, which result in reduced discrimination by the mutant polymerase as compared to the non-mutant polymerase from which it is derived.

30. The kit of claim 29, wherein said Family B DNA polymerase is a JDF-3 DNA polymerase having a sequence of SEQ ID NO:2 but comprising a substitution at L408, P410, or both L408 and P410, and further comprising a substitution at A485.

31. The kit of claim 30, wherein said JDF-3 DNA polymerase is substituted at a position corresponding to P410 of SEQ ID NO:2 with an amino acid having a non-polar side chain.

32. The kit of claim 31, wherein said amino acid having a non-polar side chain is selected from the group of methionine, glycine, alanine, valine, leucine, isoleucine, phenylalanine and proline.

33. The kit of claim 30, wherein said JDF-3 DNA polymerase has one or more of the following substitutions: L408H, L408F, A485T, or P410L.

34. The kit of claim 33, wherein said JDF-3 DNA polymerase comprises the following two amino acid mutations: P410L and A485T.

35. The kit of claim 29, wherein said Family B DNA polymerase further comprises a substitution at a position corresponding to D141 or E143 or both D141 and E143 of SEQ ID NO:2, which reduces or abolishes 3' to 5' exonuclease activity.

36. The kit of claim 29, further comprising at least one chain-terminating nucleotide analog, wherein said chain-terminating nucleotide analog is incorporated into said first primer by said Family B DNA polymerase in a template-dependent manner.

37. The kit of claim 36, wherein at least one chain-terminating nucleotide analog is labeled with a first detectable label.

38. The kit of claim 36, wherein more than one chain-terminating nucleotide analog is labeled, each chain-terminating nucleotide analog being labeled with a different first detectable label.

39. The kit of claim 36, wherein said chain-terminating nucleotide analog is a dideoxynucleotide.

40. The kit of claim 39, wherein said dideoxynucleotide is selected from the group consisting of: ddATP, ddTTP, ddCTP and ddGTP.

41. The kit of claim 36, wherein said first primer is labeled with a second detectable label.

42. The kit of claim 41, wherein first and second detectable labels generate a signal for identifying said nucleotide at the given position of the template DNA molecule.

43. The kit of claim 29, further comprising a second primer.

44. The kit of claim 43, wherein said first primer is labeled with a second detectable label and said second primer is labeled with a third detectable label, said second and third detectable labels generate a signal for identifying said nucleotide at the given position of the template DNA molecule.

45. The kit of claim 44, wherein said second primer anneals to the immediate 5' of said nucleotide at the given position of said template DNA molecule.

46. The kit of claim 45, further comprising a DNA ligase.

47. The kit of claim 29, further comprising a reaction buffer for said Family B DNA polymerase.

48. The kit of claim 29, wherein said template DNA molecule is the product of a polymerase chain reaction or a plasmid DNA.

49. The kit of claim 37, 41, or 44, wherein said first or second or third detectable label is one selected from the group consisting of: a fluorescent label, an isotope, a chemiluminescent label, a quantum dot label, an antigen, or an affinity moiety.

50. The kit of claim 49, wherein said first detectable label is a rhodamine label or a cyanine label.

51. The kit of claim 29, further comprising a control template and/or at least one control primer.

52. The kit of claim 51, comprising a control template and four control primers.

53. A kit for identifying a nucleotide at a given position of a template DNA molecule, said kit comprising a Family B DNA polymerase having reduced discrimination against non-conventional nucleotides, wherein said DNA polymerase comprises an amino acid substitution at a position corresponding to P410 of SEQ ID NO:2, which results in reduced discrimination by the mutant polymerase as compared to the non-mutant polymerase from which it is derived.

54. The kit of claim 53, wherein said amino acid substitution at a position corresponding to P410 of SEQ ID NO:2 is an amino acid substitution with an amino acid having a non polar side chain.

55. The kit of claim 54, wherein said amino acid having a non polar side chain is selected from the group of methionine, glycine, alanine, valine, leucine, isoleucine, phenylalanine and proline.

56. The kit of claim 53, further comprising an amino acid substitution at a position corresponding to A485 of SEQ ID NO:2.

57. The kit of claim 56 wherein the substitution at a position corresponding to P410 of SEQ ID NO:2 is a substitution with an amino acid with a non-polar side chain.

58. The kit of claim 57, wherein said amino acid having a non polar side chain is selected from the group of amino acid selected from the group of methionine, glycine, alanine, valine, leucine, isoleucine, phenylalanine and proline.

59. The composition of claim 1, wherein the Family B DNA polymerase is an Archaeal DNA polymerase.

60. The recombinant Family B DNA polymerase of claim 23, wherein the DNA polymerase is an Archaeal DNA polymerase.

61. The kit of claim 29, wherein the Family B DNA polymerase is an Archaeal DNA polymerase.

62. The kit of claim 53, wherein the Family B DNA polymerase is an Archaeal DNA polymerase.

63. The composition of claim 59, wherein the Archaeal DNA polymerase is selected from the group consisting of *Thermococcus litoralis* DNA polymerase (Vent); *Pyrococcus* sp. DNA polymerase (Deep Vent); *Pyrococcus furiosus* DNA polymerase (Pfu); *Pyrococcus* species strain GE 23 DNA polymerase; JDF-3 DNA polymerase; *Thermococcus gorgonanus* DNA polymerase (Tgo); *Thermococcus* species TY DNA polymerase; *Thermococcus* species strain KODI (KOD) DNA polymerase; *Thermococcus* species 9° N-7 DNA polymerase; *Pyrodictium occultum* DNA polymerase; *Sulfolobus solfataricus* DNA polymerase (Sso); *Sulfolobus acidocaldarius* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Thermococcus fumicolans* DNA polymerase; and *Aeropyrum pernix* DNA polymerase.

64. The recombinant Family B DNA polymerase of claim 60, wherein the Archaeal DNA polymerase is selected from the group consisting of: *Thermococcus litoralis* DNA polymerase (Vent); *Pyrococcus* sp. DNA polymerase (Deep Vent); *Pyrococcus furiosus* DNA polymerase (Pfu); *Pyrococcus* species strain GE 23 DNA polymerase; JDF-3 DNA polymerase; *Thermococcus gorgonanus* DNA polymerase (Tgo); *Thermococcus* species TY DNA polymerase; *Thermococcus* species strain KODI (KOD) DNA polymerase; *Thermococcus* species 9° N-7 DNA polymerase; *Pyrodictium occultum* DNA polymerase; *Sulfolobus solfataricus* DNA polymerase (Sso); *Sulfolobus acidocaldarius* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Thermococcus fumicolans* DNA polymerase; and *Aeropyrum pernix* DNA polymerase.

65. The kit of claim 61, wherein the Archaeal DNA polymerase is selected from the group consisting of: *Thermococcus litoralis* DNA polymerase (Vent); *Pyrococcus* sp. DNA polymerase (Deep Vent); *Pyrococcus furiosus* DNA polymerase (Pfu); *Pyrococcus* species strain GE 23 DNA polymerase; JDF-3 DNA polymerase; *Thermococcus gorgonanus* DNA polymerase (Tgo); *Thermococcus* species TY DNA polymerase; *Thermococcus* species strain KODI (KOD) DNA polymerase; *Thermococcus* species 9° N-7 DNA polymerase; *Pyrodictium occultum* DNA polymerase; *Sulfolobus solfataricus* DNA polymerase (Sso); *Sulfolobus acidocaldarius* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Thermococcus fumicolans* DNA polymerase; and *Aeropyrum pernix* DNA polymerase.

66. The kit of claim 62, wherein the Archaeal DNA polymerase is selected from the group consisting of *Thermococcus litoralis* DNA polymerase (Vent); *Pyrococcus* sp. DNA polymerase (Deep Vent); *Pyrococcus furiosus* DNA polymerase (Pfu); *Pyrococcus* species strain GE 23 DNA polymerase; JDF-3 DNA polymerase; *Thermococcus gorgonanus* DNA polymerase (Tgo); *Thermococcus* species TY DNA polymerase; *Thermococcus* species strain KODI (KOD) DNA polymerase; *Thermococcus* species 9° N-7 DNA polymerase; *Pyrodictium occultum* DNA polymerase; *Sulfolobus solfataricus* DNA polymerase (Sso); *Sulfolobus acidocaldarius* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Thermococcus fumicolans* DNA polymerase; and *Aeropyrum pernix* DNA polymerase.

* * * * *

UNITED STATES PATENT AND TRADEMARK OFFICE

CERTIFICATE OF CORRECTION

PATENT NO. : 8,772,006 B2
APPLICATION NO. : 11/435018
DATED : July 8, 2014
INVENTOR(S) : Joseph A. Sorge et al.

It is certified that error appears in the above-identified patent and that said Letters Patent is hereby corrected as shown below:

On the Title Page, Item (56)

On the page 2, in column 1 (Other Publications), line 21, delete "Themococcus" and insert -- Thermococcus --, therefor.

On the page 2, in column 1 (Other Publications), line 46, delete "Thermococus" and insert -- Thermococcus --, therefor.

On the page 2, in column 1 (Other Publications), line 56, delete "Deoxynucleotide" and insert -- Deoxynucleoside --, therefor.

On the page 2, in column 1 (Other Publications), line 60, delete "Shufflin," and insert -- Shuffling, --, therefor.

On the page 2, in column 1 (Other Publications), line 64, delete "Phosphocoacetic" and insert -- Phosphonoacetic --, therefor.

On the page 2, in column 2 (Other Publications), line 2, delete "Po.ymerase" and insert -- Polymerase --, therefor.

On the page 2, in column 2 (Other Publications), line 6, delete "Pyrococus" and insert -- Pyrococcus --, therefor.

On the page 2, in column 2 (Other Publications), line 11, delete "polymerae" and insert -- polymerase --, therefor.

On the page 2, in column 2 (Other Publications), line 46, delete "Polymerae" and insert -- polymerase --, therefor.

Signed and Sealed this
Thirtieth Day of September, 2014

Michelle K. Lee
*Deputy Director of the United States Patent and Trademark Office*

In the Specification

In column 1, line 10, delete "60/162,000," and insert -- 60/162,600, --, therefor.

In the Claims

In column 133, line 44, in claim 63, delete "of" and insert -- of: --, therefor.

In column 134, line 40, in claim 66, delete "of" and insert -- of: --, therefor.